US008234075B2

(12) United States Patent
Kimura et al.

(10) Patent No.: US 8,234,075 B2
(45) Date of Patent: Jul. 31, 2012

(54) APPARATUS AND METHOD FOR PROCESSING INFORMATION CONCERNING BIOLOGICAL CONDITION, SYSTEM, PROGRAM AND RECORDING MEDIUM FOR MANAGING INFORMATION CONCERNING BIOLOGICAL CONDITION

(75) Inventors: Takeshi Kimura, Kanagawa (JP); Yasushi Noguchi, Kanagawa (JP)

(73) Assignee: Ajinomoto Co., Inc., Tokyo (JP)

( * ) Notice: Subject to any disclaimer, the term of this patent is extended or adjusted under 35 U.S.C. 154(b) by 1400 days.

(21) Appl. No.: 11/148,352

(22) Filed: Jun. 9, 2005

(65) Prior Publication Data
US 2005/0283347 A1    Dec. 22, 2005

Related U.S. Application Data

(63) Continuation of application No. PCT/JP03/15713, filed on Dec. 9, 2003.

(30) Foreign Application Priority Data

Dec. 9, 2002 (JP) ................................. 2002-357042
Aug. 1, 2003 (JP) ................................. 2003-205589

(51) Int. Cl.
*G01N 33/48* (2006.01)
(52) U.S. Cl. ......................................................... 702/19
(58) Field of Classification Search ...................... 702/19
See application file for complete search history.

(56) References Cited

U.S. PATENT DOCUMENTS

| | | | |
|---|---|---|---|
| 5,054,915 A | 10/1991 | Kanda et al. |
| 5,687,716 A | 11/1997 | Kaufmann et al. |
| 5,769,074 A | 6/1998 | Barnhill et al. |
| 6,059,724 A | 5/2000 | Campell et al. |
| 6,300,136 B1 | 10/2001 | Koch et al. |
| 6,631,330 B1 | 10/2003 | Poynard |
| 6,777,197 B1 | 8/2004 | Shimoyama et al. |
| 6,925,389 B2 | 8/2005 | Hitt et al. |
| 7,290,212 B2 | 10/2007 | Fushimi et al. |
| 7,452,687 B2 | 11/2008 | Yamakoshi et al. |
| 2003/0004402 A1 | 1/2003 | Hitt et al. |
| 2003/0077833 A1 | 4/2003 | Campbell et al. |
| 2003/0158672 A1 | 8/2003 | Ramnarayan et al. |
| 2004/0022827 A1 | 2/2004 | Satomi et al. |
| 2004/0070624 A1 | 4/2004 | Fushimi et al. |
| 2004/0254122 A1 | 12/2004 | Hayes et al. |
| 2005/0043593 A9 | 2/2005 | Hitt et al. |
| 2005/0124865 A1 | 6/2005 | Kawanishi |
| 2005/0214885 A1 | 9/2005 | Yamakoshi et al. |
| 2005/0260671 A1 | 11/2005 | Hitt et al. |
| 2005/0283347 A1 | 12/2005 | Kimura et al. |
| 2006/0010090 A1 | 1/2006 | Brockway et al. |
| 2006/0170928 A1 | 8/2006 | Masilamani et al. |
| 2006/0253259 A1 | 11/2006 | Fernandez |

FOREIGN PATENT DOCUMENTS

| | | |
|---|---|---|
| EP | 0 316 812 A1 | 5/1989 |
| IN | 209084 B | 9/2007 |
| JP | 61-126472 A | 6/1986 |
| JP | 01-129837 B2 | 5/1989 |
| JP | 11-504739 A | 4/1999 |
| JP | 11-190734 A | 7/1999 |
| JP | 2002-220347 A | 8/2002 |
| JP | 2002-298147 A | 10/2002 |
| JP | 2003-159095 A | 6/2003 |
| JP | 2005-092853 A | 4/2004 |
| JP | 2004-135546 A1 | 5/2004 |
| JP | 2004-321179 A | 11/2004 |
| WO | WO 92/13273 A1 | 8/1992 |
| WO | WO 97/05553 A1 | 2/1997 |
| WO | WO 97/17891 A1 | 5/1997 |
| WO | WO 00/65472 A1 | 11/2000 |
| WO | WO 01/78652 A2 | 10/2001 |
| WO | WO 03/017177 A2 | 2/2003 |
| WO | WO 03/083133 A1 | 10/2003 |
| WO | WO 2004/038602 A1 | 5/2004 |
| WO | WO 2004/052191 A1 | 6/2004 |
| WO | WO 2005/020125 A2 | 3/2005 |
| WO | WO 2005/060608 A2 | 7/2005 |

OTHER PUBLICATIONS

Office Action mailed Jun. 2, 2009 in corresponding Japanese Application 2005-502361, 2 pages, with partial English translation, 5 pages.
Noguchi et al., "Metabolomics and its Potential for Assessment of Adequacy and Safety of Amino Acid Intake," The Journal of Nutrition, Jun. 2003, 133(6):Suppl. 1:097S-2100S, XP008088271.
Office Action mailed Mar. 11, 2009 in corresponding European Application 03 777 384.3, 8 pages.
Nefyodov et al., "New biochemical mechanisms of the anticancer effect of Ukrain in the treatment of cancer of the urinary bladder," Drugs Under Experimental and Clinical Research, 2000, XXVI(6/6):195-199, XP008088267.
Decision of a Patent Grant mailed Aug. 3, 2010, in corresponding JP 2005-502361, 1 page, with English translation, 3 pages.
Altamura et al., "Plasma concentrations of excitatory amino acids, serine, glycine, taurine and histidine in major depression," European Neuropsychopharmacology, 1995, 5(Supp):71-75.
Aoyagi et al., "Plasma Amino Acids in Patients with Crohn's Disease," JJPEN, Aug. 15, 1987, 9(4):593-599, with English translation, 10 pages.
Aoyama et al., "Plasma Amino Acid Distribution in Ulcerative Colitis," JJPEN, Jul. 10, 1994, 16(7):719-721, with English translation, 4 pages.
Argov et al., "Inflamatory Bowel Diseases as an Intermediate Stage between Normal and Cancer: A FTIR-Microspectroscopy Approach," Biopolymers, Dec. 5, 2004, 75(5):384-392.

(Continued)

*Primary Examiner* — Jerry Lin
(74) *Attorney, Agent, or Firm* — Foley and Lardner LLP

(57) ABSTRACT

A system provided in accordance with the present invention comprises a sever unit (100), which serves as an apparatus for processing information concerning a biological condition information, and a client unit (200), which serves as an information terminal of a provider of the information on the biological condition communicably connected to the server unit (100) via a network (300). The server unit (100) determines a composite index reflecting a plurality of metabolites indicative of the biological condition based on the information on the biological condition acquired from the client unit (200).

27 Claims, 57 Drawing Sheets

OTHER PUBLICATIONS

Baumgartner et al., "Supervised machine learning techniques for the classification of metabolic disorders in newborns," Bioinformatics, Nov. 22, 2004, 20(17):2985-2996.

Cascino et al., "Plasma Amino Acid Imbalance in Patients with Lung and Breast Cancer," Anticancer Research, 1995, 15(2):507-510.

Evans et al., "Perturbations in plasma amino acid profiles in small cell lung cancer (SCLC) and their response to treatment," Proc. Am. Assoc. Cancer Res. Ann. Meeting, Mar. 1988, 29:18(abstract 69).

Evans et al., "Maternal and fetal amino acid concentrations and fetal outcomes during pre-eclampsia," Reproduction, 2003, 125:785-790.

Fischer et al., "The role of plasma amino acids in hepatic encephalopathy," Surgery, Sep. 1975, 78(3):276-290.

Fukasawa et al., "Serum free amino acid content in hamsters with check pouch carcinoma," Jpn. J. Oral Biol., Oct. 20, 1992, 34:555-559, with English translation, 7 pages.

Fukui et al., "A Study of the Metabolism of Branched Chain Amino Acids in Terminal Stage Liver Cancer," Rinsho to Kenkyu, Apr. 1989, 66(4):1183-1187, with English translation.

Fukui, Shiro, "The Function and Significance of Amino Acid Transfusions (5) The capture of amino acids by the liver and amino acids in cirrhosis and hepatic carcinoma," JJPEN, 1995, 17(8):659-662.

Hirakawa et al., "Nutritional Assessment of Elemental Diet Therapy as Initial Therapy of Crohn's Disease—Plasma free amino acid, rapid turnover protein, change in clinical nutritional index," Eiyo-Hyoka to Chiryo, Japanese Journal of Nutritional Assessment, Nov. 15, 1991, 8(4):301-306, with English translation, 7 pages.

Hirayama et al., "Plasma Amino Acid Patterns in Hepatocellular Carcinoma," Biochemical Medicine and Metabolic Biology, 1987, 38(2):127-133.

Inoue et al., "Changes of Plasma Free Amino Acids in Hepatocellular Carcinoma: Clinical and Experimental Studies on Evaluation of Tyr/Phe Molar Ratio," J. Iwate Med. Assoc., Jun. 1988, 40(3):351-361, with English translation, 16 pages.

Isomaa et al., "Cardiovascular Morbidity and Mortality Associated with the Metabolic Syndrome," Diabetes Care, Apr. 2001, 24(4):683-689.

Iwagaki et al., "Observation on the Plasma Amino Acids of Patients with Colorectal Cancer," Journal of Japan Society of Coloproctology, 1991, 44(6):917-922, with English translation.

Kaneko et al., "Plasma Ratios of Tryptophan and Tyrosine to Other Large Neutral Amino Acids in Manic-Depressive Patients," The Japanese Journal of Psychiatry and Neurology, 1992, 46(3):711-720.

Kawakita, Hidenori, "Plasma-Free Amino Acids in Depressive Disorder," The Journal of Tokyo Medical University, 1994, 52(2):135-144, with English translation.

Kono et al., "Amino Acids and their Fractionation," Nippon Rinsho, 2004, 62(Supp 11):567-570, with English translation, 6 pages.

Kosaka et al., "Plasma Taurine Concentration in Patients with Crohn's Disease," Digestion & Absorption, Jan. 30, 1994, 16(2-93'):82-86, with English translation, 7 pages.

Kwon et al., "Plasma Amino Acids and Biochemical Parameters for Nutritional Assessment in Gastric Cancer Patients," Surgery, Metabolism, Nutrition, Apr. 1995, 29(2):129-134, with English translation.

Lee et al., "Identification of optimal classification functions for biological sample and state discrimination from metabolic profiling data," Bioinformatics, 2004, 20(6):959-969.

Maes et al., "Symptom Profiles of Biological Markers in Depression: A Multivariate Study," Psychoneuroendocrinology, Jan. 1, 1990, 15(1):29-37.

Matsuzawa et al. (The Examination Committee of Criteria for 'Obesity disease' in Japan, Japan Society for the Study of Obesity), "New Criteria for 'Obesity Disease' in Japan," Circ. J., 2002, 66(11):987-992.

Morita et al., "The development of dietary therapeutic agents adapted to pathological states and changes in blood amino acids in patients in the active phase of ulcerative colitis," Journal of Japanese Society of Chemical Nutrition, Oct. 20, 1999, 21(2):98, with English translation, 2 pages.

Murakami et al., "Changes of Free Amino Acids in Plasma and Tumor Tissue of Tumor-Bearing Rats with Total Parenteral Nutrition," JJPEN, Aug. 15, 1987, 9(4):615-621, with English translation, 12 pages.

Nefyodov et al., "Amino Acids and Their Derivatives in Blood Plasma of Patients with Breast Cancer Treated with Ukrain, Part V," Drugs Exptl. Clin. Res., 1996, 22(3-5):155-157.

Okuyama et al., "Study on Plasma Amino Acid Patterns in Liver Disease Using Multivariate Analysis," Liver Gall. Pancreas, 1987, 15(1):111-117, with English translation.

Pijl et al., "Insulin-Induced Decline of Plasma Amino Acid Concentrations in Obese Subjects With and Without Non-Insulin-Dependent Diabetes," Metabolism, May 1994, 43(5):640-646.

Proenza et al., "Breast and lung cancer are associated with a decrease in blood cell amino acid content," Journal of Nutritional Biochemistry, 2003, 14(3):133-138.

Proenza et al. "Blood amino acid compartmentation in men and women with different degrees of obesity," J. Nutr. Biochem., 1998, 9(12):697-704.

Rivera et al,. "Blood Amino Acid Compartmentation in Mice Bearing Lewis Lung Carcinoma," Cancer Research, Nov. 1, 1987, 47(21):5644-5646.

Roca et al., "Sex Differences in the Effect of Obesity on Human Plasma Tryptophan/Large Neutral Amino Acid Ratio," Ann. Nutr. Metab., 1999, 43(3):145-151.

Shimazaki et al., "Free Amino Acids in Normal and Tumorous Tissues of Human Kidney, Bladder, and Prostate," GANN, Oct. 1974, 65(5):455-457.

Villanueva et al., "Chromatography, Flow Injection Analysis and Electrophoresis in Computer-Assisted Comparative Biochemistry: Its Application and Possibilities in Clinical Research, Preliminary Studies on Crohn's Disease," Journal of Chromatography, 1988, 440:261-273.

Watanabe et al., "Analysis of plasma amino acids—tryptophan and tyrosine ratios to other large neutral amino acids in manic-depressive illness—," Japanese Journal of Clinical Medicine, 1994, 52(5):1152-1158, with English translation.

Wilson et al., "Free Serum Amino Acids in Patients with Advanced Cervical Carcinoma," Gynecologic Oncology, 1976, 4(3):311-313.

Yang et al., "Discrimination of Type 2 diabetic patients from healthy controls by using metabonomics method based on their serum fatty acid profiles," Journal of Chromatography B: Biomedical Sciences & Applications, Dec. 25, 2004, 813(1-2):53-58.

Anderson et al., "Decreased plasma tryptophan concentration in major depression: relationship to melancholia and weight loss," Journal of Affective Disorders, 1990, 20:185-191.

Bellodi et al., "Plasma tryptophan levels and tryptophan/neutral amino acid ratios in obsessive-compulsive patients with and without depression," Psychiatry Research, 1997, 69:9-15.

Eriksson et al., "Diurnal rhythm in absolute and relative concentrations of large neutral amino acids in human plasma," J. Psychiat. Res., 1989, 23(3/4):241-249.

Fekkes et al., "Effects of clomipramine on plasma amino acids and serotonergic parameters in panic disorder and depression," European Neuropsychopharmacology, 1997, 7:235-239.

Fortunato et al., "Multivariate Discriminant Function Based on Six Biochemical Markers in Blood can Predict the Cirrhotic Evolution of Chronic Hepatitis, " Clinical Chemistry, 2001, 47(9): 1696-1700.

Honig et al., "Amino acid levels in depression: A preliminary investigation," J. Psychiat. Res., 1988, 22(3):159-164.

Joseph et al., "Plasma $_L$-Tryptophan/Neutral Amino Acid Ratio and Dexamethasone Suppression in Depression," Psychiatry Research, 1984, 11:185-192.

Lee et al., "Plasma Amino Acid Levels in Patients with Colorectal Cancers and Liver Cirrhosis with Hepatocellular Carcinoma," Hepato-Gastroenterology, 2003, 50:1269-1273.

Lucca et al., "Plasma Tryptophan Levels and Plasma Tryptophan/neutral Amino Acids Ratio in Patients with Mood Disorder, Patients with Obsessive-Compulsive Disorder, and Normal Subjects," Psychiatry Research, 1992, 44:85-91.

Lucca et al., "Neutral Amino Acid Availability in Two Major Psychiatric Disorders," Prog. Neuro-Psychopharmacol. & Biol. Psychiat., 1995, 19:615-625.

Lucini et al., "Predictive value of tryptophan/large neutral amino acids ratio to antidepressant response," Journal of Affective Disorders, 1996, 36:129-133.

Macciardi et al., "Aminio Acid Patterns in Schizophrenia: Some New Findings," Psychiatry Research, 1990, 32:63-70.

Maes et al., "Serum levels of excitatory amino acids, serine, glycine, histidine, threonine, taurine, alanine and arginine in treatment-resistant depression: modulation by treatment with antidepressants and prediction of clinical responsivity," Acta Psychiatr. Scand., 1998, 97:302-308.

Moreno et al., "Tryptophan Depletion and Risk of Depression Relapse: A Prospective Study of Tryptophan Depletion as a Potential Predictor of Depressive Episodes," Biol. Psychiatry, 2000, 48:327-329.

Parvy et al., "A scheme for the interpretation of primary and secondary disturbances of plasma and urinary amino acid profiles. A possible way to an expert system," Clinica Chimica Acta, 1995, 235:1-10.

Russ et al., "Plasma tryptophan to large neutral amino acid ratios in depressed and normal subjects," Journal of Affective Disorders, 1990, 19:9-14.

Sanacora et al., "Subtype-Specific Alterations of γ-Aminobutyric Acid and Glutamate in Patients with Major Depression," Archives of General Psychiatry, 2004, 61:705-713.

Albright et al,. Methods for Investigation of Amino Acid and Protein Metabolism, Diabetes Mellitus, 1999, 231-247.

Fernstrom et al., "Rapid Measurement of Free Amino Acids in Serum and OSF, Using High-Performance Liquid Chromatography," Life Sciences, 1981, 29(20:2119-2130.

Franke et al., "Serum levels of total homocysteine, homocysteine metabolites and of advances glycation end-products (AGEs) in patients after renal transplantation," Clinical Nephrology, 2003, 59(2):88-97.

Ventura et al., "Plasma Homocysteine after Insulin Infusion in Type II Diabetic Patients with and without Methionine Intolerance," Exp. Clin. Endocrinol. Diabetes, 2004, 112:44-51.

Allan, Roy A., *A History of the Personal Computer, The People and The Technology*, Allan Publishing, London, Ontario, Canada, 2001.

Avogaro et al., "L-Arginine-Nitric Oxide kinetics in Normal and Type 2 Diabetic Subjects," Diabetes, Mar. 2003, 52:795-802.

Kubota et al., "Amino Acid Profiles correlate Diagnostically With Organ Site in Three Kinds of Malignant Tumors," Cancer, 1992, 69:2343-2348.

Luo et al., "Simple Blood Tests Can Predict Compensated Liver Cirrhosis in Patients with Chronic Hepatitis C," Hepato-Gastroenterology, 2002, 49:478-481.

Morgan et al., "Plasma amino-acid patterns in liver disease," Gut, 1982, 23:362-370.

Pohl et al., "Serum Aminotransferase Levels and Platelet Counts as Predictors of Degree of Fibrosis in Chronic Hepatitis C Virus Infection," American Journal of Gastroenterology, 2001, 96(11):3142-3146.

Suliman et al., "Hyperhonocysteinemia in Relation to Plasma Free Amino Acids, Biomarkers of Inflammation and Mortality in Patients with Chronic Kidney Disease Starting Dialysis Therapy," American Journal of Kidney Diseases, Sep. 2004, 44(3):455-465.

Wai et al., "A Simple Noninvasive Index Can Predict Both Significant Fibrosis and Cirrhosis in Patients with Chronic Hepatitis C," Hepatology, 2003, 38(2):518-526.

Williamson et al., "Concentrations of Free Glucogenic Amino Acids in Livers of Rats Subjected to Various Metabolic Stresses," Biochem. J., 1967, 104:497-502.

Zhang et al., "Plasma amino acid profiles applied for diagnosis of advanced liver fibrosis in patients with chronic hepatitis C infection," Hepatology Research, 2006, 34:170-177.

Caballero et al., "Plasma Amino Acid Levels in Obesity: Effects of Insulin Resistance," Amino Acids in Health and Disease: New Perspectives, 1987, 369-382.

Caballero et al., "Plasma Amino Acids and Insulin Levels in Obesity: Response to Carbohydrate Intake and Tryptophan Supplements," Metabolism, Jul. 1988, 37(7):672-676.

Caballero et al., "Differential Effects of Insulin Resistance on Leucine and Glucose Kinetics in Obesity," Metabolism, Jan. 1991, 40(1):51-58.

Caballero et al:, "Effect of Various Oral Glucose doses on Plasma Neutral Amino Acid Levels," Metabolism, Sep. 1982, 31(9):937-943.

Caballero et al., "Plasma amino acid concentrations in healthy elderly men and women," Am. J. Clin. Nutr., 1991, 53(5):1249-1252.

FIG. 1

(BASIC PRINCIPLE OF SETTING CORRELATION FORMULA) — S-1

ACQUIRE BIOLOGICAL CONDITION INFORMATION

| INDIVIDUAL (SAMPLE) NUMBER | INDEX DATA (T) OF BIOLOGICAL CONDITION | | | | GROUP OF BLOOD CONCENTRATION OF AMINO ACIDS | | | | | | |
|---|---|---|---|---|---|---|---|---|---|---|---|
| | $T_1$ | $T_2$ | $T_3$ | ... | Gly | Leu | Val | Ile | Phe | Tyr | ... |
| ⋮ | ⋮ | ⋮ | ⋮ | ⋮ | ⋮ | ⋮ | ⋮ | ⋮ | ⋮ | ⋮ | ⋮ |

S-2

DETERMINE CORRELATION OF EACH AMINO ACID WITH INDEX DATA (T)

| AMINO ACIDS | CORRELATION WITH INDEX DATA ($T_1$) |
|---|---|
| ⋮ | ⋮ |

S-3

GENERATE THE CORRELATION FORMULA (CORRELATION FUNCTION) INVOLVING A PLURALITY OF METABOLITES FOR THE BIOLOGICAL CONDITION USING PREDETERMINED CALCULATION FORMULA BASED ON THE CORRELATION

$$\text{CORRELATION FORMULA (R)} = \frac{\text{SUM OF THE AMINO ACIDS WITH POSITIVE CORRELATION}}{\text{SUM OF AMINO ACIDS WITH NEGATIVE CORRELATION}}$$

S-4

OPTIMIZE THE CORRELATION COEFFICIENT TO BE MAXIMIZED

| CORRELATION COEFFICIENT | CHANGE IN THE CALCULATION CONDITIONS (SELECTION OF AMINO ACIDS, SPLITTING OF CALCULATION FORMULAE) |
|---|---|
| $r_1$ | |
| $r_2$ | |
| ⋮ | |

S-5

THE CALCULATION CONDITION THAT MAXIMIZES THE CORRELATION COEFFICIENT CAN BE USED AS A COMPOSITE INDEX OF THE BIOLOGICAL CONDITION

EX) A COMPOSITE INDEX OF HEPATIC FIBROSIS $\dfrac{Asn}{Thr} + \dfrac{Gln}{Tau+Ser+Val+Trp}$ BIOLOGICAL CONDITION INFORMATION DB
106 b CORRELATION INFORMATION DB
106c CORRELATION INFORMATION DB
106d

FIG.17

| INDIVIDUAL (SAMPLE) NUMBER | INDEX DATA (T) OF BIOLOGICAL CONDITION | | | | BLOOD CONCENTRATION DATA GROUP OF THE AMINO ACID | | | | | | |
|---|---|---|---|---|---|---|---|---|---|---|---|
| | $T_1$ | $T_2$ | $T_3$ | ... | Gly | Leu | Val | Ile | Phe | Tyr | ... |
| A-1 | 23.4 | 62.5 | 37.1 | ... | 9.5 | 11.2 | 3.9 | 8.5 | 4.9 | 10.1 | ... |
| A-2 | 27.5 | 66.1 | 39.5 | ... | 8.5 | 10.5 | 2.7 | 9.8 | 6.1 | 15.1 | ... |
| ⋮ | ⋮ | ⋮ | ⋮ | ⋮ | ⋮ | ⋮ | ⋮ | ⋮ | ⋮ | ⋮ | ⋮ |

FIG.18

| AMINO ACIDS | CORRELATION WITH INDEX DATA ($T_1$) |
|---|---|
| Leu | -0.0199 |
| Ile | -0.069 |
| Val | -0.0722 |
| Asn | -0.0766 |
| ⋮ | ⋮ |

FIG.21

AMINO ACID (METABOLITE) INPUT SCREEN

MC-1

| UNUSED flg | Leu | Ile | Val | Asn | Arg | Trg | Met | | | | | | | |
|---|---|---|---|---|---|---|---|---|---|---|---|---|---|---|
| ☐ | 18.4 | 11.3 | 25.7 | 20.4 | 9.5 | 19.8 | 13.8 | | | | | | | |
| ☐ | 13.7 | 8.6 | 19.9 | 20.2 | 8.2 | 27.7 | 11.0 | | | | | | | |
| ☐ | 13.8 | 9.0 | 20.1 | 13.7 | 5.4 | 22.1 | 14.5 | | | | | | | |
| ☐ | 11.0 | 6.9 | 16.7 | 19.8 | 8.7 | 20.4 | 9.7 | | | | | | | |
| ☐ | 14.5 | 9.0 | 20.8 | 27.7 | 10.5 | 19.7 | 15.7 | | | | | | | |
| ☐ | 9.7 | 5.9 | 13.7 | 22.1 | 8.6 | 20.1 | 17.0 | | | | | | | |
| ☐ | 15.7 | 10.0 | 22.3 | 20.4 | 8.0 | 25.7 | 16.0 | | | | | | | |
| ☐ | 17.0 | 10.8 | 24.8 | 19.7 | 7.6 | 19.9 | 14.2 | | | | | | | |
| ☐ | 16.0 | 10.2 | 26.5 | 17.1 | 9.0 | 20.1 | 10.8 | | | | | | | |
| ☐ | 14.2 | 9.5 | 20.4 | 23.0 | 11.3 | 16.7 | 10.2 | | | | | | | |
| ☐ | 12.8 | 8.2 | 20.2 | 19.9 | 8.6 | 20.8 | 9.5 | | | | | | | |
| ☐ | 9.0 | 5.4 | 13.7 | 20.1 | 9.0 | 13.7 | 8.2 | | | | | | | |
| ☐ | 13.9 | 8.7 | 19.8 | 16.7 | 6.9 | 22.3 | 5.4 | | | | | | | |
| ☐ | 16.5 | 10.5 | 27.7 | 20.8 | 9.0 | 24.8 | 8.7 | | | | | | | |
| ☐ | 13.6 | 8.6 | 22.1 | 13.7 | 5.9 | 26.5 | 20.8 | | | | | | | |
| ☐ | 12.3 | 8.0 | 20.4 | 22.3 | 10.0 | 20.4 | 13.7 | | | | | | | |
| ☐ | 11.6 | 7.6 | 19.7 | 24.8 | 10.8 | 20.2 | 22.3 | | | | | | | |
| ☐ | 11.8 | 7.4 | 17.1 | 26.5 | 10.2 | 13.7 | 24.8 | | | | | | | |
| ☐ | 15.1 | 9.6 | 23.0 | 20.4 | 9.5 | 19.8 | 20.2 | | | | | | | |

MC-3 DATA CHECK  MC-2  MC-4 REGISTER  MC-5 GO BACK

FIG.22

BIOLOGICAL CONDITION INDEX INPUT SCREEN — MD-2

| UNUSED flg (MD-1) | BWG |
|---|---|
| ☐ | 68.7 |
| ☐ | 63.6 |
| ☐ | 66.6 |
| ☐ | 67.8 |
| ☐ | 67.9 |
| ☐ | 58.0 |
| ☐ | 67.8 |
| ☐ | 67.8 |
| ☐ | 68.4 |
| ☐ | 65.2 |
| ☐ | 67.6 |
| ☐ | 53.7 |
| ☐ | 59.5 |
| ☐ | 67.5 |
| ☐ | 57.8 |
| ☐ | 71.7 |
| ☐ | 67.0 |
| ☐ | 64.6 |
| ☐ | 58.0 |

DATA CHECK — MD-3  REGISTER — MD-4  GO BACK — MD-5

FIG.25

POSITIVE/NEGATIVE DETERMINATION CONFIRMATION SCREEN

ANALYSIS SUBJECT ITEMS: BWG

| POSITIVE/ NEGATIVE DETERMI- NATION | ANALYSIS ITEMS | CORRELATION WITH ANALYSIS SUBJECT ITEMS | USER SETTING | |
|---|---|---|---|---|
| NEGATIVE | Leu | -0.0199 | NEGATIVE | ▶ |
| NEGATIVE | Ile | -0.069 | NEGATIVE | ▶ |
| NEGATIVE | Val | -0.0532 | NEGATIVE | ▶ |
| POSITIVE | Asn | 0.0722 | POSITIVE | ▶ |
| POSITIVE | Arg | 0.0776 | POSITIVE | ▶ |
| POSITIVE | Trp | 0.3071 | POSITIVE | ▶ |
| | | | | ▶ |
| | | | | ▶ |
| | | | | ▶ |
| | | | | ▶ |

[ OK ]   [ CANCEL ]

FIG.27

RESULT (1) SHEET (RAW DATA FOR ANALYSIS)

| ANALYSIS SUBJECT ITEMS (MJ-1) | ANALYSIS ITEMS (MJ-2) | | | | | |
|---|---|---|---|---|---|---|
| BWG | Leu | Ile | Val | Met | Asn | Arg |
| 68.7 | 18.4 | 11.3 | 25.7 | 5.7 | 6.0 | 8.5 |
| 63.6 | 13.7 | 8.6 | 19.9 | 5.7 | 5.9 | 10.1 |
| 66.6 | 13.8 | 9.0 | 20.1 | 6.4 | 5.7 | 8.6 |
| 67.8 | 11.0 | 6.9 | 16.7 | 4.8 | 4.9 | 8.7 |
| 67.9 | 14.5 | 9.0 | 20.8 | 4.8 | 5.3 | 10.1 |
| 58.0 | 9.7 | 5.9 | 13.7 | 3.8 | 4.4 | 9.2 |
| 67.8 | 15.7 | 10.0 | 22.3 | 5.2 | 5.6 | 10.0 |
| 67.8 | 17.0 | 10.8 | 24.8 | 5.5 | 6.0 | 8.5 |
| 68.4 | 16.0 | 10.2 | 26.5 | 4.7 | 6.0 | 7.1 |
| 65.2 | 14.2 | 9.5 | 20.4 | 5.0 | 5.7 | 9.4 |
| 67.6 | 12.8 | 8.2 | 20.2 | 4.4 | 5.1 | 8.7 |
| 53.7 | 9.0 | 5.4 | 13.7 | 4.0 | 4.6 | 8.5 |
| 59.5 | 13.9 | 8.7 | 19.8 | 4.7 | 5.3 | 7.4 |
| 67.5 | 16.5 | 10.5 | 27.7 | 5.3 | 6.3 | 7.3 |
| 57.8 | 13.6 | 8.6 | 22.1 | 5.3 | 5.8 | 8.4 |
| 71.7 | 12.3 | 8.0 | 20.4 | 4.2 | 4.8 | 6.6 |
| 67.0 | 11.6 | 7.6 | 19.7 | 4.2 | 4.8 | 6.6 |
| 64.6 | 11.8 | 7.4 | 17.1 | 4.5 | 4.7 | 9.1 |
| 58.0 | 15.1 | 9.6 | 23.0 | 7.0 | 6.6 | 7.4 |
| 55.2 | 14.8 | 9.3 | 22.8 | 4.7 | 6.4 | 8.3 |
| 63.3 | 13.5 | 8.8 | 23.6 | 5.7 | 6.0 | 7.5 |
| 64.3 | 15.1 | 10.2 | 24.8 | 5.6 | 6.5 | 8.3 |
| 60.4 | 10.6 | 7.2 | 18.6 | 5.6 | 5.5 | 8.6 |
| 62.5 | 12.3 | 8.2 | 19.7 | 4.1 | 5.7 | 9.7 |
| 53.0 | 17.2 | 10.7 | 27.4 | 6.4 | 6.2 | 7.1 |
| 50.7 | 12.7 | 8.2 | 20.0 | 6.6 | 5.7 | 6.6 |

FIG.28

RESULT (2) SHEET (COMPOSITE INDEX SEARCH CONDITION)

ANALYSIS SUBJECT ITEMS : BWG — MK-1

| ANALYSIS ITEMS | MK-2 | MK-3 | MK-4 |
|---|---|---|---|
| | Leu | -0.0199 | NEGATIVE |
| | Ile | -0.069 | NEGATIVE |
| | Val | -0.0532 | NEGATIVE |
| | Asn | 0.0722 | POSITIVE |
| | Arg | 0.0776 | POSITIVE |
| | Trp | 0.3071 | POSITIVE |

MK-5

| CALCULATION FORMULA |
|---|
| POSITIVE + NEGATIVE |
| POSITIVE / NEGATIVE |
| NEGATIVE / POSITIVE |
| POSITIVE - NEGATIVE |

FIG.29

RESULT (3) SHEET (BEST COMPOSITE INDICES)

★RESULTS OF COMPOSITE INDEX SEARCH FOR BWG

| RANK | CORRELATION COEFFICIENT | COMPOSITE INDEX |
|---|---|---|
| 1 | 0.888 | Leu + Ile + Val / Asn + Arg + Trp |
| 2 | 0.868 | Leu + Ile + Val / Asn + Arg |
| 3 | 0.855 | Leu + Ile / Asn + Arg + Trp |
| 4 | 0.844 | Leu + Ile + Val / Asn |
| 5 | 0.832 | Leu / Asn + Arg + Trp |

FIG. 30

RESULT (4) SHEET (BEST COMPOSITE INDEX_VALUE)

| MN-1 BWG | MN-2 BEST 1 | MN-3 BEST 2 | MN-4 BEST 3 | MN-5 BEST 4 | MN-6 BEST 5 |
|---|---|---|---|---|---|
| 68.7 | 16.855 | 25.322 | -8.852 | 31.334 | -20.142 |
| 63.6 | 6.772 | 16.917 | -13.151 | 22.817 | -21.732 |
| 66.6 | 8.480 | 17.047 | -11.649 | 22.737 | -20.652 |
| 67.8 | 5.137 | 13.836 | -11.513 | 18.743 | -18.408 |
| 67.9 | 9.476 | 19.616 | -11.306 | 24.933 | -20.273 |
| 58.0 | 2.120 | 11.326 | -11.55 | 15.726 | -17.426 |
| 67.8 | 11.443 | 21.424 | -10.82 | 27.034 | -20.818 |
| 67.8 | 15.586 | 24.127 | -9.224 | 30.078 | -20.02 |
| 68.4 | 18.850 | 25.991 | -7.608 | 31.96 | -17.827 |
| 65.2 | 9.728 | 19.107 | -10.642 | 24.842 | -20.129 |
| 67.6 | 10.137 | 18.867 | -10.061 | 23.98 | -18.214 |
| 53.7 | 2.063 | 10.548 | -11.685 | 15.152 | -17.132 |
| 59.5 | 11.020 | 18.468 | -8.751 | 23.789 | -17.458 |
| 67.5 | 19.257 | 26.6 | -8.481 | 32.932 | -18.959 |
| 57.8 | 11.258 | 19.643 | -10.86 | 25.429 | -19.465 |
| 71.7 | 12.850 | 19.421 | -7.586 | 24.199 | -15.573 |
| 67.0 | 11.815 | 18.409 | -7.895 | 23.198 | -15.537 |
| 64.6 | 6.289 | 15.356 | -10.813 | 20.051 | -18.247 |
| 58.0 | 11.617 | 18.999 | -11.341 | 25.563 | -20.955 |
| 55.2 | 12.657 | 20.966 | -10.177 | 27.406 | -19.459 |
| 63.3 | 13.057 | 20.556 | -10.501 | 26.601 | -19.287 |
| 64.3 | 14.690 | 22.946 | -10.105 | 29.443 | -20.339 |
| 60.4 | 6.093 | 14.718 | -12.512 | 20.169 | -19.691 |
| 62.5 | 8.387 | 18.124 | -11.36 | 23.84 | -19.54 |
| 53.0 | 18.454 | 25.548 | -8.912 | 31.72 | -19.656 |
| 50.7 | 9.335 | 15.896 | -10.661 | 21.596 | -18.818 |

FIG.32

RESULT (6) SHEET (RAW DATA OF AMINO ACIDS (METABOLITES))

| MR-1 | | | | | | MR-2 |
|---|---|---|---|---|---|---|
| Leu | Ile | Val | Met | Asn | Arg | Met | UNUSED Flg |
| 18.4 | 11.3 | 25.7 | 5.7 | 6.0 | 8.5 | 7.3 | |
| 13.7 | 8.6 | 19.9 | 5.7 | 5.9 | 10.1 | 8.4 | |
| 13.8 | 9.0 | 20.1 | 6.4 | 5.7 | 8.6 | 6.6 | |
| 11.0 | 6.9 | 16.7 | 4.8 | 4.9 | 8.7 | 6.6 | |
| 14.5 | 9.0 | 20.8 | 4.8 | 5.3 | 10.1 | 9.1 | |
| 9.7 | 5.9 | 13.7 | 3.8 | 4.4 | 9.2 | 7.4 | |
| 15.7 | 10.0 | 22.3 | 5.2 | 5.6 | 10.0 | 8.3 | |
| 17.0 | 10.8 | 24.8 | 5.5 | 6.0 | 8.5 | 7.5 | |
| 16.0 | 10.2 | 26.5 | 4.7 | 6.0 | 7.1 | 8.3 | |
| 14.2 | 9.5 | 20.4 | 5.0 | 5.7 | 9.4 | 8.6 | |
| 12.8 | 8.2 | 20.2 | 4.4 | 5.1 | 8.7 | 9.7 | |
| 9.0 | 5.4 | 13.7 | 4.0 | 4.6 | 8.5 | 7.1 | |
| 13.9 | 8.7 | 19.8 | 4.7 | 5.3 | 7.4 | 6.6 | |
| 16.5 | 10.5 | 27.7 | 5.3 | 6.3 | 7.3 | 7.3 | |
| 13.6 | 8.6 | 22.1 | 5.3 | 5.8 | 8.4 | 8.4 | |
| 12.3 | 8.0 | 20.4 | 4.2 | 4.8 | 6.6 | 6.6 | |
| 11.6 | 7.6 | 19.7 | 4.2 | 4.8 | 6.6 | 6.6 | |
| 11.8 | 7.4 | 17.1 | 4.5 | 4.7 | 9.1 | 9.1 | |
| 15.1 | 9.6 | 23.0 | 7.0 | 6.6 | 7.4 | 7.4 | |
| 14.8 | 9.3 | 22.8 | 4.7 | 6.4 | 8.3 | 8.3 | |
| 13.5 | 8.8 | 23.6 | 5.7 | 6.0 | 7.5 | 7.5 | 1 |
| 15.1 | 10.2 | 24.8 | 5.6 | 6.5 | 8.3 | 8.3 | |
| 10.6 | 7.2 | 18.6 | 5.6 | 5.5 | 8.6 | 8.6 | |
| 12.3 | 8.2 | 19.7 | 4.1 | 5.7 | 9.7 | 9.7 | |
| 17.2 | 10.7 | 27.4 | 6.4 | 6.2 | 7.1 | 7.1 | |
| 12.7 | 8.2 | 20.0 | 6.6 | 5.7 | 6.6 | 6.6 | |

FIG.33

RESULT (7) SHEET (RAW DATA OF BIOLOGICAL CONDITION INDEX)

| MS-1 | MS-2 | |
|---|---|---|
| BWG | UNUSED Flg | |
| 68.7 | | |
| 63.6 | | |
| 66.6 | | |
| 67.8 | | |
| 67.9 | | |
| 58.0 | | |
| 67.8 | | |
| 67.8 | | |
| 68.4 | | |
| 65.2 | | |
| 67.6 | | |
| 53.7 | | |
| 59.5 | | |
| 67.5 | | |
| 57.8 | | |
| 71.7 | | |
| 67.0 | | |
| 64.6 | | |
| 58.0 | | |
| 67.8 | | |
| 67.8 | | |
| 68.4 | 1 | |
| 65.2 | | |
| 67.6 | | |
| 67.8 | | |
| 68.4 | | |

FIG.50

HEPATIC FIBROSIS INDEX DB
406c

| NUMBER | COMPOSITE INDEX | ALTERNATIVE INDEX |
|---|---|---|
| 1 | (Asn)/(Thr)+<br>(Gln)/(Tau+Ser+Val+Trp) | COMPOSITE INDEX<br>1-1~1-20 |
| 2 | (Asn+Tyr)/(Cit)+<br>(Met+Arg)/(Asp+α-ABA) | COMPOSITE INDEX<br>2-1~2-20 |
| 3 | (Tau+Gly)/(Gln)+<br>(α-ABA)/(Asp+Tyr)+<br>(His)/(Lys)+<br>(Trp)/(Thr+Asn+Cit) | COMPOSITE INDEX<br>3-1~3-20 |
| 4 | (Tau+Trp)/(Tyr)+<br>(α-ABA+His)/(Asp+Asn) | COMPOSITE INDEX<br>4-1~4-20 |
| 5 | (Leu+Val/Trp)/(Phe+Tyr)+<br>(Gly+Tau+ABA+His+Pro)/<br>(Met+Asn+Orn+Glu) | ———— |
| ⋮ | ⋮ | ⋮ |

|  | GROUP A | GROUP B | GROUP C | GROUP D |
|---|---|---|---|---|
| COMPOSITE INDEX 1 | Asn, Gln | Thr, Tau, Ser, Val, Trp | Met | Ile, α-ABA, Asp |
| COMPOSITE INDEX 2 | Asn, Met | α-ABA, Cit | Tyr, Arg | His, Thr, Trp, Asp, Glu |
| COMPOSITE INDEX 3 | α-ABA, His, Gly, Trp, Tau | Asn, Gln, Cit, Lys, Thr, Tyr |  | Met, Asp |
| COMPOSITE INDEX 4 | His, Trp | Asn, Tyr | α-ABA, Tau | Met, Asp |

US 8,234,075 B2

APPARATUS AND METHOD FOR PROCESSING INFORMATION CONCERNING BIOLOGICAL CONDITION, SYSTEM, PROGRAM AND RECORDING MEDIUM FOR MANAGING INFORMATION CONCERNING BIOLOGICAL CONDITION

TECHNICAL FIELD

The present invention relates to an apparatus and a method for processing information concerning a biological condition, as well as to a system, a program, and a recording medium for managing information concerning a biological condition. In particular, the present invention relates to an apparatus and a method for processing information concerning a biological condition, as well as to a system, a program, and a recording medium for managing such information that offer an analytical approach to determine a combination of metabolites closely related to an index associated with a particular biological condition. This approach is based on the correlation between various phenomena defining biological conditions (phenomics data) and a plurality of metabolites (metabolomics data) that can be readily measured.

The present invention also relates to an apparatus, a method, a system, a program, and a recording medium for determining hepatic-fibrosis stage. In particular, the present invention relates to an apparatus, a method, a system, a program, and a recording medium that allow the determination of a disease condition indicative of the progression of hepatic fibrosis in accordance with an index value of the disease condition of hepatic fibrosis calculated on the basis of the amounts or concentration of a plurality of metabolites (particular amino acids) that can be readily measured.

The phrase "biological condition" as used herein refers to a concept that includes healthy (normal) and diseased states. As used herein, the phrase "index data concerning a measured biological condition of an individual" refers to a concept that comprises diagnostic data of the biological condition of an individual living body. The term "index data" as used herein refers to a concept that includes both quantitative data and qualitative data (e.g., sex and presence of smoking habits).

BACKGROUND ART

Bioinformatics has given birth to rapidly developing new analytical approaches used in a variety of stages in the course of life process, from gene expression to complex phenomena in living organisms. Among such approaches are genomics, transcriptomics, proteomics, and metabolomics, each expected to have a significant impact on future bioindustries. The most important step for practical application of bioinformatics, however, is to understand mechanisms of a life process at a variety of levels associated with the life phenomenon of interest.

In the early days of genome analysis, many researchers optimistically anticipated that genome information alone would provide sufficient clues to unveil all the life processes. The anticipation soon turned out to be wrong and currently many believe that genome information alone would be insufficient, and proteome and metabolome analyses are essential to understanding life processes. This belief, however, is much the same as the previous hypothesis that genome information alone enables complete understanding of everything, only involving more information. Needless to say, complete understanding of entire life processes should allow us to determine what exact events are taking place in a living body. This approach relying on ever increasing amounts of information may sound ideal for those who are seeking ultimate goals of science, but not for businesses whose goal is to achieve practical results with limited resources and time. Nonetheless, the exhaustive collection of information may be beneficial, provided that our interests are limited to particular fields in which goals are apparent in a degree.

Understanding of life processes at gene levels requires enormous information about gene expression, translation into proteins, binding between proteins, functions of enzymes, and reaction rates of metabolites at cell levels, as well as information about communications between cells and between organs, and models to handle such information is required for accurate prediction. Thus, two techniques are required: one for obtaining information and the other for modeling such information.

As opposed to the techniques for efficiently obtaining information on life processes, which have been improved considerably, much has to be done to develop techniques for complete modeling at the level of a living system. The current modeling techniques may be effective in obtaining an amount of information sufficient to make predictions with low accuracy, but the conventional non-modeling approaches are often more effective in terms of cost effectiveness as far as low accuracy predictions are concerned.

Among the greatest concerns of medical practitioners are the correlations between clinically measurable indices and associated biological conditions of interest, such as a disease condition, and knowledge about mechanisms and treatments of these conditions derived from such correlations. Thus, it has become widely recognized that exhaustive collection of information on a living body alone is not enough, but techniques for analyzing correlations between a biological condition of interest, such as a disease condition, and various measurable indices are also required.

It has been considered that a disease marker of a particular disease condition should be specific to the disease condition and a one-to-one or similar restrictive relationship between the marker and the disease condition has been required. One disease, however, can affect many metabolites, suggesting that there is not always one-to-one relationship between the disease and the associated metabolites. Consequently, there are only limited number of simple metabolite markers. Generally understanding how the metabolism of all of metabolites changes during the course of a particular disease can provide an index defining characteristic of the metabolism of the disease. Considering the linkage of the metabolism, behavior of not all the metabolites, but some of the metabolites on a metabolic map (such as amino acids) can be tracked to determine a variation of metabolism specific to a particular disease condition.

In one conventional approach, for example, Fischer's ratio has been proposed as an index of hepatic cirrhosis. The Fischer's ratio is a ratio of the branched-chain amino acids to the aromatic amino acids or ((Ile+Leu+Val)/(Phe+Tyr)). Under the condition of hepatic cirrhosis, the branched-chain amino acids increase, whereas the aromatic amino acids decrease. Another approach relies on a trainable neural network. In this approach, various clinical indices of disease conditions and healthy subjects are entered into a computer, and the neural network is trained and optimized based on the entered data so that it can discriminate one data from another (non-linear analysis) and provide diagnoses therewith (U.S. Pat. No. 5,687,716, referred to hereinafter as Patent Document No. 1).

Patent Document No. 1: U.S. Pat. No. 5,687,716

Delivery of diagnoses using the technique described in Patent Document No. 1 requires a pre-trained neural network or a neural network having similar parameters. Thus, the diagnostic indices according to Patent Document No. 1 rely on the analytical techniques and instruments specified by the Patent Document No. 1. For this reason, the diagnostic indices according to Patent Document No. 1 cannot be used independently of the analytical techniques and instruments disclosed in the Patent Document No. 1 and cannot thus serve as universal standards for disease treatment.

Metabolites used as the diagnostic indices specified by the technique described in Patent Document No. 1 may be examined for their relationship on the metabolic map as well as for their chemical, physiological, or pharmacological findings to analyze mechanisms of diseases. The analysis by matching known metabolic findings and the like with the diagnostic indices may enable analysis of links between a disease condition and a metabolism. Such an analysis may also provide information to prove effectiveness of certain metabolites as diagnostic indices or information that provides very useful clues to make new metabological discoveries. However, with the prior-art techniques, researchers have to manually perform each of these analyses.

In view of the foregoing problems, it is an objective of the present invention to provide an apparatus and a method for processing information concerning a biological condition, as well as to a system, a program, and a recording medium for managing such information that provide an analytical approach to determine a combination of metabolites closely related to an index associated with a particular biological condition. This approach is based on the correlation between various phenomena defining biological conditions (phenomics data) and a plurality of metabolites (metabolomics data) that can be readily measured.

It is another objective of the present invention to provide to an apparatus, a method, a system, a program, and a recording medium that allow the determination of a disease condition indicative of the progression of hepatic fibrosis in accordance with an index value of the disease condition of hepatic fibrosis calculated on the basis of the amounts or concentration of a plurality of metabolites (particular amino acids) that can be readily measured.

DISCLOSURE OF THE INVENTION

The present invention has been devised based on many findings that the present inventors have found out in the course of their extensive studies. A variety of experiments have proved that amino acids are metabolites that can be measured with high accuracy, and that the deviation among the measurements is significantly smaller than the deviation among individuals.

Data as to postprandial concentration of metabolites in blood is known to reflect the change in a certain condition involved with metabolisms, such as gene expression. Blood has relations to all organs and thus may reflect a change in a certain organ.

Under a particular biological condition (for example, disease condition such as hepatic fibrosis), expression of multiple genes involved in metabolism may be affected. Also, the behavior of most of metabolites present in blood are linked to other metabolites, so that even if a metabolite most closely related to a particular biological condition is not measurable, another metabolite linked to the first metabolite may be affected.

The present inventors have found that the correlations among blood concentrations of a variety of metabolites in an individual (in particular, amino acids) serve as a highly effective index of a biological condition. That is, by analyzing the relationship between the accurately measured blood concentrations of limited range of metabolites such as amino acids and a particular biological condition, a combination of metabolites phenomenally associated with the particular biological condition can be searched. Indices that can discriminate between healthy individuals and individuals in a particular condition can be used in early diagnosis of the particular condition.

To achieve the above-described objectives, each of the apparatus for processing information concerning a biological condition, the method for processing information concerning a biological condition, and the program for allowing a computer to execute the method according to the present invention is characterized by comprising:

a correlation formula setting unit for (or a correlation formula setting step of) setting a correlation formula represented by the following formula 1 that indicates a correlation between index data concerning a biological condition measured in each individual and blood concentration data measured for each metabolite I in each individual; and a biological condition simulation unit for (or a biological condition simulation step of) simulating a biological condition of an individual to be simulated by substituting a group of blood concentration data measured for each metabolite in the individual to be simulated into the correlation formula which is set by the correlation formula setting unit (or the correlation formula setting step):

$$\sum_k G_k \frac{\sum_i \{(C_i \times A_i) + D_i\}}{\sum_j \{(E_j \times B_j) + F_j\}} + H \tag{1}$$

(wherein each of i, j, and k is a natural number; each of $A_i$ and $B_j$ is data of concentration of the metabolite in blood or values obtained from applying a function to the concentration of the metabolite in blood; and each of $C_i$, $D_i$, $E_j$, $F_j$, $G_k$ and H is a constant.)

According to the apparatus, the method, and the program described above, a correlation formula represented by the formula i that indicates a correlation between index data concerning a biological condition measured in each individual and the blood concentration data measured for each metabolite in each individual is set, and a biological condition of the individual of interest is simulated by substituting into the set correlation formula a group of blood concentration data measured for each metabolite in the individual to be simulated. Thus, the apparatus, the method, and the program enable effective simulation of the condition of health, the condition of disease progression, the condition of disease treatment, the risk of future disease, the efficacy of a drug, the side effect of a drug, and various other conditions based on the blood concentration of metabolites in the individual.

The term "simulation" as used herein refers to a concept comprising obtaining numerical values based on a set model (e.g., "correlation formula" according to the present invention) and evaluating the obtained numerical value based on a predetermined threshold value to determine the presence of a particular biological condition.

For example, the present invention can be applied to diagnosis for predicting the risk of the onset of a disease after a certain period of time. Specifically, a correlation formula is constructed based on the previously obtained data of concentrations of metabolites in blood (e.g., blood amino acid levels obtained 10 years ago) and index data concerning the current disease or health condition. By substituting the current data of concentration of metabolites in blood into the correlation formula, the future disease or health condition can be effectively simulated.

The present invention can also be used to simulate efficacy and side effects of drug administration (e.g., efficacy of drug administration such as interferons (IFNs)) and to simulate changes in biological conditions caused by stress or other factors (e.g., changes in biological conditions when the subject is stimulated by meals for example).

The correlation formula may be set by the correlation formula setting unit for (or the correlation formula setting step of) setting the formula by either of the following two approaches: first substitute the blood amino acid levels of clinical data into the formula 1 and then determine each constant in the formula 1, or use a predetermined correlation formula. In the latter approach, the correlation formulae with each constant determined by the first approach may be previously stored in a predetermined file of a memory unit and a desired correlation formula is then selected from the file, or the correlation formulae previously stored in a memory unit of another computer may be downloaded via a network.

In each of the apparatus for processing information concerning a biological condition, the method for processing information concerning a biological condition, and the program according to the next invention, the correlation formula setting unit (or the correlation formula setting step) in the apparatus, the method, or the program described above is characterized by comprising:

a correlation determining unit for (or a correlation determining step of) determining a correlation between the index data concerning the biological condition measured in each individual and each metabolite based on the index data and the group of blood concentration data measured for each metabolite in each individual;

a correlation formula generating unit for (or a correlation formula generating step of) generating a correlation formula involving a plurality of metabolites for the biological condition, the generation being carried out according to a predetermined calculation method and based on the correlation as to each metabolite determined by the correlation determining unit (or the correlation determining step); and an optimization unit (or an optimization step) for optimizing the correlation formula based on the correlation coefficient for the index data concerning the biological condition of the correlation formula determined by the correlation formula generating unit (or the correlation formula generating step).

This is a more specific example of the correlation formula setting unit (correlation formula setting step). According to the apparatus, the method, and the program described above, a correlation between index data concerning the measured biological condition of each individual and each metabolite is determined based on the index data and the group of blood concentration data measured for each metabolite in each individual, a correlation formula (correlation function) for a plurality of metabolites for the biological condition is generated by a predetermined calculation method and based on the correlation of each metabolite determined, and the correlation formula is optimized based on the correlation coefficient for the index data concerning the biological condition of the determined correlation formula. Thus, it is possible to use a formula highly correlated with the biological condition as a composite index reflecting a biological condition and allow effective calculation of the composite index, which consists of measurable metabolites highly correlated with the biological condition, such as amino acids.

As used herein, the phrase "to optimize the correlation formula based on the correlation coefficient" means to select a correlation formula, for example, so that the correlation coefficient ranks high (for example, top 20) or, preferably, is maximized.

It is also made possible to obtain a composite index for each biological condition, so that the results of a single test for, for example, blood amino acid levels may be sufficient to screen many biological conditions. This leads to a significant reduction in the cost of testing.

It is further made possible to diagnose the presence of a biological condition in the past for which the biological condition index was not available at the time of testing, by analyzing the past data once the composite index has been determined.

It is further made possible to develop a treatment for a biological condition using the composite index as a marker, because the metabolites composing the composite index for the biological condition are the potential cause or the outcome of the biological condition.

As used herein, the "index data concerning a biological condition" may be actual numerical data such as those of various measurements and test results, or it may be any numerical value assigned, for example, to a healthy or diseased condition, as shown in the following example. In the latter case, a particular disease condition can be analyzed by assigning a numerical value to the disease or the levels of the disease even if the actual numerical data are not available:
(Examples) healthy=0, obesity=1;
healthy=1, mild diabetes=2, severe diabetes=3, etc.

In case of diseases with no existing indices, the present invention also enables determination of the presence of biological conditions that have no effective diagnostic indices available and thus have been difficult to diagnose.

In each of the apparatus for processing information concerning a biological condition, the method for processing information concerning a biological condition, and the program according to the next invention, the optimization unit (or the optimization step) in the apparatus, method, or program described above is characterized by further comprising a metabolite selecting unit (metabolite selecting step) for selecting some of the metabolites, in which the plurality of metabolites selected by the metabolite selecting unit (metabolite selecting step) are used to construct the correlation formula, to calculate the correlation coefficient for the index data concerning the biological condition, and to optimize the combination of metabolites based on the correlation coefficient for the index data concerning the biological condition and the number of the metabolites.

This is a more specific example of the optimization unit (optimization step). According to the apparatus, the method, and the program described above, some of the metabolites are selected, the correlation formula is constructed using the plurality of metabolites selected, the correlation coefficient for the index data concerning the biological condition is calculated, and the combination of metabolites is optimized based on the correlation coefficient and the number of the metabolites. Thus, the apparatus, the method and the program enable exhaustive and automatic removal of selected amino acids and thus allow effective determination of a composite index for a biological condition.

As used herein, the phrase "to optimize the combination of metabolites based on the correlation coefficient and the number of the metabolites" means to select a combination of metabolites so that the correlation coefficient ranks high (for example, top 20) and the number of the metabolites is minimized. Preferably, the correlation coefficient is maximized and the number of the metabolites is minimized.

In each of the apparatus for processing information concerning a biological condition, the method for processing information concerning a biological condition, and the program according to the next invention, the optimization unit (or the optimization step) in the apparatus, method, or program described above is characterized by further comprising a calculation formula splitting unit for (calculation formula splitting step of) splitting the calculation formula, in which the calculation formula split by the calculation formula splitting unit (calculation formula splitting step) is used to calculate the correlation formula involving a plurality of metabolites for the biological condition, and the combination of the splits is optimized based on the correlation coefficient for the index data concerning the biological condition.

This is a more specific example of the optimization unit (optimization step). According to the apparatus, the method, and the program described above, the calculation formula is split, and the split calculation formula is used to calculate the correlation formula involving a plurality of metabolites for the biological condition and to optimize the combination of the splits based on the correlation coefficient for the index data concerning the biological condition. Thus, the apparatus, the method, and the program enable exhaustive and automatic splitting of each calculation formula and thus allow effective determination of a composite index for a biological condition.

As used herein, the phrase "to optimize the combination of the splits based on the correlation coefficient" means to select a combination of splits so that the correlation coefficient ranks high (for example, top 20) and, preferably, so that the correlation coefficient is maximized.

In each of the apparatus for processing information concerning a biological condition, the method for processing information concerning a biological condition, and the program according to the present invention, the optimization unit (or the optimization step) in the apparatus, method, or program described above is characterized by further comprising a metabolic map splitting unit for (or a metabolic map splitting step of) splitting the calculation formula based on the metabolic map information, in which the calculation formula split by the metabolic map splitting unit (metabolic map splitting step) is used to calculate the correlation formula involving a plurality of metabolites for the biological condition.

This is a more specific example of the optimization unit (optimization step). According to the apparatus, the method, and the program described above, the calculation formula is split based on the metabolic map information and the calculation formula split is used to calculate the correlation formula involving a plurality of metabolites for the biological condition. Thus, the apparatus, the method and the program enable automatic split of the calculation formula based on the biochemical information of the metabolic map of metabolites involved in a biological condition if such metabolic maps are already known.

Alternatively, the relationship among the metabolites in the calculated correlation formula may be converted into a numerical value, which in turn is projected onto a metabolic map to allow estimation of metabolic flux or rate-limiting steps of the metabolism.

In each of the apparatus for processing information concerning a biological condition, the method for processing information concerning a biological condition, and the program according to the next invention, the metabolite in the apparatus, method, or program described above is an amino acid.

This is a more specific example of the metabolite. Since the metabolite is an amino acid, the apparatus, the method and the program make it possible to take advantage of properties of amino acids, such as high accuracy of measurements of the metabolites and significantly smaller deviation among measurements as compared to deviation among individuals, so that reliable composite index for a biological condition can be obtained.

The present invention also relates to a system for managing information concerning a biological condition. The system is characterized by comprising:
an apparatus for processing information concerning a biological condition; and
an information terminal of a provider of information about the biological condition, the information terminal being communicably connected via a network to the apparatus for processing information;
wherein the apparatus for processing information concerning the biological condition comprises:
a correlation formula setting unit for setting a correlation formula represented by the following formula 1 that indicates a correlation between index data concerning a biological condition measured in each individual and blood concentration data measured for each metabolite in each individual;
a blood concentration data group acquiring unit for acquiring from the information terminal a group of blood concentration data measured for each metabolite in an individual to be simulated;
a biological condition simulating unit for simulating a biological condition of the individual to be simulated by substituting the group of blood concentration data measured for each metabolite in the individual to be simulated, the data being obtained at the blood concentration data group acquiring unit, into the correlation formula which is set by the correlation formula setting unit; and
an analysis result sending unit for sending the results of the simulation of the biological condition of the individual simulated by the biological condition simulating unit to the information terminal which is a sender of the group of blood concentration data;
wherein the information terminal comprises:
a sending unit for sending the group of blood concentration data to the apparatus for processing information concerning the biological condition; and
a receiving unit for receiving the results of the simulation corresponding to the group of blood concentration data that have been sent by the sending unit, from the apparatus for processing information concerning the biological condition:

$$\sum_k G_k \frac{\sum_i \{(C_i \times A_i) + D_i\}}{\sum_j \{(E_j \times B_j) + F_j\}} + H \qquad (1)$$

wherein each of i, j, and k is a natural number; each of $A_i$ and $B_j$ is data of concentration of the metabolite in blood or values obtained from applying a function to the concentration of the metabolite in blood; and each of $C_i$, $D_i$, $E_j$, $F_j$, $G_k$ and H is a constant.

According to the system described above, a correlation formula represented by the following formula 1 that indicates a correlation between index data concerning a biological condition measured in each individual and data of concentrations of metabolites in blood measured in each individual is set, a group of blood concentration data measured for each metabolite in an individual to be simulated is acquired from the information terminal, the group of blood concentration data measured for each metabolite in the individual to be simulated is substituted into the set correlation formula set to simulate a biological condition of the individual, the results of the simulation of the biological condition of the individual are sent to the information terminal to which the group of blood concentration data has been sent, the information terminal sends the group of the blood concentration data to the information processing apparatus, and the results of the simulation corresponding to the sent group of the blood concentration data are received from the information processing apparatus. Thus, the system enables effective simulation of the condition of health, the condition of disease progression, the condition of disease treatment, the risk of future disease, the efficacy of a drug, the side effect of a drug, and other conditions based on the blood concentration of metabolites in the individual.

The term "simulation" as used herein refers to a concept comprising obtaining numerical values based on a set model (e.g., correlation formula according to the present invention) and evaluating the obtained numerical value based on a predetermined threshold value to determine the presence of a particular biological condition.

For example, the present invention can be applied to diagnosis for predicting the risk of the onset of a disease after a certain period of time. Specifically, a correlation formula is constructed based on the data of previously obtained concentrations of metabolites in blood (e.g., blood amino acid levels obtained 10 years ago) and index data concerning the current disease or health condition. By substituting the current data of concentrations of metabolites in blood into the correlation formula, the future disease or health condition can be effectively simulated.

The present invention can also be used to simulate efficacy and side effects of drug administration (e.g., efficacy of drug administration such as interferons (IFNs)) and to simulate changes in biological conditions caused by stress or other factors (e.g., changes in biological conditions when the subject is stimulated by meals for example).

In the system for managing information concerning a biological condition according to the next invention, the correlation formula setting unit in the system described above is characterized by comprising:

a correlation determining unit for determining a correlation between the index data concerning the biological condition measured in each individual and each metabolite based on the index data and a group of blood concentration data measured for each metabolite in each individual;

a correlation formula generating unit for generating the correlation formula involving a plurality of metabolites for the biological condition, the generation being carried out according to a predetermined calculation method and based on the correlation as to each metabolite determined by the correlation determining unit; and an optimization unit for optimizing the correlation formula based on the correlation coefficient for the index data concerning the biological condition of the correlation formula determined by the correlation formula generating unit.

This is a more specific example of the correlation formula setting unit. According to the system described above, in the biological condition information processing apparatus, a correlation between index data concerning a measured biological condition of each individual and each metabolite is determined based on the index data and a group of blood concentration data measured for each metabolite in each individual, a correlation formula (correlation function) for a plurality of metabolites for the biological condition is generated by a predetermined calculation method and based on the correlation of each metabolite determined, and the correlation formula is optimized based on the correlation coefficient for the index data concerning the biological condition of the determined correlation formula. Thus, the system enables the use of a formula highly correlated with the biological condition as a composite index reflecting the biological condition and allows effective calculation of the composite index, which consists of measurable metabolites highly correlated with the biological condition, such as amino acids.

As used herein, the phrase "to optimize the correlation formula based on the correlation coefficient" means to select a correlation formula, for example, so that the correlation coefficient ranks high (for example, top 20) or, preferably, is maximized.

It is also made possible to obtain a composite index for each biological condition, so that the results of a single test for, for example, blood amino acid levels may be sufficient to screen many biological conditions. This leads to a significant reduction in the cost of testing.

It is further made possible to diagnose the presence of a biological condition in the past for which the biological condition index was not available at the time of testing, by analyzing the past data once the composite index has been determined.

It is further made possible to develop a treatment for a biological condition using the composite index as a marker, since the metabolites composing the composite index for the biological condition may be the potential cause or the outcome of the biological condition.

As used herein, the "index data concerning a biological condition" may be actual numerical data such as those for various measurements and test results, or it may be any numerical value assigned, for example, to a healthy or diseased condition, as shown in the following example. In the latter case, a particular disease condition can be analyzed by assigning a numerical value to the disease or the levels of the disease even if the actual numerical data are not available:

EXAMPLES healthy=0, obesity=1;
healthy=1, mild diabetes=2, severe diabetes=3, etc.

In case of diseases with no existing indices, the present invention also enables determination of the presence of biological conditions that have no effective diagnostic indices available and thus have been difficult to diagnose.

In the system for managing information concerning a biological condition according to the next invention, the optimization unit in the system described above is characterized by further comprising a metabolite selecting unit for selecting some of the metabolites, in which the plurality of metabolites selected by the metabolite selecting unit are used to construct the correlation formula, to calculate the correlation coefficient for the index data concerning the biological condition, and to optimize the combination of metabolites based on the correlation coefficient for the index data concerning the biological condition and the number of the metabolites.

This is a more specific example of the optimization unit. According to the system described above, some of the metabolites are selected, the correlation formula is constructed using the plurality of metabolites selected, the correlation coefficient for the index data concerning the biological condition is calculated, and the combination of metabolites is optimized based on the correlation coefficient and the number of the metabolites. Thus, the system enables exhaustive and automatic removal of selected amino acids and thus allows effective determination of a composite index for a biological condition.

As used herein, the phrase "to optimize the combination of metabolites based on the correlation coefficient and the number of the metabolites" means to select a combination of metabolites so that the correlation coefficient ranks high (for example, top 20) and the number of the metabolites is minimized. Preferably, the correlation coefficient is maximized and the number of the metabolites is minimized.

In the system for managing information concerning a biological condition according to the next invention, the optimization unit in the system described above is characterized by further comprising a calculation formula splitting unit for splitting the calculation formula, in which the calculation formula split by the calculation formula splitting unit is used to calculate the correlation formula involving a plurality of metabolites for the biological condition, and the combination of the splits is optimized based on the correlation coefficient for the index data concerning the biological condition.

This is a more specific example of the optimization unit. According to the system described above, the calculation formula is split, and the split calculation formula is used to calculate the correlation formula involving a plurality of metabolites for the biological condition and to optimize the combination of the splits based on the correlation coefficient for the index data concerning the biological condition. Thus, the system enables exhaustive and automatic splitting of each calculation formula and thus allows effective determination of a composite index for a biological condition.

As used herein, the phrase "to optimize the combination of the splits based on the correlation coefficient" means to select a combination of splits so that the correlation coefficient ranks high (for example, top 20) and, preferably, so that the correlation coefficient is maximized.

In the system for managing information concerning a biological condition according to the next invention, the optimization unit in the system described above is characterized by further comprising a metabolic map splitting unit for splitting the calculation formula based on the metabolic map information, in which the calculation formula split by the metabolic map splitting unit is used to calculate correlation formula involving a plurality of metabolites for the biological condition.

This is a more specific example of the optimization unit. According to the system described above, the calculation formula is split based on the metabolic map information and the calculation formula split is used to calculate the correlation formula involving a plurality of metabolites for the biological condition. Thus, the system enables automatic split of the calculation formula based on the biochemical information of the metabolic map of metabolites involved in a biological condition if such metabolic maps are already known.

Alternatively, the relationship among the metabolites in the calculated correlation formula may be converted into a numerical value, which in turn is projected onto a metabolic map to allow estimation of metabolic flux or rate-limiting steps of the metabolism.

In the system for managing information concerning a biological condition according to the next invention, the metabolite in the system described above is an amino acid.

This is a more specific example of the metabolite. Since the metabolite is an amino acid, the system makes it possible to take advantage of properties of amino acids, such as high accuracy of measurements of the metabolites and significantly smaller deviation among measurements as compared to deviation among individuals, so that reliable composite index for a biological condition can be obtained.

The present invention also relates to a recording medium that has the above-described program recorded therein.

The recording medium can provide the stored program to a computer, which reads out and executes the program to implement the same tasks, whereby the same advantage as these programs can be obtained.

The present invention also relates to an apparatus and a method for determining hepatic fibrosis stage, as well as to a program for executing the method. The apparatus, the method, and the program are characterized by comprising:

a blood concentration data acquiring unit for (or a blood concentration data acquiring step of) acquiring a group of blood concentration data measured for each metabolite in each individual;

a disease condition index value calculating unit for (or a disease condition index value calculating step of) calculating an index value indicative of the disease condition of hepatic fibrosis from the group of blood concentration data acquired by the blood concentration data acquiring unit (blood concentration data acquiring step), the calculation being performed based on at least one of the following composite indices 1 through 4:

Composite Index 1

$$(Asn)/(Thr)+(Gln)/(Tau+Ser+Val+Trp);$$

Composite Index 2

$$(Asn+Tyr)/(Cit)+(Met+Arg)/(Asp+(\alpha\text{-}ABA));$$

Composite Index 3

$$(Tau+Gly)/(Gln)+(\alpha\text{-}ABA)/(Asp+Tyr)+(His)/(Lys)+(Trp)/(Thr+Asn+Cit); \text{ and}$$

Composite Index 4

$$(Tau+Trp)/(Tyr)+((\alpha\text{-}ABA)+His)/(Asp+Asn); \text{ and}$$

a disease condition determining unit for (or a disease condition determining step of) determining the disease condition indicative of the progression of hepatic fibrosis based on the disease condition index value calculated by the disease condition index value calculating unit (or disease condition index value calculating step).

According to the apparatus, the method, and the program described above, a group of blood concentration data measured for each metabolite in each individual is acquired, an index value indicative of the disease condition of hepatic fibrosis is calculated from the acquired group of blood concentration data based on at least one of the following composite indices 1 through 4:

Composite Index 1

$$(Asn)/(Thr)+(Gln)/(Tau+Ser+Val+Trp);$$

Composite Index 2

$$(Asn+Tyr)/(Cit)+(Met+Arg)/(Asp+(\alpha\text{-}ABA));$$

Composite Index 3

$$(Tau+Gly)/(Gln)+(\alpha\text{-}ABA)/(Asp+Tyr)+(His)/(Lys)+(Trp)/(Thr+Asn+Cit); \text{ and}$$

Composite Index 4

$$(Tau+Trp)/(Tyr)+((\alpha\text{-}ABA)+His)/(Asp+Asn); \text{ and}$$

the disease condition of hepatic fibrosis is determined based on the calculated disease condition index value. Thus, the apparatus, the method, and the program make it possible to screen many individuals for hepatic fibrosis by using the results of a single test for, for example, blood amino acid levels. This leads to a significant reduction in the cost of testing.

It is also made possible to diagnose hepatic fibrosis by analyzing the data of blood amino acid level obtained in the past.

The use of one of the four composite indices 1 through 4 as a marker of hepatic fibrosis makes it possible to develop a treatment for the disease, since the metabolites composing one of the four composite indices 1 through 4 for hepatic fibrosis may be the potential cause or the outcome of the disease.

The amino acids in at least one of the four composite indices 1 through 4 may be replaced by other chemically equivalent compounds, such as other amino acids.

Specifically, at least one of the four indices 1 through 4 may be replaced by the corresponding formulae of composite indices shown below.

For example, the composite index 1 may be replaced by any of the following composite indices 1-1 through 1-20:

Composite Index 1-1

(Asn)/(Thr)+(Gln)/(Tau+Ser+Val+Trp);

Composite Index 1-2

(Asn)/(Tau+Ile)+(Gln)/(Thr+Ser+Val+Trp);

Composite Index 1-3

(Asn)/(Tau+(α-ABA)+Ile)+(Gln)/(Thr+Ser+Val+Trp);

Composite Index 1-4

(Asn)/(Asp+Thr)+(Gln)/(Tau+Ser+Val+Trp);

Composite Index 1-5

(Asn)/(Thr)+(Gln)/(Tau+Ser+Val+Ile+Trp);

Composite Index 1-6

(Asn)/(Thr)+(Gln)/(Tau+Asp+Ser+Val+Trp);

Composite Index 1-7

(Asn)/(Tau+Ile)+(Gln)/(Asp+Thr+Ser+Val+Trp);

Composite Index 1-8

(Asn)/(Tau+Ile)+(Gln+Met)/(Thr+Ser+Val+Trp);

Composite Index 1-9

(Asn)/(Tau+(α-ABA)+Ile)+(Gln)/(Asp+Thr+Ser+Val+Trp);

Composite Index 1-10

(Asn)/(Thr)+(Gln+Met)/(Tau+Ser+Val+Trp);

Composite Index 1-11

(Asn)/(Tau+Asp+(α-ABA)+Ile)+(Gln)/(Thr+Ser+Val+Trp);

Composite Index 1-12

(Asn)/(Thr)+(Gln)/(Tau+Ser+(α-ABA)+Val+Trp);

Composite Index 1-13

(Asn)/(Asp+Thr)+(Gln)/(Tau+Ser+Val+Ile+Trp);

Composite Index 1-14

(Asn)/(Tau+(α-ABA)+Ile)+(Gln+Met)/(Thr+Ser+Val+Trp);

Composite Index 1-15

(Asn)/(Tau+Asp+Ile)+(Gln)/(Thr+Ser+Val+Trp);

Composite Index 1-16

(Asn)/(Thr)+(Gln)/(Tau+Asp+Ser+Val+Ile+Trp);

Composite Index 1-17

(Asn)/(Tau+Ile)+(Gln+Met)/(Asp+Thr+Ser+Val+Trp);

Composite Index 1-18

(Asn)/(Asp+Thr)+(Gln)/(Tau+Ser+(α-ABA)+Val+Trp);

Composite Index 1-19

(Asn)/(Asp+Thr)+(Gln+Met)/(Tau+Ser+Val+Trp); and

Composite Index 1-20

(Asn)/(Thr)+(Gln)/(Tau+Ser+(α-ABA)+Val+Ile+Trp).

The composite index 2 may be replaced by any of the following composite indices 2-1 through 2-20:

Composite Index 2-1

(Asn+Tyr)/(Cit)+(Met+Arg)/(Asp+(α-ABA));

Composite Index 2-2

(Asn+Tyr)/(Cit)+(Arg)/(Asp+(α-ABA));

Composite Index 2-3

(Asn+Met+Tyr)/(Cit)+(Arg)/(Asp+(α-ABA));

Composite Index 2-4

(Asn+Met+Tyr)/(Asp+Cit)+(Arg)/(α-ABA);

Composite Index 2-5

(Asn+Met)/(Cit)+(Tyr+Arg)/(Asp+(α-ABA));

Composite Index 26

(Asn+Tyr)/(Asp+Cit)+(Arg)/(α-ABA);

Composite Index 2-7

(Asn+Tyr)/(Asp+Cit)+(Met+Arg)/(α-ABA);

Composite Index 2-8

(Asn)/(Cit)+(Tyr+Arg)/(Asp+(α-ABA));

Composite Index 2-9

(Asn)/(Thr+Cit+(α-ABA))+(Met)/(His+Trp);

Composite Index 2-10

(Ash)/(Cit)+(Met+Tyr+Arg)/(Asp+(α-ABA));

Composite Index 2-11

(Asn)/(Thr+Cit+(α-ABA))+(Met)/(Asp+His+Trp);

Composite Index 2-12

(Asn)/(Thr+Glu)+(Met)/(Cit+(α-ABA)+Trp);

Composite Index 2-13

(Asn)/(Asp+Thr+Cit+(α-ABA))+(Met)/(His+Trp);

Composite Index 2-14

(Asn)/(Thr+Cit+(α-ABA))+(Met)/(Glu+His+Trp);

Composite Index 2-15

(Asn+Met)/(Asp+Cit)+(Tyr+Arg)/(α-ABA);

Composite Index 2-16

(Asn+Met)/(Cit)+(Arg)/(Asp+(α-ABA));

Composite Index 2-17

(Asn)/(Cit+(α-ABA)+His)+(Met)/(Thr+Glu+Trp);

Composite Index 2-18

(Asn)/(Cit+(α-ABA)+His)+(Met)/(Thr+Trp);

Composite Index 2-19

(Asn)/(Cit+His+Trp)+(Met)/(Thr+(α-ABA)); and

Composite Index 2-20

(Asn+Arg)/(α-ABA)+(Met+Tyr)/(Asp+Cit).

The composite index 3 may be replaced by any of the following composite indices 3-1 through 3-20:

Composite Index 3-1

(Tau+Gly)/(Gln)+(α-ABA)/(Asp+Tyr)+(His)/(Lys)+(Trp)/(Thr+Asn+Cit);

Composite Index 3-2

(Tau+Gly)/(Gln+Met)+(α-ABA)/(Asp+Tyr)+(His)/(Lys)+(Trp)/(Thr+Asn+Cit);

Composite Index 3-3

(Tau+Gly)/(Gln)+(α-ABA)/(Thr)+(His)/(Lys)+(Trp)/(Asn+Cit+Tyr);

Composite Index 34

(Tau+Gly)/(Asp+Gln)+(α-ABA)/(Tyr)+(His)/(Lys)+(Trp)/(Thr+Asn+Cit);

Composite Index 3-5

(Tau+Gly)/(Asp+Gln+Met)+(α-ABA)/(Tyr)+(His)/(Lys)+(Trp)/(Thr+Asn+Cit);

Composite Index 3-6

(Tau+Gly)/(Gln+Met)+(α-ABA)/(Tyr)+(His)/(Lys)+(Trp)/(Thr+Asn+Cit);

Composite Index 3-7

(Tau+Gly)/(Gln+Met)+(α-ABA)/(Tyr)+(His)/(Lys)+(Trp)/(Asp+Thr+Asn+Cit);

Composite Index 3-8

(Tau+Gly)/(Gln)+(α-ABA)/(Asp+Met+Tyr)+(His)/(Lys)+(Trp)/(Thr+Asn+Cit);

Composite Index 3-9

(Tau+Gly)/(Asp+Gln)+(α-ABA)/(Met+Tyr)+(His)/(Lys)+(Trp)/(Thr+Asn+Cit);

Composite Index 3-10

(Tau+Gly)/(Gln)+(α-ABA)/(Met+Tyr)+(His)/(Lys)+(Trp)/(Asp+Thr+Asn+Cit);

Composite Index 3-11

(Tau+Gly)/(Gln)+(α-ABA)/(Met+Tyr)+(His)/(Lys)+(Trp)/(Thr+Asn+Cit);

Composite Index 3-12

(Tau+Gly)/(Gln)+(α-ABA)/(Thr)+(His)/(Asn+Cit+Tyr)+(Trp)/(Lys);

Composite Index 3-13

(Tau)/(Lys)+(Trp)/(Asn+Cit+Tyr)+(Gly+His)/(Gln)+(α-ABA)/(Asp+Thr);

Composite Index 3-14

(Tau)/(Lys)+(Trp)/(Asp+Asn+Cit+Tyr)+(Gly+His)/(Gln)+(α-ABA)/(Thr);

Composite Index 3-15

(Tau)/(Lys)+(Trp)/(Asn+Cit+Tyr)+(Gly+His)/(Gln)+(α-ABA)/(Thr);

Composite Index 3-16

(Tau)/(Asp+Asn+Lys)+(Trp)/(Cit+Tyr)+(Gly+His)/(Gln)+(α-ABA)/(Thr);

Composite Index 3-17

(Tau+Gly)/(Gln)+(α-ABA)/(Asp+Tyr)+(His)/(Thr+Asn+Cit)+(Trp)/(Lys);

Composite Index 3-18

(Tau+Gly)/(Gln+Met)+(α-ABA)/(Asp+Tyr)+(His)/(Thr+Asn+Cit)+(Trp)/(Lys);

Composite Index 3-19

(Tau+Gly)/(Gln+Met)+(α-ABA)/(Tyr)+(His)/(Asp+Cit+Lys)+(Trp)/(Thr+Asn); and

Composite Index 3-20

(Tau+Gly)/(Asp+Gln)+(α-ABA)/(Tyr)+(His)/(Thr+Asn+Cit)+(Trp)/(Lys).

The composite index 4 may be replaced by any of the following composite indices 4-1 through 4-20:

Composite Index 4-1

(Tau+Trp)/(Tyr)+((α-ABA)+His)/(Asp+Asn);

Composite Index 4-2

((α-ABA)+Trp)/(Tyr)+(His)/(Asp+Asn);

Composite Index 4-3

(Tau+(α-ABA)+Trp)/(Tyr)+(His)/(Asp+Asn);

Composite Index 4-4

(Tau+Trp)/(Tyr)+(His)/(Asp+Asn);

Composite Index 4-5

(Tau+Trp)/(Tyr)+((α-ABA)+His)/(Asn);

Composite Index 4-6

(Tau+(α-ABA)+Trp)/(Tyr)+(His)/(Asn);

Composite Index 4-7

(Tau+(α-ABA)+Trp)/(Asp+Met+Tyr)+(His)/(Asn);

Composite Index 4-8

((α-ABA)+Trp)/(Tyr)+(His)/(Asn);

Composite Index 4-9

(Tau+Trp)/(Tyr)+(α-ABA)/(Asp+Met)+(His)/(Asn);

Composite Index 4-10

(Tau+Trp)/(Tyr)+(His)/(Asn);

Composite Index 4-11

((α-ABA)+His)/(Asp+Asn)+(Trp)/(Tyr);

Composite Index 4-12

(Tau+Trp)/(Asp+Met+Tyr)+(His)/(Asn);

Composite Index 4-13

(Tau+His)/(Tyr)+((α-ABA)+Trp)/(Asp+Asn);

Composite Index 4-14

(Tau+(α-ABA))/(Asp+Asn)+(His+Trp)/(Tyr);

Composite Index 4-15

(Tau+Trp)/(Asp+Met+Tyr)+((α-ABA)+His)/(Asn);

Composite Index 4-16

(Tau+(α-ABA))/(Asn)+(His+Trp)/(Asp+Tyr);

Composite Index 4-17

((α-ABA)+Trp)/(Tyr)+(His)/(Asp+Asn+Met);

Composite Index 4-18

(Tau+(α-ABA)+His)/(Tyr)+(Trp)/(Asp+Asn);

Composite Index 4-19

(α-ABA)/(Asn)+(His+Trp)/(Asp+Met+Tyr); and

Composite Index 4-20

(Tau+His)/(Asp+Asn+Met)+((α-ABA)+Trp)/(Tyr).

The present invention also relates to a system for determining hepatic fibrosis stage. The system comprises:

a hepatic fibrosis determining apparatus for processing information concerning hepatic fibrosis; and an information terminal of a provider of information about metabolites, the information terminal being communicably connected via a network to the hepatic fibrosis determining apparatus;

wherein the hepatic fibrosis determining apparatus comprises:

a blood concentration data acquiring unit for acquiring from the information terminal a group of blood concentration data measured for each metabolite in each individual;

a disease condition index value calculating unit for calculating an index value indicative of the disease condition of the progression of hepatic fibrosis from the group of blood concentration data acquired by the blood concentration data acquiring unit, the calculation being performed based on at least one of the following composite indices 1 through 4:

Composite Index 1

(Asn)/(Thr)+(Gln)/(Tau+Ser+Val+Trp);

Composite Index 2

(Asn+Tyr)/(Cit)+(Met+Arg)/(Asp+(α-ABA));

Composite Index 3

(Tau+Gly)/(Gln)+(α-ABA)/(Asp+Tyr)+(His)/(Lys)+(Trp)/(Thr+Asn+Cit); and

Composite Index 4

(Tau+Trp)/(Tyr)+((α-ABA)+His)/(Asp+Asn);

a disease condition determining unit for determining the disease condition indicative of the progression of hepatic fibrosis based on the disease condition index value calculated by the disease condition index value calculating unit; and an analysis result sending unit for sending the results determined by the disease condition determining unit to the information terminal which is a sender of the group of blood concentration data;

wherein the information terminal comprises:

a sending unit for sending the group of blood concentration data to the hepatic fibrosis determining apparatus; and a receiving unit for receiving from the hepatic fibrosis determining apparatus the results of the determination for the group of blood concentration data having been sent by the sending unit.

According to the system described above, the hepatic fibrosis determining apparatus acquires from the information terminal a data group of metabolite concentration in blood in each individual, calculates an index value indicative of the disease condition of hepatic fibrosis from the group of blood concentration data acquired by the blood concentration data acquiring unit based on at least one of the following composite indices 1 through 4:

Composite Index 1

(Asn)/(Thr)+(Gln)/(Tau+Ser+Val+Trp);

Composite Index 2

(Asn+Tyr)/(Cit)+(Met+Arg)/(Asp+(α-ABA));

Composite Index 3

(Tau+Gly)/(Gln)+(α-ABA)/(Asp+Tyr)+(His)/(Lys)+(Trp)/(Thr+Asn+Cit); and

Composite Index 4

(Tau+Trp)/(Tyr)+((α-ABA)+His)/(Asp+Asn), determines the disease condition indicative of the progression of hepatic fibrosis based on the calculated disease condition index value, and sends the determined results to the information terminal which is a sender of the group of blood concentration data. Furthermore, the information terminal sends the group of the blood concentration data to the hepatic fibrosis determining apparatus, and receives from the hepatic fibrosis determining apparatus the results of the determination for the sent group of the blood concentration data. Thus, the system makes it possible to screen many individuals for hepatic fibrosis by using the results of a single test for, for example, blood amino acid levels. This leads to a significant reduction in the cost of testing.

It is also made possible to diagnose hepatic fibrosis by analyzing the data of blood amino acid level obtained in the past.

The use of one of the four composite indices 1 through 4 as a marker of hepatic fibrosis makes it possible to develop a treatment for the disease, since the metabolites composing one of the four composite indices 1 through 4 for hepatic fibrosis may be the potential cause or the outcome of the disease.

The amino acids in at least one of the four composite indices 1 through 4 may be replaced by other chemically equivalent compounds, such as other amino acids.

Specifically, at least one of the four indices 1 through 4 may be replaced by the corresponding formulae of composite indices shown below.

For example, the composite index 1 may be replaced by any of the following composite indices 1-1 through 1-20:

Composite Index 1-1

(Asn)/(Thr)+(Gln)/(Tau+Ser+Val+Trp);

Composite Index 1-2

(Asn)/(Tau+Ile)+(Gln)/(Thr+Ser+Val+Trp);

Composite Index 1-3

(Asn)/(Tau+(α-ABA)+Ile)+(Gln)/(Thr+Ser+Val+Trp);

Composite Index 14

(Asn)/(Asp+Thr)+(Gln)/(Tau+Ser+Val+Trp);

Composite Index 1-5

(Asn)/(Thr)+(Gln)/(Tau+Ser+Val+Ile+Trp);

Composite Index 1-6

(Asn)/(Thr)+(Gln)/(Tau+Asp+Ser+Val+Trp);

Composite Index 1-7

(Asn)/(Tau+Ile)+(Gln)/(Asp+Thr+Ser+Val+Trp);

Composite Index 1-8

(Asn)/(Tau+Ile)+(Gln+Met)/(Thr+Ser+Val+Trp);

Composite Index 1-9

(Asn)/(Tau+(α-ABA)+Ile)+(Gln)/(Asp+Thr+Ser+Val+Trp);

Composite Index 1-10

(Asn)/(Thr)+(Gln+Met)/(Tau+Ser+Val+Trp);

Composite Index 1-11

(Asn)/(Tau+Asp+(α-ABA)+Ile)+(Gln)/(Thr+Ser+Val+Trp);

Composite Index 1-12

(Asn)/(Thr)+(Gln)/(Tau+Ser+(α-ABA)+Val+Trp);

Composite Index 1-13

(Asn)/(Asp+Thr)+(Gln)/(Tau+Ser+Val+Ile+Trp);

Composite Index 1-14

(Asn)/(Tau+(α-ABA)+Ile)+(Gln+Met)/(Thr+Ser+Val+Trp);

Composite Index 1-15

(Asn)/(Tau+Asp+Ile)+(Gln)/(Thr+Ser+Val+Trp);

Composite Index 1-16

(Asn)/(Thr)+(Gln)/(Tau+Asp+Ser+Val+Ile+Trp);

Composite Index 1-17

(Asn)/(Tau+Ile)+(Gln+Met)/(Asp+Thr+Ser+Val+Trp);

Composite Index 1-18

(Asn)/(Asp+Thr)+(Gln)/(Tau+Ser+(α-ABA)+Val+Trp);

Composite Index 1-19

(Asn)/(Asp+Thr)+(Gln+Met)/(Tau+Ser+Val+Trp); and

Composite Index 1-20

(Asn)/(Thr)+(Gln)/(Tau+Ser+(α-ABA)+Val+Ile+Trp).

The composite index 2 may be replaced by any of the following composite indices 2-1 through 2-20:

Composite Index 2-1

(Asn+Tyr)/(Cit)+(Met+Arg)/(Asp+(α-ABA));

Composite Index 2-2

(Asn+Tyr)/(Cit)+(Arg)/(Asp+(α-ABA));

Composite Index 2-3

(Asn+Met+Tyr)/(Cit)+(Arg)/(Asp+(α-ABA));

Composite Index 2-4

(Asn+Met+Tyr)/(Asp+Cit)+(Arg)/(α-ABA);

Composite Index 2-5

(Asn+Met)/(Cit)+(Tyr+Arg)/(Asp+(α-ABA));

Composite Index 2-6

(Asn+Tyr)/(Asp+Cit)+(Arg)/(α-ABA);

Composite Index 2-7

(Asn+Tyr)/(Asp+Cit)+(Met+Arg)/(α-ABA);

Composite Index 2-8

(Asn)/(Cit)+(Tyr+Arg)/(Asp+(α-ABA));

Composite Index 2-9

(Asn)/(Thr+Cit+(α-ABA))+(Met)/(His+Trp);

Composite Index 2-10

(Asn)/(Cit)+(Met+Tyr+Arg)/(Asp+(α-ABA));

Composite Index 2-11

(Asn)/(Thr+Cit+(α-ABA))+(Met)/(Asp+His+Trp);

Composite Index 2-12

(Asn)/(Thr+Glu)+(Met)/(Cit+(α-ABA)+Trp);

Composite Index 2-13

(Asn)/(Asp+Thr+Cit+(α-ABA))+(Met)/(His+Trp);

Composite Index 2-14

(Asn)/(Thr+Cit+(α-ABA))+(Met)/(Glu+His+Trp);

Composite Index 2-15

(Asn+Met)/(Asp+Cit)+(Tyr+Arg)/(α-ABA);

Composite Index 2-16

(Asn+Met)/(Cit)+(Arg)/(Asp+(α-ABA));

Composite Index 2-17

(Asn)/(Cit+(α-ABA)+His)+(Met)/(Thr+Glu+Trp);

Composite Index 2-18

(Asn)/(Cit+(α-ABA)+His)+(Met)/(Thr+Trp);

Composite Index 2-19

(Asn)/(Cit+His+Trp)+(Met)/(Thr+(α-ABA)); and

Composite Index 2-20

(Asn+Arg)/(α-ABA)+(Met+Tyr)/(Asp+Cit).

The composite index 3 may be replaced by any of the following composite indices 3-1 through 3-20:

Composite Index 3-1

(Tau+Gly)/(Gln)+(α-ABA)/(Asp+Tyr)+(His)/(Lys)+(Trp)/(Thr+Asn+Cit);

Composite Index 3-2

(Tau+Gly)/(Gln+Met)+(α-ABA)/(Asp+Tyr)+(His)/(Lys)+(Trp)/(Thr+Asn+Cit);

Composite Index 3-3

(Tau+Gly)/(Gln)+(α-ABA)/(Thr)+(His)/(Lys)+(Trp)/(Asn+Cit+Tyr);

Composite Index 3-4

(Tau+Gly)/(Asp+Gln)+(α-ABA)/(Tyr)+(His)/(Lys)+(Trp)/(Thr+Asn+Cit);

Composite Index 3-5

(Tau+Gly)/(Asp+Gln+Met)+(α-ABA)/(Tyr)+(His)/(Lys)+(Trp)/(Thr+Asn+Cit);

Composite Index 3-6

(Tau+Gly)/(Gln+Met)+(α-ABA)/(Tyr)+(His)/(Lys)+(Trp)/(Thr+Asn+Cit);

Composite Index 3-7

(Tau+Gly)/(Gln+Met)+(α-ABA)/(Tyr)+(His)/(Lys)+(Trp)/(Asp+Thr+Asn+Cit);

Composite Index 3-8

(Tau+Gly)/(Gln)+(α-ABA)/(Asp+Met+Tyr)+(His)/(Lys)+(Trp)/(Thr+Asn+Cit);

Composite Index 3-9

(Tau+Gly)/(Asp+Gln)+(α-ABA)/(Met+Tyr)+(His)/(Lys)+(Trp)/(Thr+Asn+Cit);

Composite Index 3-10

(Tau+Gly)/(Gln)+(α-ABA)/(Met+Tyr)+(His)/(Lys)+(Trp)/(Asp+Thr+Asn+Cit);

Composite Index 3-11

(Tau+Gly)/(Gln)+(o-ABA)/(Met+Tyr)+(His)/(Lys)+(Trp)/(Thr+Asn+Cit);

Composite Index 3-12

(Tau+Gly)/(Gln)+(α-ABA)/(Thr)+(His)/(Asn+Cit+Tyr)+(Trp)/(Lys);

Composite Index 3-13

(Tau)/(Lys)+(Trp)/(Asn+Cit+Tyr)+(Gly+His)/(Gln)+(α-ABA)/(Asp+Thr);

Composite Index 3-14

(Tau)/(Lys)+(Trp)/(Asp+Asn+Cit+Tyr)+(Gly+His)/(Gln)+(α-ABA)/(Thr);

Composite Index 3-15

(Tau)/(Lys)+(Trp)/(Asn+Cit+Tyr)+(Gly+His)/(Gln)+(α-ABA)/(Thr);

Composite Index 3-16

(Tau)/(Asp+Asn+Lys)+(Trp)/(Cit+Tyr)+(Gly+His)/(Gln)+(α-ABA)/(Thr);

Composite Index 3-17

(Tau+Gly)/(Gln)+(α-ABA)/(Asp+Tyr)+(His)/(Thr+Asn+Cit)+(Trp)/(Lys);

Composite Index 3-18

(Tau+Gly)/(Gln+Met)+(α-ABA)/(Asp+Tyr)+(His)/(Thr+Asn+Cit)+(Trp)/(Lys);

Composite Index 3-19

(Tau+Gly)/(Gln+Met)+(α-ABA)/(Tyr)+(His)/(Asp+Cit+Lys)+(Trp)/(Thr+Asn); and

Composite Index 3-20

(Tau+Gly)/(Asp+Gln)+(α-ABA)/(Tyr)+(His)/(Thr+Asn+Cit)+(Trp)/(Lys).

The composite index 4 may be replaced by any of the following composite indices 4-1 through 4-20:

Composite Index 4-1

(Tau+Trp)/(Tyr)+((α-ABA)+His)/(Asp+Asn);

Composite Index 4-2

((α-ABA)+Trp)/(Tyr)+(His)/(Asp+Asn);

Composite Index 4-3

(Tau+(α-ABA)+Trp)/(Tyr)+(His)/(Asp+Asn);

Composite Index 4-4

(Tau+Trp)/(Tyr)+(His)/(Asp+Asn);

Composite Index 4-5

(Tau+Trp)/(Tyr)+((α-ABA)+His)/(Asn);

Composite Index 4-6

(Tau+(α-ABA)+Trp)/(Tyr)+(His)/(Asn);

Composite Index 4-7

(Tau+(α-ABA)+Trp)/(Asp+Met+Tyr)+(His)/(Asn);

Composite Index 4-8

((α-ABA)+Trp)/(Tyr)+(His)/(Asn);

Composite Index 4-9

(Tau+Trp)/(Tyr)+(α-ABA)/(Asp+Met)+(His)/(Asn);

Composite Index 4-10

(Tau+Trp)/(Tyr)+(His)/(Asn);

Composite Index 4-11

((α-ABA)+His)/(Asp+Asn)+(Trp)/(Tyr);

Composite Index 4-12

(Tau+Trp)/(Asp+Met+Tyr)+(His)/(Asn);

Composite Index 4-13

(Tau+His)/(Tyr)+((α-ABA)+Trp)/(Asp+Asn);

Composite Index 4-14

(Tau+(α-ABA))/(Asp+Asn)+(His+Trp)/(Tyr);

Composite Index 4-15

(Tau+Trp)/(Asp+Met+Tyr)+((α-ABA)+His)/(Asn);

Composite Index 4-16

(Tau+(α-ABA))/(Asn)+(His+Trp)/(Asp+Tyr);

Composite Index 4-17

((α-ABA)+Trp)/(Tyr)+(His)/(Asp+Asn+Met);

Composite Index 4-18

(Tau+(α-ABA)+His)/(Tyr)+(Trp)/(Asp+Asn);

Composite Index 4-19

(α-ABA)/(Asn)+(His+Trp)/(Asp+Met+Tyr); and

Composite Index 4-20

(Tau+His)/(Asp+Asn+Met)+((α-ABA)+Trp)/(Tyr).

The present invention also relates to a recording medium that has the above-described program recorded therein.

The recording medium can provide the stored program to a computer, which reads out and executes the program to implement the same tasks, whereby the same advantage as these programs can be obtained.

The present invention also relates to an apparatus and a method for determining hepatic fibrosis stage, as well as to a program for executing the method. The apparatus, the method and the program are characterized by comprising:

a blood concentration data acquiring unit for (or a blood concentration data acquiring step of) acquiring a group of blood concentration data measured for each metabolite in each individual;

a composite index setting unit for (or a composite index setting step of) setting a composite index for calculating an index value indicative of the disease condition of hepatic fibrosis;

a disease condition index value calculating unit for (or a disease condition index value calculating step of) calculating the index value indicative of the disease condition of hepatic fibrosis from the group of blood concentration data acquired by the blood concentration data acquiring unit (or blood concentration data acquiring step), the calculation being performed based on the composite index set by the composite index setting unit (or composite index setting step); and a disease condition determining unit for (or a disease condition determining step of) determining the disease condition indicative of the progression of hepatic fibrosis based on the disease condition index value calculated by the disease condition index value calculating unit (or disease condition index value calculating step), wherein the composite index setting unit (or composite index setting step) comprises at least one of:

a composite index 1 generating unit for (or a composite index 1 generating step of) generating a composite index 1, which consists of a single term or a summation of a plurality of terms of fractions having at least one of the blood concentration data of Asn and Gln in the numerator and at least one of the blood concentration data of Thr, Tau, Ser, Val, and Trp in the denominator (the blood concentration data of Met may be added to the numerator and the blood concentration data of any of Ile, α-ABA, and Asp may be added to the denominator);

a composite index 2 generating unit for (or a composite index 2 generating step of) generating a composite index 2, which consists of a single term or a summation of a plurality of terms of fractions having at least one of the blood concentration data of Asn and Met in the numerator and at least one of the blood concentration data of α-ABA and Cit in the denominator (the blood concentration data of any of Tyr and Arg may be further added to the numerator and the blood concentration data of any of His, Thr, Trp, Asp, and Glu may be further added to the denominator);

a composite index 3 generating unit for (or a composite index 3 generating step of) generating a composite index 3, which consists of a single term or a summation of a plurality of terms of fractions having at least one of the blood concentration data of α-ABA, His, Gly, Trp, and Tau in the numerator and at least one of the blood concentration data of Asn, Gln, Cit, Lys, Thr, and Tyr in the denominator (the blood concentration data of any of Met and Asp may be further added to the denominator); and a composite index 4 generating unit (or a composite index 4 generating step) for generating a composite index 4, which consists of a single term or a summation of a plurality of terms of fractions having at least one of the blood concentration data of His and Trp in the numerator and at least one of the blood concentration data of Asn and Tyr in the denominator (the blood concentration data of any of α-ABA and Tau may be further added to the numerator and the blood concentration data of any of Met and Asp may be further added to the denominator).

According to the apparatus, the method, and the program described above, a group of blood concentration data measured for each metabolite in each individual is acquired, a composite index for calculating an index value indicative of the disease condition of hepatic fibrosis is set, an index value indicative of the disease condition of hepatic fibrosis is calculated from the acquired group of blood concentration data based on the set composite index, and the disease condition of hepatic fibrosis is determined based on the calculated disease condition index value. Furthermore, the composite index setting is performed by generating at least one of: a composite index 1, which consists of a single term or a summation of a plurality of terms of fractions having at least one of the blood concentration data of Asn and Gln in the numerator and at least one of the blood concentration data of Thr, Tau, Ser, Val, and Trp in the denominator (the blood concentration data of Met may be added to the numerator and the blood concentration data of any of Ile, α-ABA, and Asp may be added to the denominator); a composite index 2, which consists of a single term or a summation of a plurality of terms of fractions having at least one of the blood concentration data of Asn and Met in the numerator and at least one of the blood concentration data of α-ABA and Cit in the denominator (the blood concentration data of any of Tyr and Arg may be further added to the numerator and the blood concentration data of any of His, Thr, Trp, Asp, and Glu may be further added to the denominator); a composite index 3, which consists of a single term or a summation of a plurality of terms of fractions having at least one of the blood concentration data of α-ABA, His, Gly, Trp, and Tau in the numerator and at least one of the blood concentration data of Asn, Gln, Cit, Lys, Thr, and Tyr in the denominator (the blood concentration data of any of Met and Asp may be further added to the denominator); and a composite index 4, which consists of a single term or a summation of a plurality of terms of fractions having at least one of the blood concentration data of His and Trp in the numerator and at least one of the blood concentration data of Asn and Tyr in the denominator (the blood concentration data of any of α-ABA and Tau may be further added to the numerator and the blood concentration data of any of Met and Asp may be further added to the denominator). Thus, the apparatus, the method and the program make it possible to screen many individuals for hepatic fibrosis by using the results of a single test for, for example, blood amino acid levels. This leads to a significant reduction in the cost of testing.

It is also made possible to diagnose hepatic fibrosis by analyzing the data of blood amino acid level obtained in the past.

It is further made possible to develop a treatment for hepatic fibrosis using the composite index as a marker, since the metabolites composing the composite index for hepatic fibrosis are the potential cause or the outcome of the disease.

It is further made possible to exhaustively and automatically generate the composite indices useful in the diagnosis of hepatic fibrosis.

The present invention also relates a system for determining hepatic fibrosis stage. The system is characterized by comprising:

a hepatic fibrosis determining apparatus for processing information concerning hepatic fibrosis; and an information terminal of a provider of information about metabolites, the information terminal being communicably connected via a network to the hepatic fibrosis determining apparatus;

wherein the hepatic fibrosis determining apparatus comprises:

a blood concentration data acquiring unit for acquiring a group of blood concentration data measured for each metabolite in each individual;

a composite index setting unit for setting a composite index for calculating an index value indicative of the disease condition of hepatic fibrosis;

a disease condition index value calculating unit for calculating the index value indicative of the disease condition of hepatic fibrosis from the group of blood concentration data acquired by the blood concentration data acquiring unit, the calculation being performed based on the composite index set by the composite index setting unit; and a disease condition determining unit for determining the disease condition indicative of the progression of hepatic fibrosis based on the disease condition index value calculated by the disease condition index value calculating unit, wherein the composite index setting unit comprises at least one of:

a composite index 1 generating unit for generating a composite index 1, which consists of a single term or a summation of a plurality of terms of fractions having at least one of the blood concentration data of Asn and Gln in the numerator and at least one of the blood concentration data of Thr, Tau, Ser, Val, and Trp in the denominator (the blood concentration data of Met may be added to the numerator and the blood concentration data of any of Ile, α-ABA, and Asp may be added to the denominator);

a composite index 2 generating unit for generating a composite index 2, which consists of a single term or a summation of a plurality of terms of fractions having at least one of the blood concentration data of Asn and Met in the numerator and at least one of the blood concentration data of α-ABA and Cit in the denominator (the blood concentration data of any of Tyr and Arg may be further added to the numerator and the blood concentration data of any of His, Thr, Trp, Asp, and Glu may be further added to the denominator);

a composite index 3 generating unit for generating a composite index 3, which consists of a single term or a summation of a plurality of terms of fractions having at least one of the blood concentration data of α-ABA, His, Gly, Trp, and Tau in the numerator and at least one of the blood concentration data of Asn, Gln, Cit, Lys, Thr and Tyr in the denominator (the blood concentration data of any of Met and Asp may be further added to the denominator); and a composite index 4 generating unit for generating a composite index 4, which consists of a single term or a summation of a plurality of terms of fractions having at least one of the blood concentration data of His and Trp in the numerator and at least one of the blood concentration data of Asn and Tyr in the denominator (the blood concentration data of any of α-ABA and Tau may be further added to the numerator and the blood concentration data of any of Met and Asp may be further added to the denominator); and an analysis result sending unit for sending the results determined by the disease condition determining unit to the information terminal which is a sender of the group of blood concentration data;

wherein the information terminal comprises:

a sending unit for sending the group of blood concentration data to the hepatic fibrosis determining apparatus; and a receiving unit for receiving from the hepatic fibrosis determining apparatus the results of the determination for the group of blood concentration data that have been sent by the sending unit.

According to the system described above, a group of blood concentration data measured for each metabolite in each individual is acquired, a composite index for calculating an index value indicative of the disease condition of hepatic fibrosis is set, an index value indicative of the disease condition of hepatic fibrosis is calculated from the acquired group of blood concentration data based on the set composite index, and the disease condition of hepatic fibrosis is determined based on the calculated disease condition index value. Furthermore, the composite index setting is performed by generating at least one of: a composite index 1, which consists of a single term or a summation of a plurality of terms of fractions having at least one of the blood concentration data of Asn and Gln in the numerator and at least one of the blood concentration data of Thr, Tau, Ser, Val, and Trp in the denominator (the blood concentration data of Met may be added to the numerator and the blood concentration data of any of Ile, α-ABA, and Asp may be added to the denominator); a composite index 2, which consists of a single term or a summation of a plurality of terms of fractions having at least one of the blood concentration data of Asn and Met in the numerator and at least one of the blood concentration data of α-ABA and Cit in the denominator (the blood concentration data of any of Tyr and Arg may be further added to the numerator and the blood concentration data of any of His, Thr, Trp, Asp, and Glu may be further added to the denominator); a composite index 3, which consists of a single term or a summation of a plurality of terms of fractions having at least one of the blood concentration data of α-ABA, His, Gly, Trp, and Tau in the numerator and at least one of the blood concentration data of Asn, Gln, Cit, Lys, Thr, and Tyr in the denominator (the blood concentration data of any of Met and Asp may be further added to the denominator); and a composite index 4, which consists of a single term or a summation of a plurality of terms of fractions having at least one of the blood concentration data of His and Trp in the numerator and at least one of the blood concentration data of Asn and Tyr in the denominator (the blood concentration data of any of α-ABA and Tau may be further added to the numerator and the blood concentration data of any of Met and Asp may be further added to the denominator), and the determined results is sent to the information terminal which is a sender of the group of blood concentration data. Furthermore, the information terminal sends the group of the blood concentration data to the hepatic fibrosis determining apparatus, and receives from the hepatic fibrosis determining apparatus the results of the determination for the sent group of the blood concentration data. Thus, the system makes it possible to screen many individuals for hepatic fibrosis by using the results of a single test for, for example, blood amino acid levels. This leads to a significant reduction in the cost of testing.

It is also made possible to diagnose hepatic fibrosis by analyzing the data of blood amino acid level obtained in the past.

It is further made possible to develop a treatment for hepatic fibrosis using the composite index as a marker, since the metabolites composing the composite index for hepatic fibrosis are the potential cause or the outcome of the disease.

It is further made possible to exhaustively and automatically generate the composite indices useful in the diagnosis of hepatic fibrosis.

The present invention also relates to a recording medium that has the above-described program recorded therein.

The recording medium can provide the stored program to a computer, which reads out and executes the program to implement the same tasks, whereby the same advantage as these programs can be obtained.

BRIEF DESCRIPTION OF THE DRAWINGS

FIG. 1 is a chart showing the basic principle of setting the correlation formula of the present invention.

FIG. 7 is a diagram showing one example of user information stored in a user information database 106a.

FIG. 17 is a schematic diagram showing one example of the biological condition information.

FIG. 18 is a schematic diagram showing one example of correlation between index data ($T_1$) of the determined biological condition and corresponding amino acids.

FIG. 21 shows one example of amino acid (metabolite) input screen displayed on a monitor.

FIG. 22 shows one example of biological condition index input screen displayed on a monitor.

FIG. 25 shows one example of positive/negative determination confirmation screen displayed on a monitor.

FIG. 27 shows one example of result (1) sheet (raw date for analysis) screen displayed on a monitor.

FIG. 28 shows one example of result (2) sheet (conditions for searching for a composite index) screen displayed on a monitor.

FIG. 29 shows one example of result (3) sheet (best composite indices) screen displayed on a monitor.

FIG. 30 shows one example of result (4) sheet (best composite indices_values) screen displayed on a monitor.

FIG. 32 shows one example of result (6) sheet (raw data of amino acids (metabolites)) screen displayed on a monitor screen.

FIG. 33 shows one example of result (7) sheet (raw data of biological condition indices) screen displayed on a monitor display.

FIG. 50 is a chart showing one example of information stored in a hepatic fibrosis index database 406$c$.

BEST MODE FOR CARRYING OUT THE INVENTION

[Embodiments of Biological Condition Information Management System]

A description will be now given of embodiments of the apparatus and the method for processing information concerning a biological condition, as well as the system for managing such information, the program, and the recording medium according to the present invention, with reference to the accompanying drawings. Incidentally, the embodiments are not intended to limit the scope of the invention in any way.

While the present embodiments will be mainly described by an example in which metabolites are amino acids, it may be similarly applied to any other type of metabolites.

(General Principle of the Present Invention)

Figure 57:
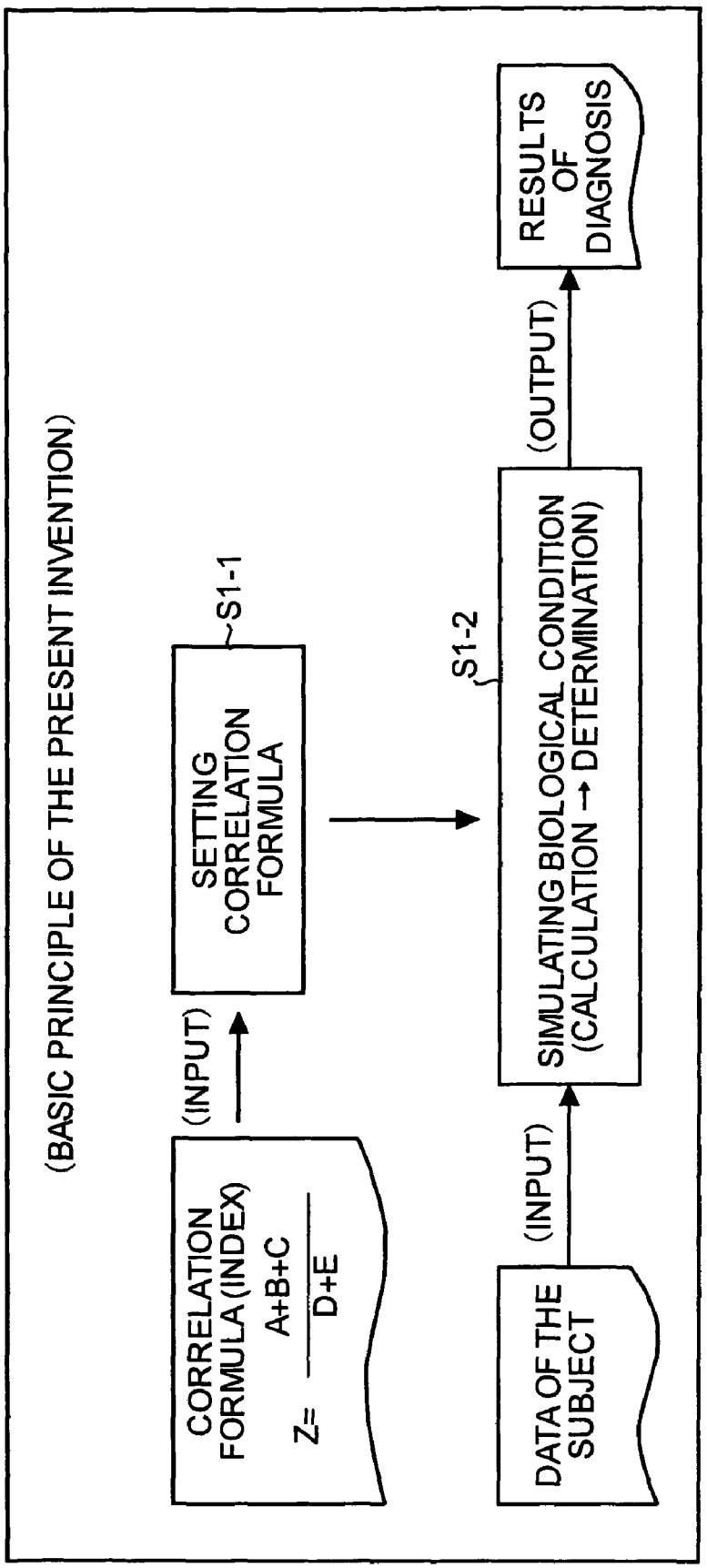
FIG. 57 is a diagram showing the basic principle of the present invention.

The present invention will be described in the following: first in its general principle, and then with respect to its detailed construction and processes involved. The basic principle of the present invention is depicted in FIG. 57.

In brief, the present invention has the following basic features: First, a correlation formula as represented by the following formula 1 is set that indicates a correlation between index data concerning a particular biological condition measured in each individual and blood concentration data (such as clinical data) measured for each metabolites in each individual (Step S1-1):

$$\sum_k G_k \frac{\sum_i \{(C_i \times A_i) + D_i\}}{\sum_j \{(E_j \times B_j) + F_j\}} + H \qquad (1)$$

(wherein each of i, j, and k is a natural number; each of $A_i$ and $B_j$ is data of concentration of the metabolite in blood or values obtained from applying a function to the concentration of the metabolite in blood; and each of $C_i$, $D_i$, $E_j$, $F_j$, $G_k$, and H is a constant.)

The correlation formula may be set by either of the following two patterns: first substitute the blood amino acid levels of clinical data into the formula 1 and then determine each constant in the formula 1 (pattern 1), or use a predetermined formula (pattern 2). In pattern 2, the correlation formula with each constant determined by pattern 1 may be stored in a predetermined file of a memory unit and a desired correlation formula is then selected from the file, or the correlation formula stored in a memory unit of another computer may be downloaded via a network.

Next, the group of blood concentration data (data obtained from subjects) measured for each metabolite in an individual to be simulated is substituted into the correlation formula set in Step S1-1 to simulate a biological condition in the individual of interest. The results of the diagnosis are then outputted (Step S1-2).

In this manner, the present invention can enable effective simulation of the condition of health, condition of disease progression, condition of disease treatment, risk of future disease, efficacy of a drug, side effect of a drug, and various other conditions based on the blood concentration of metabolites in the individual.

One example of the correlation formula setting in Step S1-1 in accordance with the aforementioned pattern 1 is now described in detail with reference to FIG. 1.

[Setting of the Correlation Formula]

FIG. 1 is a chart showing the basic principle of setting of the correlation formula of the present invention.

The setting of the correlation formula in the present invention has the following basic features: First, biological condition information is acquired. The biological condition information comprises index data concerning various biological conditions measured in each individual and group of blood concentration data measured for each metabolite in each individual (Step S-1).

One example of biological condition information is schematically shown in FIG. 17. As shown in FIG. 17, the biological condition information comprises individual (sample) numbers, index data of each biological condition (T), and groups of blood concentration data for each metabolite (for example, amino acids).

As used herein, "index data concerning a biological condition" refers to a known single index that serves as a marker of a biological condition (for example, disease conditions such as cancer, hepatic cirrhosis, dementia, and obesity).

Examples are numerical blood concentration data, enzymatic activity, gene expression level of particular metabolites, and the index of dementia (Hasegawa Dementia Scale Revised (HDSR)).

The "index data concerning a biological condition" may be obtained by assigning a numerical value to a healthy condition and a disease condition even if the actual numerical data, such as those for various measurements and test results, are not available:

(Examples) healthy=0, obesity=1; or healthy=1, mild diabetes=2, severe diabetes=3, etc.

Depending on the analysis technique, the "groups of blood concentration data" of each metabolite may be replaced by other biochemical data groups, such as gene expression levels and enzymatic activities, or combination thereof (numerical data groups combining a plurality of data groups such as metabolite level, gene expression level, and enzymatic activity).

Referring again to FIG. 1, correlation between each index data and each metabolite is then determined based on the index data concerning various biological conditions measured in each individual and the groups of blood concentration data measured for each metabolite in each individual (Step S-2).

In doing so, known correlation coefficients used to measure the strength of linear relationship between two variables x and y may be calculated to determine the correlation between each index T and each amino acid. Among such known correlation coefficients are Pearson's correlation coefficient, Spearman's correlation coefficient, and Kendall's correlation coefficient.

If a plurality of correlation formulae are obtained by using these criteria, other criteria to compare relative fitness of each correlation formula, such as Akaike's information criterion (AIC), may be used to evaluate the discrepancy of each correlation formula from the actual data and to thereby select a model.

If the "index data concerning biological condition" are to compare, as described above, between different conditions, such as healthy condition and diseased condition, the correlation ratio, the variance ratio or the Mahalanobis's generalized distance may be used to maximize and discriminate the difference between the groups. If a plurality of discrimination formulae are obtained by using these criteria, other measures such as discriminant analysis may be used to select a formula based on how effectively one condition can be discriminated from another.

Referring now to FIG. 18, one example of the correlation between index data ($T_1$) and each amino acid is conceptually shown. As shown in FIG. 18, the correlation between index data ($T_1$) of a particular biological condition and each amino acid is determined from the blood concentration data of the amino acid. The correlation may be determined by for example calculating Pearson's correlation coefficient. Pearson's correlation coefficient can take a value between −1 and 1. An absolute value of the coefficient closer to 1 indicates that the data points are more closely aligned on a straight line.

Referring again to FIG. 1, a correlation formula (correlation function) is then constructed that includes a plurality of metabolites indicative of a biological condition. This is done by using a predetermined calculation formula based on the correlation as to each metabolite determined in Step S-2 (Step S-3).

The predetermined calculation formula may be any of the following six calculation formulae:

Correlation formula ($R$)=(Sum of the amino acids with positive correlation)/(Sum of the amino acids with negative correlation);  Ex. 1)

Correlation formula ($R$)=(Sum of the amino acids with positive correlation)+(Sum of the amino acids with negative correlation);  Ex. 2)

Correlation formula ($R$)=(Sum of the amino acids with positive correlation)−(Sum of the amino acids with negative correlation);  Ex. 3)

Correlation formula ($R$)=(Sum of the amino acids with positive correlation)×(Sum of the amino acids with negative correlation);  Ex. 4)

Correlation formula ($R$)=(Sum of the amino acids with negative correlation)/(Sum of the amino acids with positive correlation)  Ex. 5)

Correlation formula ($R$)=(Sum of the amino acids with negative correlation)−(Sum of the amino acids with positive correlation).  Ex. 6)

The phrase "sum of the amino acids" in the correlation formulae above means the sum of the blood concentration of the respective amino acids.

Figure 44:
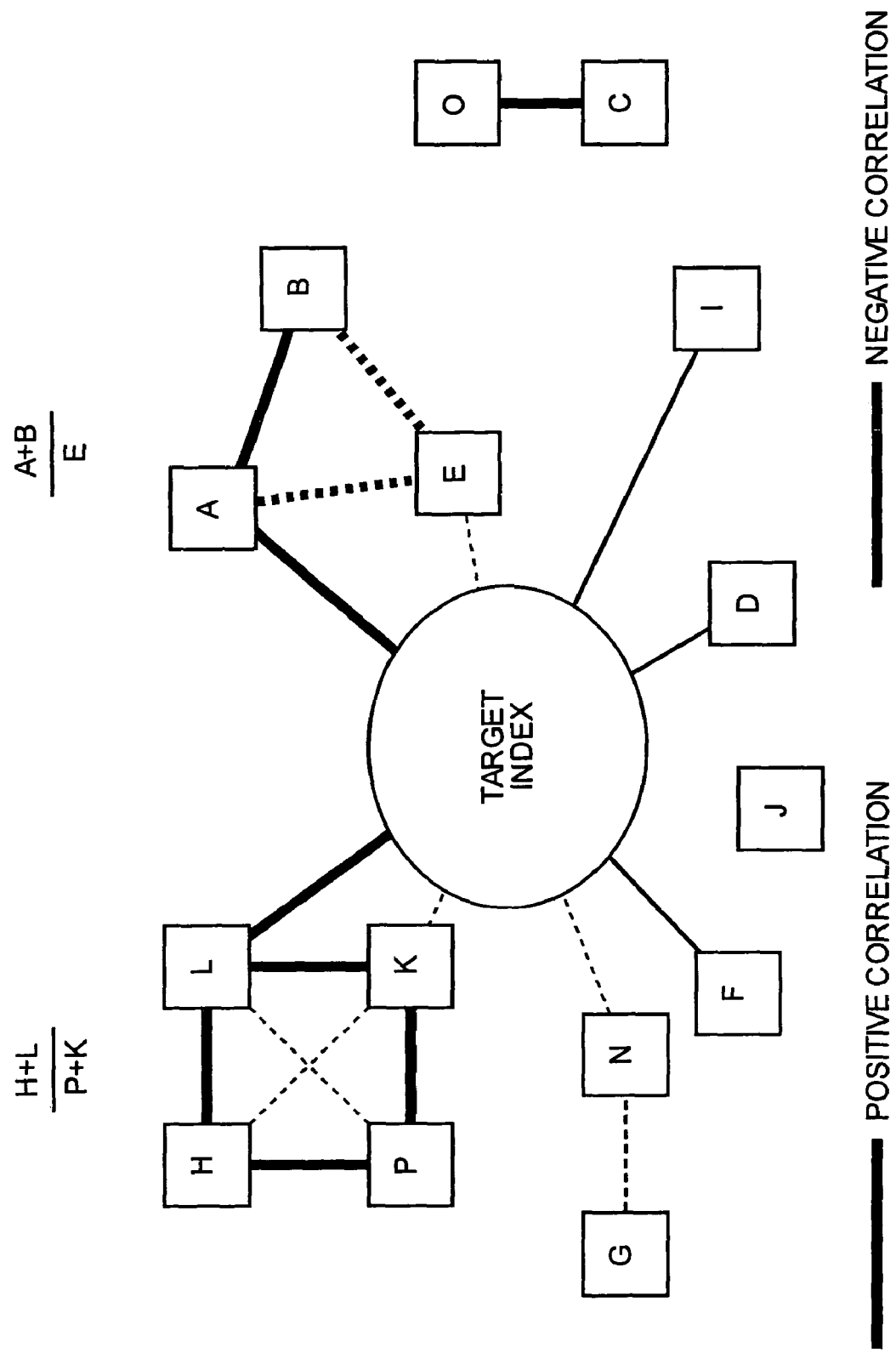
FIG. 44 is a diagram illustrating an interpretation of the calculation formula.

Referring now to FIG. 44, the interpretation of the calculation formula is conceptually illustrated. As shown in FIG. 44, the calculation formula can be considered a result of mapping of the relationship between biological indices onto a theoretical system limited to addition and subtraction etc. Thus, it is considered that the findings on the metabolic map may be further mapped with and the calculation formula.

Referring back to FIG. 1, according to the setting of the correlation formula in the present invention, the correlation formula (R) is then optimized (for example, in such a manner that the correlation coefficient ranks high (for example, top 20) or, preferably, is maximized) based on the correlation coefficient between the correlation formula (R) and the index data (T) of a biological condition determined in Step S-3 (Step S-4). The optimization may be done by either (a) selecting metabolites, such as amino acids, to be used in the calculation, (b) splitting the calculation formula, or combination of the two. We now describe these two approaches in detail.

(a) Selecting Metabolites, such as Amino Acids, to be Used in the Calculation

Figure 42:
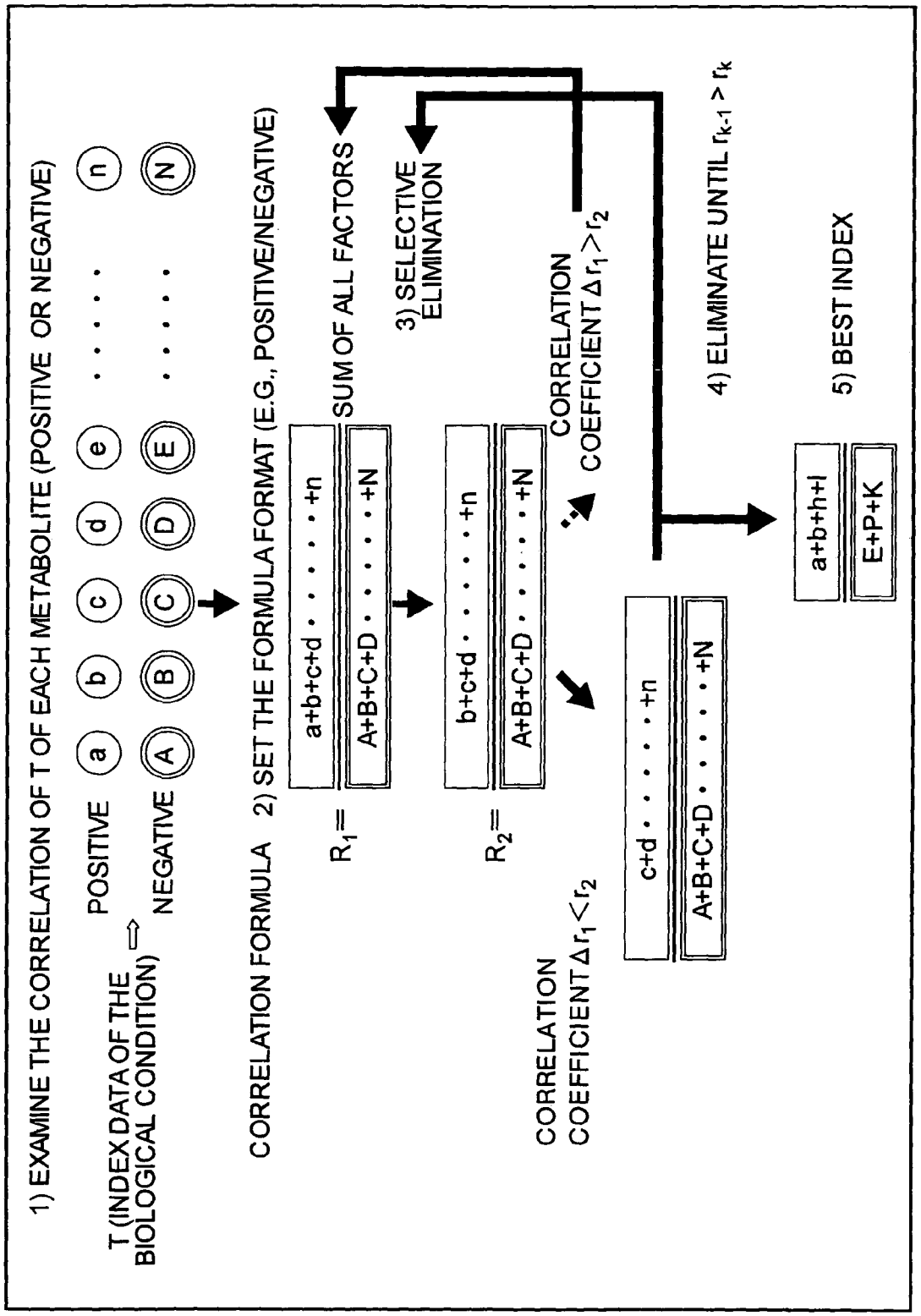
FIG. 42 is a diagram showing the concept of a procedure of calculating a correlation formula using a plurality of selected metabolites.

This approach involves selecting some of the metabolites and using the selected plurality of metabolites to calculate the correlation formula. Referring now to FIG. 42, a procedure of calculating the correlation formula using the selected plurality of metabolites is conceptually depicted. As shown in FIG. 42, the correlation between the index data (T) of a biological condition and each metabolite (for example, amino acids) is first examined to determine positively correlated metabolites (a, b, c, d, e, . . . , n) and negatively correlated metabolites (A, B, C, D, E, . . . , N).

Next, the format of the calculation formula is set. For example, the following calculation formula is selected from the above-described calculation formulae.

Correlation formula ($R_1$)=(Sum of the amino acids with positive correlation)/(Sum of the amino acids with negative correlation)

where the phrase "sum of the amino acids" means "the sum of the blood concentrations of the respective amino acids."

Next, some of the metabolites are selectively eliminated to calculate the correlation formula ($R_2$). For example, amino acid (a) may be selectively eliminated as shown in FIG. 42, more specifically, the value of the amino acid (a) is selectively removed from the calculation formula to give the correlation formula ($R_2$).

The correlation coefficient of the correlation formula ($R_1$) and the correlation coefficient of the correlation formula ($R_2$) are then compared to each other for the index data (T) of the biological condition. If the correlation coefficient of the correlation formula ($R_1$) is larger than that of the correlation formula ($R_2$), then another amino acid is selectively eliminated. The process is repeated. If, on the other hand, the correlation coefficient of the correlation formula ($R_2$) is larger than that of the correlation formula ($R_1$), then another amino acid (for example, amino acid (b)) is selectively eliminated from the calculation formula that has had the amino acid (a) eliminated. The process is repeated.

This gives a calculation formula with the maximum correlation coefficient value to the index data. If desired, a plurality of calculation formulae may be obtained: for example, top five calculation formulae with large correlation coefficients may be obtained.

(b) Splitting Calculation Formula

Figure 34:
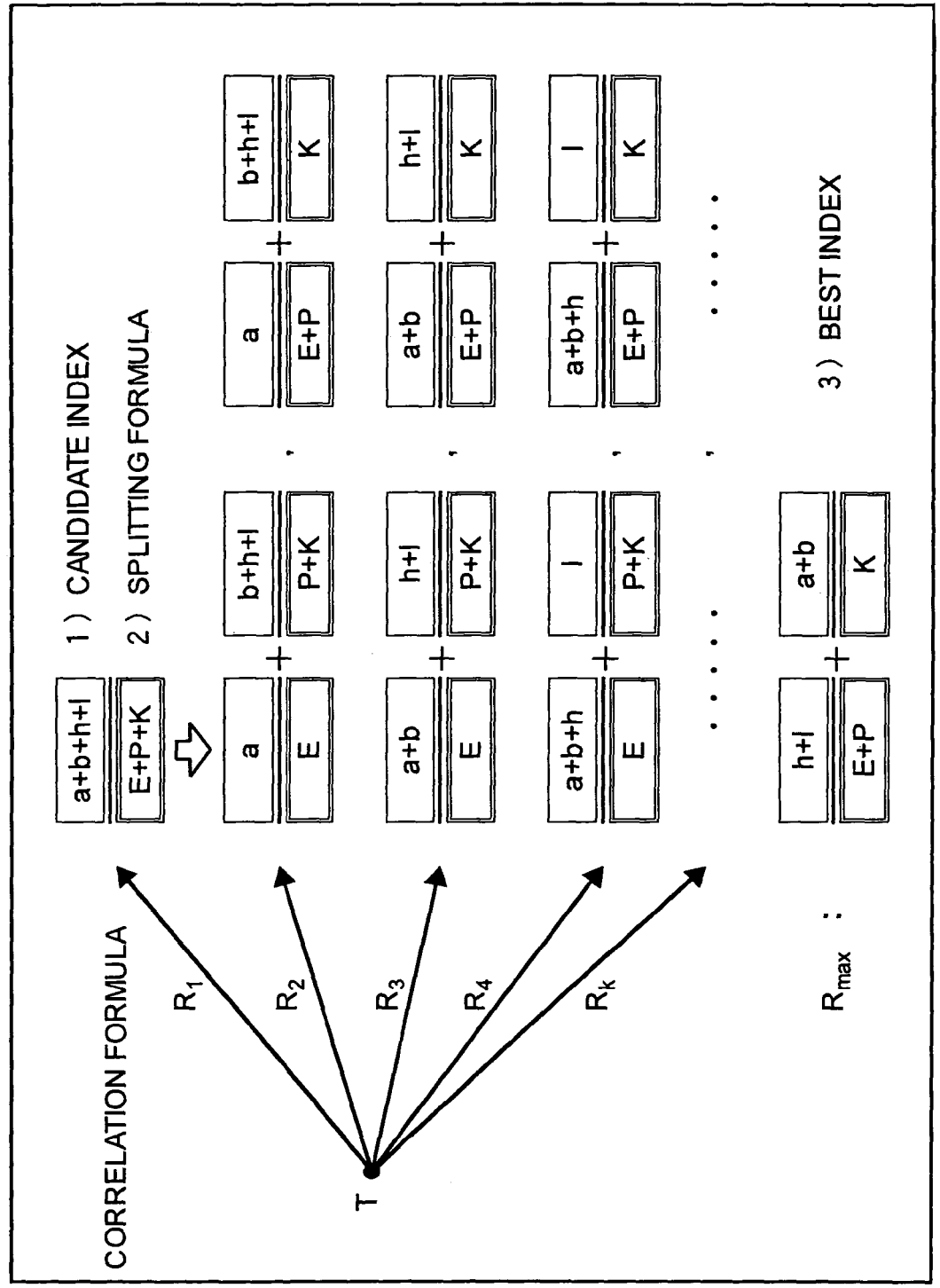
FIG. 34 is a diagram illustrating the concept of a procedure of calculating a correlation formula involving a plurality of metabolites for a biological condition by using a split calculation formula.

This approach involves splitting the calculation formula and using the split calculation formula to calculate a correlation formula including a plurality of metabolites for a biological condition. Referring to FIG. 34, a procedure is shown for calculating a correlation formula involving a plurality of metabolites for a biological condition by using the split calculation formula.

As shown in FIG. 34, correlation coefficients for the correlation formula ($R_1$), determined by a predetermined calculation formula, and the correlation formulae ($R_2$, $R_3$, $R_4$, ..., $R_k$), determined by using the calculation formula split at an arbitrary position, are first compared to one another for the index data (T) of a biological condition, thereby obtaining a calculation formula with the maximum correlation coefficients. If desired, a plurality of calculation formulae may be obtained: for example, top five calculation formulae with large correlation coefficients may be obtained.

Figure 36:
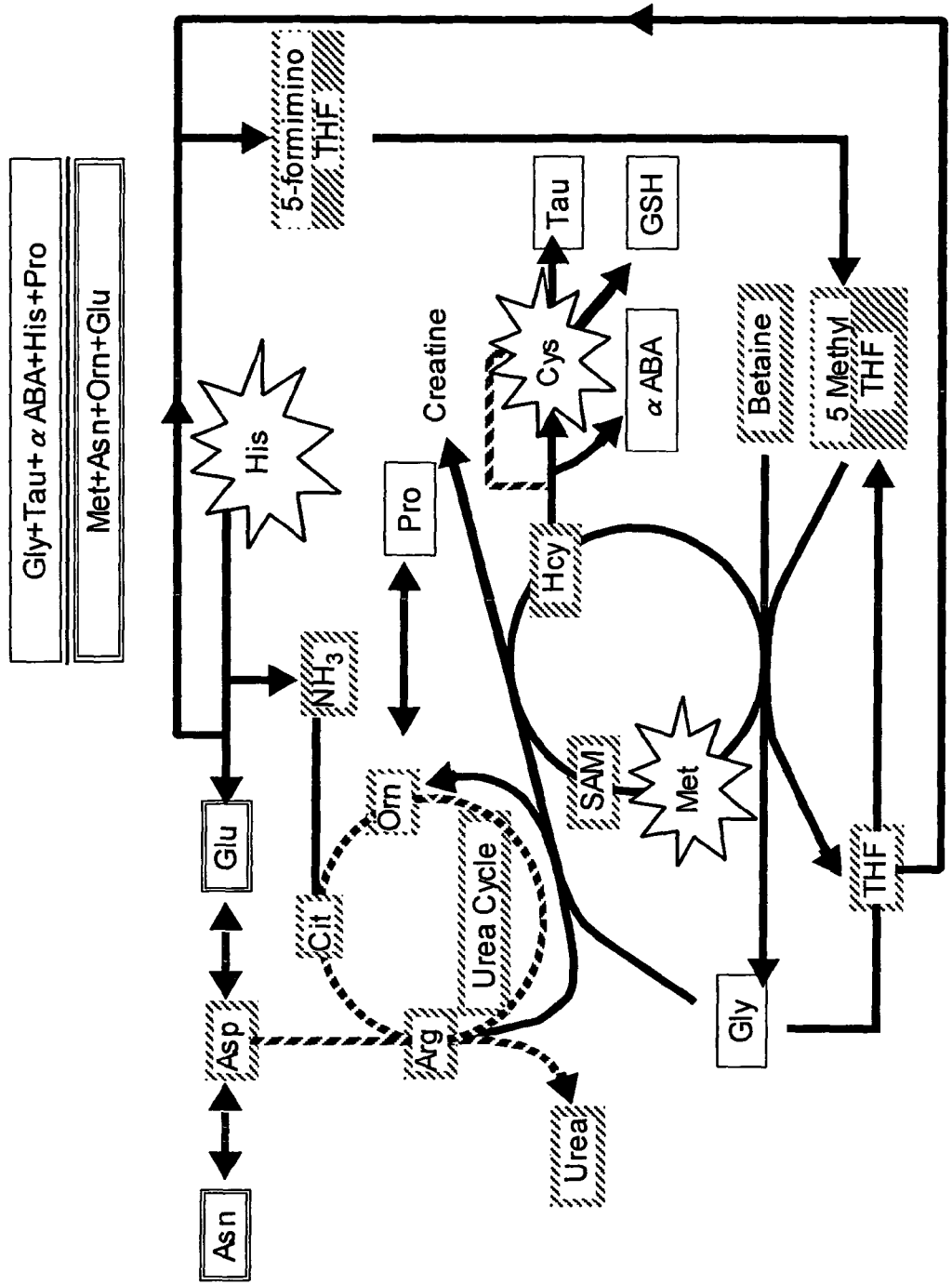
FIG. 36 is a diagram illustrating the concept of calculating the correlation formula involving a plurality of metabolites for a biological condition by using the calculation formula split based on the metabolic map information.

In doing so, the calculation formula may be split based on the metabolic map information and the split calculation formula may be used to calculate the correlation formula including a plurality of metabolites for a biological condition. Shown in FIG. 36 is the concept of calculating the correlation formula involving a plurality of metabolites for a biological condition by using the calculation formula split based on the metabolic map information. FIG. 36 illustrates one example of the relationship between a metabolic map of hepatitis and a calculation formula of a correlation formula.

As shown in FIG. 36, if a metabolic map of metabolites involved in a particular biological condition is available, the information of such a metabolic map can be used to split the calculation formula. This allows the splitting of the calculation formula based on actual biochemical findings.

When it is desired to map the calculation formula onto the metabolic map, a proper coefficient may be applied to optimize the formula so that it indicates the significance of each metabolic pathway. For example, the following formula (1) optimized for hepatic fibrosis may be subjected to multiple regression analysis to apply a coefficient to give the following formula (2), which is further optimized:

Stage (hepatic fibrosis index)=Glu/His+Met/His+Cys/
His+Orn/Pro+Asp/Glu+Asp/Asn+ABA/Met+
ABA/Thr+Tau/His+Glu/Gln; and          Formula (1):

Stage (hepatic fibrosis index)=0.590*Glu/His+
0.247*Met/His+0.250*Cys/His+0.170*Orn/Pro+
0.146*Asp/Glu+0.080*Asp/Asn+0.215*ABA/
Met+0.142*ABA/Thr+0.123*Tau/His+
0.493*Glu/Gln+ERROR.          Formula (2):

The magnitude of the partial regression coefficient can be used to test the contribution of each term. Also, mapping the partial regression coefficient onto an actual metabolic map allows extraction of factors. For example, a possible interpretation in the example of the formulae (1) and (2) may be that Glu ⇆ His or Glu <-> Gln is a potential rate-limiting step in the metabolic pathway.

Referring again to FIG. 1, according to the setting of the correlation formula in the present invention, the calculation conditions that give the maximum correlation coefficient in the optimization of the correlation formula in Step S4 may be used as the composite index for the biological condition (Step S-5). Specifically, by determining, for example, the calculation formula with the maximum correlation coefficient for each index data of each biological condition, the calculation formula can be used as the composite index reflecting a plurality of metabolites for each biological condition.

[System Configuration]

Figure 2:
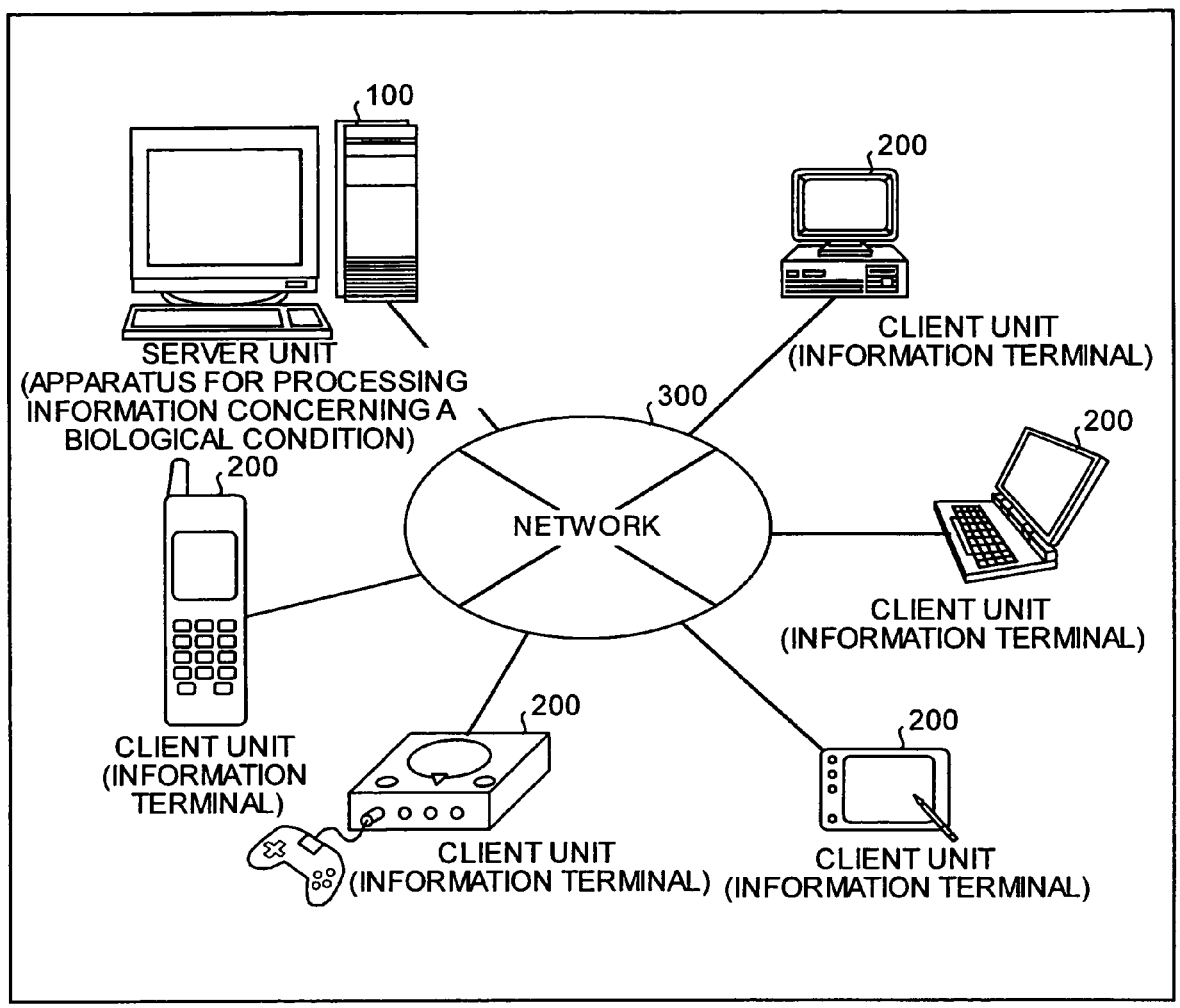
FIG. 2 is a block diagram showing an exemplary construction of the system to which the present invention is applied.

We will first describe the configuration of the system of the present invention. Shown in FIG. 2 is a block diagram of an exemplary construction of the system to which the present invention is applied. Only the part that is related to the present invention in the above construction is illustrated conceptually.

In brief, the system schematically consists of a server unit 100 and client units 200 communicably connected to the server unit 100 via a network 300. The server unit 100 is an apparatus for processing information concerning a biological condition. The client unit 200 is an information terminal of a provider of the information on the biological condition.

The system schematically has the following fundamental feature: the information about a biological condition is transmitted from the server unit 100 to the client unit 200, or vise versa, via the network 300.

The information about a biological condition is the information about values obtained for specific features of a biological condition of humans or other organisms. This information is generated by the server unit 100, the client unit 200, or other units (for example, various measurement apparatuses) and is mainly stored in the server unit 100. One example of the information about a biological condition is the information about a disease condition, which will be described later.

The server unit 100 may be integrated with various other apparatuses for analysis (for example, an amino acid analyzer).

[System Configuration—Server Unit 100]

Figure 3:
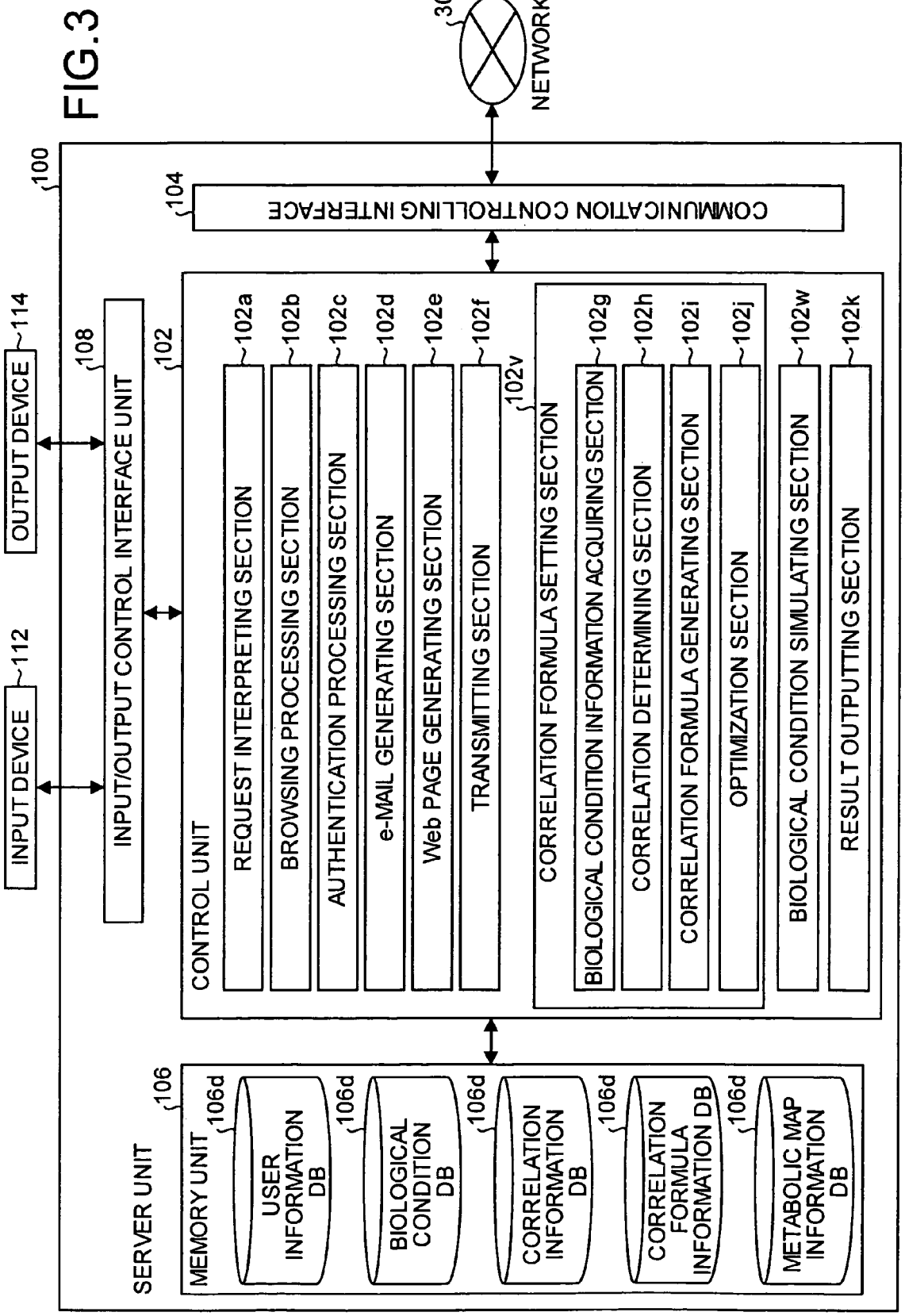
FIG. 3 is a block diagram showing an exemplary construction of a server unit 100 in the system to which the present invention is applied.

Next, we will describe the construction of the server unit 100 for use in the system of the present invention. In FIG. 3, an exemplary construction of the server unit 100 in the system of the present invention is shown in a block diagram. Only the part that is related to the present invention in the above construction is illustrated conceptually.

In FIG. 3, the server unit 100 schematically consists of a control unit 102, such as CPU, for controlling the entire server unit 100; a communication controlling interface unit 104 connected to a communication unit, such as a router (not shown), connected to a communication line; an input/output controlling interface unit 108 connected to an input device 112 or output device 114; and a memory unit 106 for storing various databases and tables. These components are communicably connected to one another via a communication pathway. The server unit 100 is further communicably connected to the network 300 via a communication device, such as a router, and a wired or wireless communication line, such as a dedicated line.

The various databases and tables (user information database 106a-metabolic map information database 106e) is stored in the memory unit 106 in FIG. 3 that is a storage unit such as a fixed disk device, which stores various programs for executing various processes, tables, files, databases, and website files.

Figure 7:
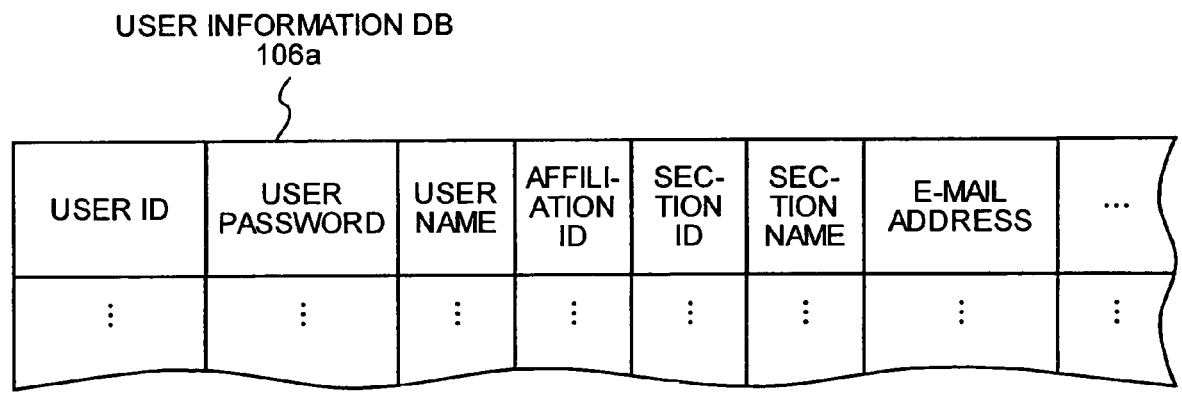

Of components of the memory unit 106, the user information database 106a serves as a user information storage unit for storing information about the user (user information). FIG. 7 shows one example of the user information stored in the user information database 106a.

As shown in FIG. 7, the information stored in the user information database 106a includes user IDs for uniquely identifying individual users; user passwords for authenticating the validity of users; names of the users; affiliation IDs for uniquely identifying which affiliation a user is belonging to; section IDs for uniquely identifying which section the affiliation of a user is belonging to; names of section; and e-mail addresses of the users. These data are shown associated with one another.

Figure 8:
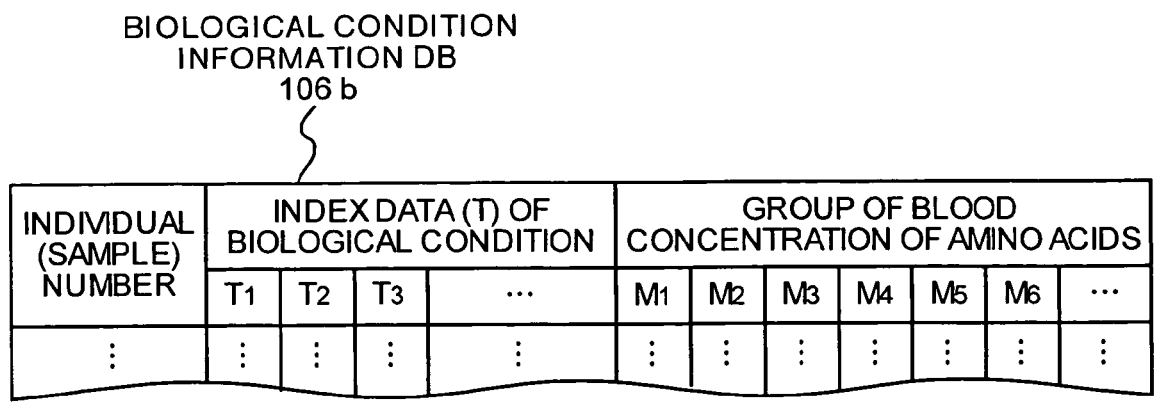
FIG. 8 is a diagram showing one example of information stored in a biological condition information database 106b.

A biological condition information database 106b serves as a biological condition information storage unit for storing information concerning, e.g., a biological condition. FIG. 8 shows one example of the information stored in the biological condition information database 106b.

As shown in, FIG. 8, the information stored in the biological condition information database 106b includes individual (sample) numbers; index data (T) for each biological condition; and groups of blood concentration data for each metabolite (for example, amino acids). These data are shown associated with one another.

Figure 9:
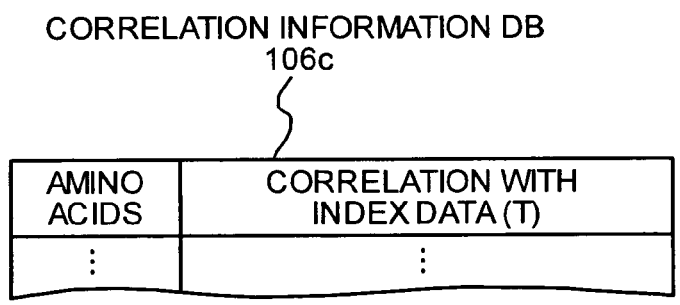
FIG. 9 is a diagram showing one example of information stored in a correlation information database 106c.

A correlation information database 106c serves as a correlation information storage unit for storing information about the correlation. FIG. 9 shows one example of the information stored in the correlation information database 106c.

As shown in FIG. 9, the information stored in the correlation information database 106c includes metabolites and correlations of the metabolites with the index data (T). These data are shown associated with one another.

Figure 10:
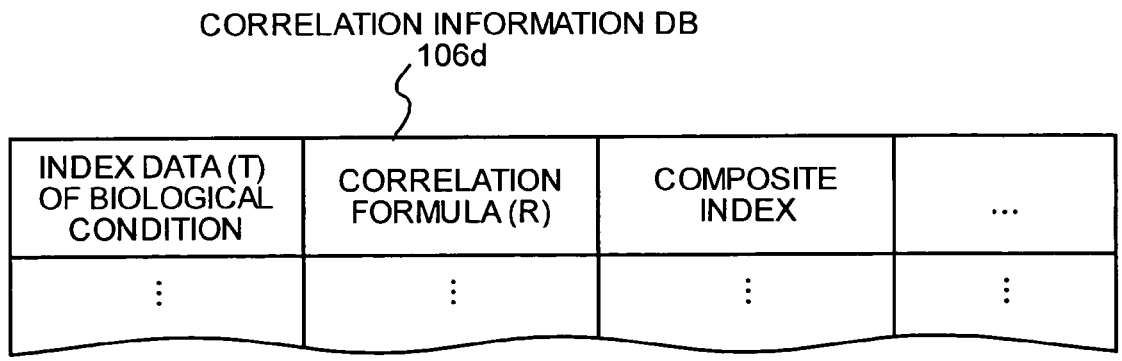
FIG. 10 is a diagram showing one example of information stored in a correlation information database 106d.

A correlation formula information database 106d serves as a correlation formula storage unit for storing information about the correlation formula. FIG. 10 shows one example of the information stored in the correlation formula database 106d.

As shown in FIG. 10, the information stored in the correlation formula information database 106d includes index data (T) of a biological condition, correlation formulae (R), and composite indices (one or more). These data are shown associated with one another.

Figure 11:
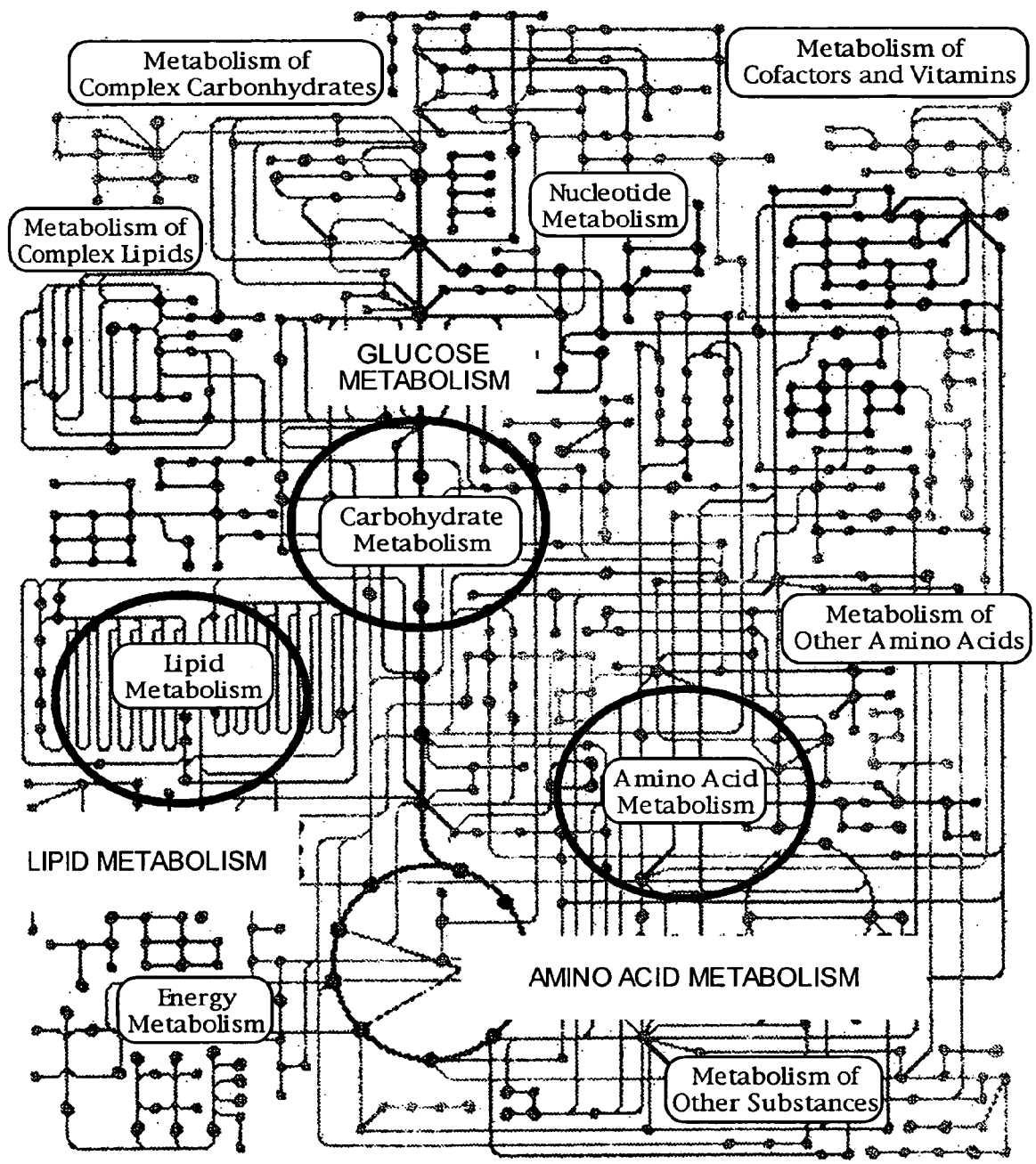
FIG. 11 is a diagram showing one example of information stored in a metabolic map information database 106e.

A metabolic map information database 106e serves as a metabolic map information storage unit for storing information about the metabolic map. FIG. 11 shows one example of the information stored in the metabolic map information database 106e.

As shown in FIG. 11, the information stored in the metabolic map information database 106e includes nodes and edges in each metabolic pathway as the information about each metabolic map. These data are shown associated with one another. The information about the metabolic map may be acquired from known metabolic maps provided by, for example, KEGG, which may be processed if desired.

The memory unit 106 of the server unit 100 stores additional information, such as various website data and CGI programs, for providing the client unit 200 with a website.

The website data includes data for displaying various Web pages, which will be described later. These data are provided in the form of text files described in HTML or XML. Also stored in the memory unit 106 are files of components and work files for constituting the website data and other temporary files.

The memory unit 106 may further store sound files, such as those created in WAVE format or AIFF format, or image files, such as still images or moving images created in JPEG format or MPEG2 format, to be sent to the client unit 200.

In FIG. 3, the communication controlling interface unit 104 controls communication between the server unit 100 and the network 300 (or communication device such as a router). In other words, the communication controlling interface unit 104 serves to transmit data to and from the other terminals via communication lines.

In FIG. 3, the input/output controlling interface unit 108 controls the input device 112 and the output device 114. The output device 114 may be a monitor (including home television monitor) or a speaker (the output device 114 may be referred to hereinafter as a monitor). The input device 112 may be a keyboard, a mouse, or a microphone. A monitor may be used in conjunction with a mouse to achieve the pointing device function.

In FIG. 3, the control unit 102 includes a control program, such as operating system (OS), a program defining steps of various processes, and an internal memory for storing the required data, and executes these programs to implement various information processes. The control unit 102 functionally includes a request interpreting section 102a, a browsing processing section 102b, an authentication processing section 102c, an e-mail generating section 102d, a Web page generating section 102e, a transmitting section 102f, a correlation formula setting section 102v, a biological condition simulating section 102w, and a result outputting section 102k.

The request interpreting section 102a serves as a request interpreting unit for interpreting the content of a request from the client unit 200 and transferring processing to other parts of the control unit depending on the result of the interpretation.

The browsing processing section 102b serves as a browsing processing unit for generating or transmitting Web data of various screens in response to a browsing request for these screens from the client unit 200.

The authentication processing section 102c serves as an authentication processing unit for making authentication in response to a request for authentication from the client unit 200.

The e-mail generating section 102d serves as an e-mail generating unit for generating an e-mail containing various information.

The Web page generating section 102e serves as a Web page generating unit for generating a Web page viewed by a user.

The transmitting section 102f serves as a transmitting unit for transmitting various information to the client unit 200 of the user, and also serves as an analysis result transmitting unit for transmitting the composite index to the client unit 200 which is a sender of the information on the biological conditions.

The correlation formula setting section 102v serves as a correlation formula setting unit for setting a correlation formula as represented by the following formula 1, which indicates the correlation between the index data concerning a biological condition measured in each individual and the blood concentration data measured for each metabolite in each individual:

$$\sum_k G_k \frac{\sum_i \{(C_i \times A_i) + D_i\}}{\sum_j \{(E_j \times B_j) + F_j\}} + H \quad (1)$$

(wherein each of i, j, and k is a natural number; each of $A_i$ and $B_j$ is data of concentration of the metabolite in blood or values obtained from applying a function to the concentration of the metabolite in blood; and each of $C_i$, $D_i$, $E_j$, $F_j$, $G_k$, and H is a constant.) The correlation formula setting section 102v further includes a biological condition information acquiring section 102g, a correlation determining section 102h, a correlation formula generating section 102i, and an optimization section 102j.

Figure 5:
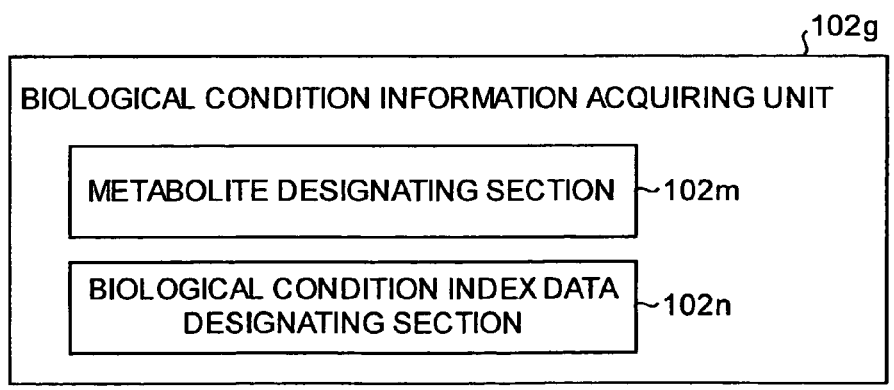
FIG. 5 is a block diagram showing an exemplary construction of a biological condition information acquiring unit 102g in the system to which the present invention is applied.

The biological condition information acquiring section 102g serves as an biological condition information acquiring unit for acquiring, from the client unit 200 or the input device 112, the biological condition information comprising the index data concerning various biological conditions measured in each individual and the group of blood concentration data measured for each metabolite in each individual. As shown in FIG. 5, the biological condition information acquiring section 102g includes a metabolite designating section 102m and a biological condition index data designating section 102n. Shown in FIG. 5 is a block diagram showing an exemplary construction of a biological condition information acquiring unit 102g in the system to which the present invention is applied. Only the part that is related to the present invention in the above construction is illustrated conceptually.

In FIG. 5, the metabolite designating section 102m serves as a metabolite designating unit for designating a desired metabolite.

The biological condition index data designating section 102n serves as a biological condition index data designating unit for designating a desired biological condition index data.

Referring again to FIG. 3, the correlation determining section 102h serves as a correlation determining unit for determining correlation between index data concerning a biological condition measured in each individual and each metabolite based on the index data and a group of blood concentration data measured for each metabolite in each individual.

Figure 6:
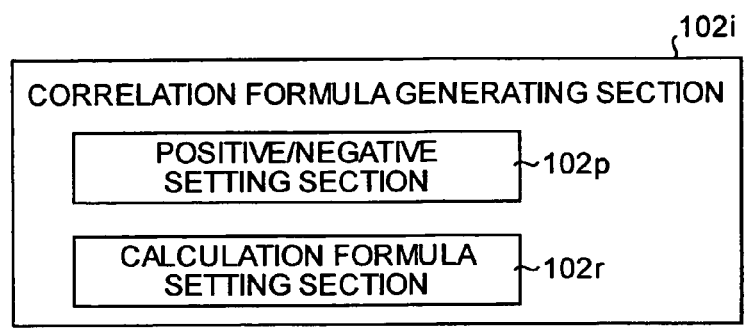
FIG. 6 is a block diagram showing an exemplary construction of a correlation formula generating section 102i in the system to which the present invention is applied.

The correlation formula generating section 102i serves as a correlation formula generating unit for generating a correlation formula (correlation function) for a plurality of metabolites for the biological condition according to a predetermined calculation method and based on the determined correlation of each metabolite. As shown in FIG. 6, the correlation formula generating section 102i includes a positive/negative setting section 102p and a calculation formula setting section 102r. FIG. 6 is a block diagram showing an exemplary construction of the correlation formula generating section 102i in the system of the present invention. Only the part that is related to the present invention in the above construction is illustrated conceptually.

In FIG. 6, the positive/negative setting section 102p serves as a positive/negative setting unit for setting positive or negative about the correlation of each metabolite.

The calculation formula setting section 102r serves as a calculation formula setting unit for setting a calculation formula required to construct a correlation formula.

Figure 43:
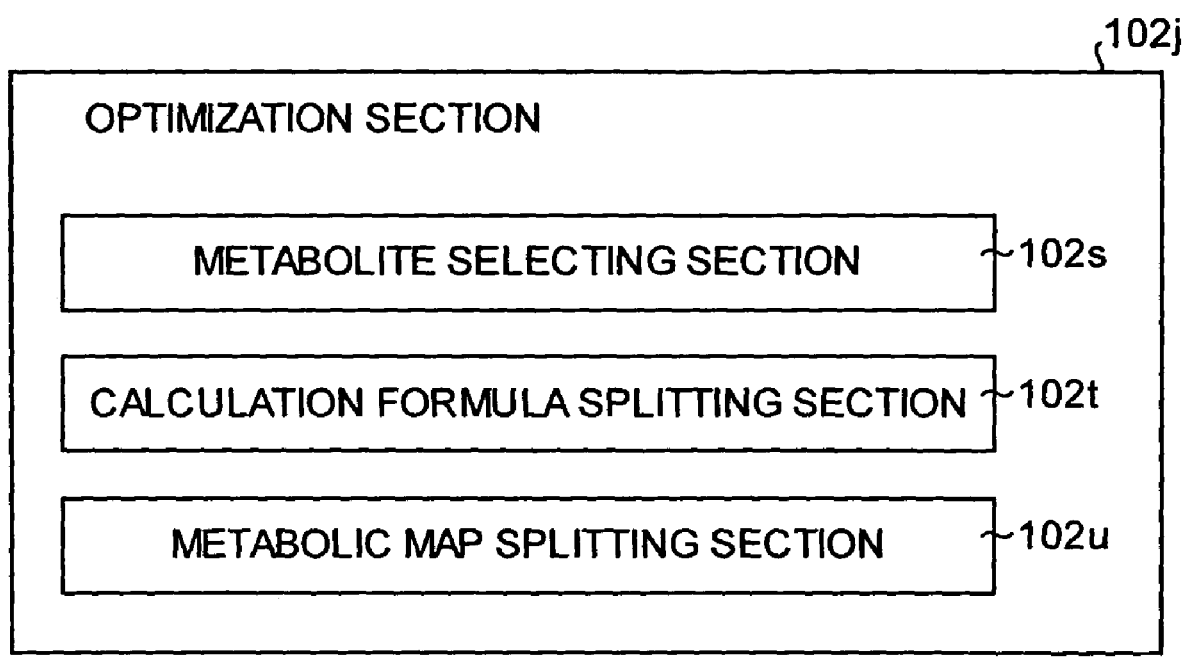
FIG. 43 is a block diagram showing an exemplary construction of optimization section 102$j$ of the system to which the present invention is applied.

Referring back to FIG. 3, the optimization section 102j serves as an optimization unit for optimizing the determined correlation formula (R) (for example, in such a manner that the correlation coefficient ranks high (for example, top 20) or, preferably, is maximized) based on the correlation coefficient indicative of the correlation between the correlation formula (R) and the index data concerning the biological condition. As shown in FIG. 43, the optimization section 102j further includes a metabolite selecting section 102s, a calculation formula splitting section 102t, and a metabolic map splitting section 102u. FIG. 43 is a block diagram showing an exemplary construction of the optimization section 102j of the system of the present invention. Only the part that is related to the present invention in this construction is illustrated conceptually.

In FIG. 43, the metabolite selecting section 102s serves as a metabolite selecting unit that selects some of the metabolites, uses the selected plurality of metabolites to construct the correlation formula, calculate the correlation coefficient for the index data concerning the biological condition, and optimizes the combination of the metabolites (for example, in such a manner that the correlation coefficient ranks high (for example, top 20) and the number of the metabolites is minimized or, preferably, in such a manner that the correlation coefficient is maximized and the number of the metabolites is minimized)) based on the correlation coefficient for the index data concerning the biological condition and the number of the metabolites.

The calculation formula splitting section 102t serves as a calculation formula splitting unit that splits the calculation formula, uses the split formula to calculate the correlation formula involving a plurality of metabolites for the biological condition, and optimizes the combination of splits (for example, in such a manner that the correlation coefficient ranks high (for example, top 20) or, preferably, is maximized) based on the correlation coefficient for the index about the biological condition.

The metabolic map splitting section 102u serves as a metabolic map splitting unit that splits the calculation formula based on the metabolic map information and uses the split calculation formula to calculate the correlation formula involving a plurality of metabolites for the biological condition.

Referring again to FIG. 3, the biological condition simulating section 102w serves as a biological condition simulation unit for simulating the biological condition in an individual of interest by substituting into the set correlation formula a group of blood concentration data measured for each metabolite in the individual of interest.

The result outputting section 102k serves as an outputting unit for outputting, for example, the results of various processings by the control unit 102 to the output device 114.

The details of the processing executed by these sections will be described later.

[System Configuration—Client Unit 200]

Figure 4:
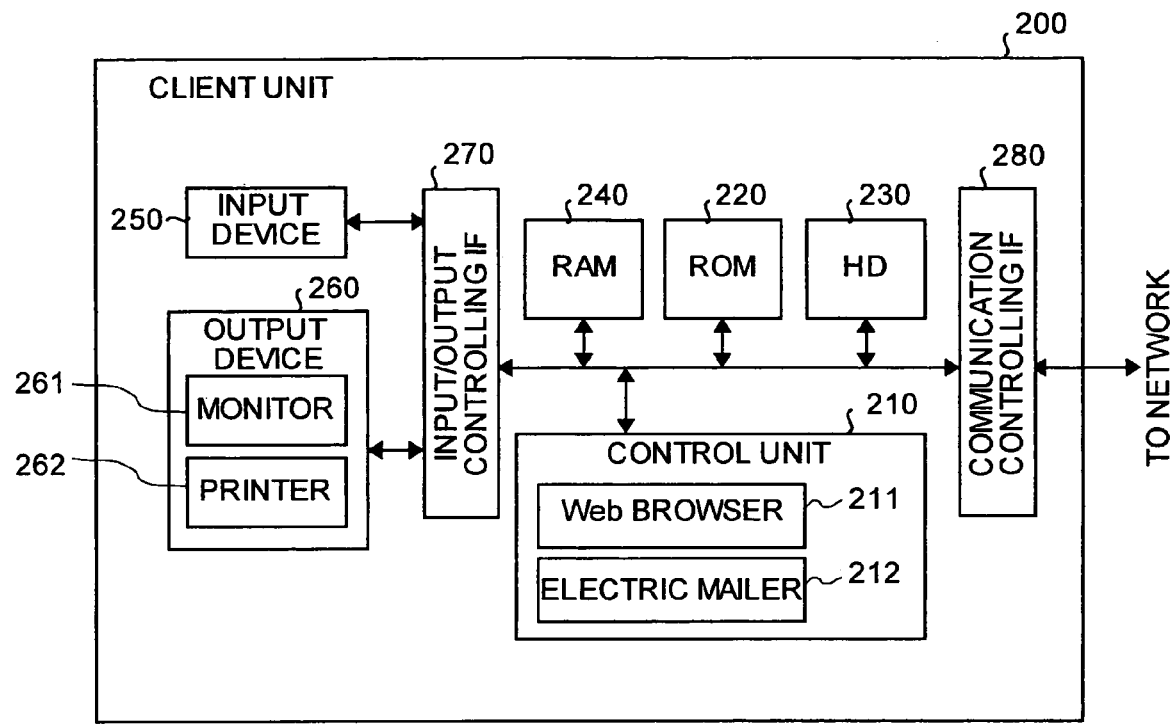
FIG. 4 is a block diagram showing an exemplary construction of a client unit 200 to which the present invention is applied.

Next, we will describe construction of the client unit 200. FIG. 4 is a block diagram showing an exemplary construction of a client unit 200 according to the present invention. Only the part that is related to the present invention in the above construction is illustrated conceptually.

As schematically shown in FIG. 4, the client unit 200 includes a control unit 210, a ROM 220, a HD 230, a RAM 240, an input device 250, an output device 260, an input/output controlling IF 270, and a communication controlling IF 280. These components are connected via a bus in a data-communicable fashion.

The control unit 210 of the client unit 200 includes a Web browser 211 and an electric mailer 212. The Web browser 211 essentially serves to interpret Web data and display it on a monitor 261 (browse process). The Web browser 211 may have various plug-in softwares, such as a stream player capable of receiving and displaying streaming images and producing a feedback. The electronic mailer 212 serves to send and receive electronic mails according to specific communication protocols such as Simple Mail Transfer Protocol (SMTP) and Post Office Protocol version 3 (POP3).

The input device 250 may be a keyboard, a mouse, or a microphone. A monitor 261, which will be described later, may be used in conjunction with a mouse to achieve the pointing device function.

A monitor 261 (including home television monitor) and a printer 262 are provided as the output device 260. A speaker may also be used as the output device 260. The output device 260 serves as an output unit for outputting the received information via the communication controlling IF 280.

The communication controlling IF 280 serves to control communication between the client unit 200 and the network 300 (or communication device such as a router). The communication controlling IF 280 serves as a receiving unit for sending information to the server unit 100 and receiving information from the server unit 100. Thus, the communication controlling IF 280 serves both as a sending unit for sending the information about the biological condition to the server unit 100 and as a receiving unit for receiving from the server unit 100 the composite index corresponding to the sent biological condition information.

Having such a construction, the client unit 200 is connected to the network 300 via a communication device, such as modem, TA, and router, and a telephone line or via a dedicated line and can access the server unit 100 according to a specific communication protocol (for example, TCP/IP Internet protocol).

[System Configuration—Network 300]

Next, we will describe the construction of the network 300. The network 300 serves to interactively connect the server unit 100 to the client unit 200. One example of the network 300 is the Internet.

[Process Performed by the System]

A detailed description is now given of one example of the process performed by the system of the present embodiment with reference to FIGS. 12 through 16.

[Biological Condition Information Analysis Service Process]

Figure 12:
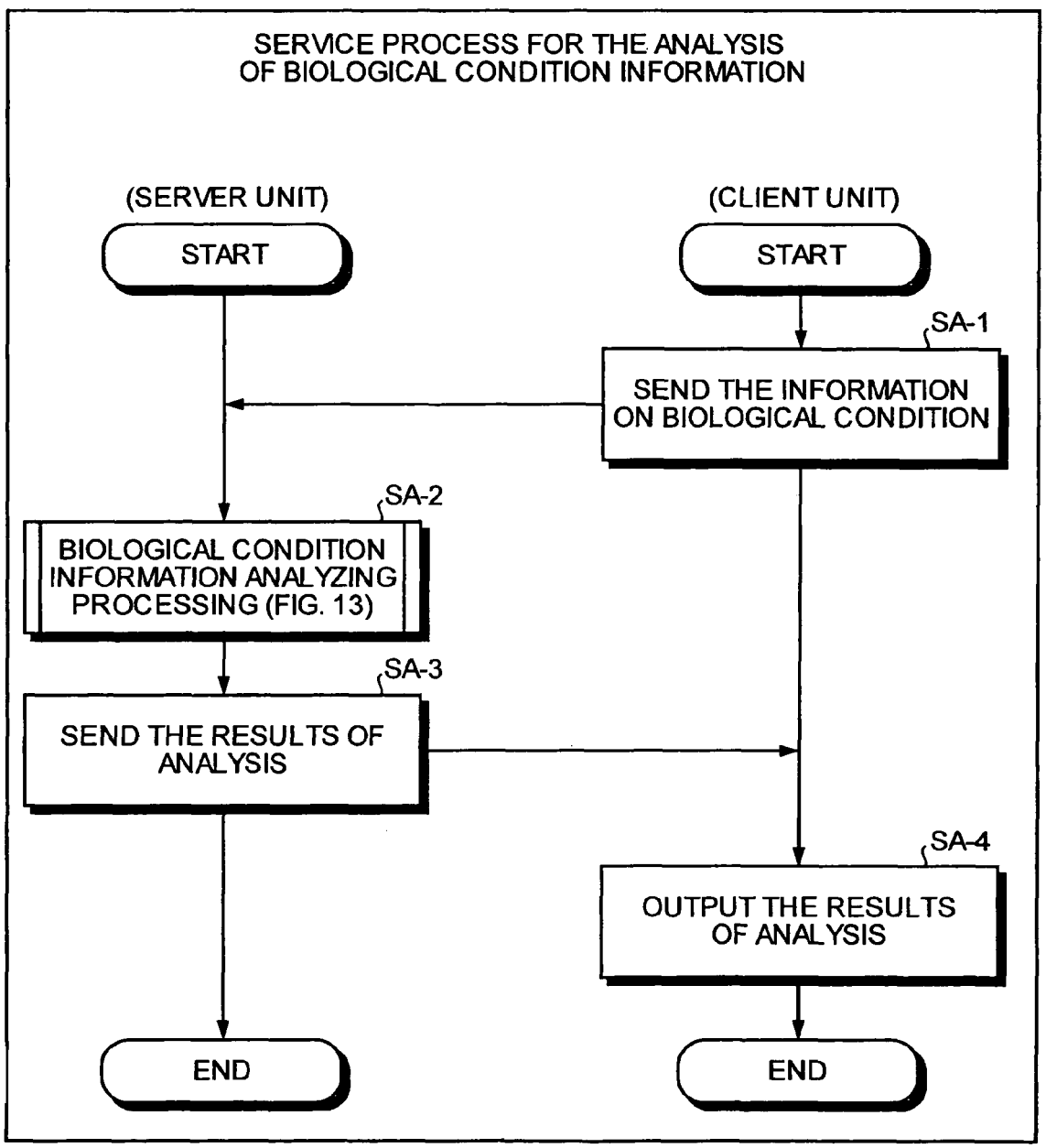
FIG. 12 is a flowchart showing one example of the service process for the analysis of biological condition information by the system of the present embodiment.

A service process for the analysis of biological condition information as the method using the present system configured above is now described in detail with reference to FIG. 12 and other figures. FIG. 12 is a flowchart showing one example of the service process for the analysis of biological condition information by the system of the present embodiment.

First, using the input device 250, a user specifies the address (e.g., URL) of a Web site provided by the server unit 100 on the Web browser 211 displayed on a screen. This causes the client unit 200 to connect to the server unit 100 via the Internet.

Specifically, the user activates the Web browser 211 on the client unit 200 and enters the URL of the transmission screen for the biological condition information into a predetermined input field of the Web browser 211. As the user renews the screen of the Web browser 211, the Web browser 211 transmits the URL according to a specific communication protocol via the communication controlling IF 280 and requests the server unit 100 to transmit the Web page of the transmission screen of the biological condition information according to the routing based on this URL.

The request interpreting section 102a of the server unit 100 monitors the transmission from the client unit 200 and, on receiving the transmission, interprets the transmission. Depending on the results of the interpretation, the request interpreting section 102a allocates the process to a corresponding section of the control unit 102. If the transmission is a request for the transmission of the Web page of the transmission screen for the biological condition information, the request interpreting section 102a, primarily under the control of the browsing processing section 102b, retrieves from the memory unit 106 the Web data required to display the Web page for transmission screen for the biological condition information, and transmits the Web data to the client unit 200 via the communication controlling interface 104. Upon transmitting the data from the server unit 100 to the client unit 200, which one of the client units 200 that the data should be transmitted to is determined by the IP address sent from the client unit 200 along with the request for the transmission.

Upon making the request for the transmission of the Web page, the user may be asked to enter a user ID and a password to allow the authentication processing section 102c to refer to the user IDs and the user passwords stored in the user information database 106a and thereby determine if the user can be approved. Only the approved users may be allowed to access the Web page (This description also applies to the following examples and the details will not be repeated).

The client unit 200 receives Web data from the server unit 100 via the communication controlling IF 280, and interprets the data on the Web browser 211, thereby displaying the Web page for biological condition information transmission screen on the monitor 261. In the following, screen request from the client unit 200 to the server unit 100, transmission of Web data from the server unit 100 to the client unit 200, and display of Web page in the client unit 200 are conducted in the similar manner, and hence detailed description thereof will be omitted.

Then, the user enters and selects biological condition information via the input device 250 of the client unit 200, and input information and an identifier for identifying the selected item are transmitted to the server unit 100 (Step SA-1).

The request interpreting section 102a of the server unit 100 analyzes the identifier to analyze the content of the request from the client unit 200 (as to identification of the content of request from the client unit 200 to the server unit 100, detailed description will be omitted hereinafter as the processing are conducted in almost the same manner).

Figure 13:
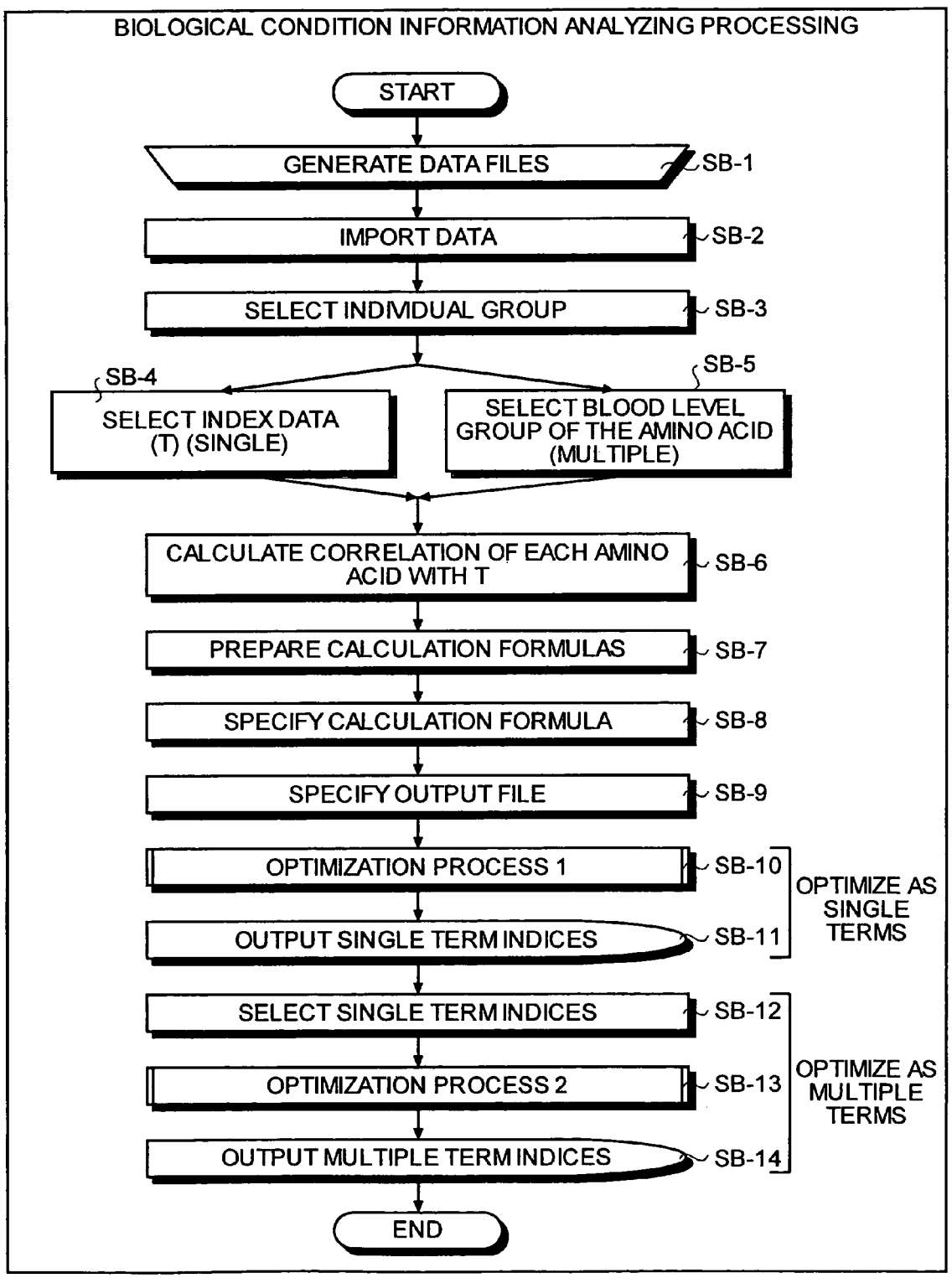
FIG. 13 is a flowchart showing one example of analysis of biological condition information by the system of the present embodiment.

Then the server unit 100 executes the biological condition information analyzing processing as will be described later using FIG. 13 or the like by a processing of each part in the control unit 102 (Step SA-2). Then the server unit 100 produces, by the processing of the Web page generating section 102e, a Web page intended to display the data of analysis result for the biological condition information sent by the user, and stores it in the memory 106.

Then the user enters a predetermined URL on the Web browser 211, and is allowed to browse the Web page for displaying the data of analysis result stored in the memory 106 after passing the authentication as described above.

That is, when the user transmits a request for browsing the Web page to the server unit 100 using the client unit 200, the server unit 100 reads out the Web page for the user from the memory 106 through the processing of the browsing processing section 102b and transmits it to the transmitting section 102f. The transmitting section 102f then transmits the Web page to the client unit 200 (Step SA-3). As a result, the user can browse the own Web page as desired (Step SA-4). Also, the user can print out the display content of the Web page with the printer 262 as necessary.

The server unit 100 may notify the user of the analysis result via an e-mail. The e-mail generating section 102d of the server unit 100 generates e-mail data containing analysis result data for the biological condition information sent by the user according to a transmission timing. Concretely, it looks up the user information stored in the user information database 106a based on the user ID of the user and calls up an e-mail address of the user.

Then it generates mail data for an e-mail which is addressed to this e-mail address and containing the name of the user and the data of analysis result for the biological condition information sent by the user, and delivers the mail data to the transmitting section 102f. Then the transmitting section 102f transmits this mail data (Step SA-3).

On the other hand, the user receives the above e-mail using the electric mailer 212 of the client unit 200 at desired timing. This e-mail is displayed on the monitor 261 based on the known function of the electric mailer 212 (Step SA-4). Also the user can prints out the display content of the e-mail with the printer 262 as is necessary.

The biological condition information analysis service processing ends here.

[Biological Condition Information Analyzing Processing]

Next, the details of an analyzing processing of biological condition information will be described with reference to FIG. 13 or the like. FIG. 13 is a flowchart showing one exemplary analyzing processing of biological condition information of the present system in the present embodiment. The present embodiment is described while taking the case where calculation and tabulation of the correlation coefficients and the correlation formulae is conducted using Excel (trade name) from Microsoft (company name) as an example, however, the present invention is not limited to that case, and may be executed using other programs.

First, the server unit 100, by the processing of the correlation formula setting section 102v, sets the correlation formula as shown by the following formula 1 (Correlation formula setting process):

$$\sum_k G_k \frac{\sum_i \{(C_i \times A_i) + D_i\}}{\sum_j \{(E_j \times B_j) + F_j\}} + H \quad (1)$$

(wherein each of i, j and k is a natural number; each of $A_i$ and $B_j$ is data of concentration of the metabolite in blood or values obtained from applying a function to the concentration of the metabolite in blood; and each of $C_i$, $D_i$, $E_j$, $F_j$, $G_k$ and H is a constant.) The correlation formula indicates the correlation between the blood concentration data measured for each metabolite in each individual and index data concerning a biological condition measured in each individual.

We will now describe in detail the process of setting the correlation formula carried out by the correlation formula setting section 102v.

First, the server unit 100 generates a data file in which the index data (T) and the groups of blood concentration data of amino acids are written in separate sheets on Excel through the processing of the biological condition information acquiring section 102g (Step SB-1).

Then the server unit 100 takes the data file generated at Step SB-1 into the memory of the control unit 102 through the processing of the biological condition information acquiring section 102g (Step SB-2).

Figure 19:
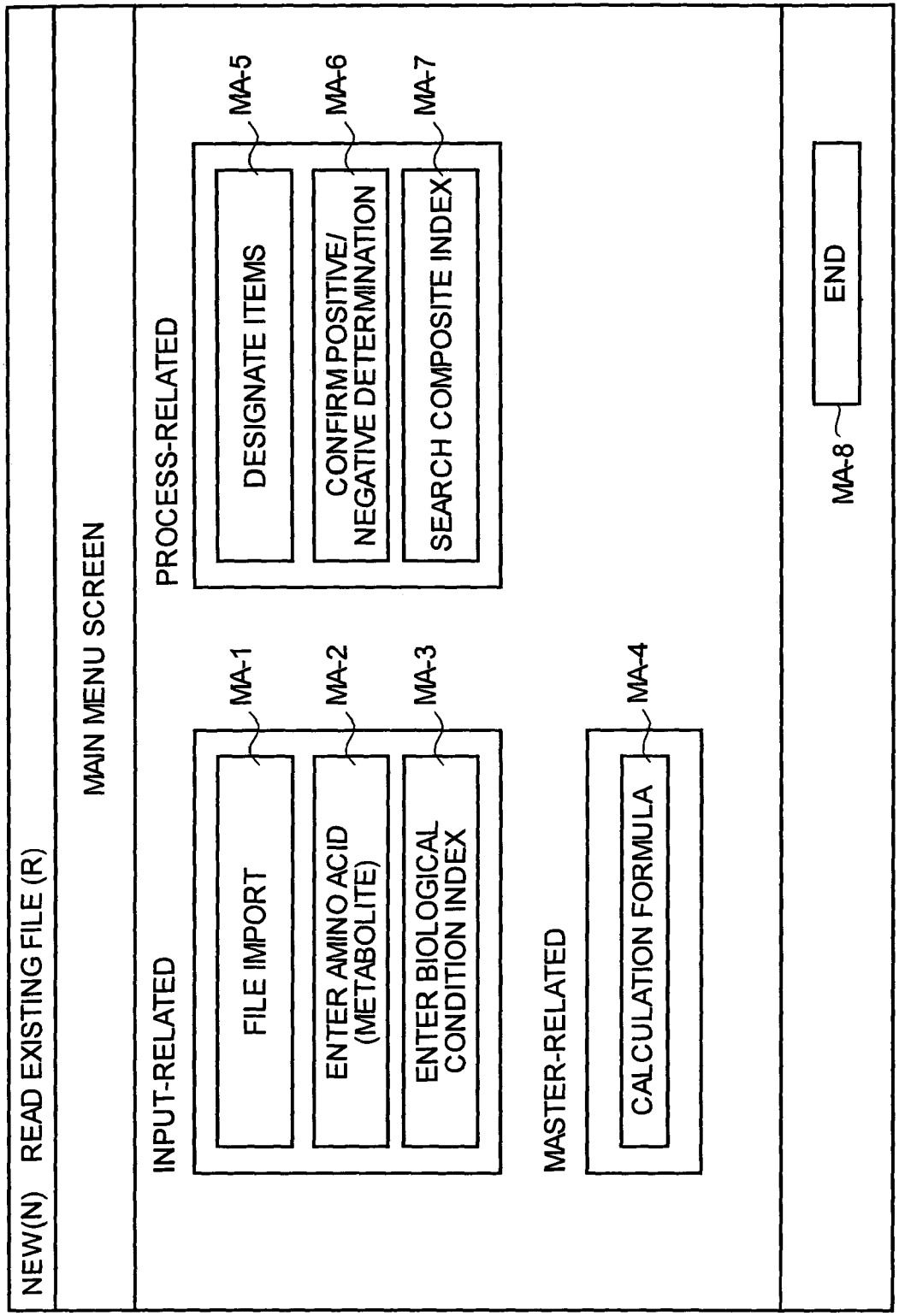
FIG. 19 shows one example of main menu screen displayed on a monitor.

FIG. 19 shows one example of a main menu screen displayed on a monitor. As shown, the main menu screen may contain the following buttons: a link button MA-1 to a file import screen (file import button), a link button MA-2 to an amino acid (metabolite) input screen (amino acid (metabolite) input button), a link button MA-3 to a biological condition index input screen (biological condition index input button), a link button MA-4 to a calculation formula master maintenance screen (calculation formula button), a link button MA-5 to an item selection screen (item designation button), a link button MA-6 to a positive/negative determination confirmation screen (positive/negative determination confirmation button), a link button MA-7 to a composite index search screen (composite index search button), and a quit button MA-8 to choose to quit the process.

Figure 20:
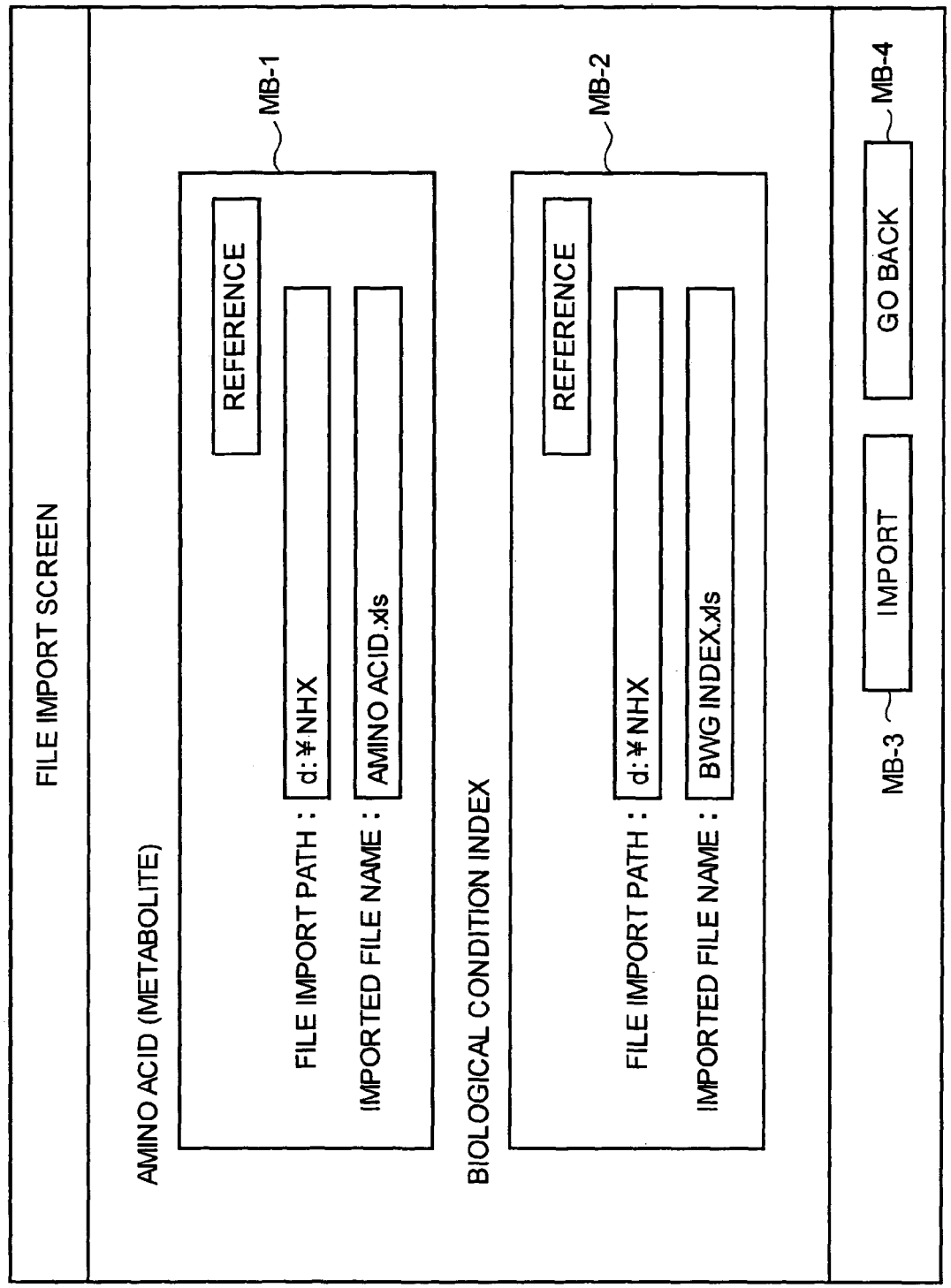
FIG. 20 shows one example of file import screen displayed on a monitor.

With regard to FIG. 19, when a user selects the file import button MA-1 in the main menu screen by means of the input device 112, a file import screen is displayed as shown in FIG. 20.

FIG. 20 shows one example of a file import screen displayed on a monitor. As shown, the file import screen may contain the following buttons: an input box group MB-1 for entering the import file paths and the import file names of amino acid (metabolite) data; an input box group MB-2 for entering the import file paths and the import file names of biological condition index data; an import button MB-3 for importing files; and a "go back" button MB-4 for going back to the main menu screen (FIG. 19).

With regard to FIG. 20, when the user selects, by means of the input device 112, an amino acid (metabolite) and a biological condition index for data import in the input box groups MB-1 and MB-2, respectively, and then selects the import button MB-3, the biological condition index data designating section 102n imports the designated amino acid (metabolite) into the memory of the control unit 102, and the metabolite designating section 102m imports the designated biological condition index data into the memory of the control unit 102.

Referring again to FIG. 13, the server unit 100 prompts, through the processing of the biological condition information acquiring unit 102g, the user to select a subject group that the user wishes to include in (or exclude from) the analysis on the amino acid (metabolite) input screen shown in FIG. 21 and the biological condition index input screen shown in FIG. 22 (Step SB-3).

FIG. 21 shows one example of an amino acid (metabolite) input screen displayed on a monitor. As shown, the amino acid (metabolite) input screen may contain the following features: unused Flg check boxes MC-1 for determining whether data for analysis is to be registered or not; a data display area MC-2; a data check button MC-3 for checking for data blanks; a register button MC-4 for registering data; and a "go back" button MC-5 for going back to the main menu screen (FIG. 19).

FIG. 22 shows one example of a biological condition index input screen displayed on a monitor. As shown, the biological condition index input screen may contain the following features: unused Flg check boxes MD-1 for determining whether data for analysis is to be registered or not; a data display area MD-2; a data check button MD-3 for checking for data blanks; a register button MD-4 for registering data; and a "go back" button MD-5 for going back to the main menu screen (FIG. 19).

With respect to FIG. 21 and FIG. 22, the user can select "unused (by checking in the box of unused Flg)" for one or more unused Flg check boxes MC-1 or MD-1 for which data is missing (blank) by checking in the boxes for the individuals. Selecting an individual to be unused (by setting the unused Flg) in one of the screens of FIG. 21 and FIG. 22 automatically causes the status of the individual to switch to "unused" in the other screen.

With respect to FIG. 21 and FIG. 22, when the user selects the data check button MC-3 or MD-3 using the input device 112, the biological condition information acquiring unit 102g automatically checks for individuals for whom the blood concentration data of an amino acid (s) (metabolites) is missing (blank) and sets the unused Flg for the individuals.

With respect to FIG. 21 and FIG. 22, when the user selects the register button MC-4 or MD-4 through the input device 112, the biological condition information acquiring unit 102g deletes the blood amino acid data designated as "unused" by the unused Flgs from the memory of the control unit 102.

Figure 24:
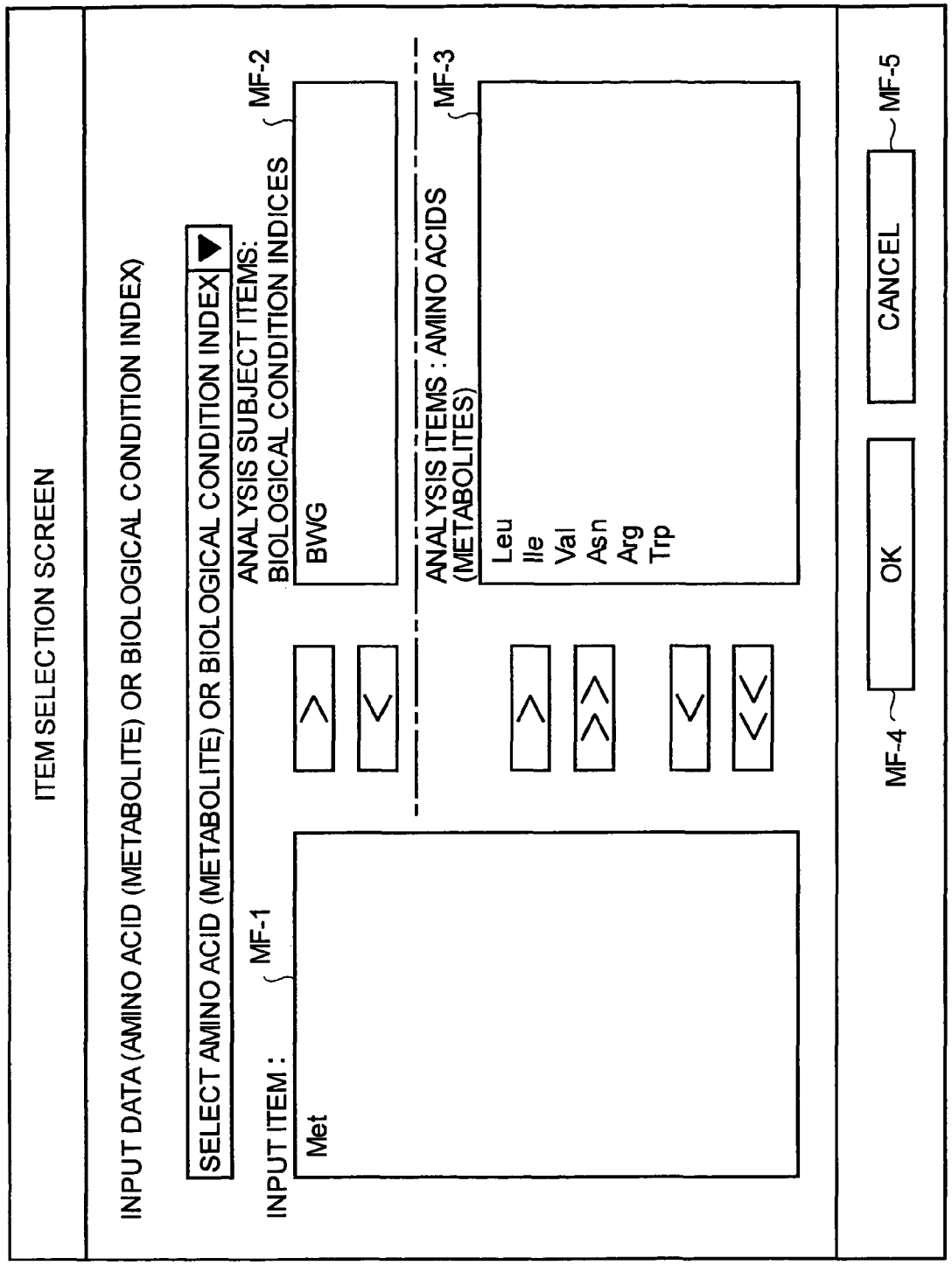
FIG. 24 shows one example of item selection screen displayed on a monitor.

Referring back to FIG. 13, the server unit 100, through the processing of the metabolite designating section 102m and the biological condition index data designating section 102n, causes the item selection screen shown in FIG. 24 to be displayed on a monitor and thereby prompts the user to select the index data (T) of a biological condition and amino acids (metabolites) for analysis (Step S-B 4 and Step SB-5).

FIG. 24 shows one example of an item selection screen displayed on a monitor. As shown, the item selection screen may contain the following features: an input item display area MF-1; a display area MF-2 for displaying items of biological condition indices to be analyzed; a display area MF-3 for displaying items of amino acids (metabolites) to be analyzed; an "OK" button MF-4 for setting the items; and a "cancel" button MF-5 for closing the item selection screen.

With respect to FIG. 24, when the user selects, by means of the input device 112, a desired biological condition index (indices) and an amino acid(s) (metabolite) from the display area MF-2 of items of the biological condition indices to be analyzed and the display area MF-3 of items of amino acids (metabolites) to be analyzed, respectively, the selected items are displayed in the input item display area MF-1. The user then selects the "OK" button MF-4 by means of the input device 112 to cause the metabolite designating section 102m and the biological condition index data designating section 102n to delete the data other than those for analysis from the memory of the control unit 102.

Referring again to FIG. 13, the server unit 100, through the processing of the correlation determining section 102h, determines the correlation of each metabolite with the index data based on the index data and the group of blood concentration data selected for analysis (Step SB-6). The server unit 100 then outputs the display screen shown in FIG. 25 on the monitor. The correlation is determined by calculating the correlation coefficient using the correl function (or PEARSON function) by Excel.

FIG. 25 shows one example of a positive/negative determination confirmation screen displayed on a monitor. As shown, the positive/negative determination confirmation screen may contain the following features: a display area MG-1 for displaying items for analysis; a positive/negative determination display area MG-2; a display area MG-3 for displaying analyzed items; a display area MG-4 for displaying the correlation with the items for analysis; a user setting display area MG-5 in which the user sets the positive/negative; an "OK" button MG-6 for setting the items; and a "cancel" button MG-7 for closing the positive/negative determination confirmation screen.

With respect to FIG. 25, the user confirms the correlation coefficient of each amino acid displayed in the display area MG-4 and confirms that each amino acid is positively or negatively correlated with the index data (T). Even when the actual correlation is positive, the user may set it as "negative," or vise versa. In such a case, the user selects, by means of the input device 112, positive or negative in the user setting display area MG-5. When the user selects the "OK" button MG-6, the positive/negative setting section 102p renews the corresponding data in the memory of the control unit.

Figure 23:
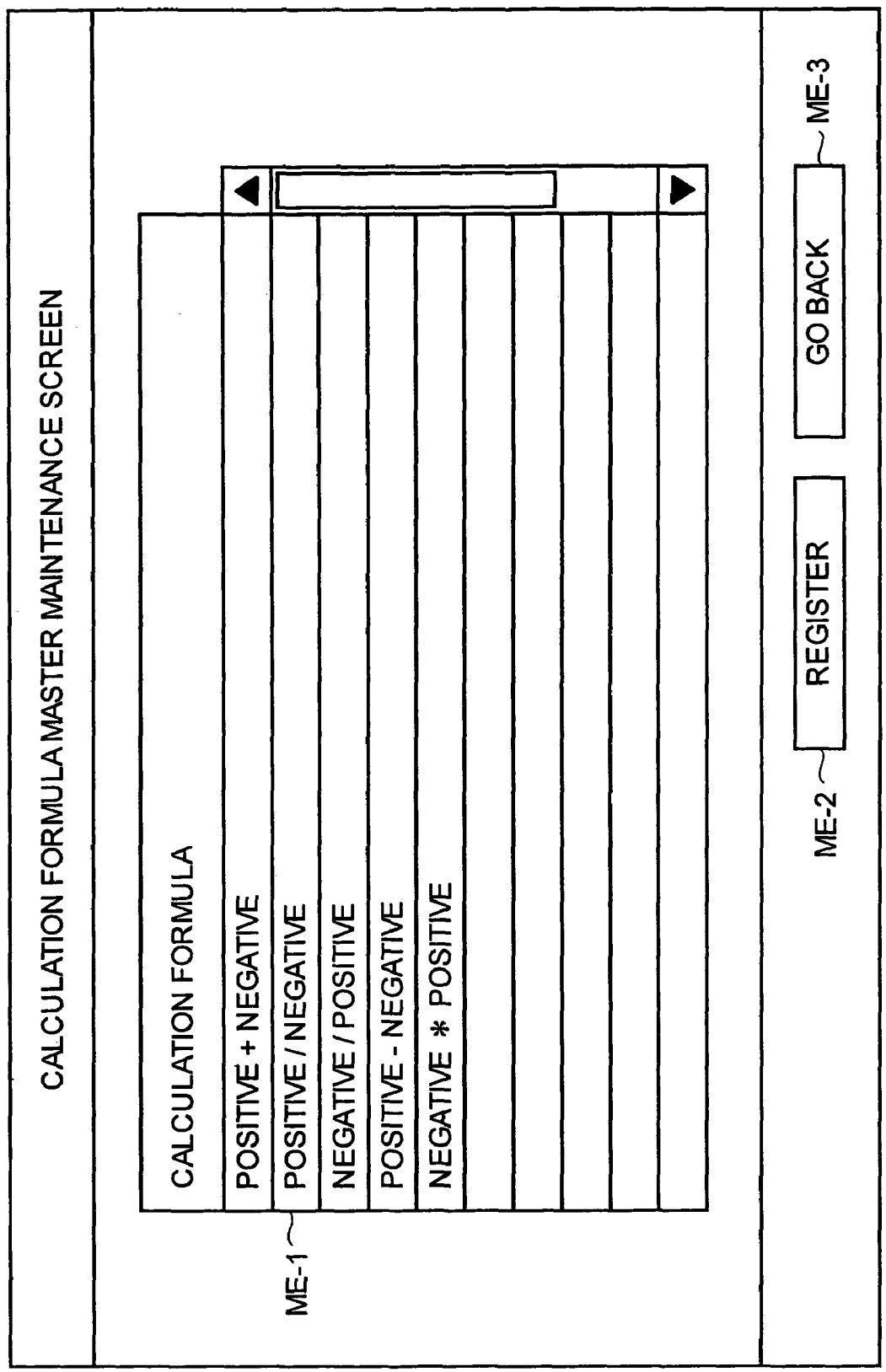
FIG. 23 shows one example of calculation formula master maintenance screen displayed on a monitor.

Referring again to FIG. 13, the server unit 100, through the processing of the calculation formula setting section 102r, displays a display screen shown in FIG. 23 to prompt the user to prepare the calculation formula for the calculation of the correlation formula (R) (Step SB-7).

FIG. 23 shows one example of the calculation formula master maintenance screen displayed on a monitor. As shown, the calculation formula master maintenance screen may contain the following features: a calculation formula input area ME-1 for entering the calculation formula for the calculation of the correlation formula (R); a register button ME-2 for registering the calculation formula; and a "go back" button ME-3 for going back to the main menu screen (FIG. 19).

With respect to FIG. 23, the user enters, by means of the input device 112, the calculation formula for calculating a desired correlation formula (R) in the calculation formula input area ME-1 and selects the register button ME-2. This causes the calculation formula setting section 102r to store the entered calculation formula in a predetermined memory area of the memory 106. The calculation formula may be defined as any of the followings, based on the sign of each correlation coefficient for each amino acid group (metabolite group) for the biological condition index data (T): (Sum of the positives)/(Sum of the negatives), (Sum of the positives)+(Sum of the negatives), (Sum of the positives)−(Sum of the negatives), (Sum of the negatives)/(Sum of the positives), (Sum of the negatives)−(Sum of the positives), and (Sum of the positives)×(Sum of the negatives).

Figure 26:
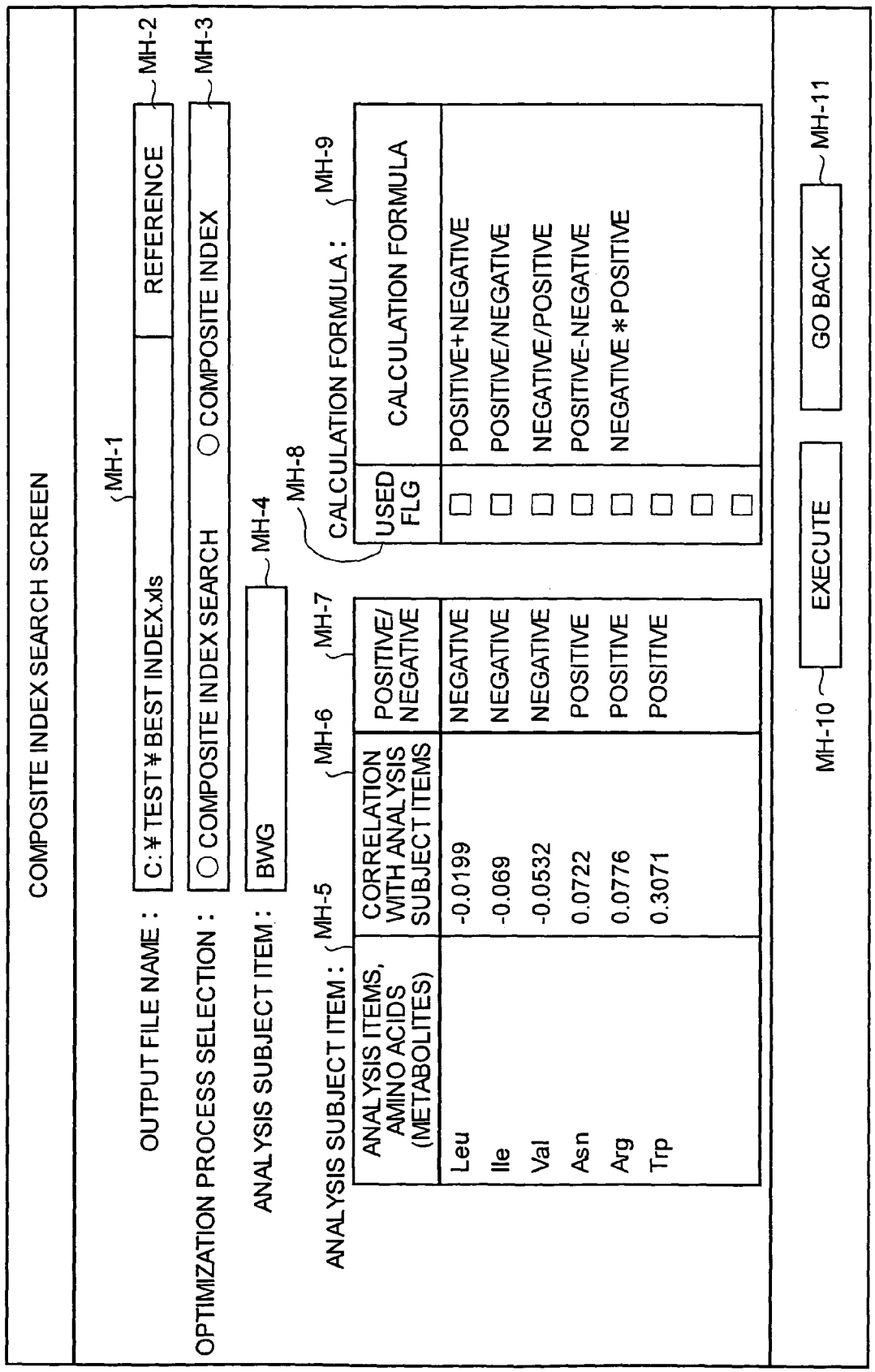
FIG. 26 shows one example of composite index search screen displayed on a monitor.

Referring again to FIG. 13, the server unit 100, through the processing of the calculation formula setting section 102r, displays a composite index search screen shown in FIG. 26. This prompts the user either to specify one or more of the calculation formulae prepared in Step SB-7 (Step SB-8) or to specify the resulting output file (Step SB-9).

FIG. 26 shows one example of the composite index search screen displayed on a monitor. As shown, the composite index search screen may contain the following features: a display and input area MH-1 for displaying and entering the name of the output file; an output file name reference button MH-2; a selection area MH-3 in which the user selects between the search for the composite index or the composite index in the optimization process; a display area MH-4 for displaying items for analysis; a display area MH-5 for displaying analyzed items; a display area MH-6 for displaying the correlation with the items for analysis; a display area MH-7 for displaying the positive/negative; a used FLG check area MH-8; a calculation formula display area MH-9; an execute button MH-10; and a "go back" button MH-11 for going back to the main menu screen (FIG. 19).

With respect to FIG. 26, the user enters or selects specific information by means of the input device 112 and then selects the execute button MH-10. This causes the server unit 100 to generate the correlation formula and then execute the optimization process 1 by the processing of the correlation formula generating section 102i and the optimization section 102j, respectively (step SB-10). The optimization process 1 will be described below with reference to FIGS. 14 and 15.

Figure 14:
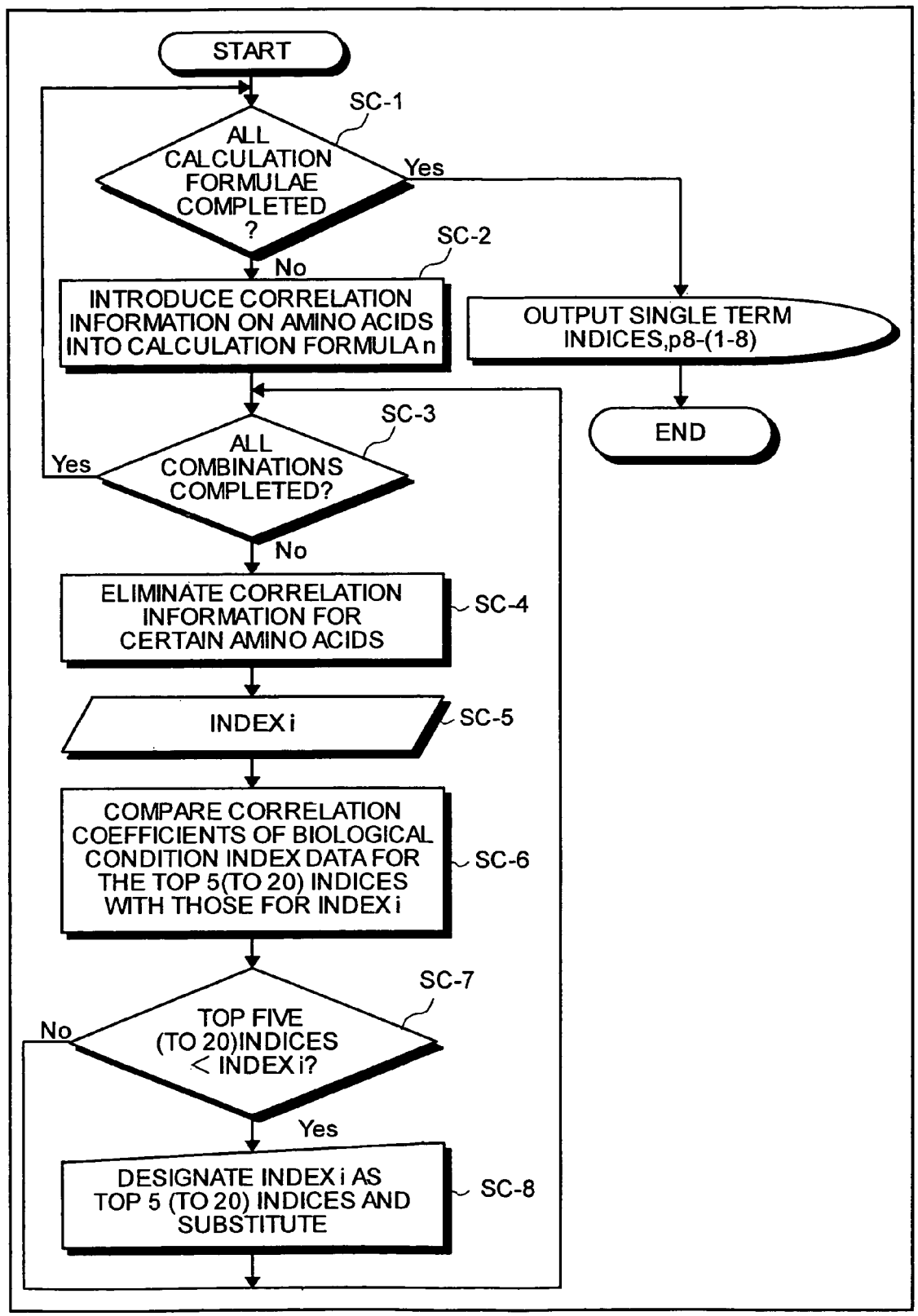
FIG. 14 is a flowchart showing one example of optimization process 1 using the exhaustive calculation technique by the system.

FIG. 14 is a flowchart showing one example of the optimization process 1 using the exhaustive calculation technique by the present system. In the exhaustive calculation technique shown in FIG. 14 (Step SC-1 through Step SC-8), the optimization section 102j calculates the unsplit composite indices. In this exhaustive calculation technique, the optimization section 102j applies the designated calculation formulae (groups) to the specified items, automatically calculates every possible combination of amino acids, and outputs the top five combinations that show the highest correlation to the index data (T) (the user can specify the top twenty combinations).

Figure 15:
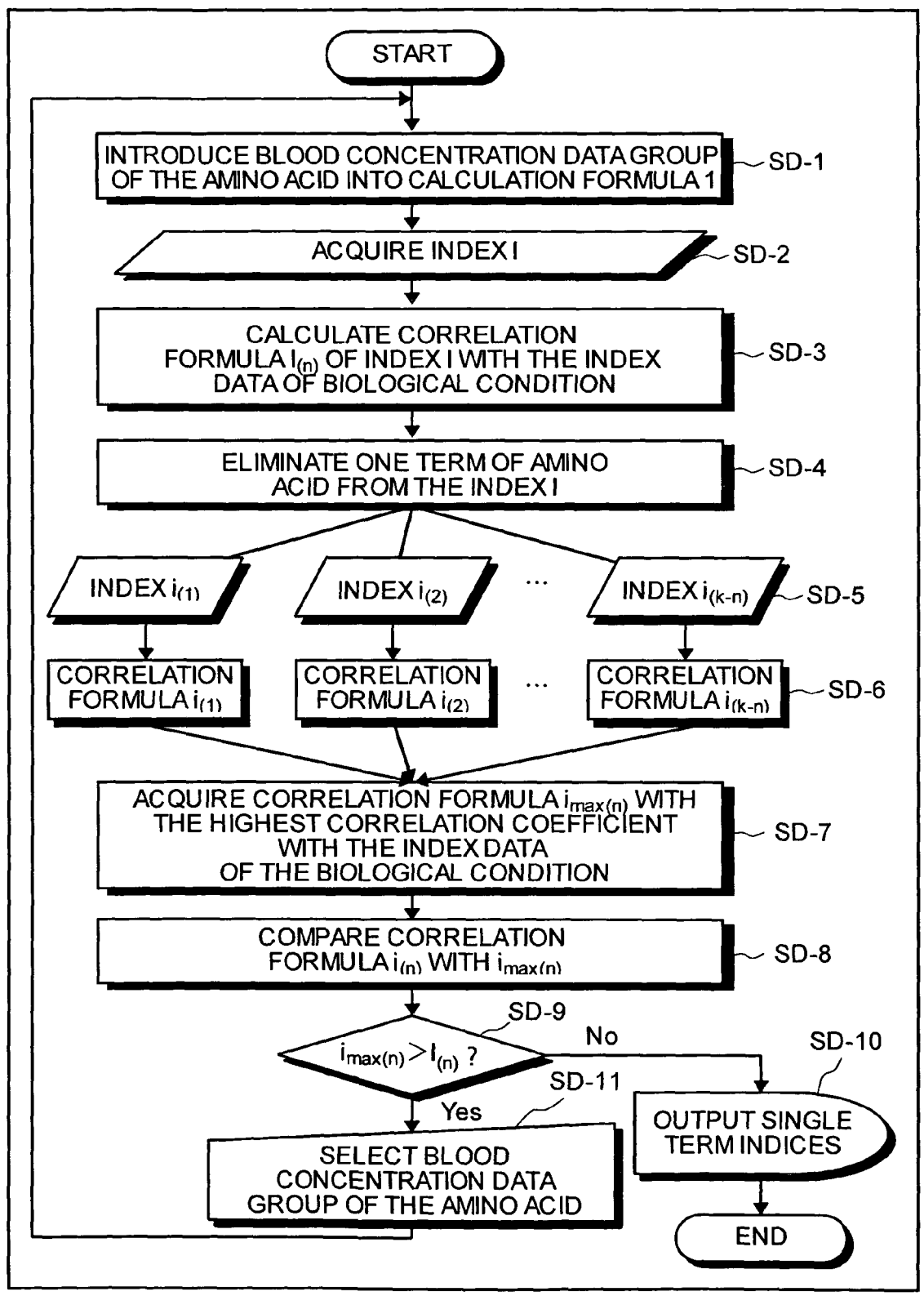
FIG. 15 is a flowchart showing one example of optimization process 1 using the best path method by the system.

FIG. 15 is a flowchart showing one example of the optimization process 1 using the best path method by the present system. In the best path method shown in FIG. 15 (Step SD-1 through Step SD-11), the optimization section 102j, through the processing of a metabolite selecting section 102s, eliminates one amino acid at a time and repeats the elimination step to obtain the optimum combination in a simplified manner.

Referring back to FIG. 13, the server unit 100, through the processing of a result outputting section 102k, outputs the results of the analysis (single term indices) to the monitor and stores the results in the memory 106 (Step SB-11).

Then, by the processing of a calculation formula splitting section 102t, the server unit 100 selects desired ones of the single term indices that are outputted in Step SB-11 (Step SB-12).

The server unit 100 then executes the optimization process 2 by the processing of the correlation formula generating section 102i and the optimization section 102j (Step SB-13). The optimization process 2 is described below with reference to FIG. 16.

Figure 16:
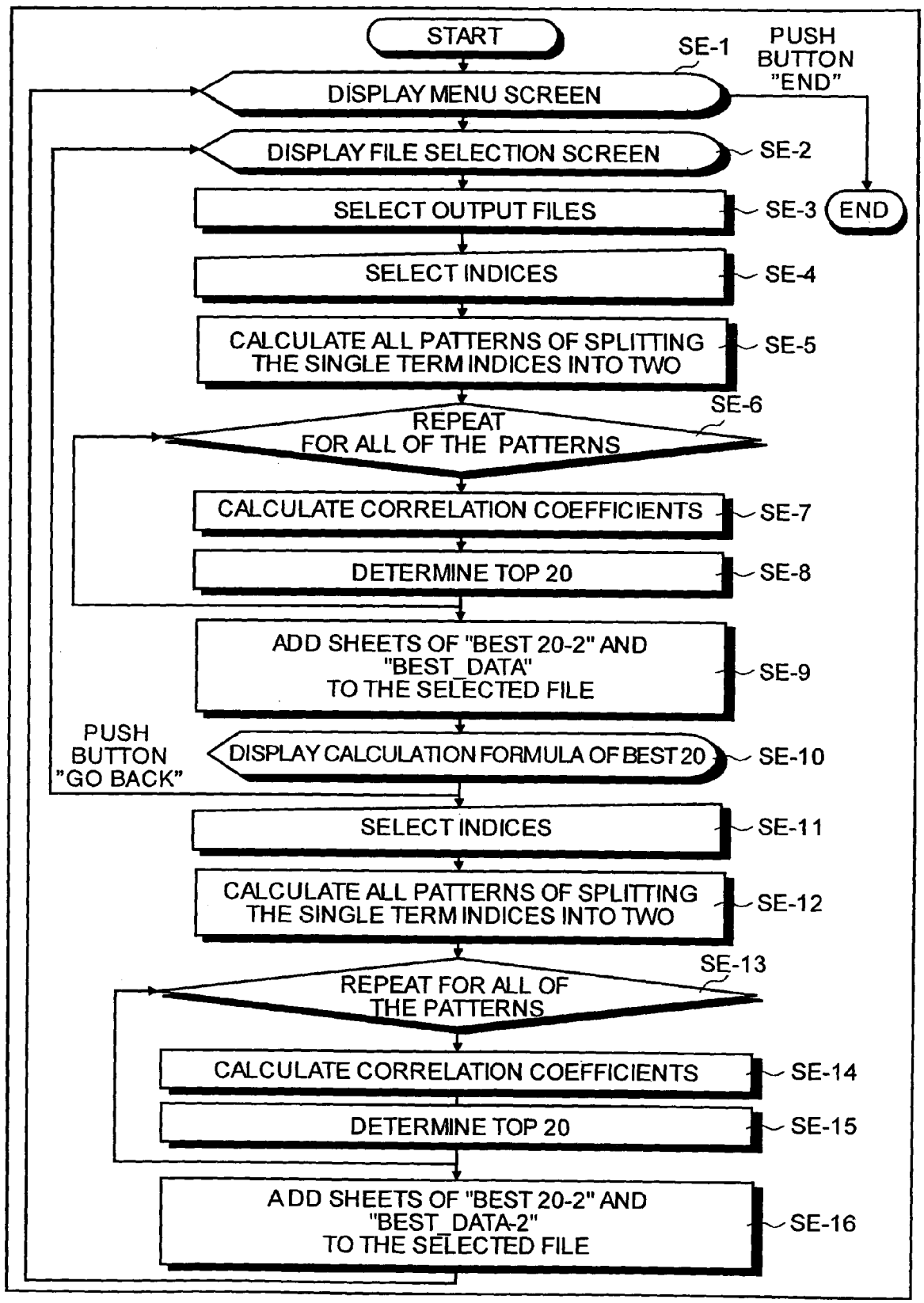
FIG. 16 is a flowchart showing one example of optimization process 2 by the system.

FIG. 16 is a flowchart showing one example of the optimization process 2 by the present system. In the optimization process 2 shown in FIG. 16 (Step SE-1 through Step SE-16), the optimization section 102j, by the processing of the calculation formula splitting section 102t, selects desired ones of the single term indices outputted in Step SB-11, determines all patterns of splitting the single term indices in two, and calculates the index that has the correlation coefficient with the largest absolute value with the index data (T). The calculation formula may be split based on the metabolic map information stored in the metabolic map information database 106e by the processing of the metabolic map splitting unit 102u.

Referring back to FIG. 13, the server unit 100, through the processing of the result outputting section 102k, outputs the result of the analysis (a plurality of term indices) to the monitor and stores the results in the memory 106 (Step SB-14). Of the split patterns, a plurality of the composite indices that show the highest correlation with the index data (T), such as top 20, may be outputted.

FIGS. 27 through 33 each show one example of the monitor display screen displaying the results of the analysis.

FIG. 27 shows one example of the result (1) sheet (raw date for analysis) screen displayed on a monitor. As shown, the result (1) sheet (raw date for analysis) screen may contain a display area MJ-1 for displaying items for analysis and a display area MJ-2 for displaying analyzed items.

FIG. 28 shows one example of the result (2) sheet (conditions for searching for a composite index) screen displayed on a monitor. As shown, the result (2) sheet (conditions for searching for a composite index) screen may contain the following features: a display area MK-1 for displaying items for analysis; a display area MK-2 for displaying the names of analyzed items; an display area MK-3 for displaying the correlation with the items for analysis; a display area MK-4 for displaying the positive/negative sign of the analyzed items; and a display area MK-5 for displaying the calculation formulae.

FIG. 29 shows one example of the result (3) sheet (best composite indices) screen displayed on a monitor. As shown, the result (3) sheet (best composite indices) screen may contain the following features: a display area MM-1 for displaying the ranks of the optimum composite indices; a display area MM-2 for displaying the correlation coefficients; and a display area MM-3 for displaying the composite indices.

FIG. 30 shows one example of the result (4) sheet (best composite indices_values) screen displayed on a monitor. As shown, the result (4) sheet (best composite indices_values) screen may contain the following features: a display area MN-1 for displaying items for analysis; a display area MN-2 for displaying the results of the calculation of the highest ranked composite indices; a display area MN-3 for displaying the results of the calculation of the second highest ranked composite indices; a display area MN-4 for displaying the results of the calculation of the third highest ranked composite indices; a display area MN-5 for displaying the results of the calculation of the fourth highest ranked composite indices; and a display area MN-6 for displaying the results of the calculation of the fifth highest ranked composite indices.

Figure 31:
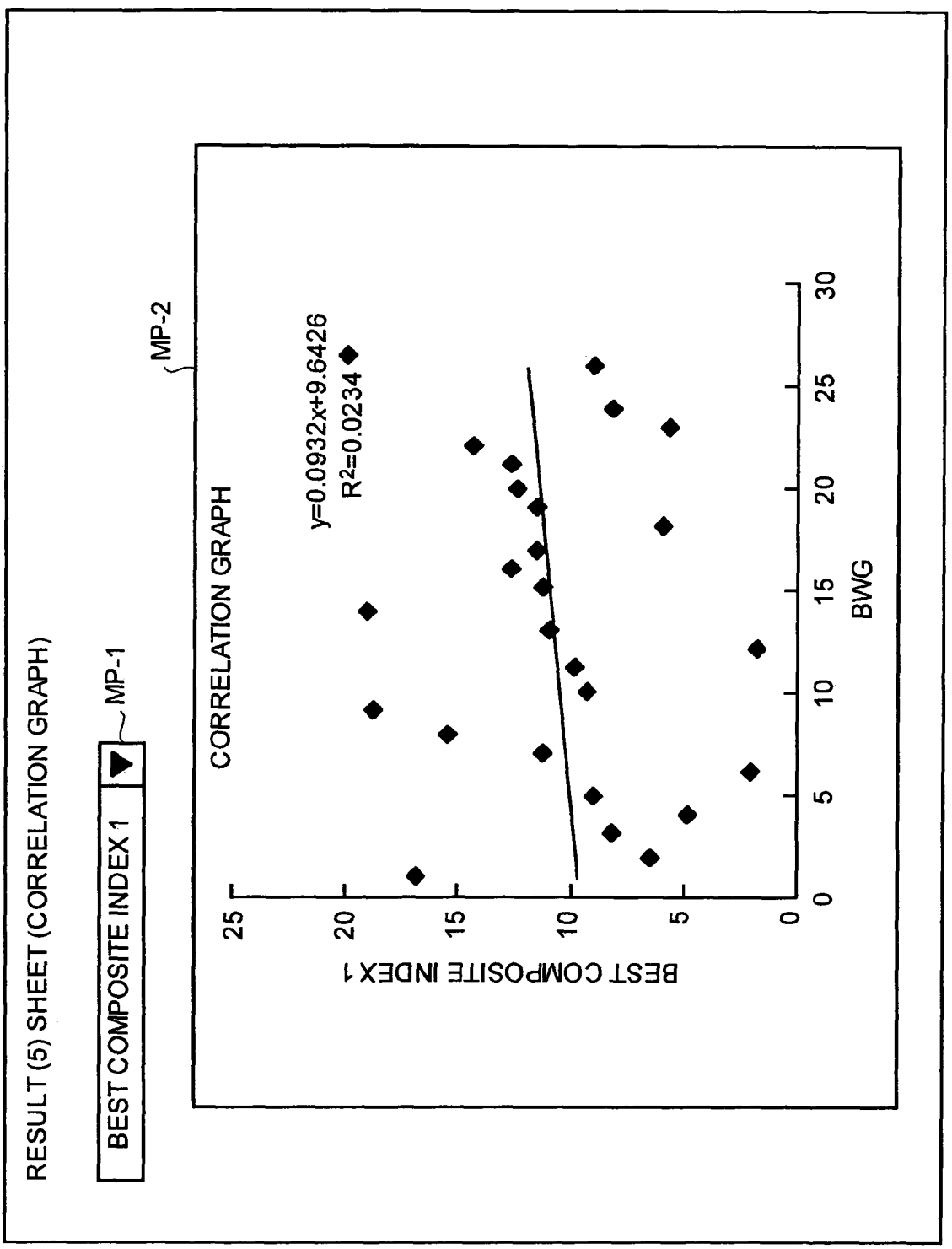
FIG. 31 shows one example of result (5) sheet (correlation graph) screen displayed on a monitor screen.

FIG. 31 shows one example of the result (5) sheet (correlation graph) screen displayed on a monitor screen. As shown, the result (5) sheet (correlation graph) screen may contain a selection area MP-1 for selecting the composite index; and a display area MP-2 for displaying the correlation graph.

FIG. 32 shows one example of result (6) sheet (raw data of amino acids (metabolites)) screen displayed on a monitor screen. As shown, the result (6) sheet (raw data of amino acids (metabolites)) screen may contain a display area MR-1 for displaying raw data of amino acids (metabolites), and a display area MR-2 for displaying unused Flg.

FIG. 33 shows one example of the result (7) sheet (raw data of biological condition indices) screen displayed on a monitor display. As shown the result (7) sheet (raw data of biological condition indices) screen may contain a display area MS-1 for displaying biological condition indices, and a display area MS-2 for displaying unused Flg.

The correlation setting process ends here.

Next, the server unit 100, through the processing of the biological condition information acquiring section 102g, acquires the groups of blood concentration data measured for each metabolite in the individual to be simulated and stores the groups of blood concentration data in a specific memory area of the memory 106.

Next, the server unit 100, through the processing of the biological condition simulating section 102w, substitutes the groups of blood concentration data measured for each metabolite in the individual to be simulated, into the correlation formula set by the correlation setting section 102v. In this manner, the biological condition of the individual of interest can be simulated.

Then the server unit 100, through the processing of the result outputting section 102k, outputs the results of the simulation of the biological condition by the biological condition simulating section 102w to the monitor and stores the results in a specific memory area of the memory 106.

The analysis of the biological condition information process ends here.

EXAMPLES

Now some examples for determination of biological condition using a composite index obtained by the present invention will be explained.

[Example of Composite Indices for Hepatic Fibrosis (Part I)]

First, example of a composite index for hepatic fibrosis (Part I) will be described in detail with reference to FIGS. 51 to 56 and Table 1. According to the forgoing method using the present system, composite index for each stage (composite indices 1 to 4) was determined by optimizing correlation of combination of plasma amino acid levels in a control group and in each stage of hepatic fibrosis using a hepatic fibrosis index in a patient with hepatitis C. In the present example, explanation will be given while taking composite indices for hepatic fibrosis in patients with hepatitis C as an example. However the subject of the present invention is not limited to patients with hepatitis C.

(Relation Between Each Composite Index and Stage of Disease Condition)

Figures 51, 52:
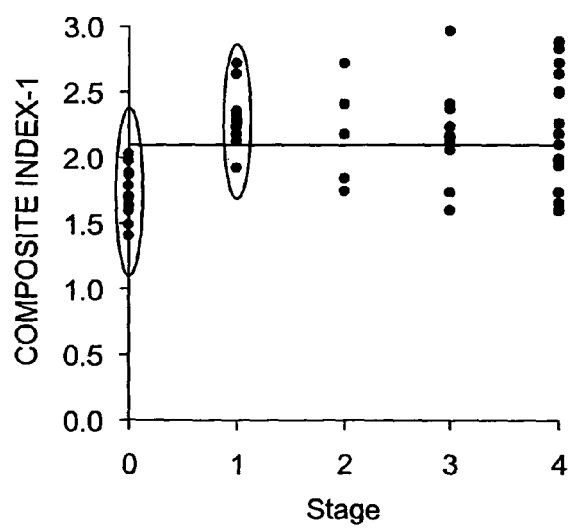
FIG. 51 is a chart showing the rule for replacing amino acids in the respective formula of composite indices 1 through 4.
FIG. 52 is a diagram showing the relationship between a composite index (composite index 1) for hepatic fibrosis as determined by the present system and disease stages, for control group and patients with hepatitis C.

FIG. 52 shows a relationship between a composite index (composite index 1) for hepatic fibrosis as determined by the present system and disease stages in a control group and in patients with hepatitis C. In this illustration, the horizontal axis represents a stage of disease condition and the vertical axis represents a value of the composite index (composite index 1) in the control group and patients with hepatitis C at each stage.

The stage of disease condition is indicated by five levels, wherein the larger the value of the stage of disease condition, the worse the disease condition is. The normal condition is indicated by "0" and the worst stage of disease condition is indicated by "4." This illustration focuses on the classification of the control group and the patients with C hepatitis at Stage 1 of hepatic fibrosis.

Figure 53:
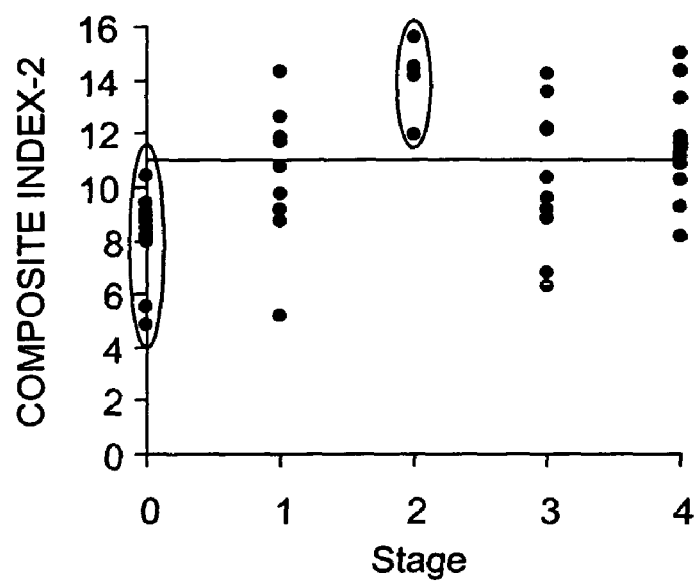
FIG. 53 is a diagram showing the relationship between a composite index (composite index 2) for hepatic fibrosis as determined by the present system and disease stages, for control group and patients with hepatitis C.

FIG. 53 shows a relationship between a composite index (composite index 2) for hepatic fibrosis as determined by the present system and disease stages in a control group and in patients with hepatitis C. In this illustration, the horizontal axis represents a stage of disease condition and the vertical axis represents a value of the composite index (composite index 2) of the control group and patients with hepatitis C at each stage.

The stage of disease condition is indicated by five levels, wherein the larger the value of the stage of disease condition, the worse the disease condition is. The normal condition is indicated by "0" and the worst stage of disease condition is indicated by "4." This illustration focuses on the classification of the control group and the patients with C hepatitis at Stage 2 of hepatic fibrosis.

Figure 54:
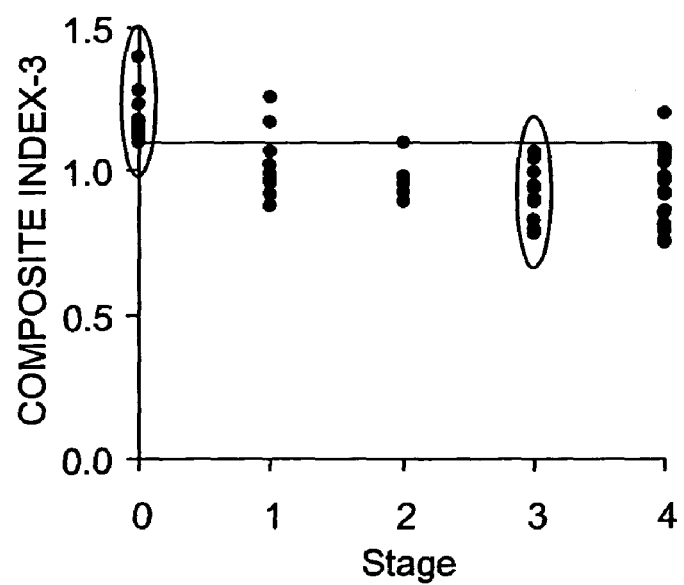
FIG. 54 is a diagram showing the relationship between a composite index (composite index 3) for hepatic fibrosis as determined by the present system and disease stages, for control group and patients with hepatitis C.

FIG. 54 shows a relationship between a composite index (composite index 3) for hepatic fibrosis as determined by the present system and disease stages in a control group and in patients with hepatitis C. In this illustration, the horizontal axis represents a stage of disease condition and the vertical axis represents a value of the composite index (composite index 3) of the control group and patients with hepatitis C at each stage.

The stage of disease condition is indicated by five levels, wherein the larger the value of the stage of disease condition, the worse the disease condition is. The normal condition is indicated by "0" and the worst stage of disease condition is indicated by "4." This illustration focuses on the classification of the control group and the patients with C hepatitis at Stage 3 of hepatic fibrosis.

Figure 55:
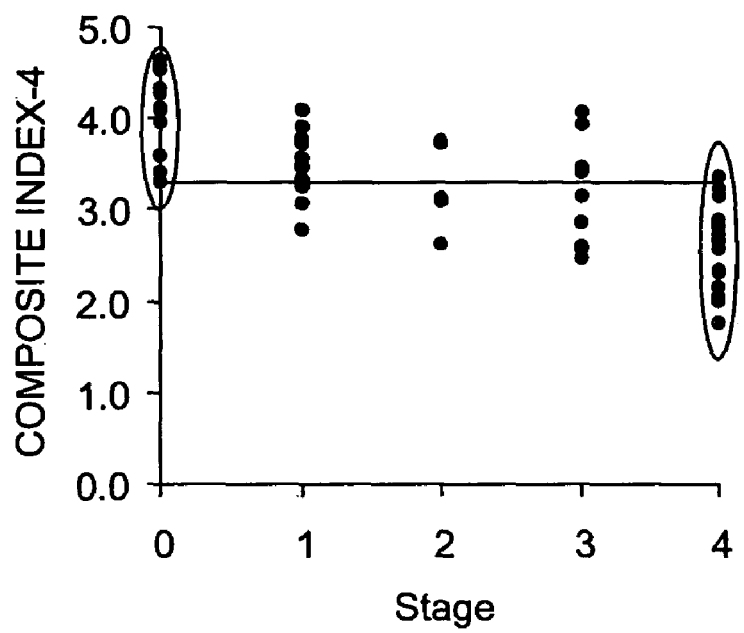
FIG. 55 is a diagram showing the relationship between a composite index (composite index 4) for hepatic fibrosis as determined by the present system and disease stages, for control group and patients with hepatitis C.

FIG. 55 shows a relationship between a composite index (composite index 4) of hepatic fibrosis as determined by the present system and disease stages in a control group and in patients with hepatitis C. In this illustration, the horizontal axis represents a stage of disease condition and the vertical axis represents a value of the composite index (composite index 4) of the control group and patients with hepatitis C at each stage.

The stage of disease-condition is indicated by five levels, wherein the larger the value of the stage of disease condition, the worse the disease condition is. The normal condition is indicated by "0" and the worst stage of disease condition is indicated by "4." This illustration focuses on the classification of the control group and the patients with C hepatitis at Stage 4 of hepatic fibrosis.

(Disease Condition Determining Method and Determination Result of Disease Condition)

Table 1 shows disease condition determining information and determination results of disease condition in a control group and patients with hepatitis C.

TABLE 1

| Patient | Stage | Fischer's ratio | Composite index 1 | Composite index 2 | Composite index 3 | Composite index 4 | Fischer's Index | Composite index 1 | Composite index 2 | Composite index 3 | Composite index 4 | SUM | General determination |
|---|---|---|---|---|---|---|---|---|---|---|---|---|---|
| | | | Minimum value in control group | | | | | | | | | | |
| | | | 1.40 | 4.81 | 1.39 | 3.31 | | | | | | | |
| | | | Maximum value in control group | | | | | | | | | | |
| | | | 2.03 | 10.41 | 1.72 | 4.62 | | | | | | | |
| 1 | 0 | 3.36 | 1.70 | 8.89 | 1.12 | 4.11 | 0 | 0 | 0 | 0 | 0 | 0 | − |
| 2 | 0 | 3.35 | 1.78 | 10.41 | 1.10 | 3.60 | 0 | 0 | 0 | 0 | 0 | 0 | − |
| 3 | 0 | 4.43 | 1.71 | 5.54 | 1.16 | 4.62 | 0 | 0 | 0 | 0 | 0 | 0 | − |
| 4 | 0 | 4.10 | 1.40 | 9.03 | 1.17 | 4.28 | 0 | 0 | 0 | 0 | 0 | 0 | − |
| 5 | 0 | 3.49 | 1.59 | 8.17 | 1.28 | 4.31 | 0 | 0 | 0 | 0 | 0 | 0 | − |
| 6 | 0 | 3.65 | 1.69 | 8.75 | 1.23 | 4.58 | 0 | 0 | 0 | 0 | 0 | 0 | − |
| 7 | 0 | 4.21 | 1.48 | 4.81 | 1.40 | 4.53 | 0 | 0 | 0 | 0 | 0 | 0 | − |
| 8 | 0 | 3.35 | 2.03 | 10.40 | 1.12 | 3.31 | 0 | 0 | 0 | 0 | 0 | 0 | − |
| 9 | 0 | 2.30 | 1.98 | 9.37 | 1.10 | 3.41 | 0 | 0 | 0 | 0 | 0 | 0 | − |
| 10 | 0 | 3.75 | 1.63 | 7.95 | 1.17 | 4.08 | 0 | 0 | 0 | 0 | 0 | 0 | − |
| 11 | 0 | 3.73 | 1.88 | 8.45 | 1.13 | 3.96 | 0 | 0 | 0 | 0 | 0 | 0 | − |
| 12 | 0 | 4.27 | 1.87 | 8.06 | 1.15 | 4.10 | 0 | 0 | 0 | 0 | 0 | 0 | − |
| 13 | 1 | 4.38 | 2.32 | 5.17 | 1.26 | 4.08 | 0 | 1 | 0 | 0 | 0 | 1 | + |
| 14 | 1 | 3.81 | 2.24 | 11.68 | 1.02 | 3.78 | 0 | 1 | 1 | 1 | 0 | 3 | + |
| 15 | 1 | 3.66 | 2.13 | 8.73 | 0.96 | 3.55 | 0 | 1 | 0 | 1 | 0 | 2 | + |
| 16 | 1 | 3.11 | 2.23 | 9.71 | 0.97 | 3.31 | 0 | 1 | 0 | 1 | 0 | 2 | + |
| 17 | 1 | 2.63 | 2.63 | 16.36 | 0.95 | 3.49 | 0 | 1 | 1 | 1 | 0 | 3 | + |
| 18 | 1 | 2.26 | 2.28 | 11.88 | 0.99 | 3.46 | 0 | 1 | 1 | 1 | 0 | 3 | + |
| 19 | 1 | 2.51 | 2.17 | 14.34 | 1.17 | 3.91 | 0 | 1 | 1 | 0 | 0 | 2 | + |
| 20 | 1 | 2.59 | 2.71 | 11.66 | 1.06 | 3.73 | 0 | 1 | 1 | 1 | 0 | 3 | + |
| 21 | 1 | 3.00 | 2.27 | 10.77 | 0.87 | 3.06 | 1 | 1 | 1 | 1 | 1 | 4 | + |
| 22 | 1 | 1.99 | 2.35 | 12.58 | 0.95 | 2.78 | 1 | 1 | 1 | 1 | 1 | 4 | + |
| 23 | 1 | 3.19 | 1.91 | 9.17 | 0.91 | 3.24 | 1 | 0 | 0 | 1 | 1 | 2 | + |
| 24 | 2 | 3.08 | 1.84 | 14.13 | 1.10 | 3.72 | 0 | 0 | 1 | 0 | 0 | 1 | + |
| 25 | 2 | 2.93 | 2.72 | 15.59 | 0.98 | 3.74 | 0 | 1 | 1 | 1 | 0 | 3 | + |

TABLE 1-continued

| | | | Composite index 1 | Composite index 2 | Composite index 3 | Composite index 4 | | | | | | | |
|---|---|---|---|---|---|---|---|---|---|---|---|---|---|
| | | | Minimum value in control group | | | | | | | | | | |
| | | | 1.40 | 4.81 | 1.39 | 3.31 | | | | | | | |
| | | | Maximum value in control group | | | | | | | | | General deter- |
| | | Fischer's | | | | | Fischer's | Composite | Composite | Composite | Composite | | |
| Patient | Stage | ratio | 2.03 | 10.41 | 1.72 | 4.62 | Index | index 1 | index 2 | index 3 | index 4 | SUM | mination |
| 26 | 2 | 3.28 | 2.18 | 14.48 | 0.89 | 3.08 | 1 | 1 | 1 | 1 | 1 | 4 | + |
| 27 | 2 | 3.00 | 1.75 | 11.94 | 0.96 | 3.12 | 1 | 0 | 1 | 1 | 1 | 3 | + |
| 28 | 2 | 2.15 | 2.40 | 14.42 | 0.92 | 2.63 | 1 | 1 | 1 | 1 | 1 | 4 | + |
| 29 | 3 | 3.24 | 1.59 | 6.24 | 1.07 | 4.07 | 0 | 0 | 0 | 1 | 0 | 1 | + |
| 30 | 3 | 2.98 | 2.24 | 8.80 | 0.94 | 3.94 | 0 | 1 | 0 | 1 | 0 | 2 | + |
| 31 | 3 | 1.80 | 2.05 | 10.37 | 0.79 | 2.86 | 1 | 1 | 0 | 1 | 1 | 3 | + |
| 32 | 3 | 2.04 | 2.96 | 12.21 | 0.90 | 3.13 | 1 | 1 | 1 | 1 | 1 | 4 | + |
| 33 | 3 | 2.41 | 2.36 | 14.26 | 0.95 | 3.14 | 1 | 1 | 1 | 1 | 1 | 4 | + |
| 34 | 3 | 3.17 | 2.41 | 6.76 | 0.99 | 3.41 | 0 | 1 | 0 | 1 | 0 | 2 | + |
| 35 | 3 | 1.96 | 2.11 | 12.14 | 0.83 | 2.45 | 1 | 1 | 1 | 1 | 1 | 4 | + |
| 36 | 3 | 3.72 | 2.16 | 9.17 | 1.04 | 3.45 | 0 | 1 | 0 | 1 | 0 | 2 | + |
| 37 | 3 | 2.68 | 2.14 | 9.57 | 0.90 | 2.57 | 1 | 1 | 0 | 1 | 1 | 3 | + |
| 38 | 3 | 2.63 | 1.74 | 13.52 | 0.79 | 2.60 | 1 | 0 | 1 | 1 | 1 | 3 | + |
| 39 | 4 | 1.91 | 1.72 | 11.62 | 0.76 | 2.30 | 1 | 0 | 1 | 1 | 1 | 3 | + |
| 40 | 4 | 2.63 | 2.18 | 11.45 | 0.98 | 3.14 | 1 | 1 | 1 | 1 | 1 | 4 | + |
| 41 | 4 | 2.35 | 1.98 | 9.23 | 0.79 | 2.79 | 1 | 0 | 0 | 1 | 1 | 2 | + |
| 42 | 4 | 1.24 | 1.93 | 11.87 | 0.86 | 2.56 | 1 | 0 | 1 | 1 | 1 | 3 | + |
| 43 | 4 | 1.98 | 2.25 | 11.86 | 0.85 | 2.82 | 1 | 1 | 1 | 1 | 1 | 4 | + |
| 44 | 4 | 0.80 | 3.14 | 18.74 | 0.81 | 1.74 | 1 | 1 | 1 | 1 | 1 | 4 | + |
| 45 | 4 | 2.76 | 1.98 | 11.16 | 0.75 | 2.65 | 1 | 0 | 1 | 1 | 1 | 3 | + |
| 46 | 4 | 0.78 | 3.47 | 14.33 | 0.97 | 2.14 | 1 | 1 | 1 | 1 | 1 | 4 | + |
| 47 | 4 | 2.46 | 2.87 | 8.11 | 0.92 | 3.23 | 1 | 1 | 0 | 1 | 1 | 3 | + |
| 48 | 4 | 1.18 | 2.72 | 11.39 | 0.76 | 2.03 | 1 | 1 | 1 | 1 | 1 | 4 | + |
| 49 | 4 | 2.46 | 2.51 | 11.08 | 1.07 | 3.34 | 0 | 1 | 1 | 1 | 0 | 3 | + |
| 50 | 4 | 0.98 | 2.49 | 21.04 | 1.20 | 1.98 | 1 | 1 | 1 | 0 | 1 | 3 | + |
| 51 | 4 | 1.38 | 2.63 | 9.26 | 1.03 | 2.88 | 1 | 1 | 0 | 1 | 1 | 3 | + |
| 52 | 4 | 4.66 | 1.72 | 44.97 | 0.70 | 2.52 | 1 | 0 | 1 | 1 | 1 | 3 | + |
| 53 | 4 | 1.72 | 2.09 | 10.27 | 1.04 | 2.83 | 1 | 1 | 0 | 1 | 1 | 3 | + |
| 54 | 4 | 2.16 | 1.64 | 10.83 | 0.96 | 2.71 | 1 | 0 | 1 | 1 | 1 | 3 | + |
| 55 | 4 | 2.38 | 1.60 | 13.28 | 0.92 | 2.67 | 1 | 0 | 1 | 1 | 1 | 3 | + |
| 56 | 4 | 1.07 | 2.83 | 14.97 | 1.06 | 2.32 | 1 | 1 | 1 | 1 | 1 | 4 | + |

For each composite index (composite indices 1 to 4), a maximum value or a minimum value in values of a respective composite index (composite indices 1 to 4) of a control group was selected as a threshold limit value. When a value of either one of the composite indices (composite indices 1 to 4) in a certain patient with hepatitis C at a certain stage is larger than the maximum value or smaller than the minimum value of the corresponding composite index of the control group, it was determined as positive "1." When the above value is between the threshold limit values of the corresponding composite index values of the control group, it was determined as negative "0." Then the sum of the values determined for each composite index (composite indices 1 to 4) was used to make general determination for each subject (subjects in a control group and subjects with hepatitis C). When the sum of the determined values was 1 or more, it was determined as positive.

As a result, all of the patients with hepatitis C in the data analyzed by the above diagnosis method were determined as positive, and all of the controls were determined as negative.

(Discussion of Determination Results (Comparison with Conventional Method))

Figure 56:
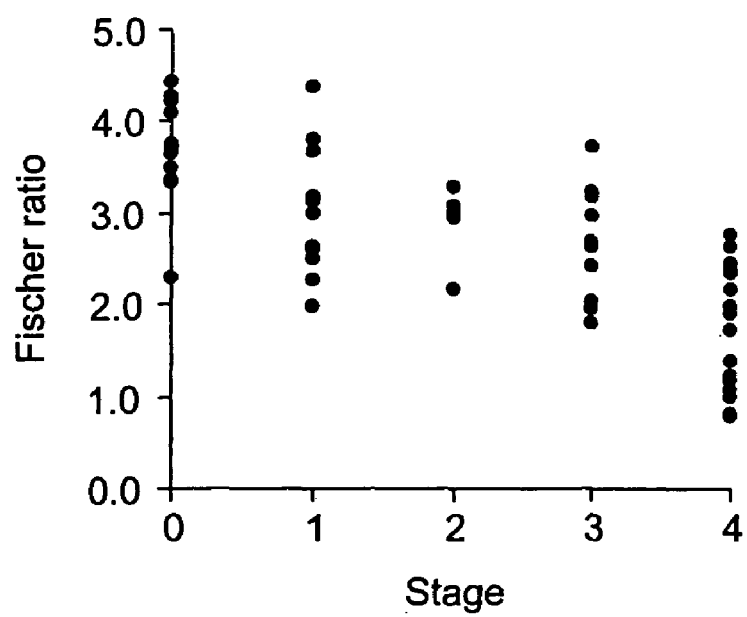
FIG. 56 is a diagram showing the relationship between Fischer's ratio and disease stages in control group and patients with hepatitis C.

FIG. 56 shows a relationship between a Fischer's ratio and a stage of disease condition in a control group and patients with hepatitis C. Likewise the composite indices calculated by the forgoing method using the present system, when a similar determination is conducted based on a Fischer's ratio conventionally used in determination of hepatitis, 66% of the patients with hepatitis turned out positive when the all of the controls were negative.

The positive determinability in each stage was 27% in Stage 1, 60% in Stage 2, 60% in Stage 3 and 94% in Stage 4, clearly showing that the above determination method is not suited for early diagnosis although it is improved as the disease proceeds (see Table 1 and FIG. 56). On the other hand, in the foregoing method using the present system and determination using the disease condition determining method of the present invention, the 100% of determinability is achieved even in early stages of the disease. This clearly shows superiority to the conventional method (determination based on a Fischer's ratio).

(Replacement of Composite Indices)

In the indices that can be derived by the above method using the present system, correlation coefficients are optimized, however, the indices can play a role as a diagnosis index even when they are not perfectly optimized. In consideration of this, we provided the following rules and formulae by analyzing the top 20 correlation coefficients.

To be more specific, for example, an amino acid in at least one formula from the composite indices 1 to 4 may be substituted in accordance with the following rules, or at least one of the composite indices 1 to 4 may be substituted by the corresponding formula as follows.

Now, the above rules will be explained with reference to FIG. 51.

FIG. 51 illustrates a rule for substituting an amino acid in each of the formulae of composite indices 1 to 4.

As seen in FIG. 51, in each of the composite indices 1 to 4, any element belonging to Group A is at the numerator, and any element belonging to Group B is at the denominator. Each of the composite indices 1 to 4 is calculated by the formula in the form of a sum of fractions including at least one fraction that divides an element belonging to Group A or a sum of elements belonging to Group A by an element belonging to Group B or a sum of elements belonging to Group B. Herein, elements belonging to Group C and elements belonging to Group D may be added to the numerator and the denominator, respectively.

The composite index 1 may be replaced, for example, by composite indices 1-1 to 1-20 recited below. The minimum value of control group and maximum value of control group represent the maximum value and the minimum value for the composite index (composite indices 1-1 to 1-20) of the control group.

(Composite index 1-1) (Minimum value of control group: 1.40, Maximum value of control group: 2.03)

(Asn)/(Thr)+(Gln)/(Tau+Ser+Val+Trp)

(Composite index 1-2) (Minimum value of control group: 1.21, Maximum value of control group: 1.84)

(Asn)/(Tau+Ile)+(Gln)/(Thr+Ser+Val+Trp)

(Composite index 1-3) (Minimum value of control group: 1.18, Maximum value of control group: 1.81)

(Asn)/(Tau+(α-ABA)+Ile)+(Gln)/(Thr+Ser+Val+Trp)

(Composite index 1-4) (Minimum value of control group: 1.39, Maximum value of control group: 2.02)

(Asn)/(Asp+Thr)+(Gln)/(Tau+Ser+Val+Trp)

(Composite index 1-5) (Minimum value of control group: 1.27, Maximum value of control group: 1.83)

(Asn)/(Thr)+(Gln)/(Tau+Ser+Val+Ile+Trp)

(Composite index 1-6) (Minimum value of control group: 1.40, Maximum value of control group: 2.02)

(Asn)/(Thr)+(Gln)/(Tau+Asp+Ser+Val+Trp)

(Composite index 1-7) (Minimum value of control group: 1.21, Maximum value of control group: 1.83)

(Asn)/(Tau+Ile)+(Gln)/(Asp+Thr+Ser+Val+Trp)

(Composite index 1-8) (Minimum value of control group: 1.26, Maximum value of control group: 1.89)

(Asn)/(Tau+Ile)+(Gln+Met)/(Thr+Ser+Val+Trp)

(Composite index 1-9) (Minimum value of control group: 1.17, Maximum value of control group: 1.80)

(Asn)/(Tau+(α-ABA)+Ile)+(Gln)/(Asp+Thr+Ser+Val+Trp)

(Composite index 1-10) (Minimum value of control group: 1.45, Maximum value of control group: 2.08)

(Asn)/(Thr)+(Gln+Met)/(Tau+Ser+Val+Trp)

(Composite index 1-11) (Minimum value of control group: 1.17, Maximum value of control group: 1.80)

(Asn)/(Tau+Asp+(α-ABA)+Ile)+(Gln)/(Thr+Ser+Val+Trp)

(Composite index 1-12) (Minimum value of control group: 2.36, Maximum value of control group: 2.00)

(Asn)/(Thr)+(Gln)/(Tau+Ser+(α-ABA)+Val+Trp)

(Composite index 1-13) (Minimum value of control group: 1.26, Maximum value of control group: 1.82)

(Asn)/(Asp+Thr)+(Gln)/(Tau+Ser+Val+Ile+Trp)

(Composite index 1-14) (Minimum value of control group: 1.23, Maximum value of control group: 1.86)

(Asn)/(Tau+(α-ABA)+Ile)+(Gln+Met)/(Thr+Ser+Val+Trp)

(Composite index 1-15) (Minimum value of control group: 1.21, Maximum value of control group: 1.83)

(Asn)/(Tau+Asp+Ile)+(Gln)/(Thr+Ser+Val+Trp)

(Composite index 1-16) (Minimum value of control group: 1.26, Maximum value of control group: 1.83)

(Asn)/(Thr)+(Gln)/(Tau+Asp+Ser+Val+Ile+Trp)

(Composite index 1-17) (Minimum value of control group: 1.26, Maximum value of control group: 1.88)

(Asn)/(Tau+Ile)+(Gln+Met)/(Asp+Thr+Ser+Val+Trp)

(Composite index 1-18) (Minimum value of control group: 1.35, Maximum value of control group: 1.88)

(Asn)/(Asp+Thr)+(Gln)/(Tau+Ser+(α-ABA)+Val+Trp)

(Composite index 1-19) (Minimum value of control group: 1.44, Maximum value of control group: 2.07)

(Asn)/(Asp+Thr)+(Gln+Met)/(Tau+Ser+Val+Trp)

(Composite index 1-20) (Minimum value of control group: 1.24, Maximum value of control group: 1.81)

(Asn)/(Thr)+(Gln)/(Tau+Ser+(α-ABA)+Val+Ile+Trp)

The composite index 2 may be replaced, for example, by composite indices 2-1 to 2-20 recited below. The minimum value of control group and maximum value of control group represent the maximum value and the minimum value for the composite index (composite indices 2-1 to 2-20) of the control group.

(Composite index 2-1) (Minimum value of control group: 4.81, Maximum value of control group: 10.41)

(Asn+Tyr)/(Cit)+(Met+Arg)/(Asp+(α-ABA))

(Composite index 2-2) (Minimum value of control group: 4.18, Maximum value of control group: 9.05)

(Asn+Tyr)/(Cit)+(Arg)/(Asp+(α-ABA))

(Composite index 2-3) (Minimum value of control group: 4.66, Maximum value of control group: 9.83)

(Asn+Met+Tyr)/(Cit)+(Arg)/(Asp+(α-ABA))

(Composite index 2-4) (Minimum value of control group: 4.63, Maximum value of control group: 10.46)

(Asn+Met+Tyr)/(Asp+Cit)+(Arg)/(α-ABA)

(Composite index 2-5) (Minimum value of control group: 5.15, Maximum value of control group: 12.23)

(Asn+Met)/(Cit)+(Tyr+Arg)/(Asp+(α-ABA))

(Composite index 2-6) (Minimum value of control group: 4.18, Maximum value of control group: 9.72)

(Asn+Tyr)/(Asp+Cit)+(Arg)/(α-ABA)

(Composite index 2-7) (Minimum value of control group: 4.88, Maximum value of control group: 12.41)

(Asn+Tyr)/(Asp+Cit)+(Met+Arg)/(α-ABA)

(Composite index 2-8) (Minimum value of control group: 4.68, Maximum value of control group: 11.41)

(Asn)/(Cit)+(Tyr+Arg)/(Asp+(α-ABA))

(Composite index 2-9) (Minimum value of control group: 0.45, Maximum value of control group: 0.67)

(Asn)/(Thr+Cit+(α-ABA))+(Met)/(His+Trp)

(Composite index 2-10) (Minimum value of control group: 5.31, Maximum value of control group: 13.40)

(Asn)/(Cit)+(Met+Tyr+Arg)/(Asp+(α-ABA))

(Composite index 2-11) (Minimum value of control group: 0.37, Maximum value of control group: 0.49)

(Asn)/(Thr+Cit+(α-ABA))+(Met)/(Asp+His+Trp)

(Composite index 2-12) (Minimum value of control group: 0.41, Maximum value of control group: 0.57)

(Asn)/(Thr+Glu)+(Met)/(Cit+(o-ABA)+Trp)

(Composite index 2-13) (Minimum value of control group: 0.37, Maximum value of control group: 0.49)

(Asn)/(Asp+Thr+Cit+(α-ABA))+(Met)/(His+Trp)

(Composite index 2-14) (Minimum value of control group: 0.34, Maximum value of control group: 0.46)

(Asn)/(Thr+Cit+(α-ABA))+(Met)/(Glu+His+Trp)

(Composite index 2-15) (Minimum value of control group: 5.44, Maximum value of control group: 15.47)

(Asn+Met)/(Asp+Cit)+(Tyr+Arg)/(α-ABA)

(Composite index 2-16) (Minimum value of control group: 3.13, Maximum value of control group: 8.06)

(Asn+Met)/(Cit)+(Arg)/(Asp+(α-ABA))

(Composite index 2-17) (Minimum value of control group: 0.37, Maximum value of control group: 0.52)

(Asn)/(Cit+(α-ABA)+His)+(Met)/(Thr+Glu+Trp)

(Composite index 2-18) (Minimum value of control group: 0.40, Maximum value of control group: 0.55)

(Asn)/(Cit+(α-ABA)+His)+(Met)/(Thr+Trp)

(Composite index 2-19) (Minimum value of control group: 0.37, Maximum value of control group: 0.49)

(Asn)/(Cit+His+Trp)+(Met)/(Thr+(α-ABA))

(Composite index 2-20) (Minimum value of control group: 5.17, Maximum value of control group: 14.31)

(Asn+Arg)/(α-ABA)+(Met+Tyr)/(Asp+Cit)

The composite index 3 may be replaced, for example, by composite indices 3-1 to 3-20 recited below. The minimum value of control group and maximum value of control group represent the maximum value and the minimum value for the composite index (composite indices 3-1 to 3-20) of the control group.

(Composite index 3-1) (Minimum value of control group: 1.39, Maximum value of control group: 1.72)

(Tau+Gly)/(Gln)+(α-ABA)/(Asp+Tyr)+(His)/(Lys)+(Trp)/(Thr+Asn+Cit)

(Composite index 3-2) (Minimum value of control group: 1.38, Maximum value of control group: 1.70)

(Tau+Gly)/(Gln+Met)+(α-ABA)/(Asp+Tyr)+(His)/(Lys)+(Trp)/(Thr+Asn+Cit)

(Composite index 3-3) (Minimum value of control group: 1.38, Maximum value of control group: 1.67)

(Tau+Gly)/(Gln)+(α-ABA)/(Thr)+(His)/(Lys)+(Trp)/(Asn+Cit+Tyr)

(Composite index 3-4) (Minimum value of control group: 1.39, Maximum value of control group: 1.74)

(Tau+Gly)/(Asp+Gln)+(α-ABA)/(Tyr)+(His)/(Lys)+(Trp)/(Thr+Asn+Cit)

(Composite index 3-5) (Minimum value of control group: 1.38, Maximum value of control group: 1.72)

(Tau+Gly)/(Asp+Gln+Met)+(α-ABA)/(Tyr)+(His)/(Lys)+(Trp)/(Thr+Asn+Cit)

(Composite index 3-6) (Minimum value of control group: 1.38, Maximum value of control group: 1.72)

(Tau+Gly)/(Gln+Met)+(α-ABA)/(Tyr)+(His)/(Lys)+(Trp)/(Thr+Asn+Cit)

(Composite index 3-7) (Minimum value of control group: 1.38, Maximum value of control group: 1.72)

(Tau+Gly)/(Gln+Met)+(α-ABA)/(Tyr)+(His)/(Lys)+(Trp)/(Asp+Thr+Asn+Cit)

(Composite index 3-8) (Minimum value of control group: 1.34, Maximum value of control group: 1.62)

(Tau+Gly)/(Gln)+(α-ABA)/(Asp+Met+Tyr)+(His)/(Lys)+(Trp)/(Thr+Asn+Cit)

(Composite index 3-9) (Minimum value of control group: 1.34, Maximum value of control group: 1.63)

(Tau+Gly)/(Asp+Gln)+(α-ABA)/(Met+Tyr)+(His)/(Lys)+(Trp)/(Thr+Asn+Cit)

(Composite index 3-10) (Minimum value of control group: 1.34, Maximum value of control group: 1.63)

(Tau+Gly)/(Gln)+(α-ABA)/(Met+Tyr)+(His)/(Lys)+(Trp)/(Asp+Thr+Asn+Cit)

(Composite index 3-11) (Minimum value of control group: 1.34, Maximum value of control group: 1.63)

(Tau+Gly)/(Gln)+(α-ABA)/(Met+Tyr)+(His)/(Lys)+(Trp)/(Thr+Asn+Cit)

(Composite index 3-12) (Minimum value of control group: 1.39, Maximum value of control group: 1.68)

(Tau+Gly)/(Gln)+(α-ABA)/(Thr)+(His)/(Asn+Cit+Tyr)+(Trp)/(Lys)

(Composite index 3-13) (Minimum value of control group: 1.23, Maximum value of control group: 1.61)

(Tau)/(Lys)+(Trp)/(Asn+Cit+Tyr)+(Gly+His)/(Gln)+(α-ABA)/(Asp+Thr)

(Composite index 3-14) (Minimum value of control group: 1.23, Maximum value of control group: 1.60)

(Tau)/(Lys)+(Trp)/(Asp+Asn+Cit+Tyr)+(Gly+His)/(Gln)+(α-ABA)/(Thr)

(Composite index 3-15)(Minimum value of control group: 1.23, Maximum value of control group: 1.61)

(Tau)/(Lys)+(Trp)/(Asn+Cit+Tyr)+(Gly+His)/(Gln)+(α-ABA)/(Thr)

(Composite index 3-16) (Minimum value of control group: 1.28, Maximum value of control group: 1.73)

(Tau)/(Asp+Asn+Lys)+(Trp)/(Cit+Tyr)+(Gly+His)/(Gln)+(α-ABA)/(Thr)

(Composite index 3-17) (Minimum value of control group: 1.28, Maximum value of control group: 1.71)

(Tau+Gly)/(Gln)+(α-ABA)/(Asp+Tyr)+(His)/(Thr+Asn+Cit)+(Trp)/(Lys)

(Composite index 3-18) (Minimum value of control group: 1.27, Maximum value of control group: 1.70)

(Tau+Gly)/(Gln+Met)+(α-ABA)/(Asp+Tyr)+(His)/(Thr+Asn+Cit)+(Trp)/(Lys)

(Composite index 3-19) (Minimum value of control group: 1.28, Maximum value of control group: 1.74)

(Tau+Gly)/(Gln+Met)+(α-ABA)/(Tyr)+(His)/(Asp+Cit+Lys)+(Trp)/(Thr+Asn)

(Composite index 3-20) (Minimum value of control group: 1.29, Maximum value of control group: 1.73)

(Tau+Gly)/(Asp+Gln)+(α-ABA)/(Tyr)+(His)/(Thr+Asn+Cit)+(Trp)/(Lys)

The composite index 4 may be replaced, for example, by composite indices 4-1 to 4-20 recited below. The minimum value of control group and maximum value of control group represent the maximum value and the minimum value for the composite index (composite indices 4-1 to 4-20) of the control group.

(Composite index 4-1) (Minimum value of control group: 3.31, Maximum value of control group: 4.62)

(Tau+Trp)/(Tyr)+((α-ABA)+His)/(Asp+Asn)

(Composite index 4-2) (Minimum value of control group: 2.46, Maximum value of control group: 3.34)

((α-ABA)+Trp)/(Tyr)+(His)/(Asp+Asn)

(Composite index 4-3) (Minimum value of control group: 3.20, Maximum value of control group: 4.62)

(Tau+(α-ABA)+Trp)/(Tyr)+(His)/(Asp+Asn)

(Composite index 4-4) (Minimum value of control group: 3.01, Maximum value of control group: 4.21)

(Tau+Trp)/(Tyr)+(His)/(Asp+Asn)

(Composite index 4-5) (Minimum value of control group: 3.42, Maximum value of control group: 4.77)

(Tau+Trp)/(Tyr)+(α-ABA)+His)/(Asn)

(Composite index 4-6) (Minimum value of control group: 3.30, Maximum value of control group: 4.70)

(Tau+(α-ABA)+Trp)/(Tyr)+(His)/(Asn)

(Composite index 4-7) (Minimum value of control group: 2.16, Maximum value of control group: 2.88)

(Tau+(α-ABA)+Trp)/(Asp+Met+Tyr)+(His)/(Asn)

(Composite index 4-8) (Minimum value of control group: 2.56, Maximum value of control group: 3.46)

((α-ABA)+Trp)/(Tyr)+(His)/(Asn)

(Composite index 4-9) (Minimum value of control group: 3.56, Maximum value of control group: 5.28)

(Tau+Trp)/(Tyr)+(α-ABA)/(Asp+Met)+(His)/(Asn)

(Composite index 4-10) (Minimum value of control group: 3.11, Maximum value of control group: 4.37)

(Tau+Trp)/(Tyr)+(His)/(Asn)

(Composite index 4-11) (Minimum value of control group: 2.49, Maximum value of control group: 3.52)

((α-ABA)+His)/(Asp+Asn)+(Trp)/(Tyr)

(Composite index 4-12) (Minimum value of control group: 2.70, Maximum value of control group: 3.63)

(Tau+Trp)/(Asp+Met+Tyr)+(His)/(Asn)

(Composite index 4-13) (Minimum value of control group: 3.21, Maximum value of control group: 4.62)

(Tau+His)/(Tyr)+((α-ABA)+Trp)/(Asp+Asn)

(Composite index 4-14) (Minimum value of control group: 3.21, Maximum value of control group: 4.62)

(Tau+(α-ABA))/(Asp+Asn)+(His+Trp)/(Tyr)

(Composite index 4-15) (Minimum value of control group: 2.93, Maximum value of control group: 4.13)

(Tau+Trp)/(Asp+Met+Tyr)+((α-ABA)+His)/(Asn)

(Composite index 4-16) (Minimum value of control group: 3.19, Maximum value of control group: 4.69)

(Tau+(α-ABA))/(Asn)+(His+Trp)/(Asp+Tyr)

(Composite index 4-17) (Minimum value of control group: 1.27, Maximum value of control group: 1.97)

((α-ABA)+Trp)/(Tyr)+(His)/(Asp+Asn+Met)

(Composite index 4-18) (Minimum value of control group: 3.18, Maximum value of control group: 4.62)

(Tau+(α-ABA)+His)/(Tyr)+(Trp)/(Asp+Asn)

(Composite index 4-19) (Minimum value of control group: 1.18, Maximum value of control group: 1.78)

(α-ABA)/(Asn)+(His+Trp)/(Asp+Met+Tyr)

(Composite index 4-20) (Minimum value of control group: 2.64, Maximum value of control group: 3.81)

(Tau+His)/(Asp+Asn+Met)+((α-ABA)+Trp)/(Tyr)

Now we finish the explanation of Example of composite indices for hepatic fibrosis (Part I).

[Example of Composite Indices for Hepatic Fibrosis (Part II)]

First, the details of Example of composite indices for hepatic fibrosis (Part II) will be explained with reference to FIG. 35. According to the forgoing method using the present system, a composite index 5 by a plurality of metabolites shown below was determined using disease condition index data regarding hepatic fibrosis.

(Composite Index 5: R=−0.80)

(Leu+Val+Trp)/(Phe+Tyr)+(Gly+Tau+ABA+His+Pro)/(Met+Asn+Orn+Glu)

Figure 35:
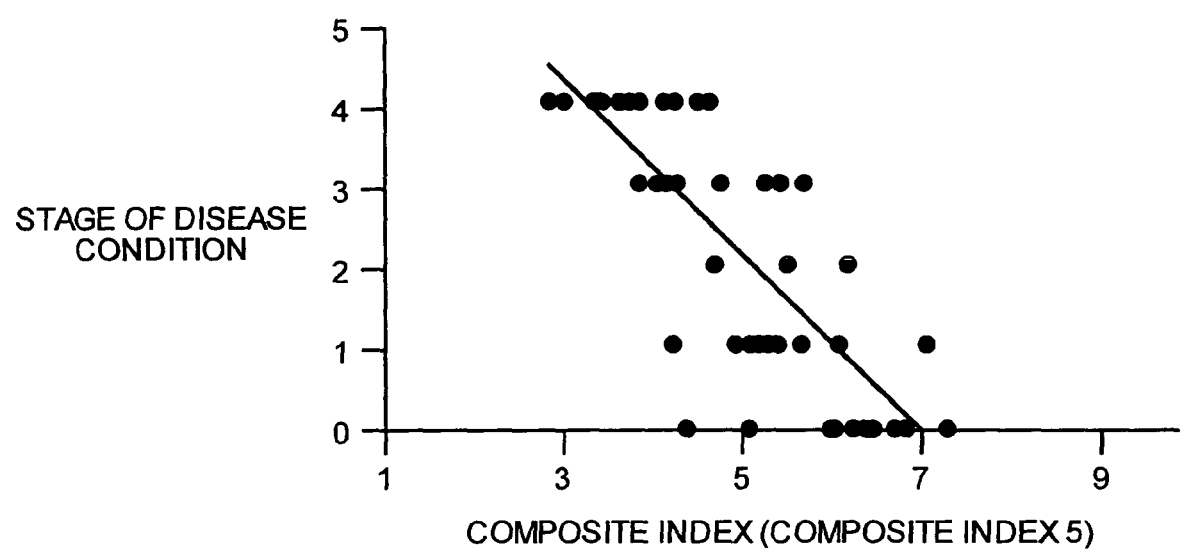
FIG. 35 is a diagram showing the relationship between a composite index (composite index 5) for hepatic fibrosis as determined by the system and disease stages.

FIG. 35 shows a relationship between a composite index (composite index 5) of hepatic fibrosis determined according to the present system and a stage of disease condition. In this graph, the horizontal axis represents a value of the composite index (composite index 5) of each sample and the vertical axis represents a stage of disease condition. The stage of disease condition is indicated by six levels, wherein the larger the value of the stage of disease condition, the worse the disease condition is. The normal condition is indicated by "0" and the worst stage of disease condition is indicated by "5."

Now we finish the explanation of Example of composite indices for hepatic fibrosis (Part II).

[Example of Composite Indices for Diabetes Model Animals]

First, the details of Example of composite indices in diabetes model animals will be explained with reference to e.g., FIGS. 37 to 39. Assigning numerals "−1 (normal)" and "1 (diabetes)" that are indicative of the disease conditions, respectively to a normal rat (Wister) and a GK (Goto-Kakizaki) rat which is a diabetes model animal, a correlation formula by blood amino acids was created according to the forgoing method using the present system, and a composite index 6 was determined.
(Composite Index 6)

(Asn+Val+Trp)/(Ser)+(Cys+Phe+Orn)/(Cit+His)+ (Ile)/(Gly)

Figure 37:
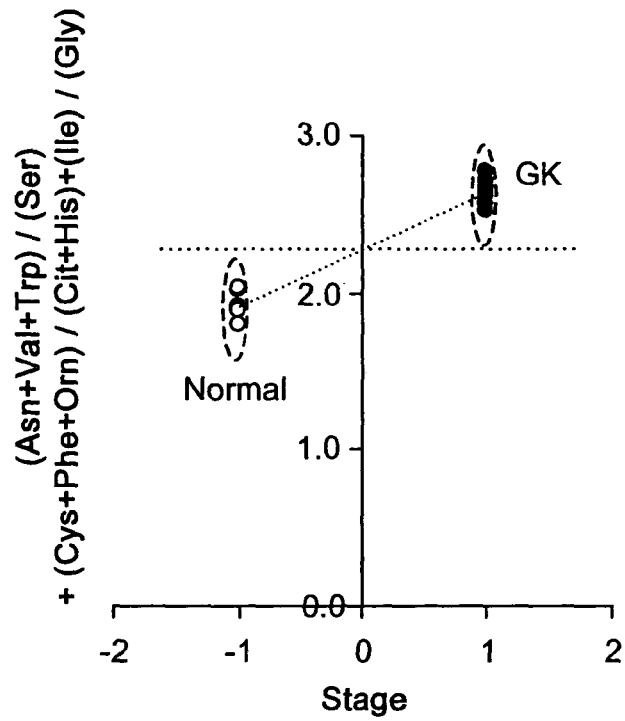
FIG. 37 is a diagram showing the relationship as determined by the system between a composite index (composite index 6) and disease stages in normal rats and diabetic (GK) rats.

FIG. 37 is a view showing a relationship between a composite index (composite index 6) and a stage of disease condition in normal (Normal) rats and diabetes (GK) rats. In this illustration, the vertical axis represents a value of composite index (composite index 6) in data of each individual of normal rats and diabetes (GK) rats, and the horizontal axis represents a stage of disease. As to the stage of disease condition, "−1" is indicative of normal, and "1" is indicative of diabetes.

Figure 38:
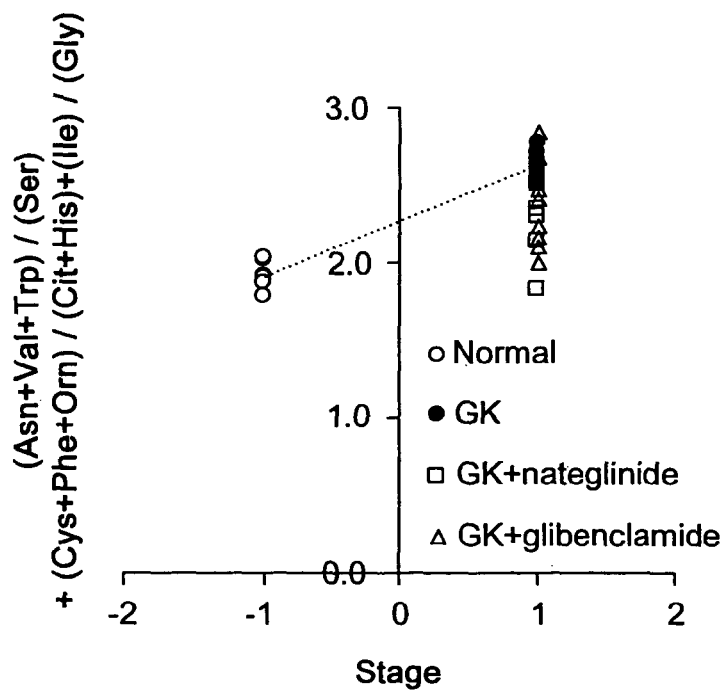
FIG. 38 is a diagram showing the relationship as determined by the system between a composite index (composite index 6) and disease stages in a normal rat, a diabetic (GK) rat, and a diabetic (GK) rat treated by administering nateglinide or glibenclamide, each a therapeutic drug for diabetes.

FIG. 38 shows a relationship between a composite index (composite index 6) and a stage of disease condition determined by the present system in a normal rat, diabetes (GK) rat and a diabetes (GK) rat treated by administration of nateglinide or glibenclamide which is a therapeutic agent for diabetes.

In this graph, the vertical axis represents a value of composite index (composite index 6) in data of each individual of the normal (Normal) rat, diabetes (GK) rat and a diabetes (GK) rat treated by administration of nateglinide or glibenclamide which is a therapeutic agent for diabetes, and the horizontal axis represent a stage of disease condition.

As to the stage of disease condition, "−1" is indicative of normal, "1" is indicative of diabetes, and diabetes treated by administration of nateglinide or glibenclamide which is a therapeutic agent for diabetes.

Figure 39:
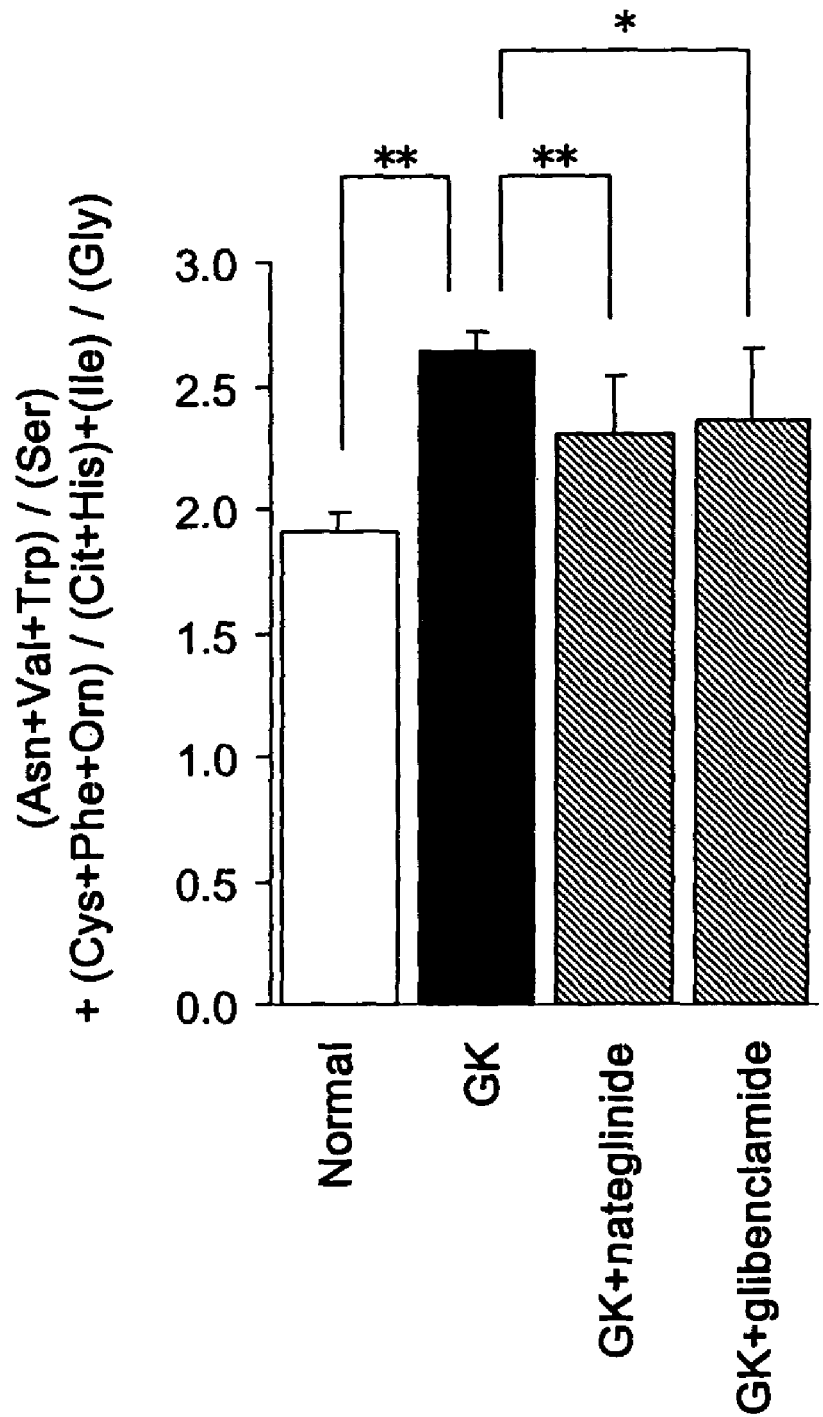
FIG. 39 is a bar graph showing the mean values (±SD) of composite index (composite index 6) as determined by the system in the groups of a normal rat, a diabetic (GK) rat, and a diabetic (GK) rat treated by administering nateglinide or glibenclamide, each a therapeutic drug for diabetes.

FIG. 39 is a bar graph showing the mean values of composite index (composite index 6) (±SD) determined by the present system of the respective individual groups including a normal rat, diabetes (GK) rat, and diabetes (GK) rat treated by administration of nateglinide or glibenclamide which is a therapeutic agent for diabetes.

In this graph, the vertical axis represents a mean value of composite index (composite index 6) values (±SD) of each of the individual groups including a normal (Normal) rat, diabetes (GK) rat and a diabetes (GK) rat treated by administration of nateglinide or glibenclamide which is a therapeutic agent for diabetes, and the horizontal axis represents each individual group.

Herein, the mean value of composite index (composite index 6) values (±SD) of the diabetes (GK) rat was significantly higher than the mean values of composite index (composite index 6) values (±SD) of the normal (Normal) rat and the diabetes (GK) rat treated by administration of nateglinide which is a therapeutic agent for diabetes with a significance level of less than 1%, and was significantly higher than the mean value of composite index (composite index 6) values of the diabetes (GK) rat treated by administration of glibenclamide which is a therapeutic agent for diabetes with a significance level of less than 5%.

Now we finish the explanation of Example of composite indices in diabetes model animals.

[1: Other Determination Examples of Disease Condition Determination Using Animal Data]

Now, an exemplary formula for discriminating an animal with a specific disease condition from a healthy animal which is a control will be explained With reference to FIGS. 58 to 64. In each formula, P-Ser represents a concentration of phosphoserine, Cys represents a concentration of cystine, and Cysthi represents a concentration of cystathionine.

(1-1: Hyperlipemia and Arteriosclerosis)

Figure 58:
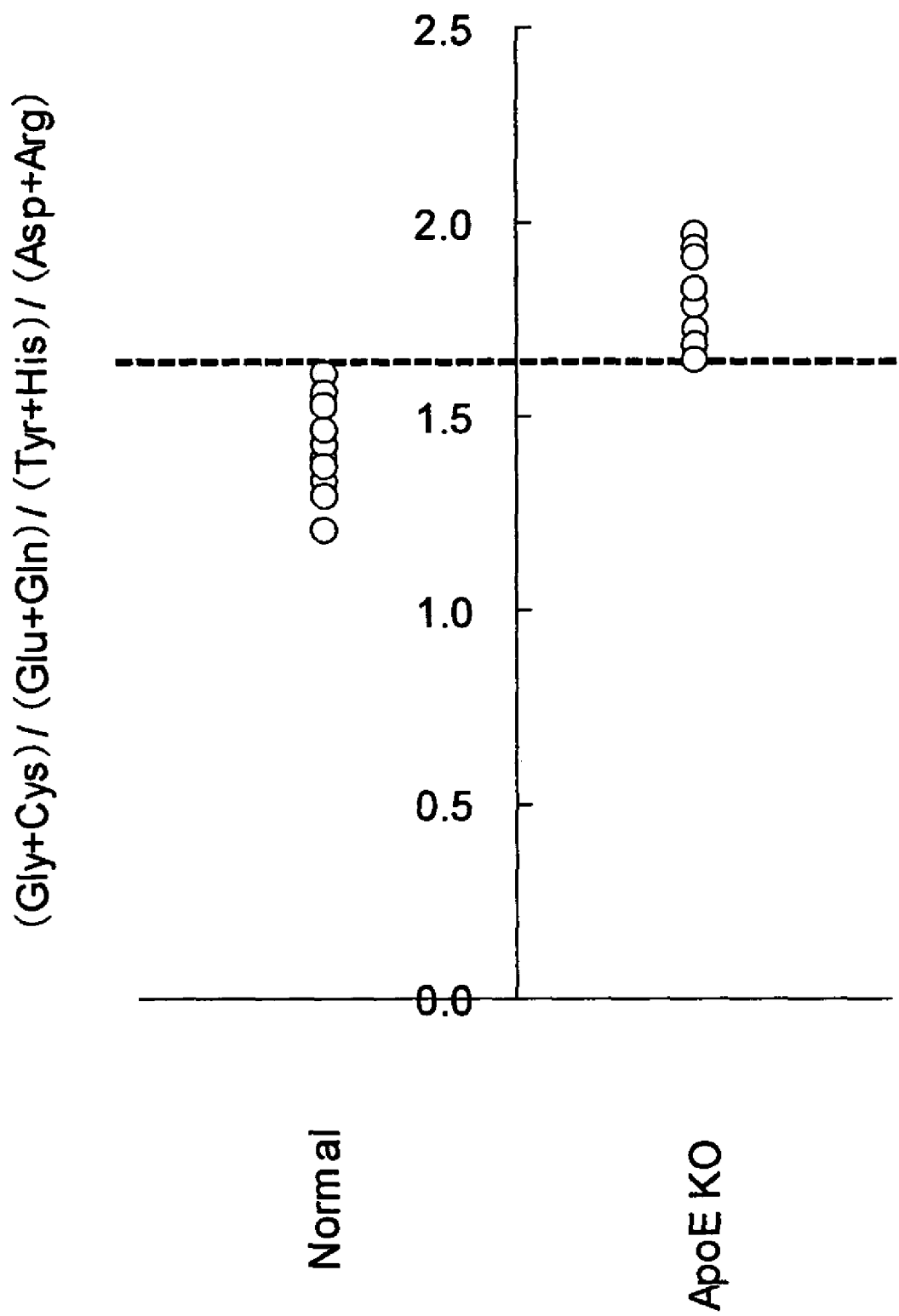
FIG. 58 is a diagram showing one example of discrimination between apo-E knockout mice (Apo-E KO) and normal mice (Normal).

An apo-E knockout mouse is known as a model animal that exhibits significant hyperlipemia and arteriosclerosis. The following is an example of a discrimination formula between an apo-E knockout mouse and a normal mouse (C57B6J) at 20 weeks old at which an initial symptom of the arteriosclerosis is observed in the apo-E knockout mouse, calculated according to the blood amino acid level (see FIG. 58). FIG. 58 is a view showing an example of discrimination between an apo-E knockout mouse (Apo-E KO) and a normal mouse. As shown in FIG. 58, an apo-E knockout mouse and a normal mouse were discriminated from each other effectively by means of the following discrimination formula.

Index: (Gly+Cys)/(Glu+Gln)+(Tyr+His)/(Asp+Arg)

(1-2: Discrimination Between Before and After Influenza Virus Infection)

Figure 59:
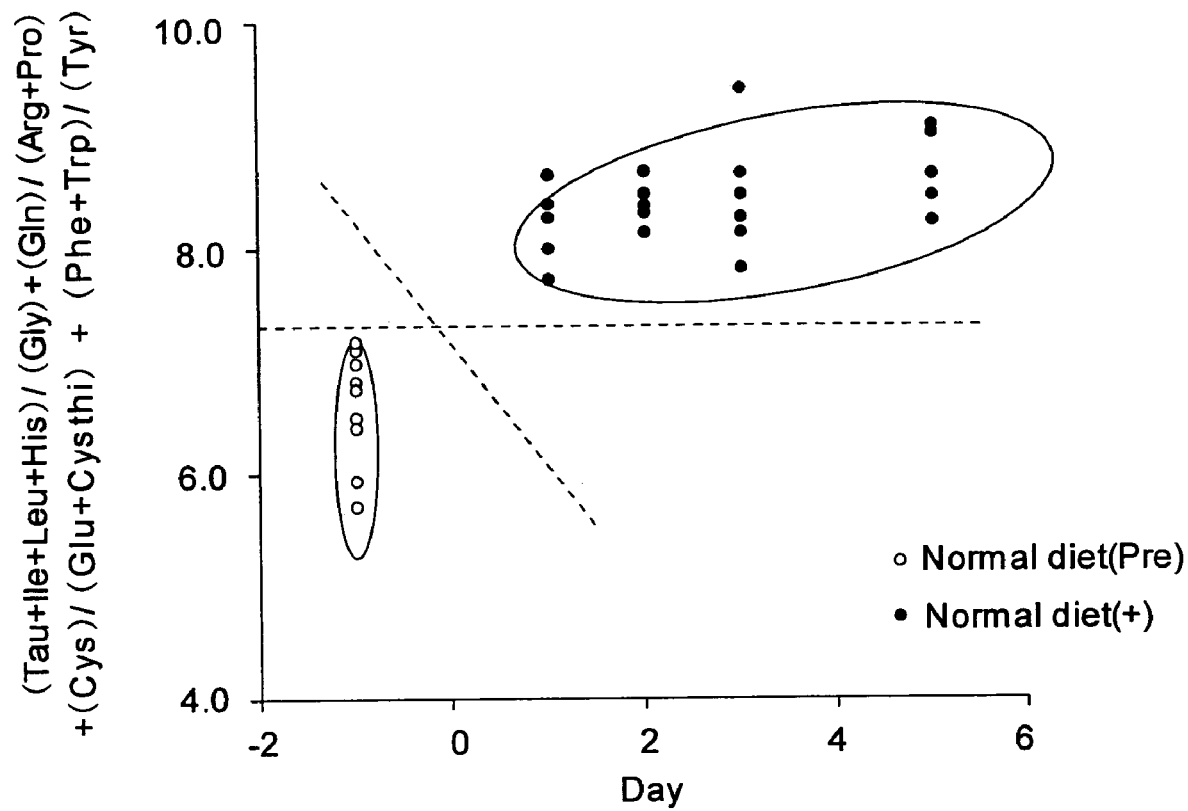
FIG. 59 is a diagram showing one example of discrimination between normal mice infected with attenuated influenza virus A/Aichi/2/68 (H3N2) and those uninfected.

Shown below is an example of discrimination formula for discriminating the uninfected condition and the infected condition with attenuated influenza virus A/Aichi/2/68 (H3N2) of a normal mouse, based on blood amino acid levels before and after (previous day and 1 to 5 days after infection) infection. An example of discrimination based on the discrimination formula is illustrated in FIG. 59. FIG. 59 is a view showing an example of discrimination between the uninfected condition and the infected condition with attenuated influenza virus A/Aichi/2/68 (H3N2) of a normal mouse. In FIG. 59, open circle represents data for a pre-infected mouse fed with a normal diet (Normal diet (pre)) and solid circle represents data for a post-infected mouse fed with a normal diet (Normal diet (+)).

Index (IFV): (Tau+Ile+Leu+His)/(Gly)+(Gln)/(Arg+ Pro)+(Cys)/(Glu+Cysthi)+(Phe+Trp)/(Tyr)

Figure 60:
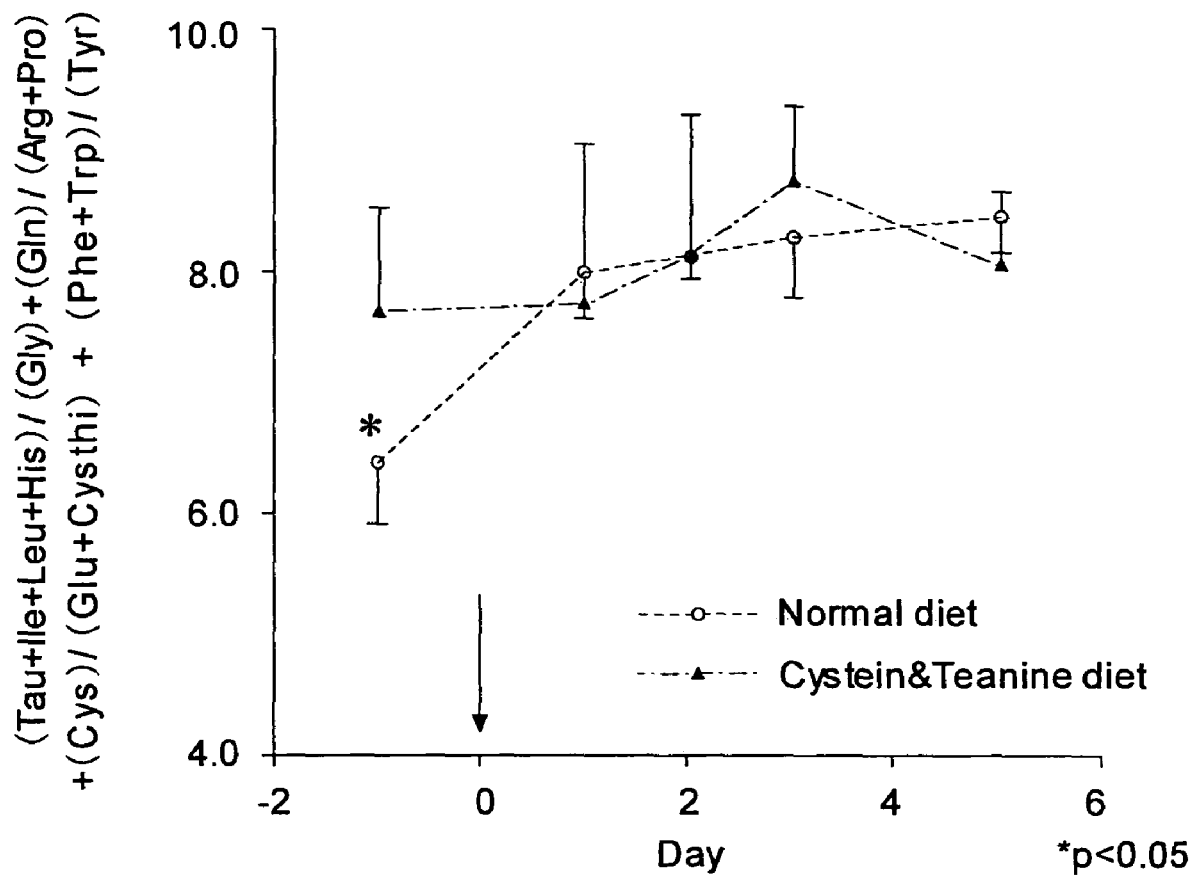
FIG. 60 is a diagram showing one example in which the variation in the value determined by the discrimination formula was compared between a group fed with cystine and teanine and then infected with the influenza virus and a group fed with normal diet.

In this experimental system, it has been reported that previous intake of cystine and theanine which are amino acids are effective in recovery from the symptom after influenza virus infection (Japanese Patent Application No. 2002-040845). In order to verify this, a change in value obtained by the above discrimination formula resulting from influenza infection after intake of cystine and theanine was compared with that obtained in the group fed with a normal diet, and an example of this comparison is shown (see FIG. 60). FIG. 60 is a view showing an example of comparing a change in value obtained by the above discrimination formula resulting from influenza infection after intake of cystine and theanine, with that obtained in the group fed with a normal diet. In FIG. 60, "open circle" represents data for the normal diet intake group (Normal diet) and "solid triangle" represents data for the cystine and theanine intake group (Cystein & Theanine diet).

As shown in FIG. 60, it was found that at points of time before virus infection (at points of time before the point of arrow in FIG. 60), values obtained by the discrimination formula in the cystine and theanine intake group exhibit significantly higher values than those obtained in the control group. This suggests the possibility of previous activation of the protective mechanism against infection.

(1-3: Diabetes)

Figure 61:
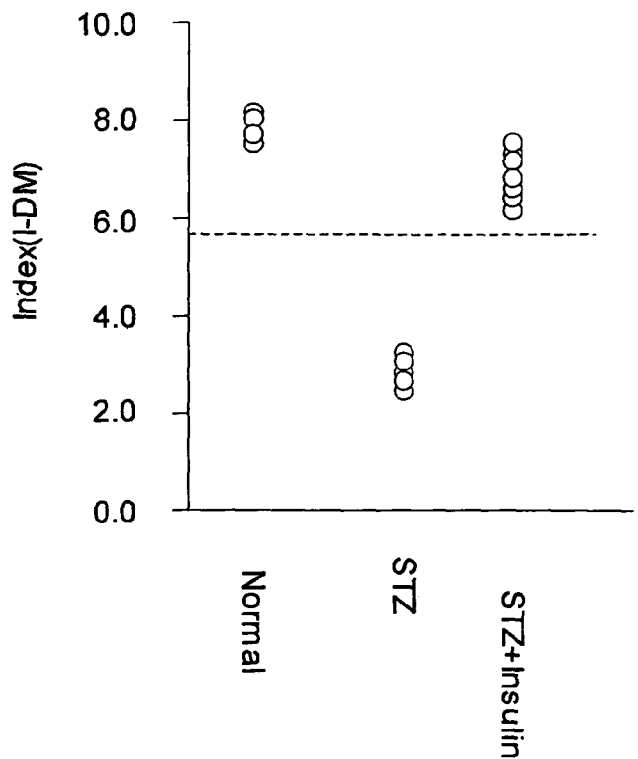
FIG. 61 is a diagram showing one example of discrimination between a streptozotocine-administered rat (STZ) to serve as an animal model for type-I diabetes and a normal rat (Normal).
Figure 62:
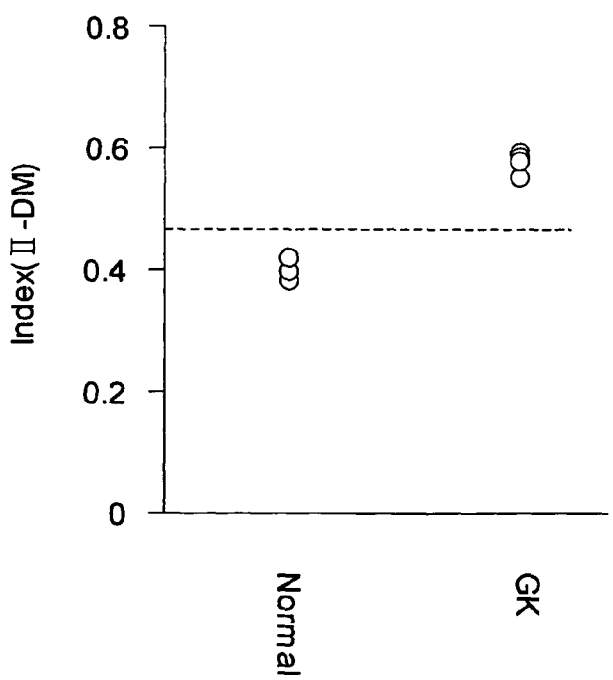
FIG. 62 is a diagram showing one example of discrimination between a GK rat (GK) to serve as an animal model for type-II diabetes and a normal rat (Normal).

Shown below are an exemplary discrimination formula calculated based on blood amino acid level of a streptozotocin-administered rat which is a model animal for type I diabetes, a GK (Goto-Kakizaki) rat which is a model animal for type II diabetes, and a control rat, and an example of discrimination according to the discrimination formula (FIGS. 61 and 62). FIG. 61 shows an example of discrimination between a streptozotocin-administered rat (STZ) which is a model animal for type I diabetes and a normal rat (Normal). FIG. 62 shows an example of discrimination between a GK rat (GK) which is a model animal for type II diabetes and a normal rat (Normal). A result for a streptozotocin-administered rat which is recovered from the disease condition by treatment with insulin (STZ+Insulin) is shown in FIG. 61 for comparison (see data of "STZ+Insulin" in FIG. 61).

Type I diabetes indices: Index (I-DM):

(Thr+Asn+Phe+Lys+Arg+Pro)/(Cit+Ile)+(Cysthi+ His)/(Asp+Met)

Type II Diabetes Indices: Index (II-DM):

(Val)/(Ser+Gly)+(Cys+Cystha+Trp)/(Cit+His+Arg)

(1-4: Obesity)

Figure 63:
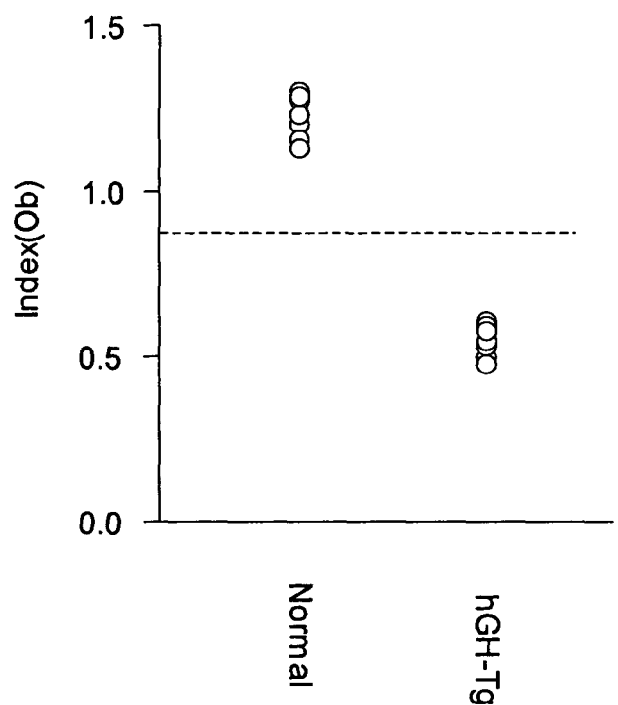
FIG. 63 is a diagram showing one example of discrimination between a human growth hormone transgenic rat (hGH-Tg rats) and a normal rat (Normal).

A human growth hormone transgenic rat (hGH-Tg rat) is reported as an obesity model animal that exhibits extreme obesity. The following discrimination formula is an example of discrimination formula calculated based on blood amino acid levels of an obesity rat and a control rat (see FIG. 63). FIG. 63 shows an example of discrimination between a human growth hormone transgenic rat (hGH-Tg rat) and a normal rat (Normal).

Obesity Index: Index (Ob):

(Gly)/(Val+Leu+Arg)+(Cit)/(Ala+Trp)+(Tyr)/(Lys)+ (His)/(Ser+Ile+Orn)

(1-5: Hepatopathy)

Figure 64:
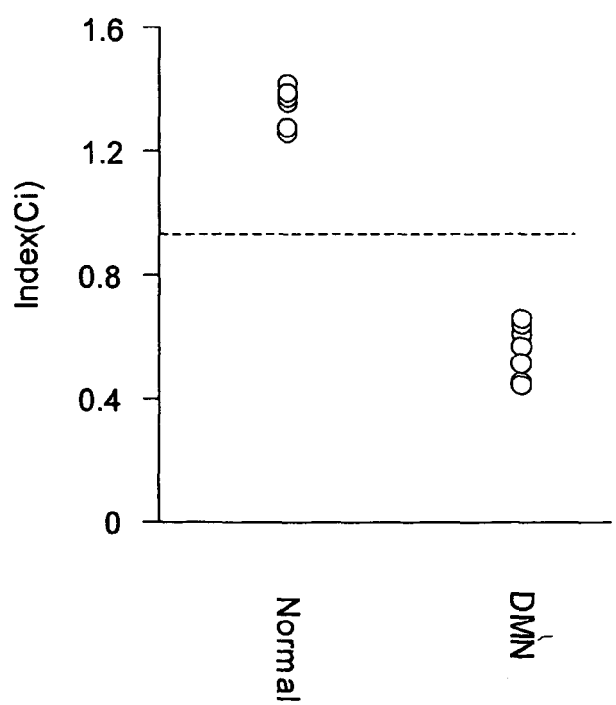
FIG. 64 is a diagram showing one example of discrimination between a model rat of hepatic fibrosis induced by dimethylnitrosamine (DMN) and a normal rat (Normal).

Shown below is an example of discrimination formula calculated based on blood amino acid levels of a hepatic fibrosis model rat created by administration of dimethylnitrosamine, and a normal rat (see FIG. 64). FIG. 64 shows an example of discrimination between a model rat of hepatic fibrosis induced by dimethylnitrosamine (DMN) and a normal rat (Normal).

Index for Hepatic Fibrosis: Index (Ci):

(Thr)/(Cit+Cys+Cysthi+Phe+Orn+His)+(Glu+Ile)/ (Tau+Gly)

[2: Example Formulating Influence of Dietary Factor on Individuals]

Figure 65:
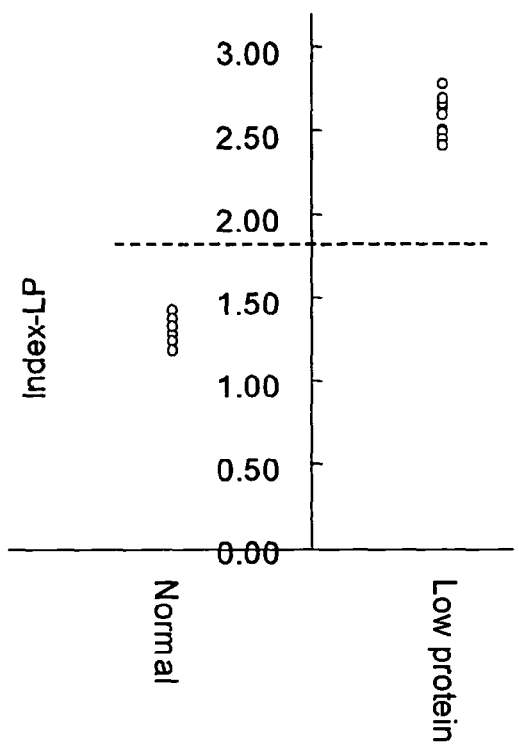
FIG. 65 is a diagram showing one example of discrimination between rats fed with a low protein diet (Low Protein) and rats fed with a normal diet (Normal).
Figure 66:
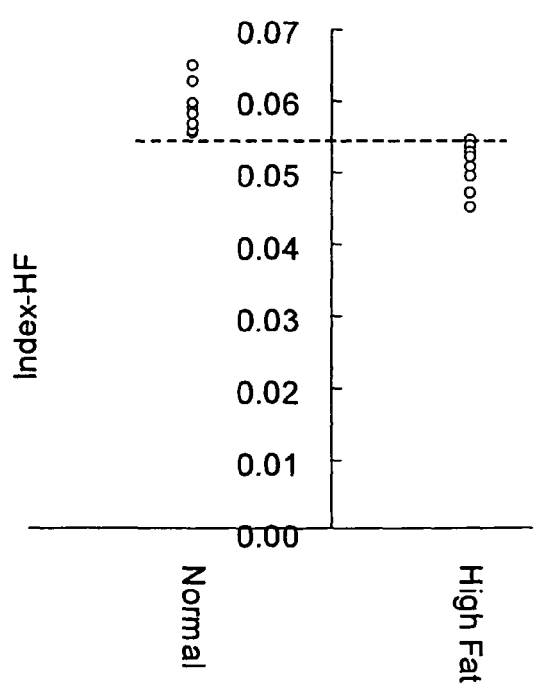
FIG. 66 is a diagram showing one example of discrimination between mice fed with a high fat diet (High Fat) and mice fed with a normal diet (Normal).

Application examples intended for determining nutritional conditions of individuals will be described below with reference to FIGS. 65 and 66. By previously formulating influence of a dietary ingredient on individuals in the following manner, it is possible to estimate the nutritional condition of a specific individual.

(2-1: Example Determining Influence of Low Protein Diet Intake on Individuals)

Shown below is an example of discrimination formula calculated based on blood amino acid levels of 6-week old rats fed for 2 weeks with a diet containing 5% protein (n=6) or with a diet containing 10% protein (n=6) (low protein diet group), and rats fed in the same manner with a diet containing 15% protein (n=6) or with a diet containing 20% protein (n=6) (control group) (see FIG. 65). FIG. 65 shows an example of discrimination between rats fed with a low protein diet (Low protein) and rats fed with a normal diet (Normal). In the formula, Cys represents a cystine concentration.

Index-LP:

(Thr+Leu)/(Ser+Gly+Orn)+(Cys)/(P-Ser+Arg)+(Val+ His)/(Lys)

(2-2: Example Determining Influence of a Dietary Lipid Amount on Individuals)

Shown below is an example of discrimination formula calculated based on blood amino acid levels and blood lipid metabolite levels of mice fed with a diet containing 20% lipids for one month (n=6) or for two months (n=6) (high fat diet group) and mice fed with a diet containing 7% lipids for one month (n=6) or for two months (n=6) (control group) (see FIG. 66). FIG. 66 shows an example of discrimination between mice fed with a high fat diet (High Fat) and mice fed with a normal diet (Normal). In the formula, α-ABA represents a concentration of α-amino butyric acid, "NEFA" represents a concentration of free fatty acid, and "TCHO" represents a total cholesterol concentration.

Index-HF:

(Met+Ile+NEFA)/(Thr+Gln+Gly+α-ABA+Val+Leu+ Tyr+Phe+His+Arg+Pro+TCHO)

[3: Use Examples of Biochemical Data as Substitutive Indices]

Examples of formulae optimized for various kinds of biochemical data are indicated in FIGS. 67 to 70. As shown herein, the following indices can be used as substitutive indices for various biochemical data in blood or organs, or various measurement items such as organ weight.

(3-1: Example of Formula Optimized to Organ Specific Biochemical Index)

Figure 67:
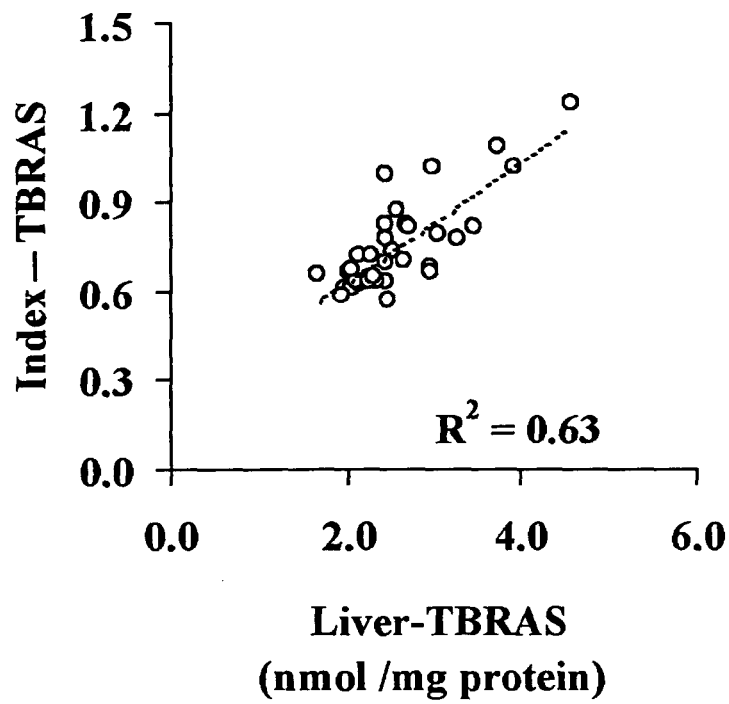
FIG. 67 is a diagram showing a correlation between the amount of peroxidated lipids in liver (Liver-TBRAS) and the value calculated based on the formula optimized for the Liver-TBRAS (Index-TBRAS).

Shown below is a formula optimized with regard to lipid peroxide (TBARS) amount in liver of each group (6 animals per group) of rats fed for two weeks with a diet of protein contents 5%, 10%, 15%, 20%, 30%, or 70% using blood amino acid level (see FIG. 67). FIG. 67 shows a correlation between a lipid peroxide amount in liver (Liver-TBRAS) and a value calculated by the formula optimized with regard to lipid peroxide amount (Index-TBRAS). In the following formula, "Cys" represents a cystine concentration, and "Cyshi" represents a cystathionine concentration.

Index-TBARS:

(Asp)/(Thr+Trp)+(Cysthi)/(Tyr)+(Cys)/(Glu+Met+ Arg)+(His)/(Cit+Phe)

(3-2: Example of Formula Optimized for Blood Biochemical Index)

Figure 68:
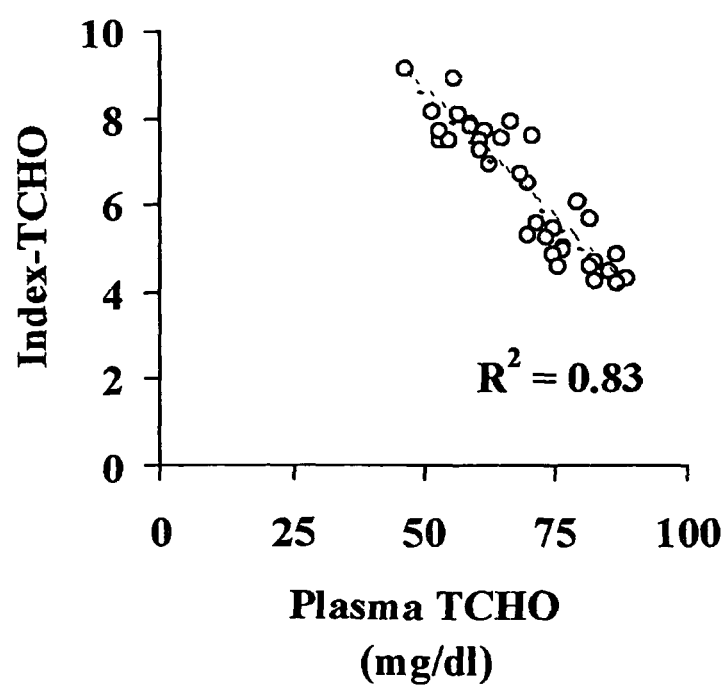
FIG. 68 is a diagram showing a correlation between a blood total cholesterol level (Plasma TCHO) and the value calculated based on the formula optimized for the plasma TCHO (Index-TCHO).

Shown below is a formula optimized for blood total cholesterol (TCHO) in the experiment of the above (3-1: Example of formula optimized for organ specific biochemical index) using blood amino acid level (see FIG. 68). FIG. 68 shows a correlation between a blood total cholesterol level (plasma TCHO) and a value calculated by the formula optimized for the blood total cholesterol level (Index-TCHO). In the following formula, "Cys" represents a cystine concentration, and "Cyshi" represents a cystathionine concentration.

Index-TCHO:

(Asn)/(Tyr)+(Gly+Pro)/(Glu)+(Val)/(Met+Arg)+(Cys+ Lys)/(Thr+Cysthi+His)

(3-3: Example of Formula Optimized for Blood Hormone Level)

Figure 69:
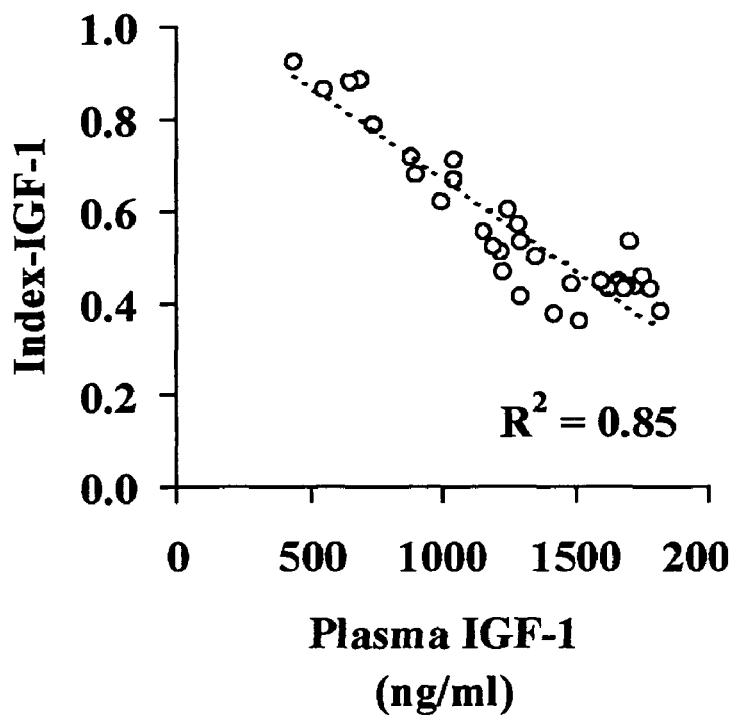
FIG. 69 is a diagram showing a correlation between a blood insulin-like growth factor-1 level (Plasma IGF-1) and the value calculated based on the formula optimized for the plasma IGF-1 (Index-IGF-1).

Shown below is a formulation optimized for a blood insulin-like growth factor level (IGF-1) in the experiment of the above (3-1: Example of formula optimized for organ specific biochemical index) using blood amino acid level (see FIG. 69). FIG. 69 shows a correlation between a blood concentration of insulin-like growth factor (Plasma IGF-1) and a value calculated by the formula optimized for the blood concentration of insulin-like growth factor (Plasma IGF-1). In the following formula, "Cys" represents a cystine concentration, and "Cyshi" represents a cystathionine concentration.

Index-IGF-1

(P-Ser)/(Glu+Cysthi)+(Ser+Gly+Cys)/(Ala+Met+ Lys+His)+(Orn)/(Asp+Thr+Cit+Trp)

(34: Example of Formula Optimized for Tissue Weight)

Figure 70:
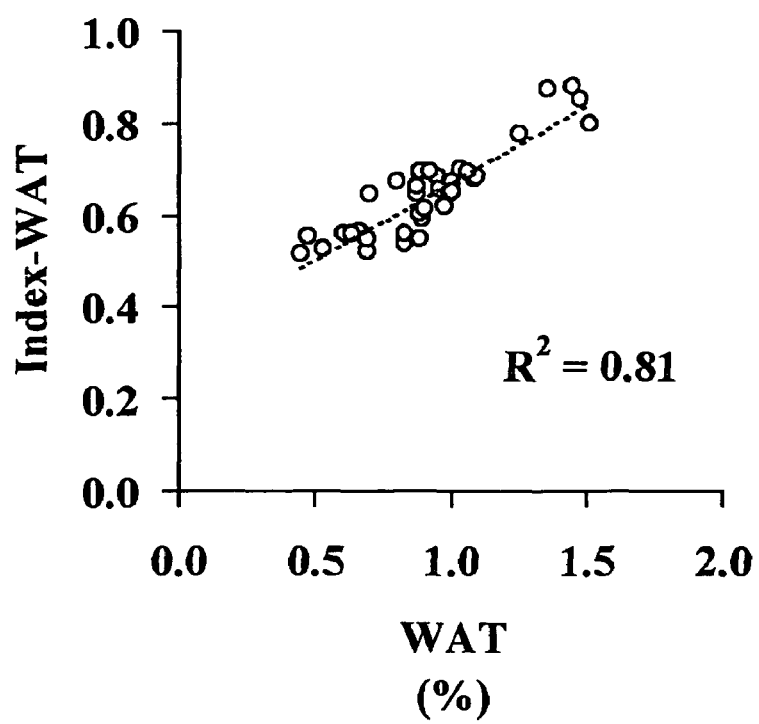
FIG. 70 is a diagram showing a correlation between the body weight ratio of epididymal fat tissue (WAT) and the value calculated based on the formula optimized for the WAT (Index-WAT).

Shown below is a formula optimized for a ratio (%) of epididymis peripheral fat to a body weight in the experiment of the above (3-1: Example of formula optimized for organ specific biochemical index) using blood amino acid level (see FIG. 70). FIG. 70 shows a correlation between a ratio of epididymis peripheral fat to body weight (WAT) and a value calculated by the formula optimized for ratio of epididymis peripheral fat to body weight (Index-WAT). In the following formula, "Cys" represents a cystine concentration, and "Cyshi" represents a cystathionine concentration.

Index-WAT:

(P-Ser+His)/(Cys+Cysthi+Phe+Arg)+(Cit)/(Asn+Val+Met+Tyr+Trp)

[4: Method of Collectively Determining Plural Physiological Conditions, Application and Usability Regarding Correlation of Plural Indices]

Figure 71:
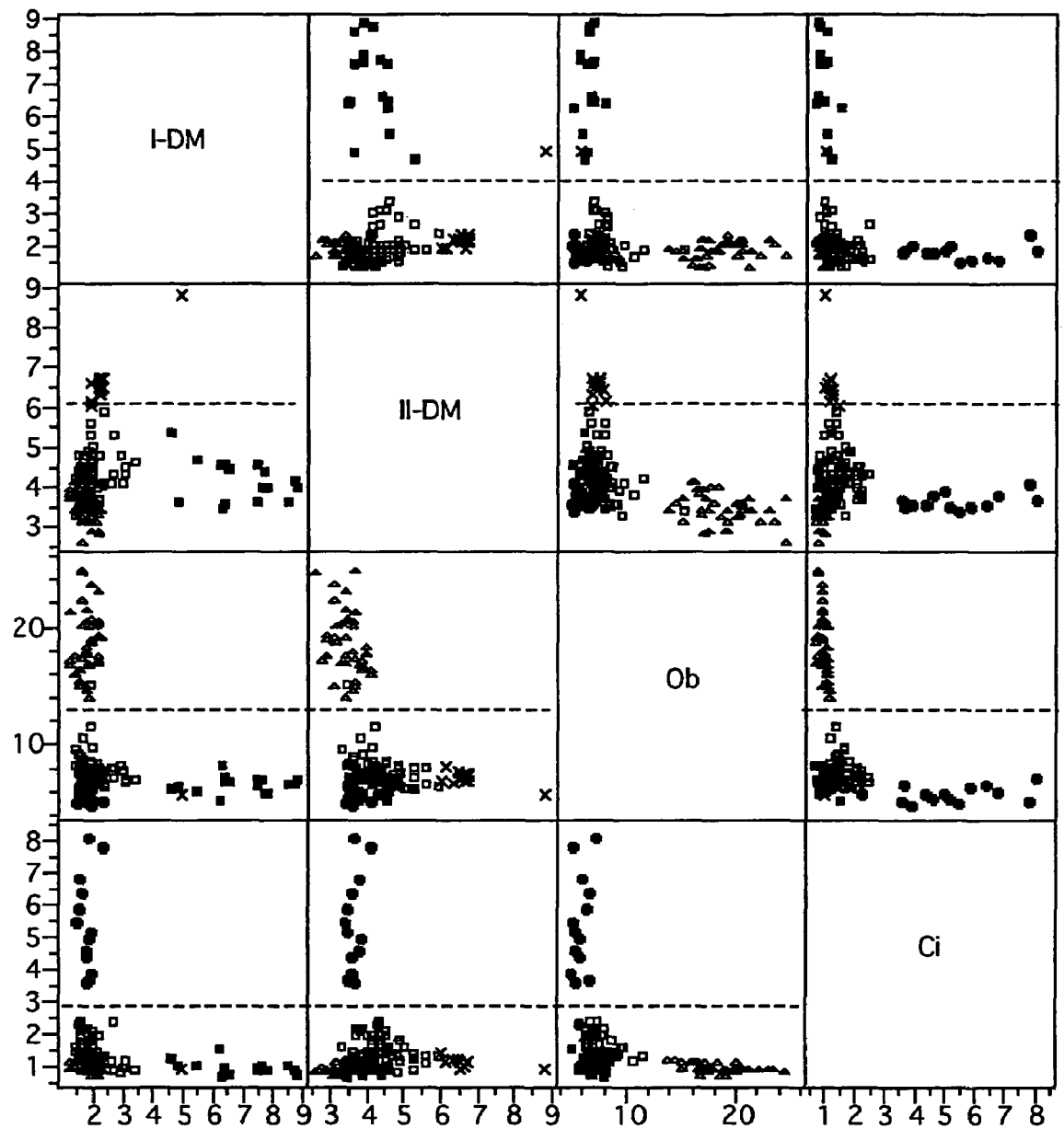
FIG. 71 is a diagram showing one example of simultaneous discrimination among streptozotocine-administered rats, GK rats, human growth hormone gene-introduced rats, hepatic fibrosis model rats, and normal rats, performed based on the blood amino acid level in respective rats.
Figure 72:
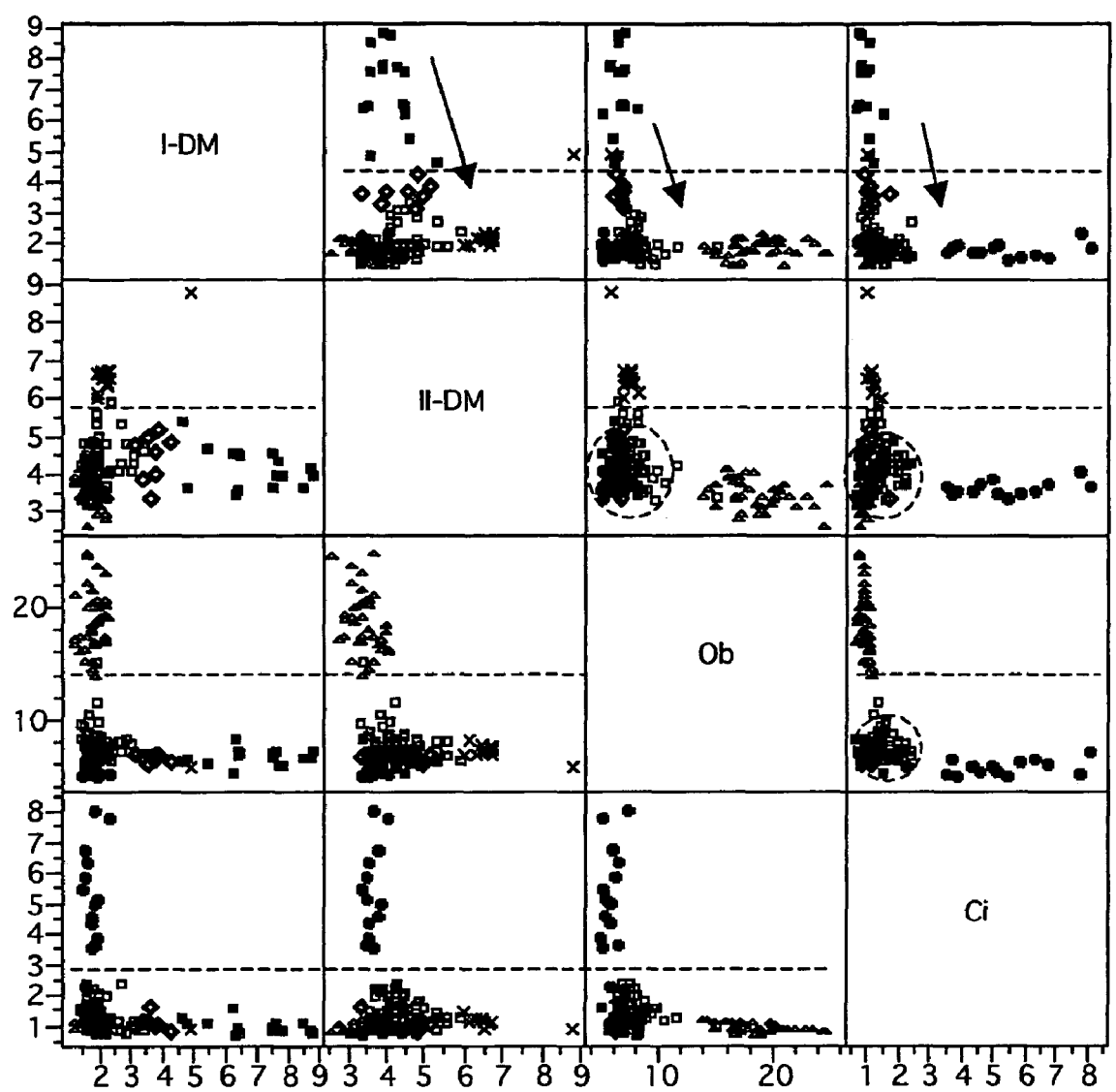
FIG. 72 is a diagram showing an example of collective examination of results of insulin treatment conducted on a rat with type I diabetes.

One exemplary approach for specifically determining a target condition by comparing the specific condition with every other different condition is shown with reference to FIG. 71 and FIG. 72.

Now we presents a description of one exemplary method of discriminating different conditions according to blood amino acid levels of a streptozotocin-administered rat which is a model animal for type I diabetes, a GK (Goto-Kakizaki) rat which is a model animal for type II diabetes, a human growth hormone transgenic rat exhibiting extreme obesity, a hepatic fibrosis model rat created by administration of dimethylnitrosamine and a normal rat (see FIG. 71).

FIG. 71 is a diagram showing one example of simultaneous discrimination among streptozotocine-administered rats, GK rats, human growth hormone gene-introduced rats, hepatic fibrosis model rats, and normal rats, performed based on the blood amino acid level in respective rats. In FIG. 71, "solid square" represents data of a streptozotocin-administered rat, "x" represents data of a GK rat, "open triangle" represents data of a human growth hormone transgenic rat, "solid circle" represents data of a hepatic fibrosis model rat and "open square" represents data of a normal rat.

The following formulae are examples of the calculated indices for specifically determining a target condition by comparing the specific condition with every other different condition.

Type I Diabetes Indices: Index (I-DM)

(Glu+Orn)/(Thr)+(lie)/(Met+His)+(Cit)/(Tau+Tyr)+(Leu)/(Gln+Pro)

Type II Diabetes Indices: Index (II-DM)

(Ser+Glu+Met+Trp)/(Cit+Pro)+(Phe)/(Orn)+(Gln)/(Tau+Tyr+Lys)

Obesity Index: Index (Ob)

(Thr+Cit)/(Tyr)+(Ser+Ala+Leu+Orn+Lys+Pro)/(Glu+Gly)

Index for Hepatic Fibrosis: Index (Ci)

(Cit+Arg)/(Tau+Thr)+(Phe)/(Gly+Ala+Val)+(Tyr)/(Ile)

FIG. 71 is a correlation chart showing correlations between each index. From such correlation between particular indices, the correlation between particular conditions becomes clear, and hence it is possible to verify the causal connection between particular conditions. For example, by calculating influences of meal-to-meal environmental factors exerted on a physiological condition as the foregoing discrimination formulae, and comparing such discrimination formulae characterizing various external factors with various disease condition-specific indices to verify the correlation therebetween, it is possible to predict risks on a disease condition by the environmental factors.

That is, as can be seen from FIG. 71, a plurality of conditions can be collectively examined with the use of these plural indices.

FIG. 72 shows an example of collective examination of results of insulin treatment conducted on a rat with type I diabetes. In FIG. 72, "solid square" represents data of a rat with type I diabetes (streptozotocin-administered rat), "x" represents data of a rat with type II diabetes (GK rat), "open triangle" represents data of an obese rat (human growth hormone transgenic rat), "solid circle" represents data of a hepatic fibrosis model rat, "open square" represents data of a normal rat, and "open diamond" represents data of a rat with type I diabetes having experienced an insulin treatment. In FIG. 72, the dotted line (ellipse) is plots of indices where a normal rat and a rat with type I diabetes is not discriminated from each other.

In FIG. 72, the results obtained through assignment to the foregoing formulae of individuals with type I diabetes treated with insulin are added to FIG. 71. This demonstrates that the insulin treatment specifically improves the corresponding determination index (I-DM). Therefore, not only a treatment effect on a target condition but also a treatment effect on other conditions can be examined in a collective manner, so that potent means for examining side effects would be provided. In other words, determination based on discrimination indices is enabled. Additionally, influences on physiologic conditions other than a treatment target can be determined concurrently.

[Example Regarding Prediction of Treatment Effect by Interferon and Ribavirin]

Interferon treatments of hepatitis C are cost consuming and cause significant side effects, and often fail to provide a treatment effect. Therefore, ability to previously expect a treatment effect is very important from the view point of mitigating a burden on a patient. The formula 3 below was used to discriminate a virus negative patient from a virus positive patient at the same point of time based on blood amino acid levels before administration in an interferon and ribavirin treatment of a patient with hepatitis C (see FIG. 73).

Figure 73:
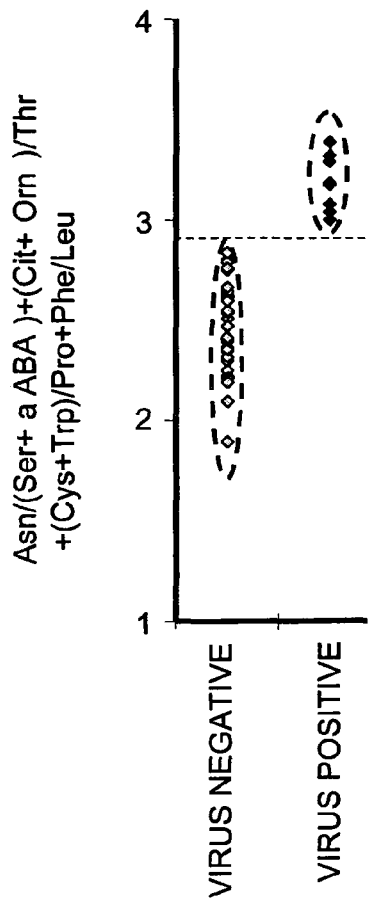
FIG. 73 is a diagram showing one example of the predicted results of treatment with interferon and ribavirin.

FIG. 73 shows one example of prediction result of an effect of an interferon and ribavirin treatment. In the present Example, the patient who turns into virus negative at 8 weeks or 12 weeks after starting of the treatment is defined as a virus negative patient. In the following formula 3 and FIG. 73, "αABA" represents a concentration of α-amino butyric acid and "Cys" represents a concentration of cystine.

FIG. 73 demonstrated that patients who benefited from the interferon and ribavirin treatment could be perfectly discriminated from patients who failed to benefit from the treatment. This result suggests the possibility of predicting efficacies, side effects and the like of various drugs by applying blood amino acid level before administrations of the drugs to the present analysis method. The present invention can be used as potent means for mitigating medical risks such as side effects.

Asn/(Ser+αABA)+(Cit+Orn)/Thr+(Cys+Trp)/Pro+Phe/Leu    Formula 3)

[Example Regarding Index for Determining Stress of Pig Before and After Transport]

Besides the situations where a blood amino acid level changes depending on the disease, medication and the like, a blood amino acid level may also change, for example, with a stress response or adaptation response to an environmental change. Pigs (n=8) loaded on a transportation truck were transported for one hour, and plasma amino acid levels of pigs measured before and after transport were analyzed, to obtain an index for determining the biological conditions of animals before and after stress application (formula 4 below).

Figure 74:
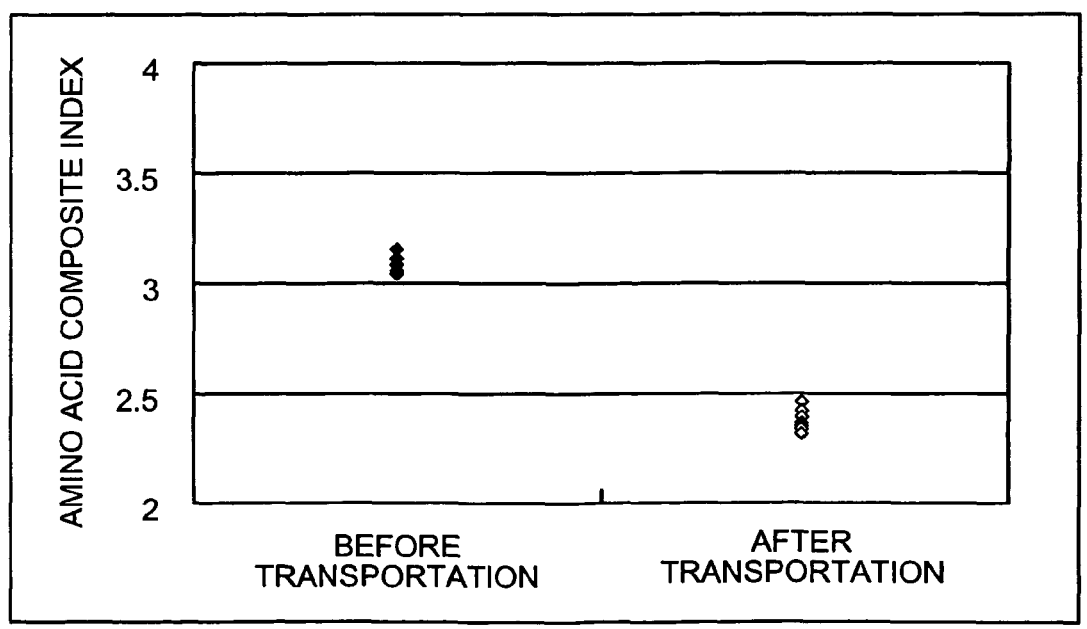
FIG. 74 is a diagram showing a composite index for amino acids before and after the transportation of swine.

FIG. 74 represents amino acid composite indices before and after transport of pigs. As shown in FIG. 74, by assigning a plasma amino acid level to the formula 4 below, it was possible to determine biological conditions of pigs before and after transport. This result suggests the possibility of mitigating the stress caused by a transport by increasing the plasma amino acid level described as a numerator of the following formula 4. This result is supported by the report that states a success in reduction of the stress caused by transport of pigs by administration of lysine (Lys) and arginine (Arg) which is a precursor of ornithine (Orn) (see "Srinongkote et al, Nutritional Neuroscience, 6, 283-289, 2003").

Formula 4) Best Index:

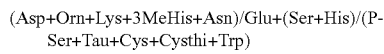

(Asp+Orn+Lys+3MeHis+Asn)/Glu+(Ser+His)/(P-Ser+Tau+Cys+Cysthi+Trp)

[Other Embodiments of Biological Condition Information Management System and the Like]

We have explained various embodiments of the present invention, however, in addition to the embodiments as described above, the present invention may be embodied in other different ways without departing from the technical idea defined in the claims.

In one embodiment of the present invention, the correlation formula selecting process executed in the correlation formula setting section 102v of the server unit 100 was explained while taking "Case where blood concentration of each amino acid included in clinical data is assigned to the formula 1, and each constant in the formula 1 is calculated again to select a correlation formula (Pattern 1)" described in the basic principal of the present invention, as an example, however, a correlation formula previously determined in the above Pattern 2 described in the basic principal of the present invention may be selected. To be more specific, correlation formulae previously calculated by the server unit 100 may be stored in a predetermined memory area in the memory 106, and a desired correlation formula may be selected and set from the memory 106 by the processing of the correlation formula setting section 102v. The server unit 100 may select and download a desired correlation formula via the network 300 from correlation formulae previously stored in other memory device such as computer unit by the processing of the correlation formula setting section 102v.

For example, the server unit 100 may execute a processing in response to a request from the client unit 200 or the like confined in another enclosure apart from the server unit 100 and returns the result of the processing to the client unit 200 or the like.

The aforementioned transmission of biological condition information (Step SA-1), transmission of analysis result (Step SA-3) and the like may be achieved by using an existing e-mail transmission technique or the like, or may be achieved in such a manner that a user or the like enters input information in a predetermined input format presented by a function of the Web site provided by the server unit 100, and the inputted information is transmitted. Alternatively, it may be achieved by known file transfer techniques such as FTP and the like.

Among each technique described in the above embodiments, the processings that were described as being conducted automatically may be fully or partly conducted manually, and the processings that were described as being conducted manually may be fully or partly conducted automatically by known methods.

In addition to the above, processing procedures, control procedures, specific names, information including parameters such as various registration data and search criteria, screen examples and database arrangement described in the above context and drawings may be arbitrarily changed unless otherwise noted.

As to the server unit 100, the elements illustrated in the drawing are given for representing functional concept, and are not necessarily structured physically as shown in the drawings.

For example, processing functions realized by particular parts or particular units in the server unit 100, especially each processing function executed in the control unit 102 may be fully or partly achieved by a CPU (Central Processing Unit) and a program that is interpreted and executed by the CPU, or may be achieved by hardware of wired logic system. Such a program is stored in a recording medium as will be described later, and is mechanically read by the server unit 100 as necessary.

In the memory 106 implemented by a ROM or a HD, a computer program for giving instructions and executing various processings in corporation with the OS (Operation System) is stored. This computer program is executed when it is loaded to a RAM or the like, and forms the control-unit 102 in corporation with the CPU. This computer program may be stored in an arbitrary application program server which is connected to the server unit 100 via the network 300. Alternatively, the whole or a part of the computer program may be downloaded as necessary.

The program of the present invention may be stored in a computer-readable recording medium. The term "recording medium" used herein includes any "portable physical medium" such as a flexible disk, a magneto optical disk, a ROM, an EPROM, an EEPROM, a CD-ROM, an MO, and a DVD and any "fixed physical medium" such as a ROM, a RAM, and a HD that are integrated in a variety of computer systems, as well as "communication medium" that temporarily holds a program such as communication line or carrier wave in the case of transmitting program over a network represented by LAN, WAN and the Internet.

The term "program" used herein refers to a data processing method descried in arbitrary language or description method, and may be described in any format including source code and binary code. "Program" is not necessarily configured as a single entity, but may be distributed as a plurality of modules or libraries, or may achieve its function in corporation with other separate programs as is represented by OS (Operating System). In each apparatus shown in the embodiments, concrete arrangements for reading recording media, reading procedures, or installing procedures after reading may be achieved using well-known arrangements or procedures.

Various databases stored in the memory 106 of the server unit 100 (user information database 106a to metabolism map information database 106e) are storage units that are implemented by memory devices such as a RAM and a ROM, fixed disk devices such as a hard disk, a flexible disk, an optical disk, and the like, and store various programs used for various processings or for providing Web sites, tables, files, databases and files for Web pages.

The server unit 100 may be realized by mounting software (including program, data and the like) that achieves the method of the present invention, on an information processing device structured by connecting peripheral devices such as a printer, a monitor and a image scanner to an existent information processing terminal such as a personal computer and a work station.

Furthermore, concrete forms in terms of integration/distribution of the server unit 100 are not limited to those illustrated in drawings, and the whole or a part thereof may be functionally or physically distributed or integrated in any units depending on various types of loads and the like. For example, each database may be independently arranged as an independent database device, and a part of processing may be realized by using the CGI (Common Gateway Interface).

The client unit 200 may be realized by mounting software (including program, data and the like) that achieves a Web information browsing function and an e-mail function, on an information processing device such as information processing terminals like an existent personal computer, a work station, a home-use game machine, an Internet TV, a PHS terminal, a cellular phone terminal, a mobile communication terminal, and a PDA, to which peripheral devices such as a printer, a monitor, an image scanner, and the like are connected as necessary.

The control unit 210 of the client unit 200 may be realized fully or partly by a CPU, a program, and a program interpreted and executed by the CPU. In other words, the ROM or HD stores a computer program for giving instructions to the CPU and executing various processings in corporation with the OS (Operating System). This computer program is executed when it is loaded to the RAM and forms the control unit together with the CPU.

However, this computer program may be stored in an arbitrary application program server which is connected to the client unit 200 via an arbitrary network, or the whole or a part of the computer program may be downloaded as necessary. Alternatively, the whole or an arbitrary part of each control unit may be realized by hardware based on the wired logic or the like.

The network 300 connects the server unit 100 and the client unit 200, and may include any one of the Internet, intranets, LANs (including both wired and wireless), VANs, PC communication networks, public telecommunication networks (including both analogue and digital), dedicated line networks (including both analogue and digital), CATV networks, mobile line switching networks/mobile packet switching networks of, for example, IMT 2000 system, GSM system, or PDC/PDC-P system, radio calling networks, local radio networks such as Bluetooth, PHS networks, satellite communication networks such as CS, BS or ISDB. That is, the present system can transmit/receive various data over any networks regardless of whether radio transmission or fixed-line communication.

[Embodiments of Hepatic Fibrosis Determining System and the Like]

Now, embodiments of a hepatic fibrosis determining apparatus, hepatic fibrosis determining method, hepatic fibrosis determining system, program and recording medium of the present invention will be explained in detail with reference to the drawings. It is to be noted that the present invention is not limited to these embodiments.

[System Arrangement—Hepatic Fibrosis Determination Apparatus 400]

Figure 45:
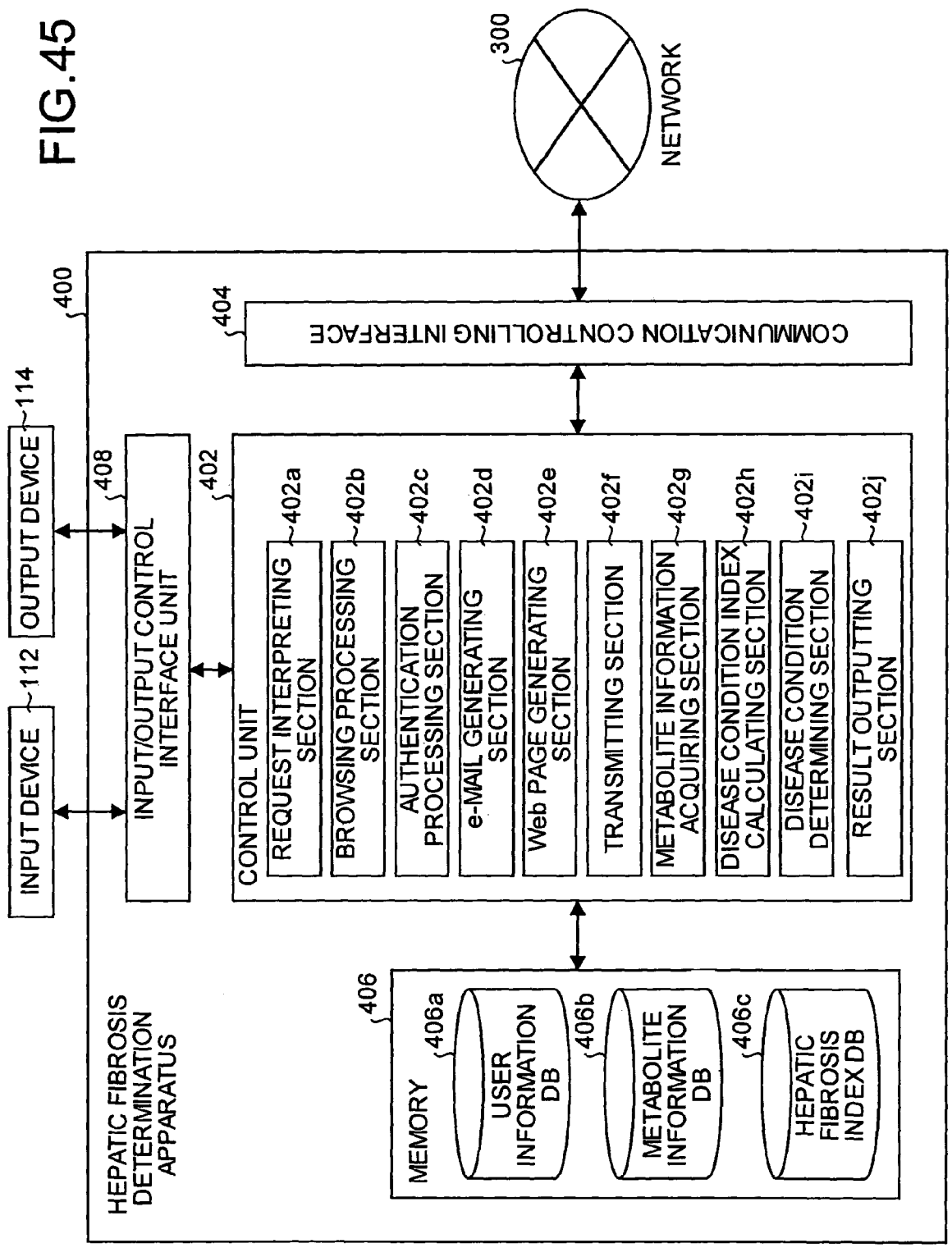
FIG. 45 is a block diagram showing an exemplary construction of a hepatic fibrosis determining apparatus 400 in the system to which the present invention is applied.

Next, an arrangement of the hepatic fibrosis determination apparatus 400 in the present system will be explained. FIG. 45 is a block diagram of one exemplary arrangement of the hepatic fibrosis determination apparatus 400 of the present invention to which the present invention is applied. Only the part that is related to the present invention in the above arrangement is illustrated conceptually.

In FIG. 45, the hepatic fibrosis determination apparatus 400 generally includes the control unit 402 such as CPU that controls the overall hepatic fibrosis determination apparatus 400; the communication controlling interface 404 connected with a communication device (not shown) such as router that is connected to a communication line or the like; the input/output controlling interface 408 connected with the input device 112 or the output device 114; and the memory 406 storing a variety of databases and tables, which are communicatively connected one another via arbitrary communication channels. Further, the hepatic fibrosis determination apparatus 400 is communicatively connected with the network 300 via a communication device such as router and a wireless or wired communication line such as dedicated line.

Various databases and tables (user information database 406a, metabolite information database 406b and hepatic fibrosis index database 406c) stored in the memory 406 of FIG. 45 are storage units such as fixed disk device or the like, and store e.g., various programs, tables, files, databases used for a variety of processings and files for Web pages.

Figure 47:
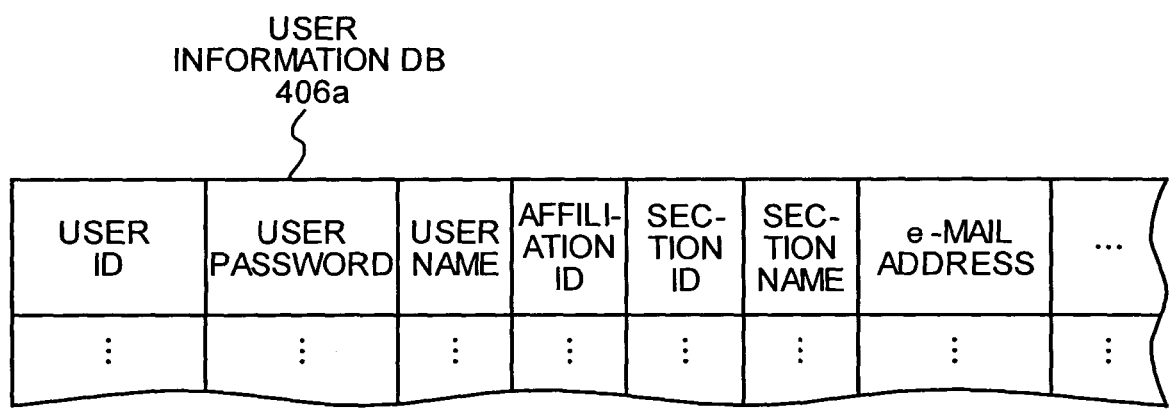
FIG. 47 is a chart showing one example of user information stored in a user information database 406$a$.

Among these elements constituting the memory 406, the user information database 406a is a user information storage unit that stores information about users (user information). FIG. 47 shows one example of user information stored in the user information database 406a.

The information stored in the user information database 406a includes, as shown in FIG. 47, user IDs for uniquely identifying each user; user password for authenticating the validity of each user; name of each user; affiliation ID for uniquely identifying the affiliation to which each user belongs; section ID for uniquely identifying the section name to which the affiliation of each user belongs; section name; and e-mail address of each user which are correlated to one another.

Figure 48:
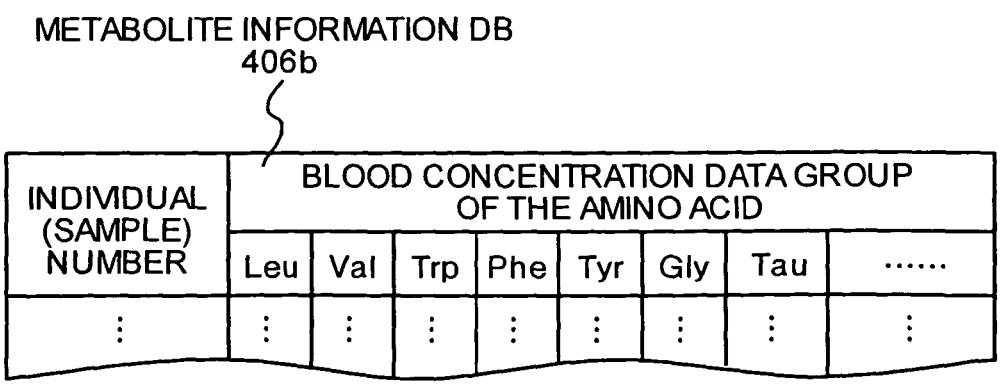
FIG. 48 is a chart showing one example of information stored in a metabolite information database 406$b$.

The metabolite information database 406b is a metabolite information storage unit that stores metabolite information and the like. FIG. 48 shows one example of information stored in the metabolite information database 406b.

The information stored in the metabolite information database 406b includes, as shown in FIG. 48, individual (sample) number; and blood concentrate data of each metabolite (for example, amino acid), which are correlated to each other.

The hepatic fibrosis index database 406c is a hepatic fibrosis index storage unit that stores hepatic fibrosis indices and the like. In this database, optimized indices that are optimized for each stage of each disease condition outputted by the processing of the result outputting section 102k of the server unit 100 are stored as composite indices, while related with top level indices as alternative indices. FIG. 50 shows one example of information stored in the hepatic fibrosis index database 406c. FIG. 50 shows one exemplary case where indices of the foregoing examples (Example of composite indices for hepatic fibrosis (Part I) and Example of composite indices for hepatic fibrosis (Part II)) are stored.

The information stored in the hepatic fibrosis index database 406c includes, as shown in FIG. 50, number, composite index and alternative index which are correlated one another.

In addition to the above information, the memory 406 of the hepatic fibrosis determination apparatus 400 also stores various Web data, CGI program or the like for providing the client unit 200 with Web sites.

The Web data includes data for displaying a variety of Web pages as will be described later, and such data is in the form of a text file described in HTML or XML. Component files, work files and other temporary files for generating the Web data are also stored in the memory 406.

In addition to the above, audio for transmission to the client unit 200 may be stored in an audio file of WAVE format or AIFF format, and a still image or a moving image may be stored in an image file of JPEG format or MPEG2 format as is necessary.

In FIG. 45, the communication controlling interface 404 controls communication between the hepatic fibrosis determination apparatus 400 and the network 300 (or communication device such as router). In other words, the communication controlling interface 404 enables data communication with other terminals via communication lines.

In FIG. 45, the input/output controlling interface 408 controls the input device 112 and the output device 114.

In FIG. 45, the control unit 402 has an internal memory for storing a control program such as OS (Operating System), a program defining a variety of procedures and required data, and executes information processings for executing a variety of processings by way of these programs. The control unit 402 includes a request interpreting section 402a, a browsing processing section 402b, an authentication processing section 402c, an e-mail generating section 402d, a Web page generating section 402e, a transmitting section 402f, a metabolite information acquiring section 402g, a disease condition index value calculating section 402h, a disease condition determining section 402i and a result outputting section 402j all of which are named for their functional concepts.

Among these, the request interpreting section 402a is a request interpreting unit that interprets the content of a request from the client unit 200 and transfers processings to other parts of the control unit depending on the result of the interpretation.

The browsing processing section 402b is a browsing processing unit that generates or transmits Web data of various screens in response to a browsing request for these screens from the client unit 200.

The authentication processing section 402c is an authentication processing unit that makes authentication in response to a request for authentication from the client unit 200.

The e-mail generating section 402d is an e-mail generating unit that generates an e-mail containing various information.

The Web page generating section 402e is a Web page generating unit that generates a Web page viewed by a user.

The transmitting section 402f is a transmitting unit that transmits various information to the client unit 200 of the user, and also is an analysis result transmitting unit that transmits a hepatic fibrosis determination result to the client unit 200 which is a sender of the metabolite information.

Figure 46:
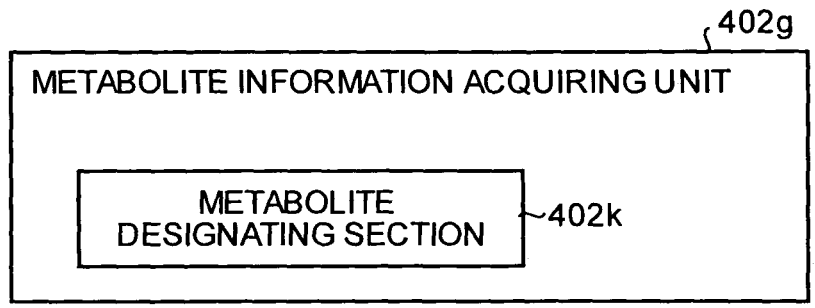
FIG. 46 is a block diagram showing an exemplary construction of a metabolite information acquiring unit 402$g$ in the system to which the present invention is applied.

The metabolite information acquiring section 402g is a metabolite information acquiring unit that acquires metabolite information including a group of blood concentration data measured for each metabolite in each individual from the client unit 200, the input device 112 or the like. The metabolite information acquiring section 402g further includes a metabolite designating section 402k as shown in FIG. 46. FIG. 46 is a block diagram showing one exemplary arrangement of the metabolite information acquiring section 402g of the present system to which the present invention is applied. Only the part that is related to the present invention in the above arrangement is illustrated conceptually.

In FIG. 46, the metabolite designating section 402k is a metabolite designating unit that designates a desired metabolite.

Referring again to FIG. 45, the disease condition index value calculating section 402h is a disease condition index value calculating unit that calculates a disease condition index value for hepatic fibrosis from metabolite information including a group of blood concentration data measured for each metabolite in each individual acquired by the metabolite information acquiring section 402g, based on at least one of the composite indices 1 to 4 stored in the hepatic fibrosis index database 406c or based on the composite index 5 stored in the hepatic fibrosis index database 406c, and is also a composite index setting unit that sets a composite index for calculating a disease condition index value for hepatic fibrosis. Herein the composite index setting unit comprises at least one selected from: a composite index 1 generating unit that generates the composite index 1 which is a fractional expression of single term or a fractional expression summing a plurality of terms, the fractional expression having at least one of blood concentration data of Asn and Gin as its numerator and at least one of blood concentration of Thr, Tau, Ser, Val and Trp as its denominator (optionally, blood concentration data of Met may be added to the numerator, and blood concentration data of any of Ile, α-ABA or Asp may be added to the denominator); a composite index 2 generating unit that generates the composite index 2 which is a fractional expression of single term or a fractional expression summing a plurality of terms, the fractional expression having at least one of blood concentration data of Asn and Met as its numerator and at least one of blood concentration of α-ABA and Cit as its denominator (optionally, blood concentration data of any of Tyr or Arg may be added to the numerator, and blood concentration data of any of His, Thr, Trp, Asp or Glu may be added to the denominator); a composite index 3 generating unit that generates the composite index 3 which is a fractional expression of single term or a fractional expression summing a plurality of terms, the fractional expression having at least one of blood concentration data of α-ABA, His, Gly, Trp and Tau as its numerator and at least one of blood concentration of Asn, Gin, Cit, Lys, Thr and Tyr as its denominator (optionally, blood concentration data of any of Met or Asp may be added to the denominator); and a composite index 4 generating unit that generates the composite index 4 which is a fractional expression of single term or a fractional expression summing a plurality of terms, the fractional expression having at least one of blood concentration data of His and Trp as its numerator and at least one of blood concentration of Asn and Tyr as its denominator (optionally, blood concentration data of any of α-ABA or Tau may be added to the numerator and blood concentration data of any of Met or Asp may be added to the denominator).

An amino acid in at least one formula of composite indices 1 to 4 may be replaced by an amino acid or the like having an equivalent chemical property.

To be more specific, for example, an amino acid in at least one formula of composite indices 1 to 4 may be replaced in accordance with the following rules, or at least one of the composite indices 1 to 4 may be replaced by the corresponding formulae as shown below.

The aforementioned rules will be described with reference to FIG. 51.

FIG. 51 represents rules for replacing an amino acid in each of the formulae for the composite indices 1 to 4.

As shown in FIG. 51, in each of the composite indices 1 to 4, any element belonging to Group A is at the numerator, and any element belonging to Group B is at the denominator. And each of the composite indices 1 to 4 is calculated by the formula in the form of a sum of fractions including at least one fraction that divides an element belonging to Group A or a sum of elements belonging to Group A by an element belonging to Group B or a sum of elements belonging to Group B. Herein, elements belonging to Group C and elements belonging to Group D may be added to the numerator and the denominator, respectively.

Each of the composite indices 1 to 4 may be replaced, for example, by the respective alternative indices (composite indices 1-1 to 1-20, composite indices 2-1 to 2-20, composite indices 3-1 to 3-20, composite indices 4-1 to 4-20) stored in the hepatic fibrosis index database 406c.

The disease condition determining section 402i is a disease condition determining unit that determines a disease condition indicative of the progression of hepatic fibrosis according to the disease condition index value calculated by the disease condition index value calculating section 402h.

The result outputting section 402j is an outputting unit that outputs e.g., processing results of processings in the control unit 402.

The details of the processings executed at these sections will be described later.

Explanation about the client unit 200 and the network 300 will be omitted because they are arranged in the same manner as described above.

[System Processings]

Figure 40:
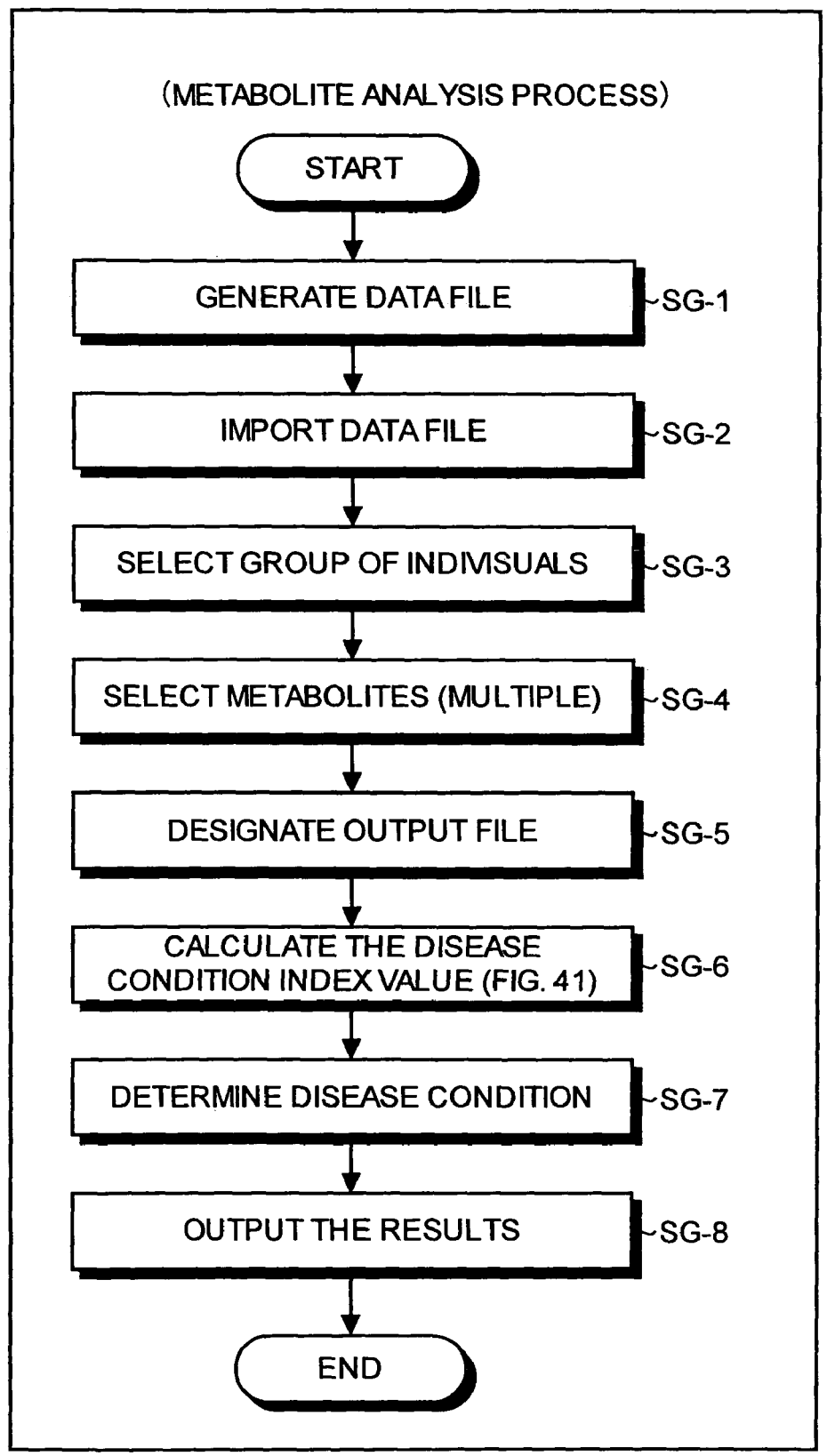
FIG. 40 is a flowchart showing one example of analysis process of the metabolite information by the system according to the present embodiment.
Figure 49:
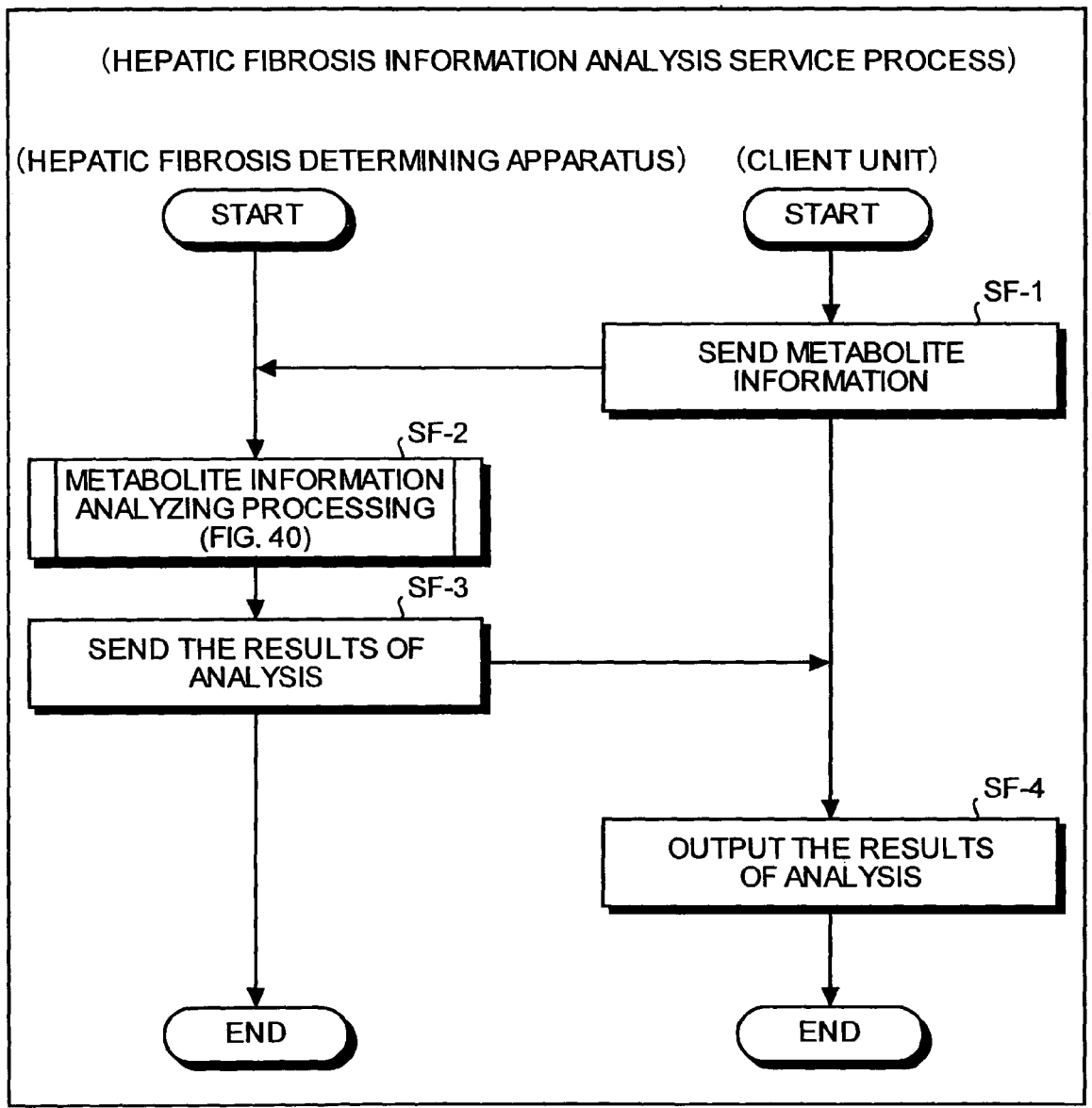
FIG. 49 is a flow chart showing one example of the service process of hepatic fibrosis information analysis in the system according to the present embodiment.

Next, examples of processings in the present system of the present embodiment arranged as described above will be explained in detail with reference to FIG. 40, FIG. 41, FIG. 49 and so on.

[Hepatic Fibrosis Information Analysis Service Processing]

Now the details of the hepatic fibrosis information analysis service processing which is the present method conducted using the present system arranged as describe above will be explained with reference to FIG. 49. FIG. 49 is a flowchart showing one example of a hepatic fibrosis information analysis service processing of the present system in the present embodiment.

First, a user designates an address of Web site (e.g. URL) provided by the hepatic fibrosis determination apparatus 400 via the input device 250 on the screen where the Web browser 211 is displayed, and the client unit 200 comes into connection with the hepatic fibrosis determination apparatus 400 via the Internet.

Specifically, a user starts up the Web browser 211 in the client unit 200, and enters a predetermined URL corresponding to the metabolite information sending screen of the present system in a predetermined entry field of the Web browser 211. When the user designates updating of the screen of the Web browser 211, the Web browser 211 transmits the URL via the communication controlling IF 280 in accordance with a predetermined communication protocol, and requests for the hepatic fibrosis determination apparatus 400 to transmit a Web page for metabolite information sending screen according to the routing based on this URL.

Then, upon detection of a transmission, the request interpreting section 402a of the hepatic fibrosis determination apparatus 400 that monitors whether or not a transmission is made from the client unit 200 analyzes the content of the transmission, and makes a respective part in the control unit 402 to conduct a processing depending on the result of the analysis. When the content of the transmission is a request for transmission of a Web page for metabolite information sending screen, Web data for displaying the Web page for metabolite information sending screen is acquired from the memory 406 mainly under the control of the browsing processing section 402a, and the Web data is transmitted to the client unit 200 via the communication controlling interface 404. The client unit 200 to which data is transmitted from the hepatic fibrosis determination apparatus 400 is identified from the IP address that is transmitted from the client unit 200 together with the transmission request.

When a user requests for transmission of a Web page, the user is requested to enter a user ID and a password, which is then authenticated by the authentication processing section 402c based on user IDs and user pass words stored in the user information database 406a. The Web page may be allowed to browse only when the authentication is valid (the details will be omitted in the following description because similar processings are repeated).

The client unit 200 receives Web data from the hepatic fibrosis determination apparatus 400 via the communication controlling IF 280, and interprets the data on the Web browser 211, thereby displaying the Web page for metabolite information sending screen on the monitor 261 in the following, screen request from the client unit 200 to the hepatic fibrosis determination apparatus 400, transmission of Web data from the hepatic fibrosis determination apparatus 400 to the client unit 200, and display of Web page in the client unit 200 are conducted in the similar manner, and hence detailed description thereof will be omitted.

Then, the user enters and selects metabolite information via the input device 250 of the client unit 200, and input information and an identifier for identifying the selected item are transmitted to the hepatic fibrosis determination apparatus 400 (Step SF-1).

The request interpreting section 402a of the hepatic fibrosis determination apparatus 400 interprets the identifier and analyzes the content of the request from the client unit 200 (as to identification of the content of request from the client unit 200 to the hepatic fibrosis determination apparatus 400, detailed description will be omitted hereinafter as the processings are conducted in almost the same manner).

Then the hepatic fibrosis determination apparatus 400 executes the metabolite information analyzing processing as will be described later using FIG. 40 or the like by a processing of each part in the control unit 402 (Step SF-2). Then the hepatic fibrosis determination apparatus 400 produces, by the processing of the Web page generating section 402e, a Web page intended to display the data of analysis result for the metabolite information sent by the user, and stores it in the memory 406.

Then the user enters a predetermined URL on the Web browser 211, and is allowed to browse the Web page for displaying the data of analysis result stored in the memory 406 after passing the authentication as described above.

That is, when the user transmits a request for browsing the Web page to the hepatic fibrosis determination apparatus 400 using the client unit 200, the hepatic fibrosis determination apparatus 400 reads out the Web page for the user from the memory 406 through the processing of the browsing processing section 402b and transmits it to the transmitting section 402f. The transmitting section 402f then transmits the Web page to the client unit 200 (Step SF-3). As a result, the user can browse the own Web page as desired (Step SF-4). Also, the user can print out the display content of the Web page with the printer 262 as necessary.

The hepatic fibrosis determination apparatus 400 may notify the user of the analysis result via an e-mail. The e-mail generating section 402d of the hepatic fibrosis determination apparatus 400 generates e-mail data containing analysis result data for the metabolite information sent by the user according to transmission timing. Concretely, it looks up the user information stored in the user information database 406a based on the user ID of the user and calls up an e-mail address of the user.

Then it generates mail data for an e-mail which is addressed to this e-mail address and containing the name of the user and the data of analysis result for the metabolite information sent by the user, and delivers the mail data to the transmitting section 402f. Then the transmitting section 402f transmits this mail data (Step SF-3).

On the other hand, the user receives the above e-mail using the electric mailer 212 of the client unit 200 at desired timing. This e-mail is displayed on the monitor 261 based on the known function of the electric mailer 212 (Step SF-4). Also the user can prints out the display content of the e-mail with the printer 262 as is necessary.

The hepatic fibrosis information analysis service processing ends here.

[Metabolite Information Analyzing Processing]

Next, the details of an analyzing processing of metabolite information will be described with reference to FIG. 40 or the like. FIG. 40 is a flowchart showing one exemplary analyzing processing of metabolite information of the present system in the present embodiment. The present embodiment is described while taking the case where tabulation is conducted using EXCEL (trade name) from Microsoft (company name) as an example, however, the present is not limited to that case, and may be executed using other programs.

First, the hepatic fibrosis determination apparatus 400 generates a data file in which groups of blood concentration data of amino acid are written in separate sheets on the Excel through the processing of the metabolite information acquiring section 402g (Step SG-1).

Then the hepatic fibrosis determination apparatus 400 takes the data file generated at Step SG-1 into the memory of the control unit 402 through the processing of the metabolite information acquiring section 402g (Step SG-2).

Next, the hepatic fibrosis determination apparatus 400 makes the user select a group of individuals to be analyzed (or a group of individuals to be excluded) through the processing of the metabolite information acquiring section 402g (Step SG-3).

Next, the hepatic fibrosis determination apparatus 400 makes the user select an amino acid to be analyzed through the processing of the metabolite designating section 402k (Step SG-4).

Next, the hepatic fibrosis determination apparatus 400 makes the user designate a file to which a result is outputted (Step SG-5).

Next, the hepatic fibrosis determination apparatus 400 calculates a disease condition index value through the processing of the disease condition index value calculating section 402h as will be described later using FIG. 41 (Step SG-6).

Figure 41:
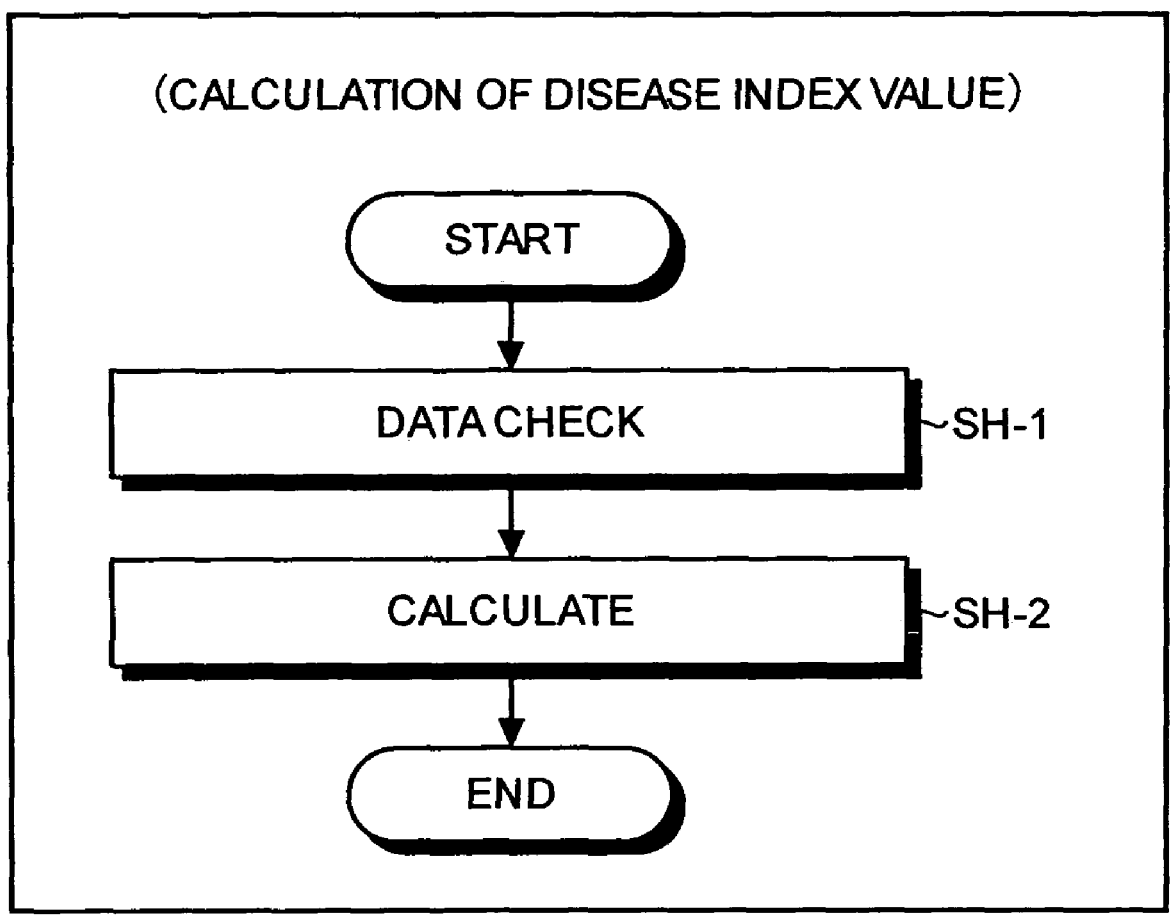
FIG. 41 is a flowchart showing one example of calculation process of disease condition index value by the system according to the present embodiment.

FIG. 41 is a flowchart showing one example of calculation of a disease condition index value in the present system in the present embodiment.

In calculation of a disease condition index value, first the hepatic fibrosis determination apparatus 400 checks metabolite information through the processing of the disease condition index value calculating section 402h (Step SH-1), and then calculates a disease condition index value based on at least one of the composite indices 1 to 4 stored in the hepatic fibrosis index database 406c or based on the composite index 5 stored in the hepatic fibrosis index database 406c (Step SH-2).

An amino acid in at least one formula of composite indices 1 to 5 may be replaced by an amino acid or the like having an equivalent chemical property.

To be more specific, for example, an amino acid in at least one formula of composite indices 1 to 4 may be replaced in accordance with the following rules, or at least one of the composite indices 1 to 4 may be replaced by the corresponding formulae as shown below.

The aforementioned rules will be described with reference to FIG. 51.

FIG. 51 represents rules for replacing an amino acid in each of the formulae for the composite indices 1 to 4.

As shown in FIG. 51, in each of the composite indices 1 to 4, any element belonging to Group A is at the numerator, and any element belonging to Group B is at the denominator. And each of the composite indices 1 to 4 is calculated by the formula in the form of a sum of fractions including at least one fraction that divides an element belonging to Group A or a sum of elements belonging to Group A by an element belonging to Group B or a sum of elements belonging to Group B. Herein, elements belonging to Group C and elements belonging to Group D may be added to the numerator and the denominator, respectively. In this manner, the disease condition index value calculating section 402h may generate the composite indices 1 to 4 according to these rules.

Each of the composite indices 1 to 4 may be replaced, for example, by the respective alternative indices (composite indices 1-1 to 1-20, composite indices 2-1 to 2-20, composite indices 3-1 to 3-20, composite indices 4-1 to 4-20) stored in the hepatic fibrosis index database 406c.

Referring again to FIG. 40, the hepatic fibrosis determination apparatus 400 determines the disease condition according to the disease condition index value calculated by the processing of the disease condition index value calculating section 402h through the processing of the disease condition determining section 402i (Step SG-7).

Next, the hepatic fibrosis determination apparatus 400 outputs the analysis result on a monitor through the processing of the result outputting section 402j and stores the analysis result in the memory 406 (Step SG-8).

The analyzing processing of metabolite information ends here.

[Other Embodiments of Hepatic Fibrosis Determining System and the Like]

In the foregoing description, embodiments of the present invention have been explained, however, the present invention may be embodied in various ways without departing from the scope of technical idea defined in the above claims besides the foregoing embodiments.

For example, the hepatic fibrosis determination apparatus 400 may execute the processing in response to a request from the client unit 200 or the like confined in another enclosure apart from the hepatic fibrosis determination apparatus 400, and may return the result of the processing to the client unit 200 or the like.

The aforementioned transmission of metabolite information (Step SF-1), transmission of analysis result (step SF-3) and the like may be achieved by using an existing electric mail transmission technique or the like, or may be achieved in such a manner that a user or the like inputs information in a predetermined input format presented by a function of the Web site provided by hepatic fibrosis determination apparatus 400, an the inputted information is transmitted. Alternatively, it may be achieved by known file transfer techniques such as FTP and the like.

Among each technique described in the above embodiments, the processings that were described as being conducted automatically may be fully or partly conducted manually, and the processings that were described as being conducted manually may be fully or partly conducted automatically by known methods.

In addition to the above, processing procedures, control procedures, specific names, information including parameters such as various registration data and search criteria, screen examples and database arrangement described in the above context and drawings may be arbitrarily changed unless otherwise noted.

As to hepatic fibrosis determination apparatus 400, the elements illustrated in the drawing are given as representation of functional concept, and are not necessarily structured physically as shown in the drawings.

For example, processing functions realized by particular parts or particular nits in hepatic fibrosis determination apparatus 400, especially each processing unction executed in the control unit 402 may be fully or partly achieved by a CPU (Central Processing Unit) and a program that is interpreted and executed by the CPU, or may be achieved by hardware of wired logic system. Such a program is stored in a recording medium as will be described later, and is mechanically read by the hepatic fibrosis determination apparatus 400 as necessary.

In the memory 406 implemented by ROM or HD, a computer program for giving instructions and executing various processings in corporation with the OS (Operation System) is stored. This computer program is executed when it is loaded to a RAM or the like, and forms the control unit 402 in corporation with the CPU. This computer program may be stored in an arbitrary application program server which is connected to the hepatic fibrosis determination apparatus 400 via the network 300. Alternatively, the whole or a part of the computer program may be downloaded as necessary.

The program of the present invention may be stored in a computer-readable recording medium. The term "recording medium" used herein includes any "portable physical medium" such as a flexible disk, a magneto optical disk, a ROM, an EPROM, an EEPROM, a CD-ROM, an MO, a and a DVD and any "fixed physical medium" such as a ROM, a RAM, and a HD that are integrated in a variety of computer systems, as well as "communication medium" that temporarily holds a program such as communication line or carrier wave in the case of transmitting program over a network represented by LAN, WAN and the Internet.

The term "program" used herein refers to a data processing method descried in arbitrary language or description method, and may be described in any format regardless of whether source code or binary code. "Program" is not necessarily configured as a single entity, but may be distributed as a plurality of modules or libraries, or may achieve its function in corporation with other separate programs as is represented by OS (Operating System). In each device shown in the embodiments, concrete arrangements for reading recording media, reading procedures or installing procedures after reading may be achieved using well-known arrangements or procedures.

Various databases stored in the memory 406 of the hepatic fibrosis determination apparatus 400 (user information database 406a, metabolite information database 406b, and hepatic fibrosis index database 406c) are storage units implemented by memory devices such as a RAM and a ROM, fixed disk devices such as a hard disk, a flexible disk, and an optical disk, and store various programs used for various processings or for providing Web sites, tables, files, databases and files for Web pages.

The hepatic fibrosis determination apparatus 400 may be realized by mounting software (including program, data and the like) that achieves the method of the present invention, on an information processing device structured by connecting peripheral devices such as a printer, a monitor and a image scanner to an existent information processing terminal such as a personal computer and a work station.

Furthermore, concrete forms in terms of integration/disintegration of the hepatic fibrosis determination apparatus 400 are not limited to those illustrated in drawings, and the whole or a part thereof may be functionally or physically distributed or integrated in any units depending on various types of loads and the like. For example, each database may be independently arranged as an independent database device, and a part of processing may be realized by using the CGI (Common Gateway Interface).

The network 300 connects the hepatic fibrosis determination apparatus 400 and the client unit 200, and may include any one of the Internet, intranets, LANs (including both wired and wireless), VANs, PC communication networks, public telecommunication networks (including both analogue and digital), dedicated line networks (including both analogue and digital), CATV networks, mobile line switching networks/mobile packet switching networks of, for example, IMT 2000 system, GSM system or PDC/PDC-P system, radio calling networks, local radio networks such as Bluetooth, PHS networks, satellite communication networks such as CS, BS or ISDB. That is, the present system can transmit/receive various data over any of the radio or fixed-line networks.

As is in the above detailed description, according to the present invention, after setting a correlation formula represented by the formula 1 which indicates a correlation between index data concerning a biological condition measured in each individual and blood concentration data measured for each metabolite in each individual; and a group of blood concentration data measured for each metabolite in an individual to be simulated is substituted into the set correlation formula, thereby simulating a biological condition of the individual to be simulated. Therefore, it is possible to provide an apparatus and a method for processing information concerning a biological condition, a system for managing information concerning a biological condition, a program, and a recording medium capable of effectively simulating the health condition, proceeding of disease, curing state of disease, future risk to disease, efficacy of drug, side effect of drug and the like on the basis of blood concentrations of metabolites in individuals.

According to the present invention, on the basis of index data concerning biological condition measured in each individual and a group of blood concentration data measured for each metabolite in each individual, a correlation of each metabolite with index data is determined; on the basis of the determined correlation of each metabolite, a correlation formula (correlation function) by a plurality of metabolites, relative to biological condition is created according to a predetermined calculation method; and on the basis of correlation coefficients for index data concerning biological condition in the determined correlation formula, the correlation formula is optimized (for example, in such a manner that the correlation coefficient is ranked in the top levels (e.g., top 20 levels), preferably the correlation coefficient is maximum), resulting that it is possible to use a calculation formula of high correlation as a composite index reflecting biological condition. Therefore, it is possible to provide an apparatus and a method for processing information concerning a biological condition, a system for managing information on a biological condition, a program, and a recording medium capable of effectively calculate a composite index composed of measurable metabolites such as amino acids having high correlation with biological conditions.

Further, according to the present invention, since composite indices for each biological condition can be individually determined, a number of disease conditions can be screened using one measurement result of e.g., blood amino acid level. Therefore, it is possible to provide an apparatus and a method for processing information concerning a biological condition, a system for managing information on a biological condition, a program, and a recording medium capable of largely reducing the testing cost.

Further, according to the present invention, it is possible to provide an apparatus and a method for processing information concerning a biological condition, system for managing information on a biological condition, a program, and a recording medium enabling a biological condition whose biological condition index is not available at the time of measurement, to be diagnosed by analyzing past data at the time when a composite index becomes clear.

Further, according to the present invention, since each metabolite composing a composite index for a biological condition is possibly a cause or a result of the biological condition, it is possible to provide an apparatus and a method for processing information concerning a biological condition, a system for managing information on a biological condition, a program, and a recording medium enabling development of a therapeutic method of biological condition using the composite index as a marker.

Further, according to the present invention, some of metabolites are selected; a correlation formula is established using a plurality of the selected metabolites; the correlation coefficient for index data concerning biological condition is calculated; and on the basis of the correlation coefficient for the index data concerning biological condition and the number of metabolites, combination of metabolites is optimized (for example, in such a manner that the correlation coefficient is ranked in top levels (e.g., in the top 20 levels) and the number of metabolites is minimum, preferably, the correlation coefficient is maximum and the number of metabolites is minimum), whereby selective removal of each amino acid is conducted exhaustively and automatically. Therefore, it is possible to provide an apparatus and a method for processing information concerning a biological condition, a system for managing information on a biological condition, a program, and a recording medium capable of efficiently determining a composite index regarding biological condition.

Further, according to the present invention, a calculation formula is split; a correlation formula regarding biological condition made up of a plurality of metabolites is calculated using the split calculation formula; and on the basis of the correlation coefficient for an index regarding biological condition, combination of the splitting is optimized (for example, in such a manner that the correlation coefficient is ranked in top levels (for example, top 20 levels), preferably the correlation coefficient is maximum); so that it is possible to split each calculation formula exhaustively and automatically. Therefore, it is possible to provide an apparatus and a method for processing information concerning a biological condition, a system for managing information on a biological condition, a program, and a recording medium capable of efficiently determining a composite index regarding biological condition.

Further, according to the present invention, since a calculation formula is split based on metabolism map information; and on the basis of the split formula, a correlation function for biological condition made up of a plurality of metabolites is calculated, it is possible to provide an apparatus and a method for processing information concerning a biological condition, a system for managing information on a biological condition, a program, and a recording medium capable of automatically splitting a calculation formula based on biochemical findings if the metabolism maps of metabolites in relation to biological conditions is already known.

Further, when an amino acid is selected as a metabolite in the present invention, it is possible to provide an apparatus and a method for processing information concerning a biological condition, a system for managing information on a biological condition, a program, and a recording medium capable of obtaining a composite index for biological condition having high reliability by utilizing the advantageous physical properties of amino acid, e.g. high accuracy in metabolite measurement and relatively small deviation resulting from measurement compared to deviation resulting from individual difference.

Further, according to the present invention, since a group of blood concentration data measured for each metabolite in each individual is acquired; a disease condition index value for hepatic fibrosis is calculated from the acquired group of blood concentration data based on at least one of the composite indices 1 to 4:

Composite Index 1:

$$(Asn)/(Thr)+(Gln)/(Tau+Ser+Val+Trp)$$

Composite Index 2:

$$(Asn+Tyr)/(Cit)+(Met+Arg)/(Asp+(\alpha\text{-}ABA))$$

Composite Index 3:

$$(Tau+Gly)/(Gln)+(\alpha\text{-}ABA)/(Asp+Tyr)+(His)/(Lys)+(Trp)/(Thr+Asn+Cit)$$

Composite Index 4:

$$(Tau+Trp)/(Tyr)+((\alpha\text{-}ABA)+His)/(Asp+Asn); \text{ and}$$

a disease condition of hepatic fibrosis is determined according to the calculated disease condition index value, a number of screenings for hepatic fibrosis can be conducted using one measurement result of e.g., blood amino acid level. Therefore, it is possible to provide an apparatus, a method, a system, a program, and a recording medium for determining hepatic fibrosis stage, capable of largely reducing the testing cost.

Further, according to the present invention, it is possible to provide an apparatus, a method, a system, a program, and a recording medium for determining hepatic fibrosis stage enabling diagnosis by analysis of past data.

Further, according to the present invention, since each metabolite composing at least one of the composite indices 1 to 4 for hepatic fibrosis is possibly a cause or result of the hepatic fibrosis, it is possible to provide an apparatus, a method, a system, a program, and a recording medium for determining hepatic fibrosis stage enabling development of a therapeutic method of hepatic fibrosis using at least one of the composite indices 1 to 4 as a marker.

Further, according to the present invention, a group of blood concentration data measured for each metabolite in each individual is acquired; a composite index for calculating a disease condition index value for hepatic fibrosis is set; on the basis of the set composite index, a disease condition index value for hepatic fibrosis is calculated from the acquired group of blood concentration data; a disease condition of hepatic fibrosis is determined in accordance with the calculated disease condition index value; and in the setting of the composite index, at least one of the following composite indices 1 to 4 is created: composite index 1 which is a fractional expression of single term or a fractional expression summing a plurality of terms, the fractional expression having at least one of blood concentration data of Asn and Gin as its numerator and at least one of blood concentration of Thr, Tau, Ser, Val and Trp as its denominator (blood concentration data of Met may be added to the numerator, and blood concentration data of any of lie, α-ABA or Asp may be added to the denominator); composite index 2 which is a fractional expression of single term or a fractional expression summing a plurality of terms, the fractional expression having at least one of blood concentration data of Asn and Met as its numerator and at least one of blood concentration of α-ABA and Cit as its denominator (blood concentration data of any of Tyr or Arg may be added to the numerator, and blood concentration data of any of His, Thr, Trp, Asp or Glu may be added to the denominator); composite index 3 which is a fractional expression of single term or a fractional expression summing a plurality of terms, the fractional expression having at least one of blood concentration data of α-ABA, His, Gly, Trp and Tau as its numerator and at least one of blood concentration of Asn, Gln, Cit, Lys, Thr and Tyr as its denominator (blood concentration data of any of Met or Asp may be added to the denominator); and composite index 4 which is a fractional expression of single term or a fractional expression summing a plurality of terms, the fractional expression having at least one of blood concentration data of His and Trp as its numerator and at least one of blood concentration of Asn and Tyr as its denominator (blood concentration data of any of α-ABA or Tau may be added to the numerator and blood concentration data of any of Met or Asp may be added to the denominator). Hence, a number of screenings for hepatic fibrosis can be conducted using one measurement result of e.g., blood amino acid level, and it is possible to provide an apparatus, a method, a system, a program, and a recording medium for determining hepatic fibrosis stage capable of largely reducing the testing cost.

Further, according to the present invention, it is possible to provide an apparatus, a method, a system, a program, and a recording medium for determining hepatic fibrosis stage enabling diagnosis by analysis of past measuring result data such as blood amino acid level.

Further, according to the present invention, since each metabolite composing a composite index for hepatic fibrosis is possibly a cause or a result of the hepatic fibrosis, it is possible to provide an apparatus, a method, a system, a program, and a recording medium for determining hepatic fibrosis stage enabling development of a therapeutic method of hepatic fibrosis using the composite index as a marker.

Further, according to the present invention, it is possible to provide an apparatus, a method, a system, a program, and a recording medium for determining hepatic fibrosis stage capable of creating a composite index which is useful in hepatic fibrosis exhaustively and automatically.

INDUSTRIAL APPLICABILITY

As described above, an apparatus and a method for processing information concerning a biological condition, as well as a system for managing information concerning a biological condition, a program, and a recording medium of the present invention can provide an analyzing methodology that derives a combination of metabolites having high relationship with a specific biological condition index, based on a correlation between various phenomena defining conditions of biological body (phenomics data) and a plurality of metabolites that can be readily measured (metabolomics data).

Further, an apparatus, a method, a system for determining hepatic fibrosis stage, a program, and a recording medium of the present invention can calculate a disease condition index value for hepatic fibrosis from a plurality of metabolites (specific amino acid) that can be readily measured, and determine a disease condition indicative of the progression of hepatic fibrosis according to the calculated disease condition index value.

Accordingly, the apparatus and the method for processing information concerning a biological condition, the system for managing information concerning a biological condition, the apparatus, the method and the system for determining hepatic fibrosis stage, and program and recording medium of the present invention are extremely useful in the bioinformatics field conducting diagnosis of disease condition, diagnosis of disease risk, proteome and metabolome analyses and the like.

The present invention is extremely useful because it has wide practicability in a large number of industrial fields, particularly, in pharmaceutical, food, cosmetic and medical fields.

The invention claimed is:

1. An apparatus for processing information concerning a biological condition, comprising:
a correlation formula setting unit that sets a correlation formula represented by the following formula 1, which correlates (i) index data concerning a biological condition measured in each individual with (ii) blood concentration data measured for each metabolite in each individual;

$$\sum_k G_k \frac{\sum_i \{(C_i \times A_i) + D_i\}}{\sum_j \{(E_j \times B_j) + F_j\}} + H \qquad (1)$$

(wherein each of i, j, and k is a natural number; each of $A_i$ and $B_j$ is data of concentration of the metabolite in blood or values obtained from applying a function to the concentration of the metabolite in blood; and each of $C_i$, $D_i$, $E_j$, $F_j$, $G_k$, and H is a constant); and
a biological condition simulation unit that simulates a biological condition of an individual to be simulated by substituting a group of blood concentration data measured for each metabolite in the individual to be simulated into the correlation formula set by the correlation formula setting unit.

2. The apparatus for processing information concerning a biological condition according to claim 1, wherein the correlation formula setting unit further comprises:
a correlation determining unit that determines a correlation between the index data concerning the biological condition measured in each individual and each metabolite based on the index data and the group of blood concentration data measured for each metabolite in each individual;
a correlation formula generating unit that generates a correlation formula involving a plurality of metabolites for the biological condition, the generation being carried out according to a predetermined calculation method and based on the correlation as to each metabolite determined by the correlation determining unit; and
an optimization unit that optimizes the correlation formula based on the correlation coefficient for the index data concerning the biological condition of the correlation formula determined by the correlation formula generating unit.

3. The apparatus for processing information concerning a biological condition according to claim 2, wherein the optimization unit further comprises:
a metabolite selecting unit that selects some of the metabolites, wherein the plurality of metabolites selected by the metabolite selecting unit are used to construct the correlation formula, to calculate the correlation coefficient for the index data concerning the biological condition, and to optimize the combination of metabolites based on the correlation coefficient for the index data concerning the biological condition and the number of the metabolites.

4. The apparatus for processing information concerning a biological condition according to claim 1, wherein the metabolite is an amino acid.

5. The apparatus for processing information concerning a biological condition according to claim 2, wherein the optimization unit further comprises:
   a calculation formula splitting unit that splits a calculation formula of the correlation formula, wherein the calculation formula split by the calculation formula splitting unit is used to calculate the correlation formula involving a plurality of metabolites for the biological condition, and the combination of the splits is optimized based on the correlation coefficient for the index data concerning the biological condition.

6. The apparatus for processing information concerning a biological condition according claim 5, wherein the optimization unit further comprises:
   a metabolic map splitting unit that splits the calculation formula based on the metabolic map information, wherein the calculation formula split by the metabolic map splitting unit is used to calculate the correlation formula involving a plurality of metabolites for the biological condition.

7. A method for processing information concerning a biological condition, comprising:
   a correlation formula setting step of setting a correlation formula represented by the following formula 1, which correlates (i) index data concerning a biological condition measured in each individual and with (ii) blood concentration data measured for each metabolite in each individual;

$$\sum_k G_k \frac{\sum_i \{(C_i \times A_i) + D_i\}}{\sum_j \{(E_j \times B_j) + F_j\}} + H \quad (1)$$

(wherein each of i, j and k is a natural number; each of $A_i$ and $B_j$ is data of concentration of the metabolite in blood or values obtained from applying a function to the concentration of the metabolite in blood; and each of $C_i$, $D_i$, $E_j$, $F_j$, $G_k$ and H is a constant), and
   a biological condition simulation step of simulating a biological condition, by one or more computers, of an individual to be simulated by substituting a group of blood concentration data measured for each metabolite in the individual to be simulated into the correlation formula which is set by the correlation formula setting step.

8. The method for processing information concerning a biological condition according to claim 5, wherein the correlation formula setting step further comprises:
   a correlation determining step of determining a correlation between the index data concerning the biological condition measured in each individual and each metabolite based on the index data and the group of blood concentration data measured for each metabolite in each individual;
   a correlation formula generating step of generating a correlation formula involving a plurality of metabolites for the biological condition, the generation being carried out according to a predetermined calculation method and based on the correlation as to each metabolite determined in the correlation determining step; and
   an optimization step of optimizing the correlation formula, by one or more computers, based on the correlation coefficient for the index data concerning the biological condition of the correlation formula determined in the correlation formula generating step.

9. The method for processing information concerning a biological condition according to claim 6, wherein the optimization step further comprises:
   a metabolite selecting step of selecting some of the metabolites, wherein the plurality of metabolites selected in the metabolite selecting step are used to construct the
   a metabolite selecting step of selecting some of the metabolites, wherein the plurality of metabolites selected in the metabolite selecting step are used to construct the correlation formula, to calculate the correlation coefficient for the index data concerning the biological condition, and to optimize the combination of metabolites based on the correlation coefficient for the index data concerning the biological condition and the number of the metabolites.

10. The method for processing information concerning a biological condition according to claim 8, wherein the optimization step further comprises:
    a calculation formula splitting step of splitting a calculation formula of the correlation formula, wherein the calculation formula split in the calculation formula splitting step is used to calculate the correlation formula involving a plurality of metabolites for the biological condition, and the combination of the splits is optimized based on the correlation coefficient for the index data concerning the biological condition.

11. The method for processing information concerning a biological condition according to claim 10, wherein the optimization step further comprises:
    a metabolic map splitting step of splitting the calculation formula based on the metabolic map information, wherein the calculation formula split in the metabolic map splitting step is used to calculate the correlation formula involving a plurality of metabolites for the biological condition.

12. The method for processing information concerning a biological condition according to claim 7, wherein the metabolite includes at least an amino acid.

13. A system for managing information concerning a biological condition, comprising:
    an apparatus that processes information concerning a biological condition; and
    an information terminal, the information terminal being communicably connected via a network to the apparatus for processing information;
    wherein the apparatus that processes information concerning the biological condition comprises:
       a correlation formula setting unit that sets a correlation formula represented by the following formula 1, which correlates (i) index data concerning a biological condition measured in each individual with (ii) a blood concentration data measured for each metabolite in each individual;

$$\sum_k G_k \frac{\sum_i \{(C_i \times A_i) + D_i\}}{\sum_j \{(E_j \times B_j) + F_j\}} + H \quad (1)$$

(wherein each of i, j and k is a natural number; each of $A_i$ and $B_j$ is data of concentration of the metabolite in blood or values obtained from applying a function to the concentration of the metabolite in blood; and each of $C_i$, $D_i$, $E_j$, $F_j$, $G_k$ and H is a constant)

a blood concentration data group acquiring unit that acquires from the information terminal a group of blood concentration data measured for each metabolite in an individual to be simulated;

a biological condition simulating unit that simulates a biological condition of the individual to be simulated by substituting the group of blood concentration data measured for each metabolite in the individual to be simulated, the data being obtained at the blood concentration data group acquiring unit, into the correlation formula which is set by the correlation formula setting unit; and an analysis result sending unit that sends the results of the simulation of the biological condition of the individual simulated by the biological condition simulating unit to the information terminal which is the sender of the group of blood concentration data;

wherein the information terminal comprises:
a sending unit that sends the group of blood concentration data to the apparatus for processing information concerning the biological condition; and
a receiving unit that receives the results of the simulation corresponding to the group of blood concentration data that have been sent by the sending unit, from the apparatus for processing information concerning the biological condition.

14. The system for managing information concerning a biological condition according to claim 13, wherein the correlation formula setting unit further comprises:
a correlation determining unit that determines a correlation between the index data concerning the biological condition measured in each individual and each metabolite based on the index data and the group of blood concentration data measured for each metabolite in each individual;
a correlation formula generating unit that generates a correlation formula involving a plurality of metabolites for the biological condition, the generation being carried out according to a predetermined calculation method and based on the correlation as to each metabolite determined by the correlation determining unit; and
an optimization unit that optimizes the correlation formula based on the correlation coefficient for the index data concerning the biological condition of the correlation formula determined by the correlation formula generating unit.

15. The system for managing information concerning a biological condition according to claim 14, wherein the optimization unit further comprises:
a metabolite selecting unit that selects some of the metabolites, wherein the plurality of metabolites selected by the metabolite selecting unit are used to construct the correlation formula, to calculate the correlation coefficient for the index data concerning the biological condition, and to optimize the combination of metabolites based on the correlation coefficient for the index data concerning the biological condition and the number of the metabolites.

16. The system for managing information concerning a biological condition according to claim 14, wherein the optimization unit further comprises:
a calculation formula splitting unit that splits a calculation formula of the correlation formula, wherein the calculation formula split by the calculation formula splitting unit is used to calculate the correlation formula involving a plurality of metabolites for the biological condition, and the combination of the splits is optimized based on the correlation coefficient for the index data concerning the biological condition.

17. The system for managing information concerning a biological condition according to claim 16, wherein the optimization unit further comprises:
a metabolic map splitting unit that splits the calculation formula based on the metabolic map information, wherein the calculation formula split by the metabolic map splitting unit is used to calculate the correlation formula involving a plurality of metabolites for the biological condition.

18. The system for managing information concerning a biological condition according to claim 13, wherein the metabolite includes at least an amino acid.

19. A tangible computer-readable medium having a program for executing on a computer a method for processing information concerning a biological condition, the method comprising:
a correlation formula setting step of setting a correlation formula represented by the following formula 1, which correlates (i) index data concerning a biological condition measured in each individual with (ii) blood concentration data measured for each metabolite in each individual;

$$\sum_k G_k \frac{\sum_i \{(C_i \times A_i) + D_i\}}{\sum_j \{(E_j \times B_j) + F_j\}} + H \quad (1)$$

(wherein each of i, j and k is a natural number; each of $A_i$ and $B_j$ is data of concentration of the metabolite in blood or values obtained from applying a function to the concentration of the metabolite in blood; and each of $C_i$, $D_i$, $E_j$, $F_j$, $G_k$ and H is a constant), and a biological condition simulation step of simulating a biological condition of an individual to be simulated by substituting a group of blood concentration data measured for each metabolite in the individual to be simulated into the correlation formula which is set in the correlation formula setting step.

20. The tangible computer-readable medium according to claim 19, wherein the correlation formula setting step further comprises:
a correlation determining step of determining a correlation between the index data concerning the biological condition measured in each individual and each metabolite based on the index data and the group of blood concentration data measured for each metabolite in each individual;

a correlation formula generating step of generating a correlation formula involving a plurality of metabolites for the biological condition, the generation being carried out according to a predetermined calculation method and based on the correlation as to each metabolite determined in the correlation determining step; and an optimization step of optimizing the correlation formula based on the correlation coefficient for the index data concerning the biological condition of the correlation formula determined in the correlation formula generating step.

21. The tangible computer-readable medium according to the claim 20, wherein the optimization step further comprises:

a metabolite selecting step of selecting some of the metabolites, wherein the plurality of metabolites selected in the metabolite selecting step are used to construct the correlation formula, to calculate the correlation coefficient for the index data concerning the biological condition, and to optimize the combination of metabolites based on the correlation coefficient for the index data concerning the biological condition and the number of the metabolites.

22. The tangible computer-readable medium according to claim 20 wherein the optimization step further comprises:

a calculation formula splitting step of splitting a calculation formula of the correlation formula, wherein the calculation formula split in the calculation formula splitting step is used to calculate the correlation formula involving a plurality of metabolites for the biological condition, and the combination of the splits is optimized based on the correlation coefficient for the index data concerning the biological condition.

23. The tangible computer-readable medium according to claim 22, wherein the optimization step further comprises:

a metabolic map splitting step of splitting the calculation formula based on the metabolic map information, wherein the calculation formula split in the metabolic map splitting step is used to calculate the correlation formula involving a plurality of metabolites for the biological condition.

24. The tangible computer-readable medium according to claim 19, wherein the metabolite includes at least an amino acid.

25. An apparatus for processing information concerning a biological condition, comprising:

a correlation formula setting unit that sets a correlation formula represented by the following formula 1, which correlates (i) index data concerning a biological condition measured in each individual with (ii) blood concentration data measured for each metabolite in each individual; said setting being performed by selecting the formula from formulae previously stored in a memory unit;

$$\sum_k G_k \frac{\sum_i \{(C_i \times A_i) + D_i\}}{\sum_j \{(E_j \times B_j) + F_j\}} + H \quad (1)$$

(wherein each of i, j, and k is a natural number; each of $A_i$ and $B_j$ is data of concentration of the metabolite in blood or values obtained from applying a function to the concentration of the metabolite in blood; and each of $C_i$, $D_i$, $E_j$, $F_j$, $G_k$, and H is a constant); and a biological condition simulation unit that simulates a biological condition of an individual to be simulated by substituting a group of blood concentration data measured for each metabolite in the individual to be simulated into the correlation formula which is set by the correlation formula setting unit.

26. An information terminal communicably connected via a network to an apparatus for processing information concerning a biological condition, comprising:

a sending unit that sends a group of blood concentration data measured for each metabolite in each individual to be simulated to the apparatus; and a receiving unit that receives results of a simulation corresponding to the group of blood concentration data that have been sent by the sending unit, from the apparatus, wherein the results of the simulation is the results of setting a correlation formula represented by the following formula 1, which correlates (i) index data concerning the biological condition measured in each individual with (ii) the blood concentration data measured for each metabolite in each individual, and simulating the biological condition of the individual to be simulated by substituting the group of blood concentration data measured for each metabolite in the individual to be simulated into the correlation formula $$\sum_k G_k \frac{\sum_i \{(C_i \times A_i) + D_i\}}{\sum_j \{(E_j \times B_j) + F_j\}} + H \quad (1)$$

(wherein each of i, j and k is a natural number; each of $A_i$ and $B_j$ is data of concentration of the metabolite in blood or values obtained from applying a function to the concentration of the metabolite in blood; and each of $C_i$, $D_i$, $E_j$, $F_j$, $G_k$ and H is a constant).

27. An apparatus for processing information communicably connected via a network to an information terminal, comprising:

a correlation formula setting unit that sets a correlation formula represented by the following formula 1, which correlates (i) index data concerning a biological condition measured in each individual with (ii) the blood concentration data measured for each metabolite in each individual:

$$\sum_k G_k \frac{\sum_i \{(C_i \times A_i) + D_i\}}{\sum_j \{(E_j \times B_j) + F_j\}} + H \quad (1)$$

(wherein each of i, j and k is a natural number; each of $A_i$ and $B_j$ is data of concentration of the metabolite in blood or values obtained from applying a function to the concentration of the metabolite in blood; and each of $C_i$, $D_i$, $E_j$, $F_j$, $G_k$ and H is a constant);

a blood concentration data group acquiring unit that acquires from the information terminal a group of blood concentration data measured for each metabolite in an individual to be simulated;

a biological condition simulating unit that simulates a biological condition of the individual to be simulated by substituting the group of blood concentration data measured for each metabolite in the individual to be simulated, the data being obtained at the blood concentration data group acquiring unit, into the correlation formula; and an analysis result sending unit that sends results of the simulation of the biological condition of the individual simulated by the biological condition simulating unit to the information terminal.

* * * * *